United States Patent
Schrader et al.

(10) Patent No.: US 12,054,487 B2
(45) Date of Patent: Aug. 6, 2024

(54) MUSCARINIC ACETYLCHOLINE $M_1$ RECEPTOR ANTAGONISTS

(71) Applicant: Contineum Therapeutics, Inc., San Diego, CA (US)

(72) Inventors: Thomas Schrader, San Diego, CA (US); Yifeng Xiong, San Diego, CA (US); Jill Baccei, San Diego, CA (US); Jeffrey Roppe, San Diego, CA (US); Austin Chen, San Diego, CA (US)

(73) Assignee: Contineum Therapeutics, Inc., San Diego, CA (US)

( * ) Notice: Subject to any disclaimer, the term of this patent is extended or adjusted under 35 U.S.C. 154(b) by 684 days.

(21) Appl. No.: 17/267,677

(22) PCT Filed: Sep. 3, 2019

(86) PCT No.: PCT/US2019/049374
§ 371 (c)(1),
(2) Date: Feb. 10, 2021

(87) PCT Pub. No.: WO2020/051153
PCT Pub. Date: Mar. 12, 2020

(65) Prior Publication Data
US 2021/0155629 A1    May 27, 2021

Related U.S. Application Data

(60) Provisional application No. 62/726,915, filed on Sep. 4, 2018.

(51) Int. Cl.
*C07D 487/04* (2006.01)
*A61K 45/06* (2006.01)
*C07D 519/00* (2006.01)
*A61P 25/00* (2006.01)

(52) U.S. Cl.
CPC ............ *C07D 487/04* (2013.01); *A61K 45/06* (2013.01); *C07D 519/00* (2013.01); *A61P 25/00* (2018.01); *C07B 2200/05* (2013.01)

(58) Field of Classification Search
CPC .... C07D 487/04; C07D 519/00; A61K 45/06; A61P 25/00; C07B 2200/05
See application file for complete search history.

(56) References Cited

U.S. PATENT DOCUMENTS

| | | | |
|---|---|---|---|
| 4,803,203 | A | 2/1989 | Caprathe et al. |
| 4,873,331 | A | 10/1989 | Childers, Jr. et al. |
| 5,089,497 | A | 2/1992 | Jaen et al. |
| 7,071,335 | B2 | 7/2006 | Kyle et al. |
| 8,648,074 | B2 | 2/2014 | Li et al. |
| 8,999,974 | B2 | 4/2015 | Morita et al. |
| 11,512,090 | B2 | 11/2022 | Xiong et al. |
| 11,752,149 | B2 | 9/2023 | Xiong et al. |
| 2006/0233843 | A1 | 10/2006 | Conn et al. |
| 2007/0129378 | A1 | 6/2007 | Siddiqui et al. |
| 2013/0178458 | A1 | 7/2013 | Lindsley et al. |
| 2013/0289019 | A1 | 10/2013 | Chau |
| 2018/0258085 | A1 | 9/2018 | Brown et al. |
| 2020/0181166 | A1 | 6/2020 | Lindsley et al. |
| 2020/0231592 | A1 | 7/2020 | Lindsley et al. |
| 2021/0155629 | A1 | 5/2021 | Schrader et al. |
| 2021/0161889 | A1 | 6/2021 | Xiong et al. |
| 2023/0089921 | A1 | 3/2023 | Baccei et al. |
| 2023/0364082 | A1 | 11/2023 | Xiong et al. |

FOREIGN PATENT DOCUMENTS

| | | |
|---|---|---|
| CN | 108349936 A | 7/2018 |
| WO | WO-97/23482 A1 | 7/1997 |
| WO | WO-2006/010751 A1 | 2/2006 |
| WO | WO-2007/077508 A2 | 7/2007 |
| WO | WO-2007/077508 A3 | 7/2007 |
| WO | WO-2013/103931 A1 | 7/2013 |
| WO | WO-2017/079641 A1 | 5/2017 |
| WO | WO-2018/089433 A1 | 5/2018 |
| WO | WO-2019/158572 A1 | 8/2019 |
| WO | WO-2019/212937 A1 | 11/2019 |
| WO | WO-2019/241131 A1 | 12/2019 |
| WO | WO-2020/051153 A1 | 3/2020 |
| WO | WO-2021/071843 A1 | 4/2021 |

OTHER PUBLICATIONS

Zuev, D. et al. Stereoselective Synthesis of New Conformationally Restricted Analogues of a Potent CGRP Receptor Antagonist. Organic Letters 2005 vol. 7, No. 12, p. 2465-2468 (Year: 2005).*
Xi Liu. et al. Parkinsonism Caused by Viral Encephalitis Affecting the Bilateral Substantia Nigra. Clin Neuroradiol (2019) 29:571-573 (Year: 2019).*
Gregory A. Jicha. et al. Hippocampal Sclerosis, Argyrophilic Grain Disease, and Primary Age-Related Tauopathy. Continuum ( MINNEAP MINN) 2019;25(1, Dementia):208-233. (Year: 2019).*
Merilee Teylan. et al. Clinical diagnoses among individuals with primary age-related tauopathy versus Alzheimer's neuropathology. Laboratory Investigation (2019) 99:1049-1055 https://doi.org/10.1038/s41374-019-0186-0 (Year: 2019).*
Klein, J. Can a person prevent multiple sclerosis? Medical News Today. Apr. 29, 2020. pp. 1-9 (Year: 2020).*
Sasha Smith. et al. Prevention and Management Strategies for Diabetic Neuropathy. Life 2022, 12, 1185. https://doi.org/10.3390/life12081185 p. 1-28 (Year: 2022).*
Extended European Search Report mailed on Oct. 10, 2023, for EP Patent Application No. 20875038.0, 7 pages.

(Continued)

*Primary Examiner* — Noble E Jarrell
*Assistant Examiner* — Richard Grant Peckham
(74) *Attorney, Agent, or Firm* — Mintz, Levin, Cohn, Ferris, Glovsky and Popeo, P.C.

(57) ABSTRACT

Provided, inter alia, are compounds which are useful as antagonists of the muscarinic acetylcholine receptor M1 (mAChR M1); synthetic methods for making the compounds; pharmaceutical compositions comprising the compounds; and methods of treating neurological and psychiatric disorders associated with muscarinic acetylcholine receptor dysfunction using the compounds and compositions.

18 Claims, No Drawings

(56) References Cited

OTHER PUBLICATIONS

Bender, A.M. et al. (Aug. 1, 2017, e-published May 15, 2017). "Discovery and optimization of 3-(4-aryl/heteroarylsulfonyl)piperazin-1-yl)-6-(piperidin-1-yl)pyridazines as novel, CNS penetrant pan-muscarinic antagonists," *Bioorg Med Chem Lett* 27(15):3576-3581.

International Search Report mailed Oct. 18, 2019, for PCT Application No. PCT/US2019/036345, filed Jun. 10, 2019, 4 pages.

International Search Report mailed on Nov. 21, 2019, for PCT Application No. PCT/US2019/049374, filed Sep. 3, 2019, 3 pages.

International Search Report mailed on Dec. 29, 2020 for PCT Application No. PCT/US2020/054412, filed Oct. 6, 2020, 3 pages.

Melancon, B.J. et al. (Jan. 15, 2012, e-published Dec. 6, 2011). "Development of a more highly selective M1 antagonist from the continued optimization of the MLPCN Probe ML012," *Bioorg Med Chem Lett* 22(2):1044-1048.

Melancon, B.J. et al. (Aug. 1, 2012, e-published Jun. 15, 2012). "Development of novel M1 antagonist scaffolds through the continued optimization of the MLPCN probe ML012," *Bioorg Med Chem Lett* 22(15):5035-5040.

PubChem CID 70746046, (Create Date Mar. 4, 2013), located at <https://pubchem.ncbi.nlm.nih.gov/compound/70746046>, 5 pages.

PubChem CID 101131894, (Create Date Dec. 17, 2015), located at <https://pubchem.ncbi.nlm.nih.gov/compound/101131894>, 7 pages.

PubChem CID 101131895, (Create Date Dec. 17, 2015), located at <https://pubchem.ncbi.nlm.nih.gov/compound/101131895>, 8 pages.

PubChem CID 102350371, (Create Date Dec. 25, 2015), located at <https://pubchem.ncbi.nlm.nih.gov/compound/102350371>, 7 pages.

Sheffler, D.J. et al. (Aug. 2009, e-published Apr. 30, 2009). "A novel selective muscarinic acetylcholine receptor subtype 1 antagonist reduces seizures without impairing hippocampus-dependent learning," *Mol Pharmacol* 76(2):356-368.

Written Opinion mailed Oct. 18, 2019, for PCT Application No. PCT/US2019/036345, filed Jun. 10, 2019, 6 pages.

Written Opinion mailed on Nov. 21, 2019, for PCT Application No. PCT/US2019/049374, filed Sep. 3, 2019, 4 pages.

Written Opinion mailed on Dec. 29, 2020 for PCT Application No. PCT/US2020/054412, filed Oct. 6, 2020, 3 pages.

Extended European Search Report mailed on May 6, 2022, for EP Patent Application No. 19857624.1, 8 pages.

Manetti, D. et al. (May 18, 2000). "Design, synthesis, and preliminary pharmacological evaluation of 1, 4-diazabicyclo[4.3.0]nonan-9-ones as a new class of highly potent nootropic agents," *Journal of Medicinal Chemistry* 43(10):1969-1974.

Weaver, C.D. et al. (2009). "Discovery and development of a potent and highly selective small molecule muscarinic acetylcholine receptor subtype I (mAChR 1 or M1) antagonist in vitro and in vivo probe," *Current Topics in Medicinal Chemistry* 9(13):1217-1226.

International Search Report mailed on Jul. 15, 2022, for PCT Application No. PCT/US2022/024684, filed on Apr. 13, 2022, 2 pages.

Written Opinion mailed on Jul. 15, 2022, for PCT Application No. PCT/US2022/024684, filed on Apr. 13, 2022, 3 pages.

\* cited by examiner

MUSCARINIC ACETYLCHOLINE M₁ RECEPTOR ANTAGONISTS

CROSS-REFERENCES TO RELATED APPLICATIONS

This application is the national stage filing under 35 U.S.C. § 371 of International Application No. PCT/US2019/049374 filed Sep. 3, 2019, which claims the benefit of U.S. Provisional Application No. 62/726,915, filed on Sep. 4, 2018, which are herein incorporated by reference in their entirety.

BACKGROUND

The human muscarinic acetylcholine receptor $M_1$ (mAChR $M_1$) is a protein of 479 amino acids encoded by the CHRM1 gene. The mAChR $M_1$ is one of five member of the family of muscarinic acetylcholine receptors ($M_1$-$M_5$), which are widely expressed throughout the body where they have varying roles in cognitive, sensory, motor, and autonomic functions. The $M_1$ mAChR is found in both the central and peripheral nervous systems, particularly in the cerebral cortex and sympathetic ganglia. Based on the potential role of mAChR $M_1$ in seizure activity and motor control, highly selective mAChR $M_1$ antagonists may have potential utility in the treatment of some epileptic disorders, as well as certain movement disorders, including Parkinson's disease, dystonia, and fragile X syndrome.

SUMMARY

This disclosure provides, for example, compounds and compositions which are antagonists of the muscarinic acetylcholine $M_1$ receptor (mAChR $M_1$), and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of muscarinic acetylcholine M1 receptor activity in patients.

In one aspect is provided a compound of Formula (IA):

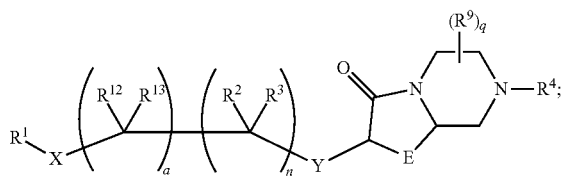

Formula (IA)

wherein: E is —CH₂—, —CH₂CH₂—, —O—CH₂—, or —CH₂—O—; X is a bond,

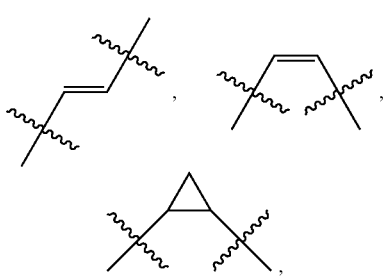

—C≡C—, —C(=O)—, —CH₂O—, —CH₂CH₂O—, —O—, —N(R⁷)—, —S(O)₂—, —CH₂N(R⁷)—, or —CH₂CH₂N(R⁷)—; Y is a bond, —O—, or —N(R⁸)—; $R^1$ is

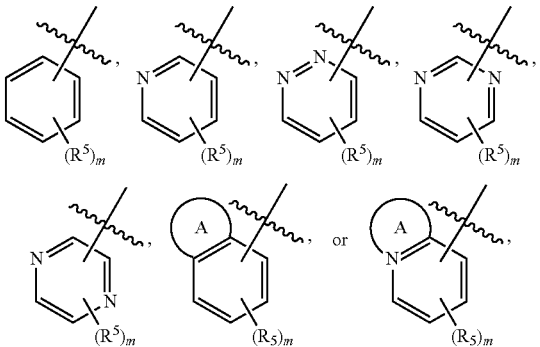

wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N(R¹⁰)₂, $C_{1-6}$ alkyl, $C_{1-6}$ alkyl-OH, $C_{1-6}$ alkoxy, $C_{1-6}$ haloalkyl, or $C_{1-6}$ haloalkoxy; each $R^2$ is independently selected from hydrogen, deuterium, halogen, —OH, and $C_{1-6}$ alkyl; each $R^3$ is independently selected from hydrogen, deuterium, halogen, —OH, and $C_{1-6}$ alkyl; $R^4$ is

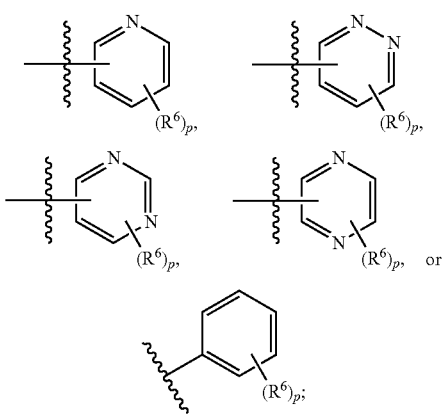

each $R^5$ is independently selected from halogen, —CN, $C_{1-6}$ alkyl, $C_{1-6}$ cycloalkyl, $C_{1-6}$ alkoxy, $C_{1-6}$ haloalkyl, and $C_{1-6}$ haloalkoxy; each $R^6$ is independently selected from hydrogen, deuterium, halogen, —CN, —N(R¹⁰)₂, $C_{1-6}$ alkyl, $C_{1-6}$ cycloalkyl, $C_{1-6}$ alkoxy, $C_{1-6}$ haloalkyl, $C_{1-6}$ haloalkoxy, —C(=O)($C_{1-6}$ alkyl), —(C(R¹⁰)₂)$_q$—O—($C_{1-6}$ alkyl) and —S(O)₂R¹¹; $R^7$ is hydrogen or $C_{1-6}$ alkyl; $R^8$ is hydrogen or $C_{1-6}$ alkyl; $R^9$ is hydrogen or $C_{1-6}$ alkyl; each $R^{10}$ is independently selected from H and $C_{1-6}$ alkyl; $R^{11}$ is $C_{1-6}$ alkyl; each $R^{12}$ is independently selected from hydrogen, deuterium, halogen, —OH, and $C_{1-6}$ alkyl; each $R^{13}$ is independently selected from hydrogen, deuterium, halogen, —OH, and $C_{1-6}$ alkyl; a is 1, 2, 3, 4, or 5; m is 0, 1, 2, or 3; n is 1, 2, 3, 4, or 5; p is 0, 1, 2, or 3; and each q is independently 0, 1, 2, 3, or 4; or a pharmaceutically acceptable salt or solvate thereof.

In some embodiments is a compound of Formula (IA) wherein $R^4$ is

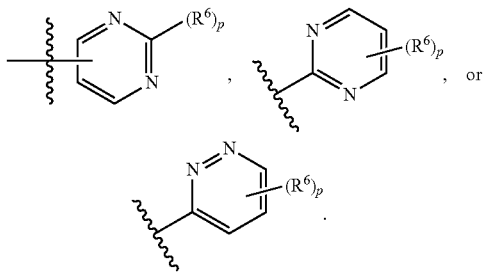

In one aspect is provided a compound of Formula (I):

Formula (I)

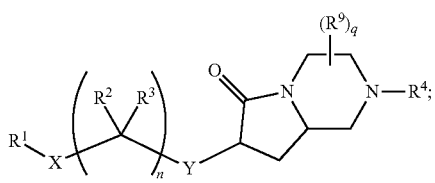

wherein:
X is a bond, —CH$_2$O—, —CH$_2$CH$_2$O—, —O—, —N(R$^7$)—, —S(O)$_2$—, —CH$_2$N(R$^7$)—, or —CH$_2$CH$_2$N(R$^7$)—;
Y is a bond, —O—, or —N(R$^8$)—;
$R^1$ is

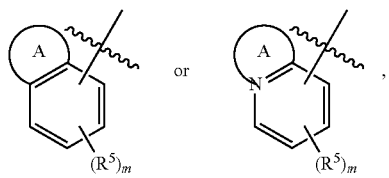

wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy;
each $R^2$ is independently selected from H and C$_{1-6}$ alkyl;
each $R^3$ is independently selected from H and C$_{1-6}$ alkyl;
$R^4$ is

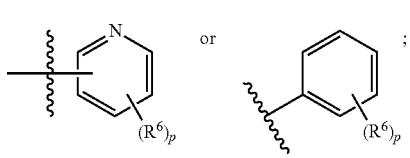

each $R^5$ is independently selected from halogen, —CN, C$_{1-6}$ alkyl, C$_{1-6}$ alkoxy, C$_{1-6}$ haloalkyl, and C$_{1-6}$ haloalkoxy;
each $R^6$ is independently selected from halogen, —CN, —N(R$^{10}$)$_2$, C$_{1-6}$ alkyl, C$_{1-6}$ alkoxy, C$_{1-6}$ haloalkyl, C$_{1-6}$ haloalkoxy, and —S(O)$_2$R$^{11}$;

$R^7$ is hydrogen or C$_{1-6}$ alkyl;
$R^8$ is hydrogen or C$_{1-6}$ alkyl;
$R^9$ is C$_{1-6}$ alkyl;
each $R^{10}$ is independently selected from H and C$_{1-6}$ alkyl;
$R^{11}$ is C$_{1-6}$ alkyl;
m is 0, 1, 2, or 3;
n is 1, 2, 3, 4, or 5;
p is 0, 1, 2, or 3; and
q is 0, 1, 2, 3, or 4;
or a pharmaceutically acceptable salt or solvate thereof.

In some embodiments is a compound of Formula (I), or a pharmaceutically acceptable salt or solvate thereof, having the structure of Formula (Ia), or a pharmaceutically acceptable salt or solvate thereof:

Formula (Ia)

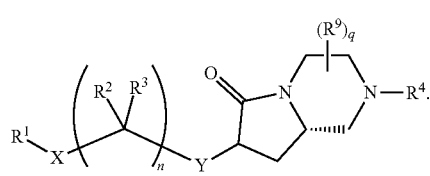

In some embodiments is a compound of Formula (I), or a pharmaceutically acceptable salt or solvate thereof, having the structure of Formula (Ib), or a pharmaceutically acceptable salt or solvate thereof:

Formula (Ib)

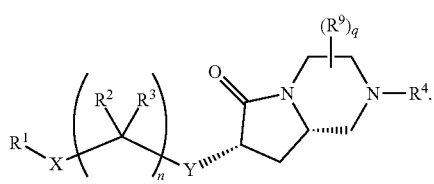

In some embodiments is a compound of Formula (I), or a pharmaceutically acceptable salt or solvate thereof, having the structure of Formula (Ic), or a pharmaceutically acceptable salt or solvate thereof:

Formula (Ic)

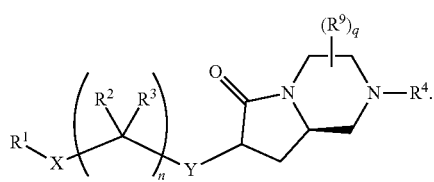

In some embodiments is a compound of Formula (I), or a pharmaceutically acceptable salt or solvate thereof, having the structure of Formula (Id), or a pharmaceutically acceptable salt or solvate thereof:

Formula (Id)

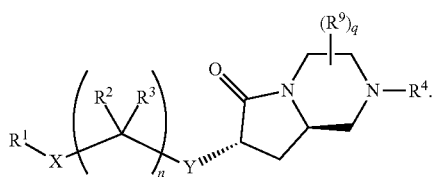

In some embodiments of a compound of Formula (I), (Ia), (Ib), (Ic), or (Id), or a pharmaceutically acceptable salt or solvate thereof, $R^1$ is

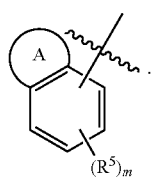

In some embodiments of a compound of Formula (I), (Ia), (Ib), (Ic), or (Id), or a pharmaceutically acceptable salt or solvate thereof, ring A is 5- or 6-membered heteroaryl ring. In some embodiments of a compound of Formula (I), (Ia), (Ib), (Ic), or (Id), or a pharmaceutically acceptable salt or solvate thereof, $R^1$ is

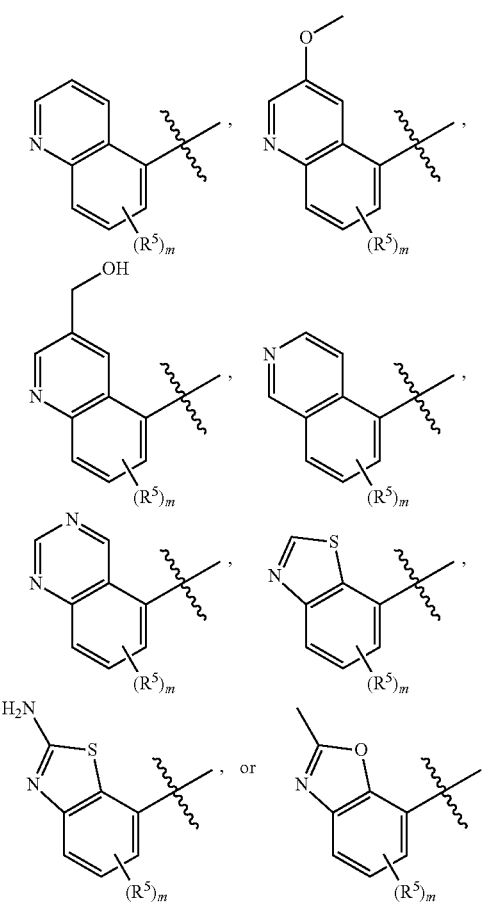

In some embodiments of a compound of Formula (I), (Ia), (Ib), (Ic), or (Id), or a pharmaceutically acceptable salt or solvate thereof, $R^1$ is

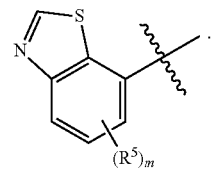

In some embodiments of a compound of Formula (I), (Ia), (Ib), (Ic), or (Id), or a pharmaceutically acceptable salt or solvate thereof, ring A is a 5- or 6-membered heterocycloalkyl ring or a 4-, 5-, or 6-membered cycloalkyl ring. In some embodiments of a compound of Formula (I), (Ia), (Ib), (Ic), or (Id), or a pharmaceutically acceptable salt or solvate thereof, $R^1$ is

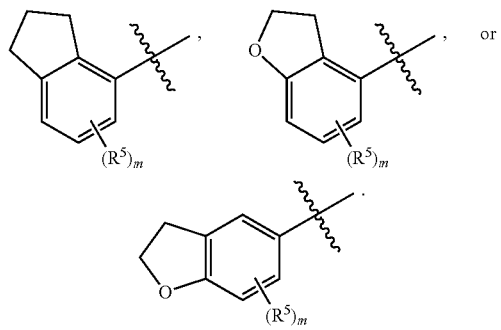

In some embodiments of a compound of Formula (I), (Ia), (Ib), (Ic), or (Id), or a pharmaceutically acceptable salt or solvate thereof, $R^1$ is

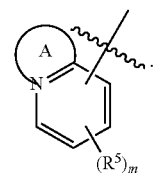

In some embodiments of a compound of Formula (I), (Ia), (Ib), (Ic), or (Id), or a pharmaceutically acceptable salt or solvate thereof, $R^1$ is

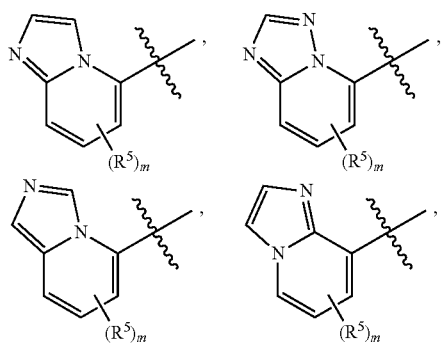

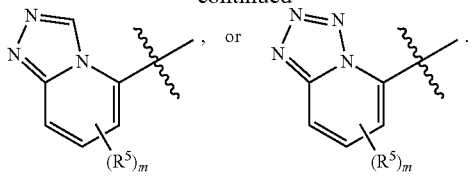

In some embodiments of a compound of Formula (I), (Ia), (Ib), (Ic), or (Id), or a pharmaceutically acceptable salt or solvate thereof, $R^1$ is

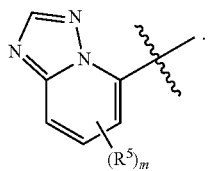

In some embodiments of a compound of Formula (I), (Ia), (Ib), (Ic), or (Id), or a pharmaceutically acceptable salt or solvate thereof, m is 0. In some embodiments of a compound of Formula (I), (Ia), (Ib), (Ic), or (Id), or a pharmaceutically acceptable salt or solvate thereof, q is 0.

In some embodiments of a compound of Formula (I), (Ia), (Ib), (Ic), or (Id), or a pharmaceutically acceptable salt or solvate thereof, X is a bond and Y is a bond. In some embodiments of a compound of Formula (I), (Ia), (Ib), (Ic), or (Id), or a pharmaceutically acceptable salt or solvate thereof, X is a bond and Y is —O—. In some embodiments of a compound of Formula (I), (Ia), (Ib), (Ic), or (Id), or a pharmaceutically acceptable salt or solvate thereof, X is a bond and Y is —N(H)—. In some embodiments of a compound of Formula (I), (Ia), (Ib), (Ic), or (Id), or a pharmaceutically acceptable salt or solvate thereof, X is a —CH$_2$N(H)— and Y is a bond. In some embodiments of a compound of Formula (I), (Ia), (Ib), (Ic), or (Id), or a pharmaceutically acceptable salt or solvate thereof, X is a —S(O)$_2$— and Y is a bond. In some embodiments of a compound of Formula (I), (Ia), (Ib), (Ic), or (Id), or a pharmaceutically acceptable salt or solvate thereof, each $R^2$ and each $R^3$ are H. In some embodiments of a compound of Formula (I), (Ia), (Ib), (Ic), or (Id), or a pharmaceutically acceptable salt or solvate thereof, n is 1, 2, or 3. In some embodiments of a compound of Formula (I), (Ia), (Ib), (Ic), or (Id), or a pharmaceutically acceptable salt or solvate thereof, n is 3. In some embodiments of a compound of Formula (I), (Ia), (Ib), (Ic), or (Id), or a pharmaceutically acceptable salt or solvate thereof, n is 2. In some embodiments of a compound of Formula (I), (Ia), (Ib), (Ic), or (Id), or a pharmaceutically acceptable salt or solvate thereof, n is 1. In some embodiments of a compound of Formula (I), (Ia), (Ib), (Ic), or (Id), or a pharmaceutically acceptable salt or solvate thereof, $R^4$ is

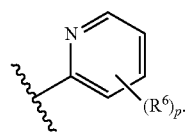

In some embodiments of a compound of Formula (I), (Ia), (Ib), (Ic), or (Id), or a pharmaceutically acceptable salt or solvate thereof, $R^4$ is

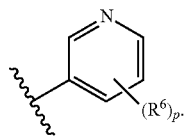

In some embodiments of a compound of Formula (I), (Ia), (Ib), (Ic), or (Id), or a pharmaceutically acceptable salt or solvate thereof, $R^4$ is

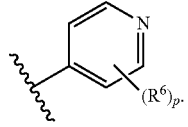

In some embodiments of a compound of Formula (I), (Ia), (Ib), (Ic), or (Id), or a pharmaceutically acceptable salt or solvate thereof, $R^4$ is

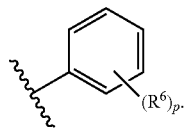

In some embodiments of a compound of Formula (I), (Ia), (Ib), (Ic), or (Id), or a pharmaceutically acceptable salt or solvate thereof, each $R^6$ is independently selected from halogen, —CN, —N($R^{10}$)$_2$, and —S(O)$_2R^{11}$. In some embodiments of a compound of Formula (I), (Ia), (Ib), (Ic), or (Id), or a pharmaceutically acceptable salt or solvate thereof, each $R^6$ is independently selected from halogen and —CN. In some embodiments of a compound of Formula (I), (Ia), (Ib), (Ic), or (Id), or a pharmaceutically acceptable salt or solvate thereof, p is 1 or 2. In some embodiments of a compound of Formula (I), (Ia), (Ib), (Ic), or (Id), or a pharmaceutically acceptable salt or solvate thereof, p is 2. In some embodiments of a compound of Formula (I), (Ia), (Ib), (Ic), or (Id), or a pharmaceutically acceptable salt or solvate thereof, p is 1. In some embodiments of a compound of Formula (I), (Ia), (Ib), (Ic), or (Id), or a pharmaceutically acceptable salt or solvate thereof, p is 0.

Any combination of the groups described above or below for the various variables is contemplated herein. Throughout the specification, groups and substituents thereof are chosen by one skilled in the field to provide stable moieties and compounds.

In another aspect is a pharmaceutical composition comprising a compound of Formula (I), (Ia), (Ib), (Ic), or (Id), or a pharmaceutically acceptable salt or solvate thereof, and at least one pharmaceutically acceptable excipient.

In another aspect is a method of treating a neurodegenerative disorder in a subject in need thereof, comprising administering to subject a therapeutically effective amount of a compound of Formula (I), (Ia), (Ib), (Ic), or (Id), or a pharmaceutically acceptable salt or solvate thereof.

In another aspect is a method of treating neuropathy in a subject in need thereof, comprising administering to subject a therapeutically effective amount of a compound of Formula (I), (Ia), (Ib), (Ic), or (Id), or a pharmaceutically acceptable salt or solvate thereof. In some embodiments is a method of treating neuropathy in a subject in need thereof, comprising administering to the subject a therapeutically effective amount of a compound of Formula (I), (Ia), (Ib), (Ic), or (Id), or a pharmaceutically acceptable salt or solvate thereof, wherein the neuropathy is peripheral neuropathy. In some embodiments is a method of treating neuropathy in a subject in need thereof, comprising administering to the subject a therapeutically effective amount of a compound of Formula (I), (Ia), (Ib), (Ic), or (Id), or a pharmaceutically acceptable salt or solvate thereof, wherein the neuropathy is diabetic neuropathy.

In another aspect is a method of treating a demyelinating disease in a subject in need thereof, comprising administering to the subject a therapeutically effective amount of a compound of Formula (I), (Ia), (Ib), (Ic), or (Id), or a pharmaceutically acceptable salt or solvate thereof. In some embodiments is a method of treating a demyelinating disease in a subject in need thereof, comprising administering to the subject a therapeutically effective amount of a compound of Formula (I), (Ia), (Ib), (Ic), or (Id), or a pharmaceutically acceptable salt or solvate thereof, wherein the demyelinating disease is a demyelinating disease of the central nervous system. In some embodiments is a method of treating a demyelinating disease in a subject in need thereof, comprising administering to the subject a therapeutically effective amount of a compound of Formula (I), (Ia), (Ib), (Ic), or (Id), or a pharmaceutically acceptable salt or solvate thereof, wherein the demyelinating disease is multiple sclerosis. In some embodiments is a method of treating a demyelinating disease in a subject in need thereof, comprising administering to the subject a therapeutically effective amount of a compound of Formula (I), (Ia), (Ib), (Ic), or (Id), or a pharmaceutically acceptable salt or solvate thereof, wherein the demyelinating disease is a demyelinating disease of the peripheral nervous system.

In some embodiments of the methods described herein, the method further comprises the administration of one or more immunomodulatory agents. In some embodiments, the one or more immunomodulatory agents are selected from: an IFN-β 1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or FTY720 or other S1P1 functional modulator; a dimethyl fumarate; an antibody to the alpha subunit of the IL-2 receptor of T cells (CD25) or daclizumab; an antibody against CD52 or alemtuzumab; an antibody against CD20; and an inhibitor of a dihydroorotate dehydrogenase or teriflunomide.

In another aspect is a method of modulating muscarinic acetylcholine receptor $M_1$ activity in a subject comprising administering to the subject a compound of Formula (I), (Ia), (Ib), (Ic), or (Id), or a pharmaceutically acceptable salt or solvate thereof. In some embodiments, the compound of Formula (I), (Ia), (Ib), (Ic), or (Id), or a pharmaceutically acceptable salt or solvate thereof, acts as a selective M1 antagonist

DETAILED DESCRIPTION

This disclosure is directed, at least in part, to compounds capable of inhibiting the muscarinic acetylcholine M1 receptor.

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, heteroaryl, or heteroarylalkyl, and each R$^f$ is independently alkyl, fluoroalkyl, cycloalkyl, aryl, aralkyl, heterocycloalkyl, heteroaryl, or heteroarylalkyl.

Alkoxy" refers to a radical bonded through an oxygen atom of the formula —O— alkyl, where alkyl is an alkyl chain as defined above.

Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^f$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, heteroaryl, or heteroarylalkyl, and each R$^f$ is independently alkyl, fluoroalkyl, cycloalkyl, aryl, aralkyl, heterocycloalkyl, heteroaryl, or heteroarylalkyl.

Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, heteroaryl, or heteroarylalkyl, and each R$^f$ is independently alkyl, fluoroalkyl, cycloalkyl, aryl, aralkyl, heterocycloalkyl, heteroaryl, or heteroarylalkyl.

Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O) R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocycloalkyl, heteroaryl, or heteroarylalkyl, each R$^b$ is independently a direct bond or a straight or branched alkylene or alkenylene chain, and R$^c$ is a straight or branched alkylene or alkenylene chain.

Aryloxy" refers to a radical bonded through an oxygen atom of the formula —O-aryl, where aryl is as defined above.

Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

Aralkyloxy" refers to a radical bonded through an oxygen atom of the formula —O-aralkyl, where aralkyl is as defined above.

Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Unless otherwise stated specifically in the specification, the term "cycloalkyl" is meant to include cycloalkyl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Haloalkoxy" refers to an alkoxy radical, as defined above, that is substituted by one or more halo radicals, as defined above.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-C(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Mickel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^a-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula $-R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

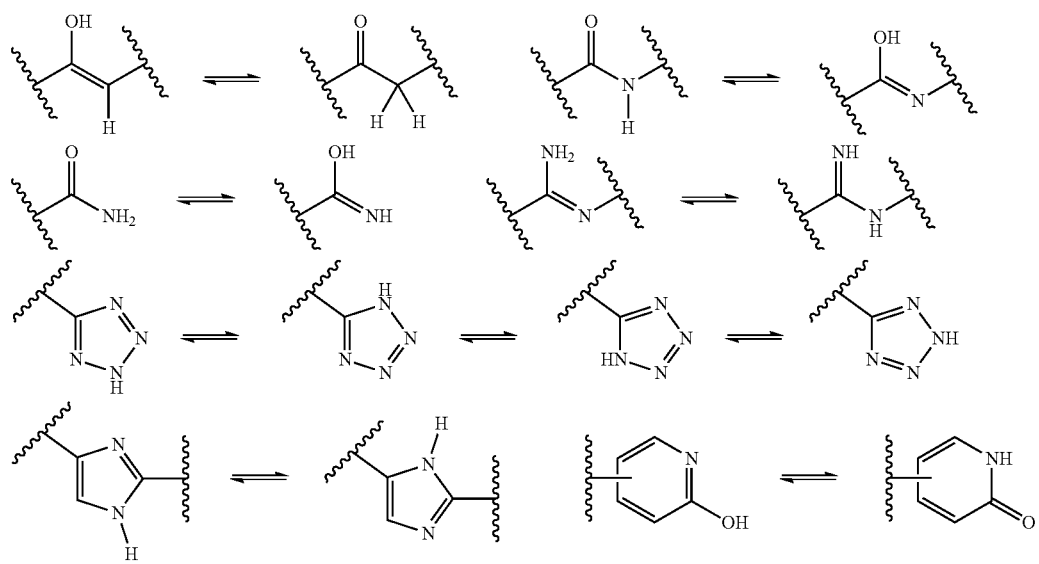

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M et al., "Pharmaceutical Salts," *Journal of Pharmaceutical Science,* 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. "Hydrates" are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The terms "allosteric site" and "allosteric binding site" refer to a ligand binding site that is topographically distinct from the orthosteric binding site.

The term "ligand" refers to a natural or synthetic molecule that is capable of binding to or associating with a receptor to form a complex and mediate, prevent, or modify a biological effect. The term "ligand" is meant to encompass allosteric modulators, inhibitors, activators, agonists, antagonists, natural substrates, and analogs of natural substrates.

The terms "natural ligand" and "endogenous ligand" refer to a naturally occurring ligand which binds to a receptor.

The terms "orthosteric site" and "orthosteric binding site" refer to the primary binding site on a receptor that is recognized by an endogenous ligand or agonist for the receptor. For example, the orthosteric site on the muscarinic acetylcholine M1 receptor is the site that acetylcholine binds.

The term "mAChR $M_1$ receptor antagonist" refers to any exogenously administered compound or agent that is capable of partially or completely inhibiting, or reversing, the effect of an agonist (e.g. acetylcholine) on the mAChR $M_1$ receptor. The term is inclusive of compounds or agents characterized or described as antagonists, partial antagonists, and negative allosteric modulators. For example, mAChR $M_1$ receptor antagonists can mediate their effects by binding to the orthosteric site or to allosteric sites, or they may interact at unique binding sites not normally involved in the biological regulation of the receptor's activity. Thus, a mAChR $M_1$ receptor antagonist directly or indirectly inhibits the activity of the mAChR $M_1$ receptor in the presence or in the absence of acetylcholine, or another agonist, in an animal, in particular a mammal, for example a human. In various aspects, a mAChR $M_1$ receptor antagonist decreases the activity of the mAChR $M_1$ receptor in a cell in the presence of extracellular acetylcholine. In some embodiments, a compound that is a "mAChR $M_1$ receptor antagonist" includes a compound that is a "mAChR $M_1$ receptor competitive antagonist," a "mAChR $M_1$ receptor noncompetitive antagonist," a "mAChR $M_1$ receptor partial antagonist," or a "mAChR $M_1$ receptor negative allosteric modulator."

The term "mAChR $M_1$ receptor competitive antagonist" refers to any exogenously administered compound or agent that is capable of binding to the orthosteric site of mAChR $M_1$ receptors without activating the receptor. Thus, a competitive antagonist can interact with a mAChR $M_1$ receptor and compete with the endogenous ligand, acetylcholine, for binding to the receptor and decrease the ability of the receptor to transduce an intracellular signal in response to endogenous ligand binding.

The term "mAChR $M_1$ receptor noncompetitive antagonist" refers to any exogenously administered compound or agent that binds to site that is not the orthosteric binding site of mAChR $M_1$ receptors, and is capable of partially or completely inhibiting, or reversing, the effect of an agonist (e.g. acetylcholine) on the mAChR $M_1$ receptor. Thus, a non-competitive antagonist can interact with a mAChR $M_1$ receptor and decrease the binding of the endogenous ligand, acetylcholine, to the receptor and/or decrease the ability of the receptor to transduce an intracellular signal in response to endogenous ligand binding.

The term "mAChR $M_1$ partial antagonist" refers to any exogenously administered compound or agent that can bind to an orthosteric or an allosteric site, but the effect of binding is to only partially block effect of mAChR $M_1$ receptor response to an agonist, e.g. acetylcholine. Thus, a partial antagonist can interact with a mAChR $M_1$ receptor and but is not capable of fully inhibiting the response of the mAChR $M_1$ receptor to an agonist, e.g. acetylcholine.

The term "mAChR $M_1$ negative allosteric modulator" refers to any exogenously administered compound or agent that binds an allosteric site that directly or indirectly inhibits the activity of the mAChR $M_1$ receptor in the presence of acetylcholine, or another agonist, in an animal, in particular a mammal, for example a human. For example, while not intended to be limiting towards the present disclosure, a selective muscarinic $M_1$ negative allosteric modulator can preferentially bind to the muscarinic $M_1$ receptor and decrease muscarinic $M_1$ signaling by acting as a non-competitive antagonist. In one aspect, a mAChR $M_1$ receptor negative allosteric modulator decreases the activity of the mAChR $M_1$ receptor in a cell in the presence of extracellular acetylcholine.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the subject is a human.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

As used herein, "$EC_{50}$" is intended to refer to the concentration of a substance (e.g., a compound or a drug) that is required for 50% activation or enhancement of a biological process, or component of a process, including a protein, subunit, organelle, ribonucleoprotein, etc. For example, $EC_{50}$ can refer to the concentration of agonist that provokes a response halfway between the baseline and maximum response in an in vitro assay. In some embodiments, in vitro assay systems utilize a cell line that either expresses endogenously a target of interest, or has been transfected with a suitable expression vector that directs expression of a recombinant form of the target.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. For example, $IC_{50}$ refers to the half maximal (50%) inhibitory concentration (IC) of a substance as determined in a suitable assay. For example, an $IC_{50}$ for mAChR $M_1$ receptor can be determined in an in vitro assay system.

Compounds

This disclosure provides, compounds which are antagonists of the muscarinic acetylcholine $M_1$ receptor (mAChR $M_1$). These compounds, and compositions comprising these compounds, are useful for the treatment or prevention of neurological disorders. In some embodiments, the compounds described herein are useful for treating Parkinson's disease.

In some embodiments provided herein is a compound having the structure of Formula (I):

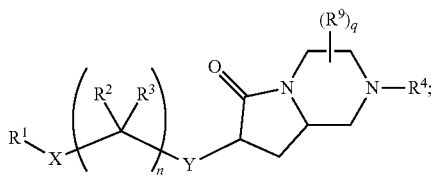

Formula (I)

wherein:
X is a bond, —CH$_2$O—, —CH$_2$CH$_2$O—, —O—, —N(R$^7$)—, —S(O)$_2$—, —CH$_2$N(R$^7$)—, or —CH$_2$CH$_2$N(R$^7$)—;
Y is a bond, —O—, or —N(R$^8$)—;
R$^1$ is

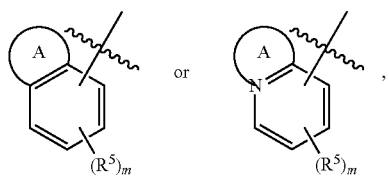

wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy;
each R$^2$ is independently selected from H and C$_{1-6}$ alkyl;
each R$^3$ is independently selected from H and C$_{1-6}$ alkyl;
R$^4$ is

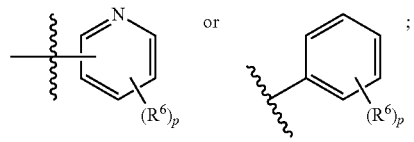

each R$^5$ is independently selected from halogen, —CN, C$_{1-6}$ alkyl, C$_{1-6}$ alkoxy, C$_{1-6}$ haloalkyl, and C$_{1-6}$ haloalkoxy;
each R$^6$ is independently selected from halogen, —CN, —N(R$^{10}$)$_2$, C$_{1-6}$ alkyl, C$_{1-6}$ alkoxy, C$_{1-6}$ haloalkyl, C$_{1-6}$ haloalkoxy, and —S(O)$_2$R$^{11}$;
R$^7$ is hydrogen or C$_{1-6}$ alkyl;
R$^8$ is hydrogen or C$_{1-6}$ alkyl;
R$^9$ is C$_{1-6}$ alkyl;
each R$^{10}$ is independently selected from H and C$_{1-6}$ alkyl;
R$^{11}$ is C$_{1-6}$ alkyl;
m is 0, 1, 2, or 3;
n is 1, 2, 3, 4, or 5;
p is 0, 1, 2, or 3; and
q is 0, 1, 2, 3, or 4;
or a pharmaceutically acceptable salt or solvate thereof.

In some embodiments provided herein is a compound having the structure of Formula (Ia):

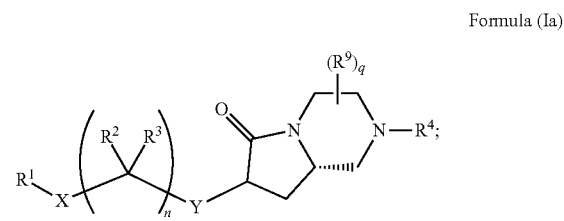

Formula (Ia)

wherein:
X is a bond, —CH$_2$O—, —CH$_2$CH$_2$O—, —O—, —N(R$^7$)—, —S(O)$_2$—, —CH$_2$N(R$^7$)—, or —CH$_2$CH$_2$N(R$^7$)—;
Y is a bond, —O—, or —N(R$^8$)—;
R$^1$ is

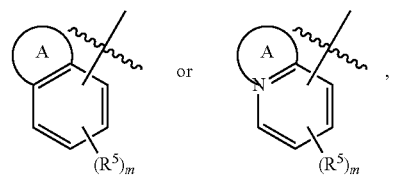

wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy;
each R$^2$ is independently selected from H and C$_{1-6}$ alkyl;
each R$^3$ is independently selected from H and C$_{1-6}$ alkyl;

R⁴ is

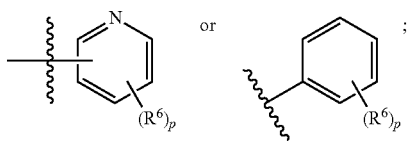

or each $R^5$ is independently selected from halogen, —CN, $C_{1-6}$ alkyl, $C_{1-6}$ alkoxy, $C_{1-6}$ haloalkyl, and $C_{1-6}$ haloalkoxy;

each $R^6$ is independently selected from halogen, —CN, —N($R^{10}$)$_2$, $C_{1-6}$ alkyl, $C_{1-6}$ alkoxy, $C_{1-6}$ haloalkyl, $C_{1-6}$ haloalkoxy, and —S(O)$_2$$R^{11}$;

$R^7$ is hydrogen or $C_{1-6}$ alkyl;

$R^8$ is hydrogen or $C_{1-6}$ alkyl;

$R^9$ is $C_{1-6}$ alkyl;

each $R^{10}$ is independently selected from H and $C_{1-6}$ alkyl;

$R^{11}$ is $C_{1-6}$ alkyl;

m is 0, 1, 2, or 3;

n is 1, 2, 3, 4, or 5;

p is 0, 1, 2, or 3; and q is 0, 1, 2, 3, or 4;

or a pharmaceutically acceptable salt or solvate thereof.

In some embodiments provided herein is a compound having the structure of Formula (Ib):

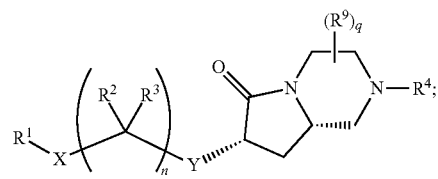

Formula (Ib)

wherein:

X is a bond, —CH$_2$O—, —CH$_2$CH$_2$O—, —O—, —N($R^7$)—, —S(O)$_2$—, —CH$_2$N($R^7$)—, or —CH$_2$CH$_2$N($R^7$)—;

Y is a bond, —O—, or —N($R^8$)—;

$R^1$ is

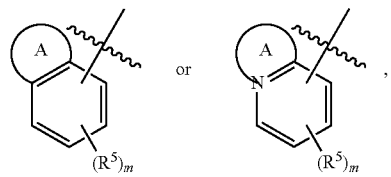

or wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N($R^{10}$)$_2$, $C_{1-6}$ alkyl, $C_{1-6}$ alkyl-OH, $C_{1-6}$ alkoxy, $C_{1-6}$ haloalkyl, or $C_{1-6}$ haloalkoxy;

each $R^2$ is independently selected from H and $C_{1-6}$ alkyl;

each $R^3$ is independently selected from H and $C_{1-6}$ alkyl;

R⁴ is

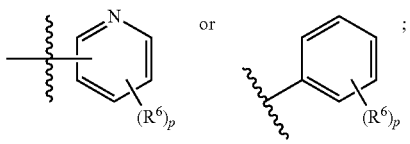

or each $R^5$ is independently selected from halogen, —CN, $C_{1-6}$ alkyl, $C_{1-6}$ alkoxy, $C_{1-6}$ haloalkyl, and $C_{1-6}$ haloalkoxy;

each $R^6$ is independently selected from halogen, —CN, —N($R^{10}$)$_2$, $C_{1-6}$ alkyl, $C_{1-6}$ alkoxy, $C_{1-6}$ haloalkyl, $C_{1-6}$ haloalkoxy, and —S(O)$_2$$R^{11}$;

$R^7$ is hydrogen or $C_{1-6}$ alkyl;

$R^8$ is hydrogen or $C_{1-6}$ alkyl;

$R^9$ is $C_{1-6}$ alkyl;

each $R^{10}$ is independently selected from H and $C_{1-6}$ alkyl;

$R^{11}$ is $C_{1-6}$ alkyl;

m is 0, 1, 2, or 3;

n is 1, 2, 3, 4, or 5;

p is 0, 1, 2, or 3; and q is 0, 1, 2, 3, or 4;

or a pharmaceutically acceptable salt or solvate thereof.

In some embodiments provided herein is a compound having the structure of Formula (Ic):

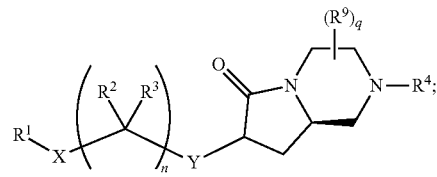

Formula (Ic)

wherein:

X is a bond, —CH$_2$O—, —CH$_2$CH$_2$O—, —O—, —N($R^7$)—, —S(O)$_2$—, —CH$_2$N($R^7$)—, or —CH$_2$CH$_2$N($R^7$)—;

Y is a bond, —O—, or —N($R^8$)—;

$R^1$ is

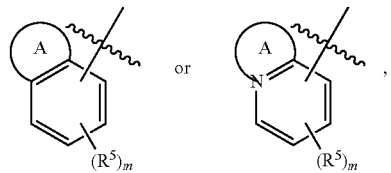

or wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N($R^{10}$)$_2$, $C_{1-6}$ alkyl, $C_{1-6}$ alkyl-OH, $C_{1-6}$ alkoxy, $C_{1-6}$ haloalkyl, or $C_{1-6}$ haloalkoxy;

each $R^2$ is independently selected from H and $C_{1-6}$ alkyl;

each $R^3$ is independently selected from H and $C_{1-6}$ alkyl;

$R^4$ is

[structure: pyridinyl with $(R^6)_p$] or [structure: phenyl with $(R^6)_p$];

each $R^5$ is independently selected from halogen, —CN, $C_{1-6}$ alkyl, $C_{1-6}$ alkoxy, $C_{1-6}$ haloalkyl, and $C_{1-6}$ haloalkoxy;

each $R^6$ is independently selected from halogen, —CN, —N($R^{10}$)$_2$, $C_{1-6}$ alkyl, $C_{1-6}$ alkoxy, $C_{1-6}$ haloalkyl, $C_{1-6}$ haloalkoxy, and —S(O)$_2$$R^{11}$;

$R^7$ is hydrogen or $C_{1-6}$ alkyl;

$R^8$ is hydrogen or $C_{1-6}$ alkyl;

$R^9$ is $C_{1-6}$ alkyl;

each $R^{10}$ is independently selected from H and $C_{1-6}$ alkyl;

$R^{11}$ is $C_{1-6}$ alkyl;

m is 0, 1, 2, or 3;

n is 1, 2, 3, 4, or 5;

p is 0, 1, 2, or 3; and q is 0, 1, 2, 3, or 4;

or a pharmaceutically acceptable salt or solvate thereof.

In some embodiments provided herein is a compound having the structure of Formula (Id):

Formula (Id)

[chemical structure]

wherein:

X is a bond, —CH$_2$O—, —CH$_2$CH$_2$O—, —O—, —N($R^7$)—, —S(O)$_2$—, —CH$_2$N($R^7$)—, or —CH$_2$CH$_2$N($R^7$)—;

Y is a bond, —O—, or —N($R^8$)—;

$R^1$ is

[two structures showing ring A with $(R^5)_m$]

wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N($R^{10}$)$_2$, $C_{1-6}$ alkyl, $C_{1-6}$ alkyl-OH, $C_{1-6}$ alkoxy, $C_{1-6}$ haloalkyl, or $C_{1-6}$ haloalkoxy;

each $R^2$ is independently selected from H and $C_{1-6}$ alkyl;

each $R^3$ is independently selected from H and $C_{1-6}$ alkyl;

$R^4$ is

[structure: pyridinyl with $(R^6)_p$] or [structure: phenyl with $(R^6)_p$];

each $R^5$ is independently selected from halogen, —CN, $C_{1-6}$ alkyl, $C_{1-6}$ alkoxy, $C_{1-6}$ haloalkyl, and $C_{1-6}$ haloalkoxy;

each $R^6$ is independently selected from halogen, —CN, —N($R^{10}$)$_2$, $C_{1-6}$ alkyl, $C_{1-6}$ alkoxy, $C_{1-6}$ haloalkyl, $C_{1-6}$ haloalkoxy, and —S(O)$_2$$R^{11}$;

$R^7$ is hydrogen or $C_{1-6}$ alkyl;

$R^8$ is hydrogen or $C_{1-6}$ alkyl;

$R^9$ is $C_{1-6}$ alkyl;

each $R^{10}$ is independently selected from H and $C_{1-6}$ alkyl;

$R^{11}$ is $C_{1-6}$ alkyl;

m is 0, 1, 2, or 3;

n is 1, 2, 3, 4, or 5;

p is 0, 1, 2, or 3; and q is 0, 1, 2, 3, or 4;

or a pharmaceutically acceptable salt or solvate thereof.

In some embodiments of a compound of Formula (I), (Ia), (Ib), (Ic), or (Id), or a pharmaceutically acceptable salt or solvate thereof, $R^1$ is

[structure showing ring A with $(R^5)_m$].

In some embodiments of a compound of Formula (I), (Ia), (Ib), (Ic), or (Id), or a pharmaceutically acceptable salt or solvate thereof, $R^1$ is

[structure showing ring A with N and $(R^5)_m$].

In some embodiments of a compound of Formula (I), (Ia), (Ib), (Ic), or (Id), or a pharmaceutically acceptable salt or solvate thereof, ring A is a 5- or 6-membered heteroaryl ring optionally substituted with halogen, —CN, —N($R^{10}$)$_2$, $C_{1-6}$ alkyl, $C_{1-6}$ alkyl-OH, $C_{1-6}$ alkoxy, $C_{1-6}$ haloalkyl, or $C_{1-6}$ haloalkoxy. In some embodiments, ring A is a 5-membered heteroaryl ring optionally substituted with halogen, —CN, —N($R^{10}$)$_2$, $C_{1-6}$ alkyl, $C_{1-6}$ alkyl-OH, $C_{1-6}$ alkoxy, $C_{1-6}$ haloalkyl, or $C_{1-6}$ haloalkoxy. In some embodiments, ring A is a 6-membered heteroaryl ring optionally substituted with halogen, —CN, —N($R^{10}$)$_2$, $C_{1-6}$ alkyl, $C_{1-6}$ alkyl-OH, $C_{1-6}$ alkoxy, $C_{1-6}$ haloalkyl, or $C_{1-6}$ haloalkoxy. In some embodiments, ring A is a heteroaryl ring optionally substituted with halogen, —CN, —N($R^{10}$)$_2$, $C_{1-6}$ alkyl, $C_{1-6}$ alkyl-OH, $C_{1-6}$ alkoxy, $C_{1-6}$ haloalkyl, or $C_{1-6}$ haloalkoxy, wherein the heteroaryl ring is selected from the group consisting of pyrrolyl, pyrazolyl, imidazolyl, furanyl, thiophenyl, oxazolyl, isoxazolyl, thiazolyl, isothiazolyl, pyridinyl, pyridazinyl, pyrimidinyl, and pyrazinyl. In some embodiments, ring A is a heteroaryl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy, wherein the heteroaryl ring is selected from the group consisting of pyrrolyl, pyrazolyl, imidazolyl, furanyl, thiophenyl, oxazolyl, isoxazolyl, thiazolyl, and isothiazolyl. In some embodiments, ring A is a heteroaryl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy, wherein the heteroaryl ring is selected from the group consisting of imidazolyl, oxazolyl, and thiazolyl. In some embodiments, ring A is a imidazolyl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy. In some embodiments, ring A is a oxazolyl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy. In some embodiments, ring A is a thiazolyl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy. In some embodiments, ring A is a heteroaryl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy, wherein the heteroaryl ring is selected from the group consisting of pyridinyl, pyridazinyl, pyrimidinyl, and pyrazinyl. In some embodiments, ring A is a heteroaryl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy, wherein the heteroaryl ring is selected from the group consisting of pyridinyl and pyrimidinyl. In some embodiments, ring A is a pyridyl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy. In some embodiments, ring A is a pyrimidinyl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy. In some embodiments, ring A is optionally substituted with —N(R$^{10}$)$_2$, C$_{1-6}$ alkyl, C$_{1-6}$ alkyl-OH, or C$_{1-6}$ alkoxy. In some embodiments, ring A is optionally substituted with —NH$_2$, methyl, —CH$_2$OH, or methoxy. In some embodiments, ring A is unsubstituted.

In some embodiments of a compound of Formula (I), (Ia), (Ib), (Ic), or (Id), or a pharmaceutically acceptable salt or solvate thereof, R$^1$ is

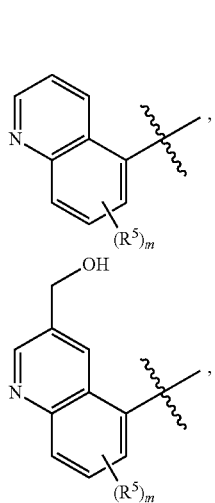,

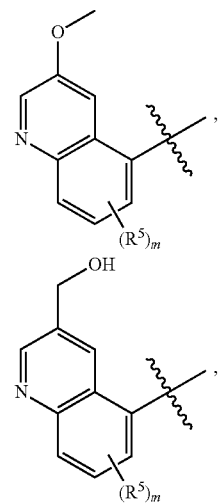,

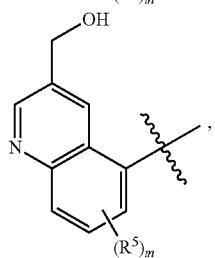,

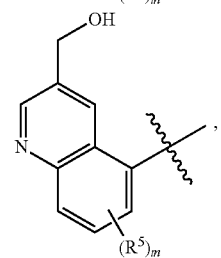,

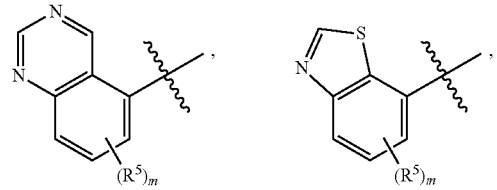

In some embodiments, R$^1$ is

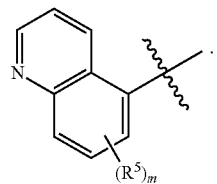.

In some embodiments, R$^1$ is

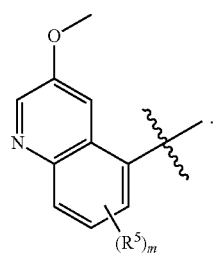.

In some embodiments, R$^1$ is

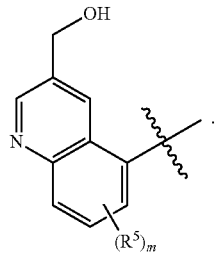.

In some embodiments, R¹ is

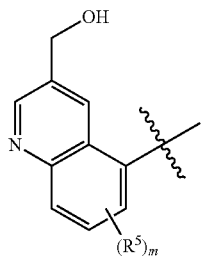

In some embodiments, R¹ is

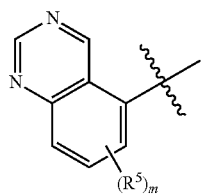

In some embodiments, R¹ is

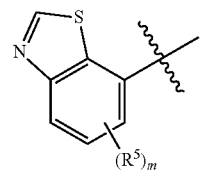

In some embodiments, R¹ is

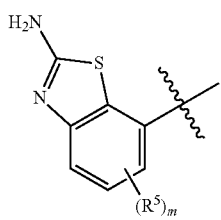

In some embodiments, R¹ is

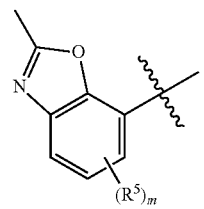

In some embodiments, R¹ is

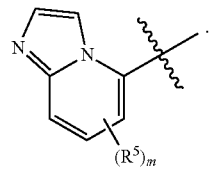

In some embodiments of a compound of Formula (I), (Ia), (Ib), (Ic), or (Id), or a pharmaceutically acceptable salt or solvate thereof, ring A is a 5- or 6-membered heterocycloalkyl ring optionally substituted with halogen, —CN, —N(R¹⁰)₂, $C_{1-6}$ alkyl, $C_{1-6}$ alkyl-OH, $C_{1-6}$ alkoxy, $C_{1-6}$ haloalkyl, or $C_{1-6}$ haloalkoxy. In some embodiments of a compound of Formula (I), (Ia), (Ib), (Ic), or (Id), or a pharmaceutically acceptable salt or solvate thereof, ring A is a 5-membered heterocycloalkyl ring optionally substituted with halogen, —CN, —N(R¹⁰)₂, $C_{1-6}$ alkyl, $C_{1-6}$ alkyl-OH, $C_{1-6}$ alkoxy, $C_{1-6}$ haloalkyl, or $C_{1-6}$ haloalkoxy. In some embodiments of a compound of Formula (I), (Ia), (Ib), (Ic), or (Id), or a pharmaceutically acceptable salt or solvate thereof, ring A is a 6-membered heterocycloalkyl ring optionally substituted with halogen, —CN, —N(R¹⁰)₂, $C_{1-6}$ alkyl, $C_{1-6}$ alkyl-OH, $C_{1-6}$ alkoxy, $C_{1-6}$ haloalkyl, or $C_{1-6}$ haloalkoxy. In some embodiments of a compound of Formula (I), (Ia), (Ib), (Ic), or (Id), or a pharmaceutically acceptable salt or solvate thereof, ring A is

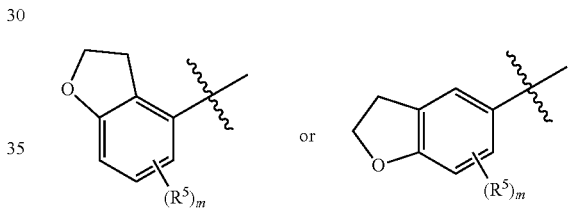

In some embodiments of a compound of Formula (I), (Ia), (Ib), (Ic), or (Id), or a pharmaceutically acceptable salt or solvate thereof, ring A is an unsubstituted 5- or 6-membered heterocycloalkyl ring. In some embodiments of a compound of Formula (I), (Ia), (Ib), (Ic), or (Id), or a pharmaceutically acceptable salt or solvate thereof, ring A is an unsubstituted 5-membered heterocycloalkyl ring. In some embodiments of a compound of Formula (I), (Ia), (Ib), (Ic), or (Id), or a pharmaceutically acceptable salt or solvate thereof, ring A is an unsubstituted 6-membered heterocycloalkyl ring.

In some embodiments of a compound of Formula (I), (Ia), (Ib), (Ic), or (Id), or a pharmaceutically acceptable salt or solvate thereof, ring A is a 4-, 5-, or 6-membered cycloalkyl ring optionally substituted with halogen, —CN, —N(R¹⁰)₂, $C_{1-6}$ alkyl, $C_{1-6}$ alkyl-OH, $C_{1-6}$ alkoxy, $C_{1-6}$ haloalkyl, or $C_{1-6}$ haloalkoxy. In some embodiments of a compound of Formula (I), (Ia), (Ib), (Ic), or (Id), or a pharmaceutically acceptable salt or solvate thereof, ring A is a 4-membered cycloalkyl ring optionally substituted with halogen, —CN, —N(R¹⁰)₂, $C_{1-6}$ alkyl, $C_{1-6}$ alkyl-OH, $C_{1-6}$ alkoxy, $C_{1-6}$ haloalkyl, or $C_{1-6}$ haloalkoxy. In some embodiments of a compound of Formula (I), (Ia), (Ib), (Ic), or (Id), or a pharmaceutically acceptable salt or solvate thereof, ring A is a 5-membered cycloalkyl ring optionally substituted with halogen, —CN, —N(R¹⁰)₂, $C_{1-6}$ alkyl, $C_{1-6}$ alkyl-OH, $C_{1-6}$ alkoxy, $C_{1-6}$ haloalkyl, or $C_{1-6}$ haloalkoxy. In some embodiments of a compound of Formula (I), (Ia), (Ib), (Ic), or (Id), or a pharmaceutically acceptable salt or solvate thereof, ring A is a 6-membered cycloalkyl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy. In some embodiments of a compound of Formula (I), (Ia), (Ib), (Ic), or (Id), or a pharmaceutically acceptable salt or solvate thereof, ring A is an unsubstituted 4-, 5-, or 6-membered cycloalkyl ring. In some embodiments of a compound of Formula (I), (Ia), (Ib), (Ic), or (Id), or a pharmaceutically acceptable salt or solvate thereof, ring A is

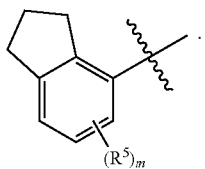

In some embodiments of a compound of Formula (I), (Ia), (Ib), (Ic), or (Id), or a pharmaceutically acceptable salt or solvate thereof, ring A is an unsubstituted 4-, 5-, or 6-membered cycloalkyl ring. In some embodiments of a compound of Formula (I), (Ia), (Ib), (Ic), or (Id), or a pharmaceutically acceptable salt or solvate thereof, ring A is

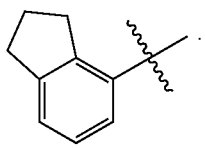 [SMILES: *c1cccc2c1CCC2]

In some embodiments of a compound of Formula (I), (Ia), (Ib), (Ic), or (Id), or a pharmaceutically acceptable salt or solvate thereof, each R$^5$ is independently selected from halogen, —CN, C$_{1-6}$ alkyl, C$_{1-6}$ alkoxy, C$_{1-6}$ haloalkyl, and C$_{1-6}$ haloalkoxy. In some embodiments, each R$^5$ is independently selected from halogen, —CN, C$_{1-6}$ alkyl, and C$_{1-6}$ alkoxy.

In some embodiments of a compound of Formula (I), (Ia), (Ib), (Ic), or (Id), or a pharmaceutically acceptable salt or solvate thereof, m is 0, 1, 2, or 3. In some embodiments, m is 0 to 1, 0 to 2, 0 to 3, 1 to 2, 1 to 3, or 2 to 3. In some embodiments, m is 0. In some embodiments, m is 1. In some embodiments, m is 2. In some embodiments, m is 3.

In some embodiments of a compound of Formula (I), (Ia), (Ib), (Ic), or (Id), or a pharmaceutically acceptable salt or solvate thereof, R$^1$ is

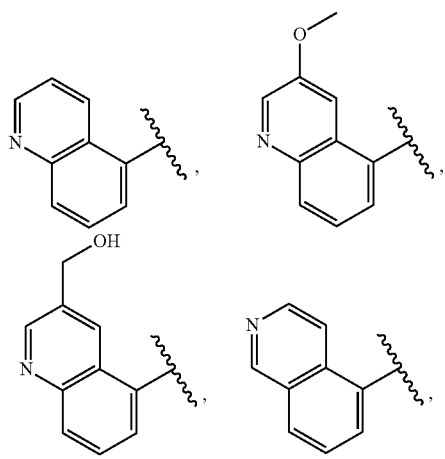

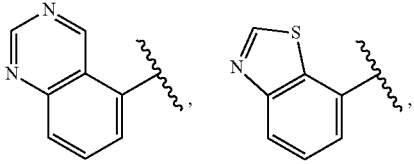

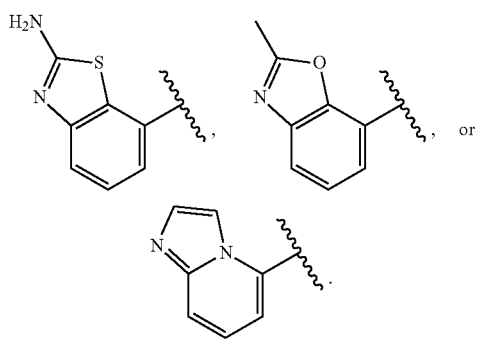

In some embodiments, R$^1$ is

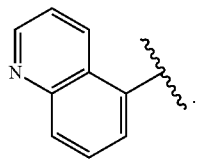 [SMILES: *c1cccc2ncccc12]

In some embodiments, R$^1$ is

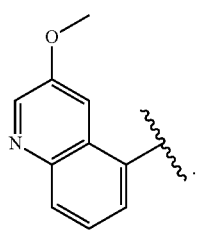 [SMILES: *c1cccc2ncc(OC)cc12]

In some embodiments, R$^1$ is

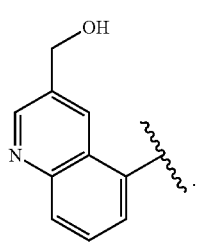 [SMILES: *c1cccc2ncc(CO)cc12]

In some embodiments, R¹ is

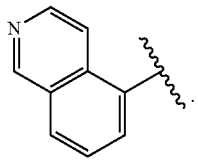 [SMILES: *c1cccc2cnccc12]

In some embodiments, R¹ is

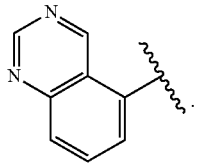 [SMILES: *c1cccc2ncncc12]

In some embodiments, R¹ is

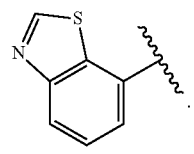

In some embodiments, R¹ is

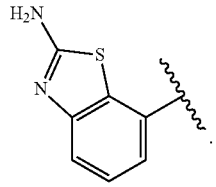

In some embodiments, R¹ is

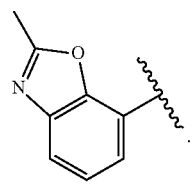

In some embodiments, R¹ is

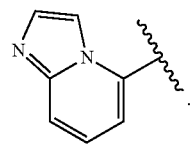

In some embodiments of a compound of Formula (I), (Ia), (Ib), (Ic), or (Id), or a pharmaceutically acceptable salt or solvate thereof, ring A is

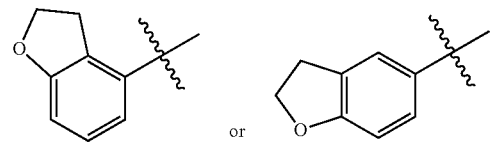

In some embodiments is a compound of Formula (II), or a pharmaceutically acceptable salt or solvate thereof:

Formula (II)

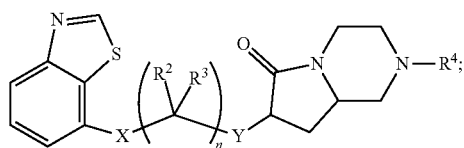

X is a bond, —CH₂O—, —CH₂CH₂O—, —O—, —N(R⁷)—, —S(O)₂—, —CH₂N(R⁷)—, or —CH₂CH₂N(R⁷)—;

Y is a bond, —O—, or —N(R⁸)—;

each R² is independently selected from H and $C_{1-6}$ alkyl;

each R³ is independently selected from H and $C_{1-6}$ alkyl;

R⁴ is

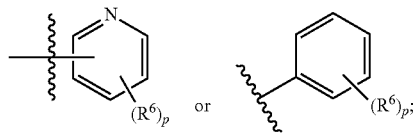

each R⁶ is independently selected from halogen, —CN, —N(R¹⁰)₂, $C_{1-6}$ alkyl, $C_{1-6}$ alkoxy, $C_{1-6}$ haloalkyl, $C_{1-6}$ haloalkoxy, and —S(O)₂R¹¹;

R⁷ is hydrogen or $C_{1-6}$ alkyl;

R⁸ is hydrogen or $C_{1-6}$ alkyl;

n is 1, 2, 3, 4, or 5; and p is 0, 1, 2, or 3.

In some embodiments is a compound of Formula (IIa), or a pharmaceutically acceptable salt or solvate thereof:

Formula (IIa)

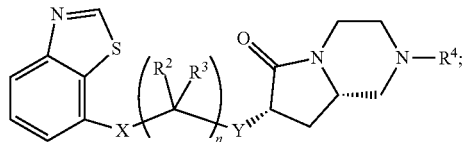

X is a bond, —CH₂O—, —CH₂CH₂O—, —O—, —N(R⁷)—, —S(O)₂—, —CH₂N(R⁷)—, or —CH₂CH₂N(R⁷)—;

Y is a bond, —O—, or —N(R⁸)—;

each R² is independently selected from H and $C_{1-6}$ alkyl;

each R³ is independently selected from H and $C_{1-6}$ alkyl;

R⁴ is

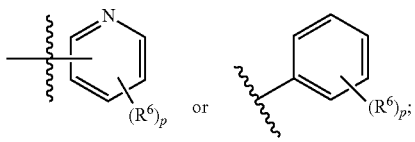

each R⁶ is independently selected from halogen, —CN, —N(R¹⁰)₂, C₁₋₆ alkyl, C₁₋₆ alkoxy, C₁₋₆ haloalkyl, C₁₋₆ haloalkoxy, and —S(O)₂R¹¹;
R⁷ is hydrogen or C₁₋₆ alkyl;
R⁸ is hydrogen or C₁₋₆ alkyl;
n is 1, 2, 3, 4, or 5; and
p is 0, 1, 2, or 3.

In some embodiments is a compound of Formula (III), or a pharmaceutically acceptable salt or solvate thereof:

Formula (III)

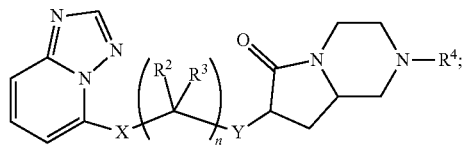

X is a bond, —CH₂O—, —CH₂CH₂O—, —O—, —N(R⁷)—, —S(O)₂—, —CH₂N(R⁷)—, or —CH₂CH₂N(R⁷)—;
Y is a bond, —O—, or —N(R⁸)—;
each R² is independently selected from H and C₁₋₆ alkyl;
each R³ is independently selected from H and C₁₋₆ alkyl;
R⁴ is

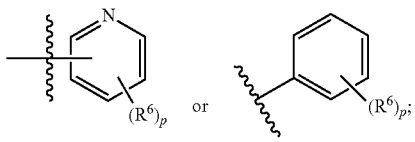

each R⁶ is independently selected from halogen, —CN, —N(R¹⁰)₂, C₁₋₆ alkyl, C₁₋₆ alkoxy, C₁₋₆ haloalkyl, C₁₋₆ haloalkoxy, and —S(O)₂R¹¹;
R⁷ is hydrogen or C₁₋₆ alkyl;
R⁸ is hydrogen or C₁₋₆ alkyl;
n is 1, 2, 3, 4, or 5; and
p is 0, 1, 2, or 3.

In some embodiments is a compound of Formula (IIIa), or a pharmaceutically acceptable salt or solvate thereof:

Formula (IIIa)

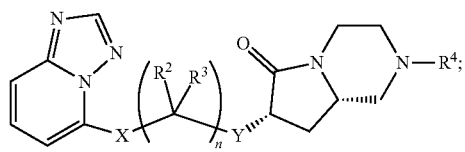

X is a bond, —CH₂O—, —CH₂CH₂O—, —O—, —N(R⁷)—, —S(O)₂—, —CH₂N(R⁷)—, or —CH₂CH₂N(R⁷)—;
Y is a bond, —O—, or —N(R⁸)—;
each R² is independently selected from H and C₁₋₆ alkyl;
each R³ is independently selected from H and C₁₋₆ alkyl;
R⁴ is

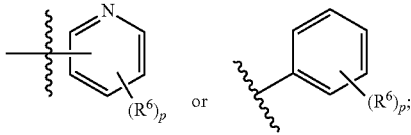

each R⁶ is independently selected from halogen, —CN, —N(R¹⁰)₂, C₁₋₆ alkyl, C₁₋₆ alkoxy, C₁₋₆ haloalkyl, C₁₋₆ haloalkoxy, and —S(O)₂R¹¹;
R⁷ is hydrogen or C₁₋₆ alkyl;
R⁸ is hydrogen or C₁₋₆ alkyl;
n is 1, 2, 3, 4, or 5; and
p is 0, 1, 2, or 3.

In some embodiments of a compound of Formula (I), (Ia), (Ib), (Ic), (Id), (II), (IIa), (III), or (IIIa), or a pharmaceutically acceptable salt or solvate thereof, R⁴ is

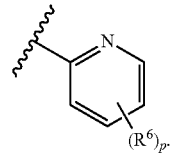

In some embodiments, R⁴ is

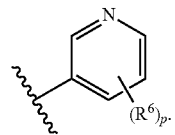

In some embodiments, R⁴ is

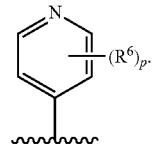

In some embodiments of a compound of Formula (I), (Ia), (Ib), (Ic), (Id), (II), (IIa), (III), or (IIIa), or a pharmaceutically acceptable salt or solvate thereof, R⁴ is

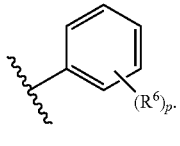

In some embodiments of a compound of Formula (I), (Ia), (Ib), (Ic), (Id), (II), (IIa), (III), or (IIIa), or a pharmaceutically acceptable salt or solvate thereof, each R⁶ is independently selected from halogen, —CN, —N(R¹⁰)₂, C₁₋₆ alkyl, $C_{1-6}$ alkoxy, $C_{1-6}$ haloalkyl, $C_{1-6}$ haloalkoxy, and —S(O)$_2$R$^{11}$. In some embodiments of a compound of Formula (I), (Ia), (Ib), (Ic), (Id), (II), (IIa), (III), or (IIIa), or a pharmaceutically acceptable salt or solvate thereof, each R$^6$ is independently selected from halogen, —CN, —N(R$^{10}$)$_2$, $C_{1-6}$ alkyl, $C_{1-6}$ alkoxy, $C_{1-6}$ haloalkyl, and $C_{1-6}$ haloalkoxy. In some embodiments of a compound of Formula (I), (Ia), (Ib), (Ic), (Id), (II), (IIa), (III), or (IIIa), or a pharmaceutically acceptable salt or solvate thereof, each R$^6$ is independently selected from —F, —Cl, —Br, —CN, $C_{1-4}$alkyl, $C_{1-4}$alkoxy, and $C_{1-4}$haloalkyl. In some embodiments of a compound of Formula (I), (Ia), (Ib), (Ic), (Id), (II), (IIa), (III), or (IIIa), or a pharmaceutically acceptable salt or solvate thereof, each R$^6$ is independently selected from —F, —Cl, —CN, methyl, methoxy, and trifluoromethyl. In some embodiments of a compound of Formula (I), (Ia), (Ib), (Ic), (Id), (II), (IIa), (III), or (IIIa), or a pharmaceutically acceptable salt or solvate thereof, each R$^6$ is halogen. In some embodiments of a compound of Formula (I), (Ia), (Ib), (Ic), (Id), (II), (IIa), (III), or (IIIa), or a pharmaceutically acceptable salt or solvate thereof, each R$^6$ is —F. In some embodiments of a compound of Formula (I), (Ia), (Ib), (Ic), (Id), (II), (IIa), (III), or (IIIa), or a pharmaceutically acceptable salt or solvate thereof, each R$^6$ is —Cl. In some embodiments of a compound of Formula (I), (Ia), (Ib), (Ic), (Id), (II), (IIa), (III), or (IIIa), or a pharmaceutically acceptable salt or solvate thereof, each R$^6$ is —NH$_2$. In some embodiments of a compound of Formula (I), (Ia), (Ib), (Ic), (Id), (II), (IIa), (III), or (IIIa), or a pharmaceutically acceptable salt or solvate thereof, each R$^6$ is —S(O)$_2$CH$_3$.

In some embodiments of a compound of Formula (I), (Ia), (Ib), (Ic), (Id), (II), (IIa), (III), or (IIIa), or a pharmaceutically acceptable salt or solvate thereof, p is 0, 1, 2, or 3. In some embodiments, p is 0 to 1, 0 to 2, 0 to 3, 1 to 2, 1 to 3, or 2 to 3. In some embodiments, p is 0. In some embodiments, p is 1. In some embodiments, p is 2. In some embodiments, p is 3.

In some embodiments of a compound of Formula (I), (Ia), (Ib), (Ic), (Id), (II), (IIa), (III), or (IIIa), or a pharmaceutically acceptable salt or solvate thereof, R$^4$ is

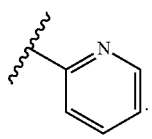

In some embodiments, R$^4$ is

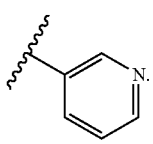

In some embodiments, R$^4$ is

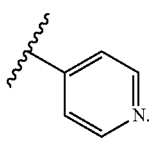

In some embodiments of a compound of Formula (I), (Ia), (Ib), (Ic), (Id), (II), (IIa), (III), or (IIIa), or a pharmaceutically acceptable salt or solvate thereof, R$^4$ is

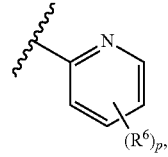

p is 1, and R$^6$ is selected from halogen, —CN, —N(R$^{10}$)$_2$, $C_{1-6}$ alkyl, $C_{1-6}$ alkoxy, $C_{1-6}$ haloalkyl, $C_{1-6}$ haloalkoxy, and —S(O)$_2$R$^{11}$. In some embodiments, R$^4$ is

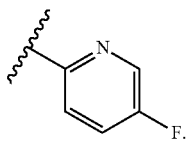 [SMILES: *c1ccc(F)cn1]

In some embodiments, R$^4$ is

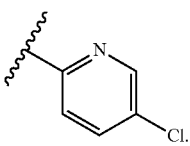 [SMILES: *c1ccc(Cl)cn1]

In some embodiments, R$^4$ is

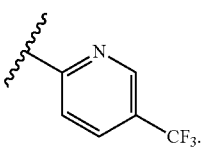 [SMILES: *c1ccc(C(F)(F)F)cn1]

In some embodiments, R$^4$ is

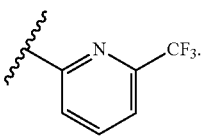 [SMILES: *c1cccc(C(F)(F)F)n1]

In some embodiments, R$^4$ is

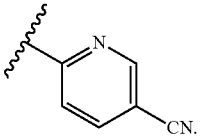 [SMILES: *c1ccc(C#N)cn1]

In some embodiments, R⁴ is

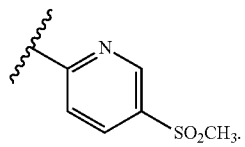 [SMILES: *c1ccc(S(C)(=O)=O)cn1]

In some embodiments, R⁴ is

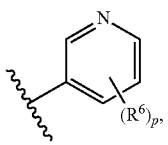

p is 1, and R⁶ is selected from halogen, —CN, —N(R¹⁰)₂, $C_{1-6}$ alkyl, $C_{1-6}$ alkoxy, $C_{1-6}$ haloalkyl, $C_{1-6}$ haloalkoxy, and —S(O)₂R¹¹. In some embodiments, R⁴ is

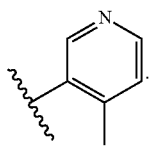 [SMILES: *c1cnccc1C]

In some embodiments, R⁴ is

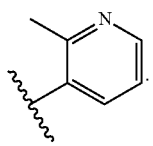 [SMILES: *c1cccnc1C]

In some embodiments, R⁴ is

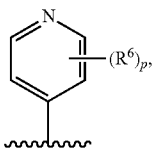

and each R⁶ is independently selected from halogen, —CN, —N(R¹⁰)₂, $C_{1-6}$ alkyl, $C_{1-6}$ alkoxy, $C_{1-6}$ haloalkyl, $C_{1-6}$ haloalkoxy, and —S(O)₂R¹¹. In some embodiments, R⁴ is

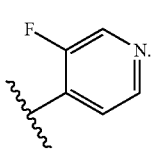 [SMILES: *c1ccncc1F]

In some embodiments, R⁴ is

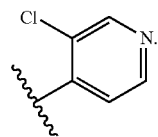

In some embodiments, R⁴ is

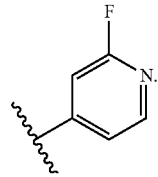

In some embodiments, R⁴ is

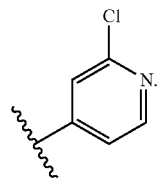

In some embodiments, R⁴ is

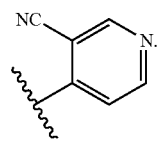

In some embodiments, R⁴ is

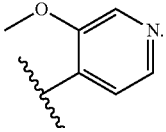 [SMILES: *c1ccncc1OC]

In some embodiments, R⁴ is

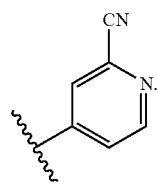

In some embodiments, R⁴ is

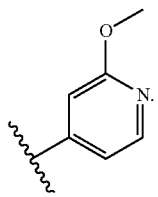 [SMILES: *c1ccnc(OC)c1]

In some embodiments, R⁴ is

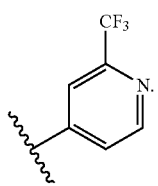 [SMILES: *c1ccnc(C(F)(F)F)c1]

In some embodiments, R⁴ is

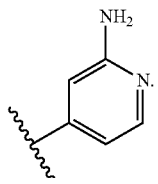 [SMILES: *c1ccnc(N)c1]

In some embodiments of a compound of Formula (I), (Ia), (Ib), (Ic), (Id), (II), (IIa), (III), or (IIIa), or a pharmaceutically acceptable salt or solvate thereof, R⁴ is

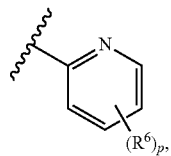

p is 2, and each R⁶ is independently selected from halogen, —CN, —N(R¹⁰)₂, C₁₋₆ alkyl, C₁₋₆ alkoxy, C₁₋₆ haloalkyl, C₁₋₆ haloalkoxy, and —S(O)₂R¹¹. In some embodiments, R⁴ is

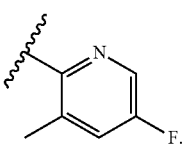 [SMILES: *c1ncc(F)cc1C]

In some embodiments, R⁴ is

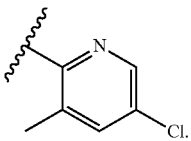

In some embodiments, R⁴ is

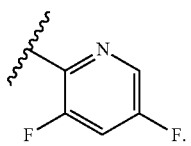 [SMILES: *c1ncc(F)cc1F]

In some embodiments, R⁴ is

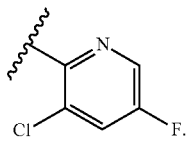 [SMILES: *c1ncc(F)cc1Cl]

In some embodiments, R⁴ is

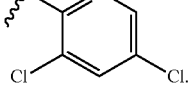

In some embodiments, R⁴ is

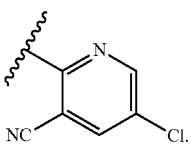 [SMILES: *c1ncc(Cl)cc1C#N]

In some embodiments of a compound of Formula (I), (Ia), (Ib), (Ic), (Id), (II), (IIa), (III), or (IIIa), or a pharmaceutically acceptable salt or solvate thereof, R⁴ is

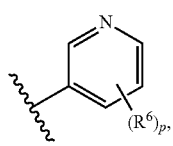

p is 2, and each $R^6$ is independently selected from halogen, —CN, —N($R^{10}$)$_2$, $C_{1-6}$ alkyl, $C_{1-6}$ alkoxy, $C_{1-6}$ haloalkyl, $C_{1-6}$ haloalkoxy, and —S(O)$_2R^{11}$. In some embodiments of a compound of Formula (I), (Ia), (Ib), (Ic), (Id), (II), (IIa), (III), or (IIIa), or a pharmaceutically acceptable salt or solvate thereof, $R^4$ is

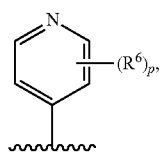

p is 2, and each $R^6$ is independently selected from halogen, —CN, —N($R^{10}$)$_2$, $C_{1-6}$ alkyl, $C_{1-6}$ alkoxy, $C_{1-6}$ haloalkyl, $C_{1-6}$ haloalkoxy, and —S(O)$_2R^{11}$.

In some embodiments of a compound of Formula (I), (Ia), (Ib), (Ic), (Id), (II), (IIa), (III), or (IIIa), or a pharmaceutically acceptable salt or solvate thereof, $R^4$ is

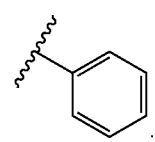

In some embodiments of a compound of Formula (I), (Ia), (Ib), (Ic), (Id), (II), (IIa), (III), or (IIIa), or a pharmaceutically acceptable salt or solvate thereof, $R^4$ is

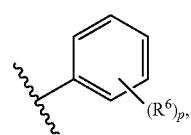

p is 1, and $R^6$ is selected from halogen, —CN, —N($R^{10}$)$_2$, $C_{1-6}$ alkyl, $C_{1-6}$ alkoxy, $C_{1-6}$ haloalkyl, $C_{1-6}$ haloalkoxy, and —S(O)$_2R^{11}$. In some embodiments, $R^4$ is

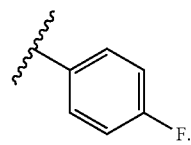 [SMILES: *c1ccc(F)cc1]

In some embodiments, $R^4$ is

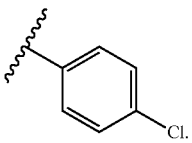 [SMILES: *c1ccc(Cl)cc1]

In some embodiments, $R^4$ is

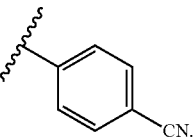 [SMILES: *c1ccc(C#N)cc1]

In some embodiments, $R^4$ is

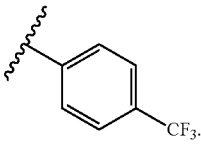

In some embodiments of a compound of Formula (I), (Ia), (Ib), (Ic), (Id), (II), (IIa), (III), or (IIIa), or a pharmaceutically acceptable salt or solvate thereof, $R^4$ is

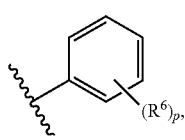

p is 2, and $R^6$ is selected from halogen, —CN, —N($R^{10}$)$_2$, $C_{1-6}$ alkyl, $C_{1-6}$ alkoxy, $C_{1-6}$ haloalkyl, $C_{1-6}$ haloalkoxy, and —S(O)$_2R^{11}$. In some embodiments, $R^4$ is

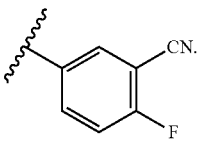 [SMILES: *c1ccc(F)c(C#N)c1]

In some embodiments, $R^4$ is

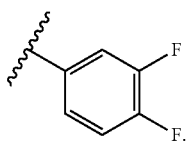 [SMILES: *c1ccc(F)c(F)c1]

In some embodiments of a compound of Formula (I), (Ia), (Ib), (Ic), (Id), (II), (IIa), (III), or (IIIa), or a pharmaceutically acceptable salt or solvate thereof, each $R^2$ is independently selected from H and $C_{1-4}$ alkyl. In some embodiments, each $R^2$ is independently selected from H and methyl.

In some embdodiments, each $R^2$ is H. In some embdodiments, each $R^2$ is $C_{1-4}$ alkyl. In some embdodiments, each $R^2$ is methyl.

In some embodiments of a compound of Formula (I), (Ia), (Ib), (Ic), (Id), (II), (IIa), (III), or (IIIa), or a pharmaceutically acceptable salt or solvate thereof, each $R^3$ is independently selected from H and $C_{1-4}$ alkyl. In some embodiments, each $R^3$ is independently selected from H and methyl. In some embodiments, each $R^3$ is H. In some embdodiments, each $R^3$ is $C_{1-4}$ alkyl. In some embdodiments, each $R^3$ is methyl.

In some embodiments of a compound of Formula (I), (Ia), (Ib), (Ic), (Id), (II), (IIa), (III), or (IIIa), or a pharmaceutically acceptable salt or solvate thereof, each $R^2$ and $R^3$ is H.

In some embodiments of a compound of Formula (I), (Ia), (Ib), (Ic), (Id), (II), (IIa), (III), or (IIIa), or a pharmaceutically acceptable salt or solvate thereof, X is a bond. In some embodiments, X is —$CH_2O$—. In some embodiments, X is —$CH_2CH_2O$—. In some embodiments, X is —O—. In some embodiments, X is —$N(R^7)$—. In some embodiments, X is $S(O)_2$. In some embodiments, X is —$CH_2N(R^7)$—. In some embodiments, X is —$CH_2CH_2N(R^7)$—. In some embodiments, X is —NH—. In some embodiments, X is —$CH_2NH$—. In some embodiments, X is —$CH_2CH_2NH$—. In some embodiments, X is —$N(CH_3)$—. In some embodiments, X is —$CH_2N(CH_3)$—. In some embodiments, X is —$CH_2CH_2N(CH_3)$—.

In some embodiments of a compound of Formula (I), (Ia), (Ib), (Ic), (Id), (II), (IIa), (III), or (IIIa), or a pharmaceutically acceptable salt or solvate thereof, Y is a bond. In some embodiments, Y is —$N(R^8)$—. In some embodiments, Y is or —NH—. In some embodiments, Y is or —$N(CH_3)$—.

In some embodiments of a compound of Formula (I), (Ia), (Ib), (Ic), (Id), (II), (IIa), (III), or (IIIa), or a pharmaceutically acceptable salt or solvate thereof, n is 1, 2, 3, 4, or 5. In some embodiments, n is 1 to 2, 1 to 3, 1 to 4, 1 to 5, 2 to 3, 2 to 4, 2 to 5, 3 to 4, 3 to 5, or 4 to 5. In some embodiments, n is 1. In some embodiments, n is 2. In some embodiments, n is 3. In some embodiments, n is 4 In some embodiments, n is 5.

In some embodiments of a compound of Formula (I), (Ia), (Ib), (Ic), (Id), (II), (IIa), (III), or (IIIa), or a pharmaceutically acceptable salt or solvate thereof, X is bond and Y is a bond.

In some embodiments of a compound of Formula (I), (Ia), (Ib), (Ic), (Id), (II), (IIa), (III), or (IIIa), or a pharmaceutically acceptable salt or solvate thereof, X is bond and Y is —O—.

In some embodiments of a compound of Formula (I), (Ia), (Ib), (Ic), (Id), (II), (IIa), (III), or (IIIa), or a pharmaceutically acceptable salt or solvate thereof, X is bond and Y is —N(H)—.

In some embodiments of a compound of Formula (I), (Ia), (Ib), (Ic), (Id), (II), (IIa), (III), or (IIIa), or a pharmaceutically acceptable salt or solvate thereof, X is —$CH_2O$— and Y is a bond.

In some embodiments of a compound of Formula (I), (Ia), (Ib), (Ic), (Id), (II), (IIa), (III), or (IIIa), or a pharmaceutically acceptable salt or solvate thereof, X is —$CH_2CH_2N(H)$— and Y is a bond.

In some embodiments of a compound of Formula (I), (Ia), (Ib), (Ic), (Id), (II), (IIa), (III), or (IIIa), or a pharmaceutically acceptable salt or solvate thereof, X is —$CH_2N(H)$— and Y is a bond.

In some embodiments of a compound of Formula (I), (Ia), (Ib), (Ic), (Id), (II), (IIa), (III), or (IIIa), or a pharmaceutically acceptable salt or solvate thereof, X is $S(O)_2$ and Y is a bond.

In some embodiments of a compound of Formula (I), (Ia), (Ib), (Ic), (Id), (II), (IIa), (III), or (IIIa), or a pharmaceutically acceptable salt or solvate thereof, wherein

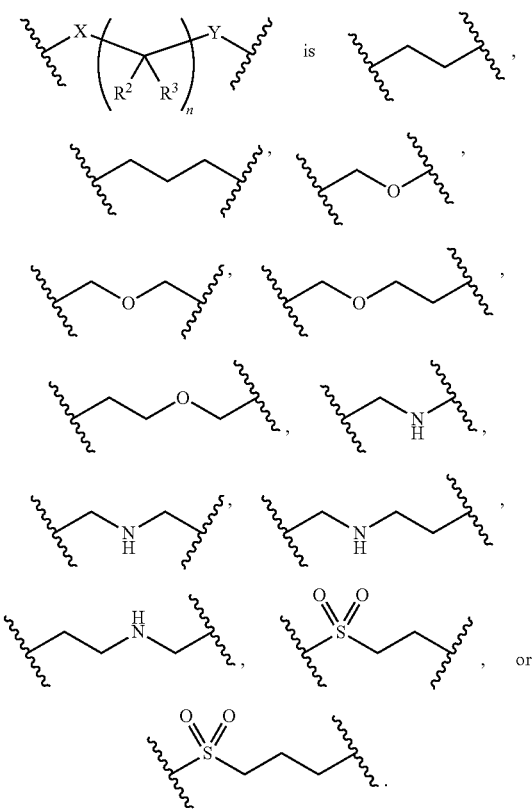

In some embodiments,

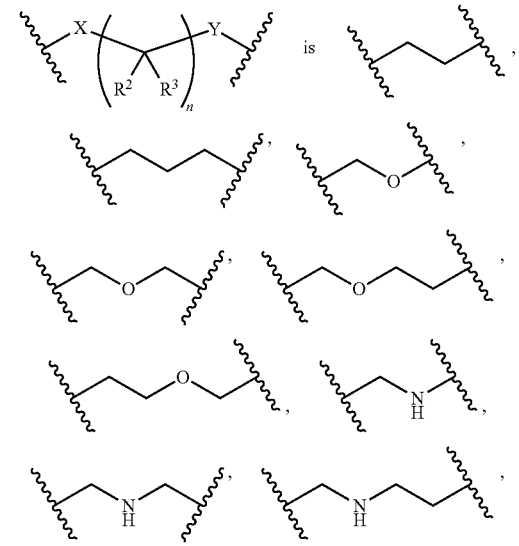

-continued
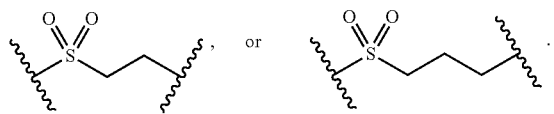
In some embodiments,
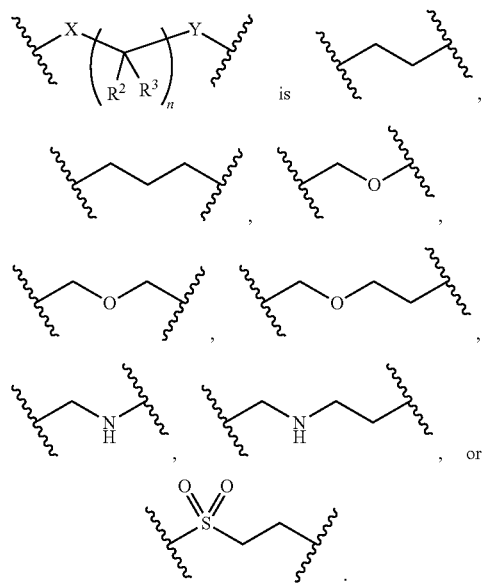
In some embodiments,
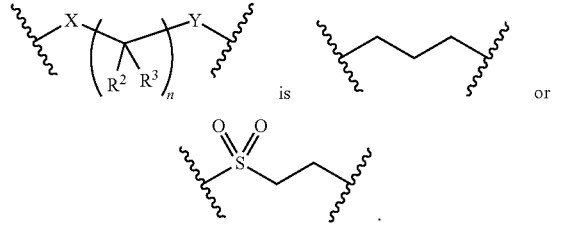
In some embodiments,
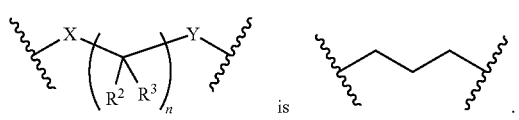
In some embodiments,
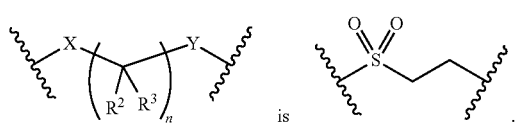
In some embodiments,
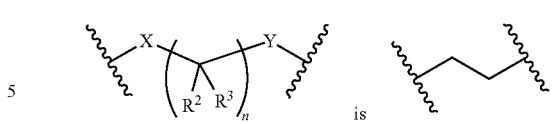
In some embodiments,
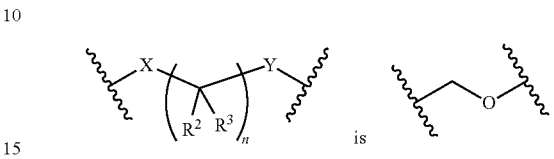
In some embodiments,
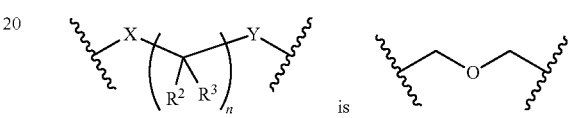
In some embodiments,
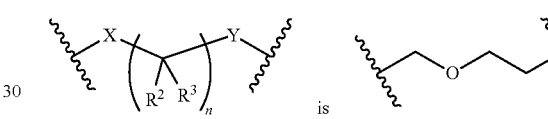
In some embodiments,
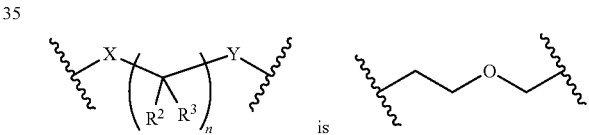
In some embodiments,
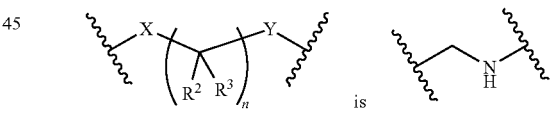
In some embodiments,
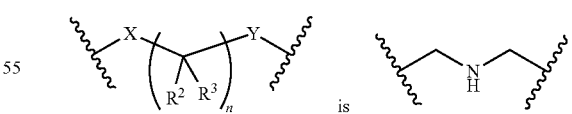
In some embodiments,
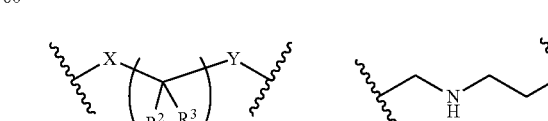

In some embodiments,
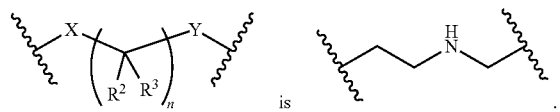
is .
In some embodiments,
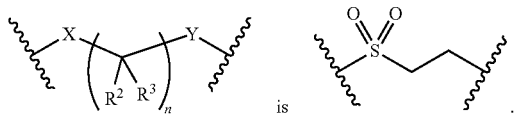
is .
Any combination of the groups described above for the various variables is contemplated herein. Throughout the specification, groups and substituents thereof can be chosen to provide stable moieties and compounds.
In some embodiments is a compound selected from:
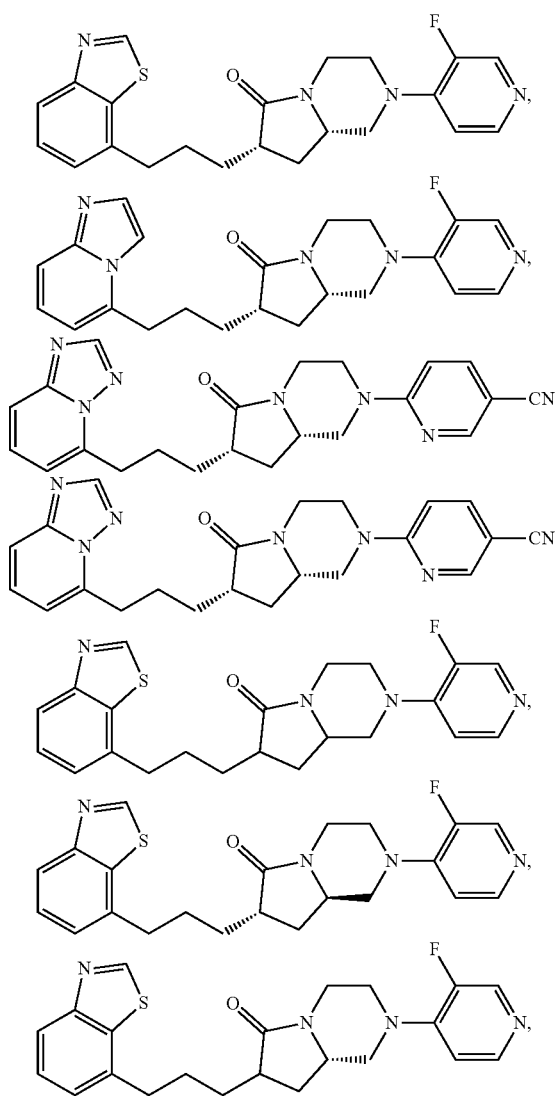
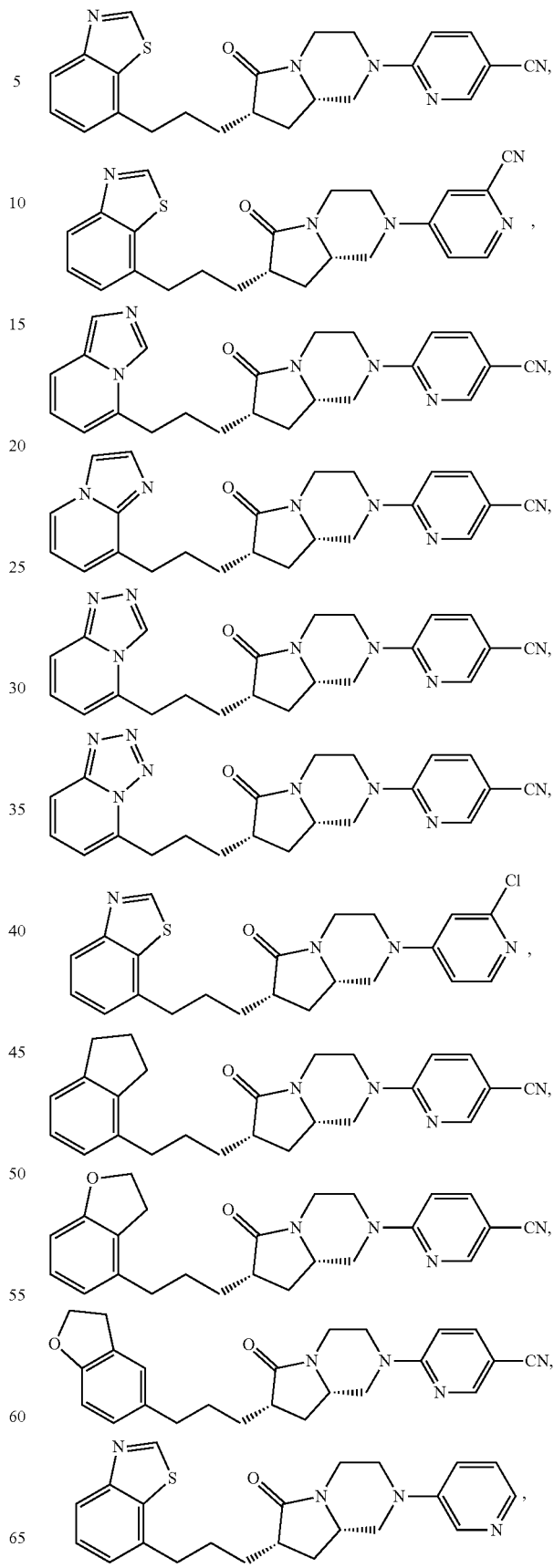

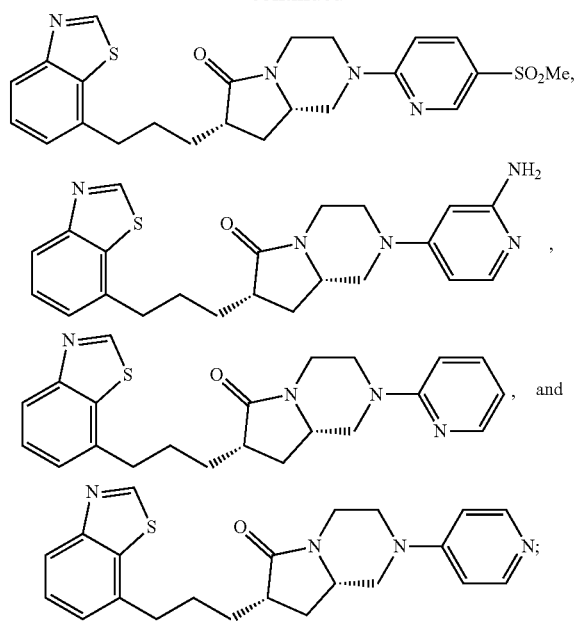
or a pharmaceutically acceptable salt or solvate thereof.
In some embodiments is a compound selected from:
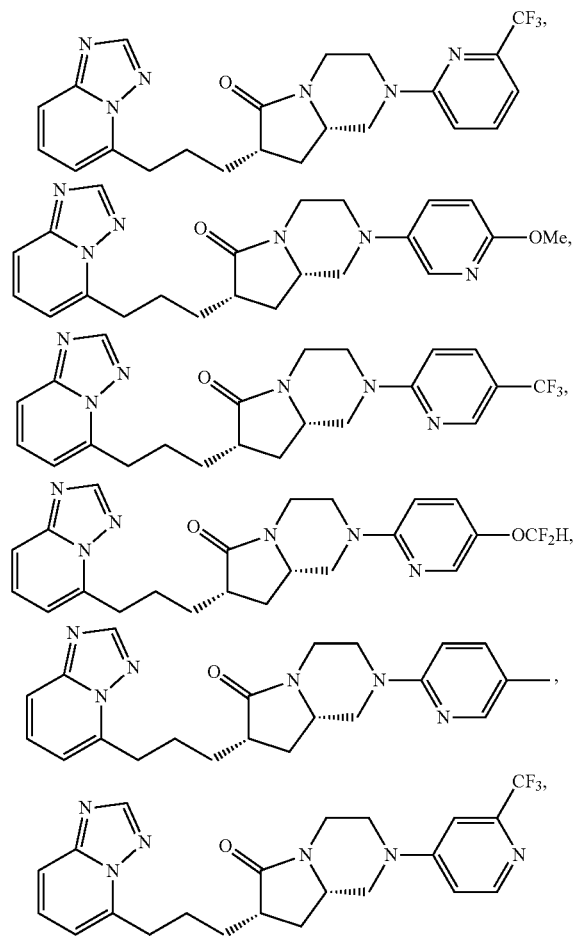
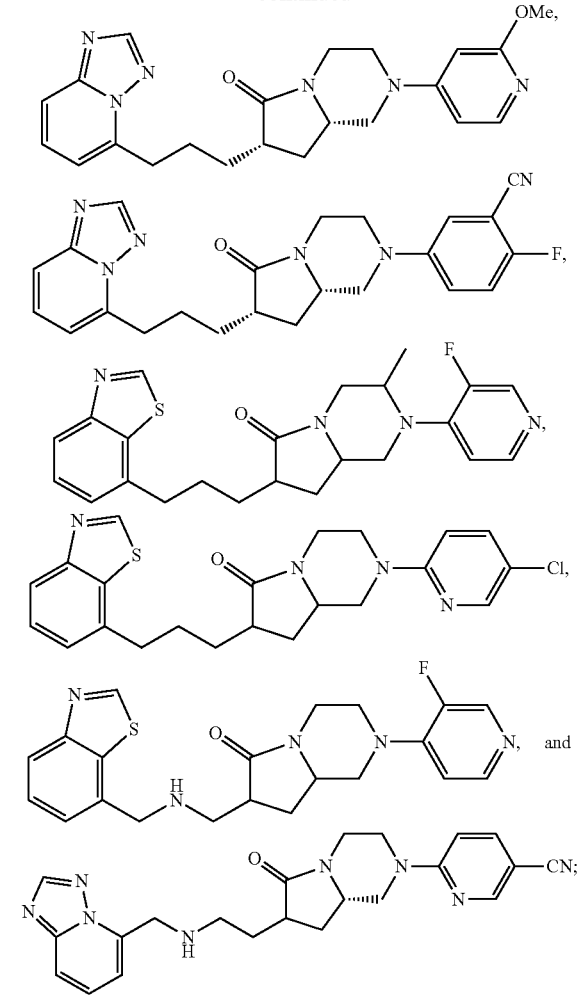
or a pharmaceutically acceptable salt or solvate thereof.
In some embodiments is a compound selected from:
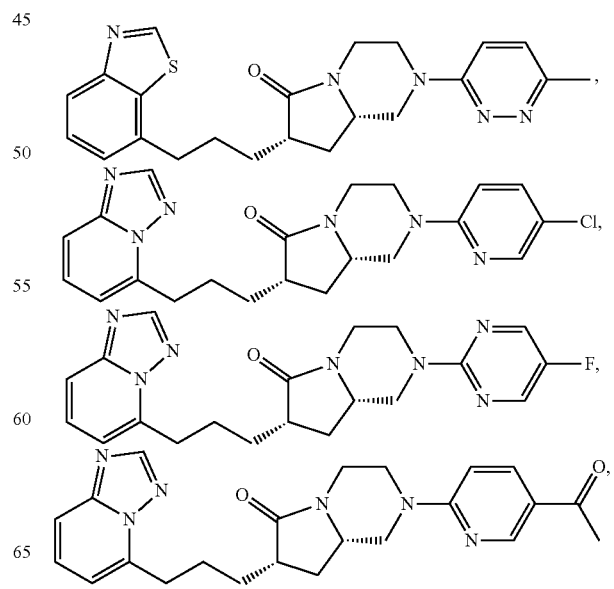

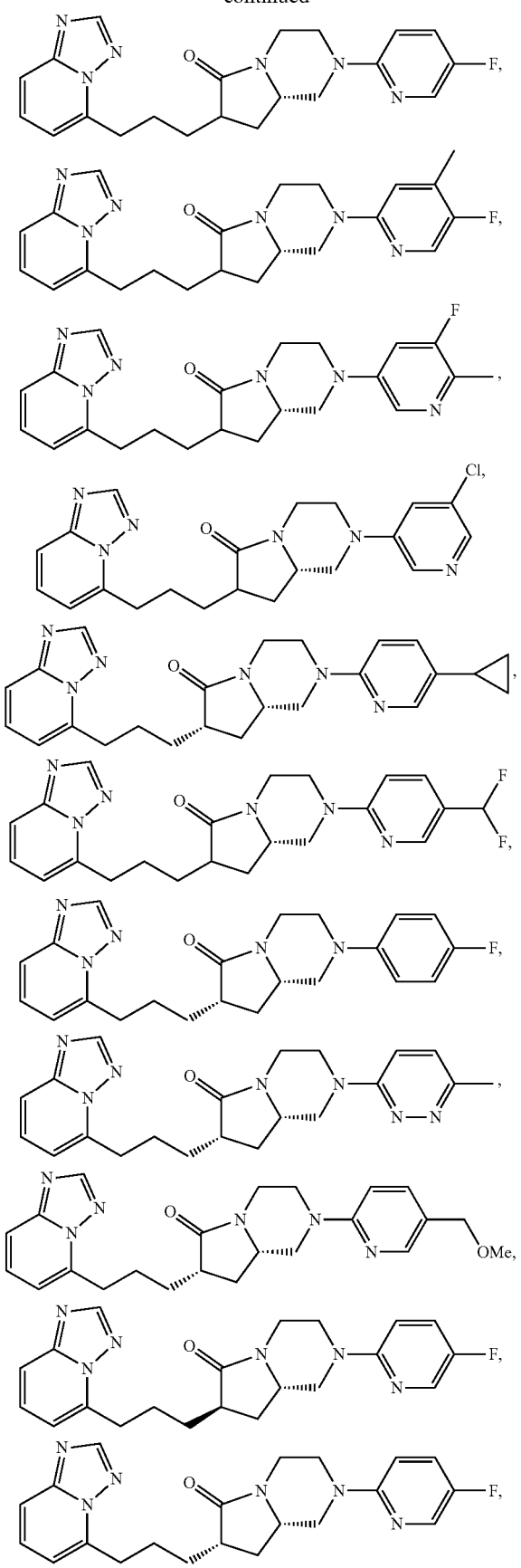
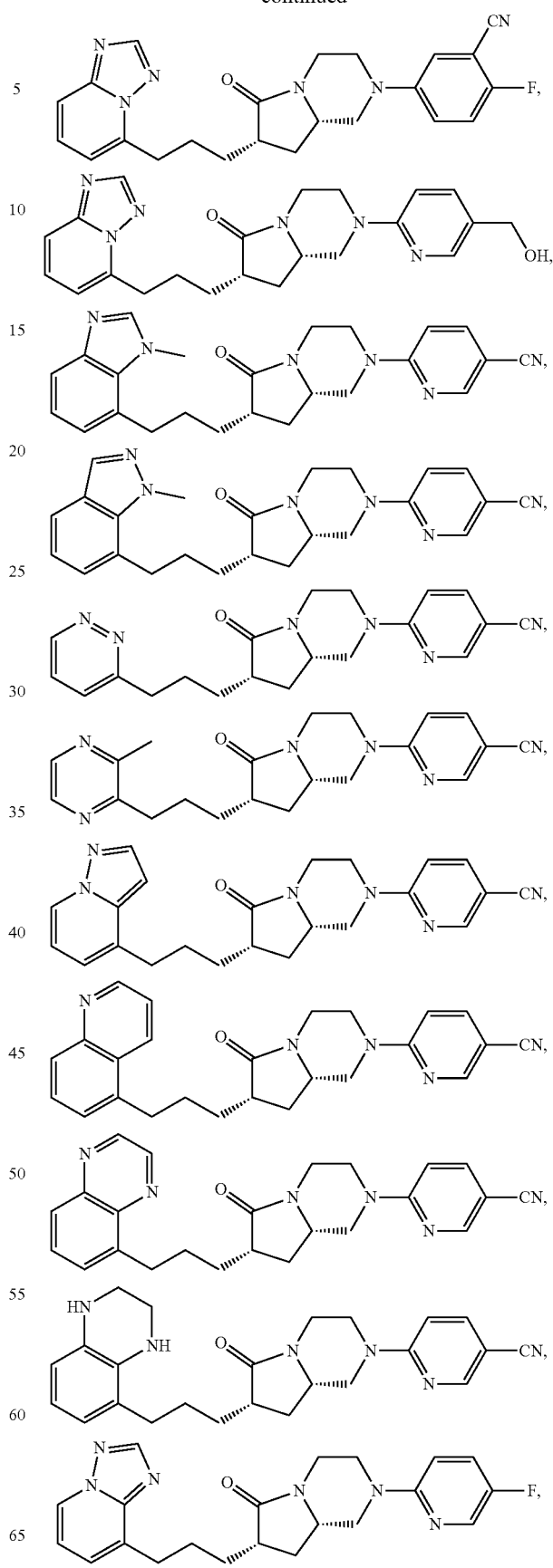

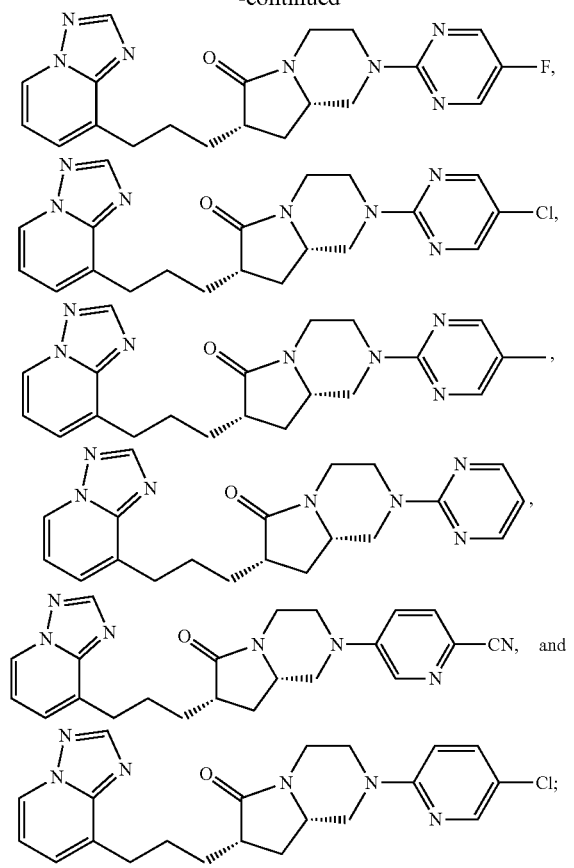
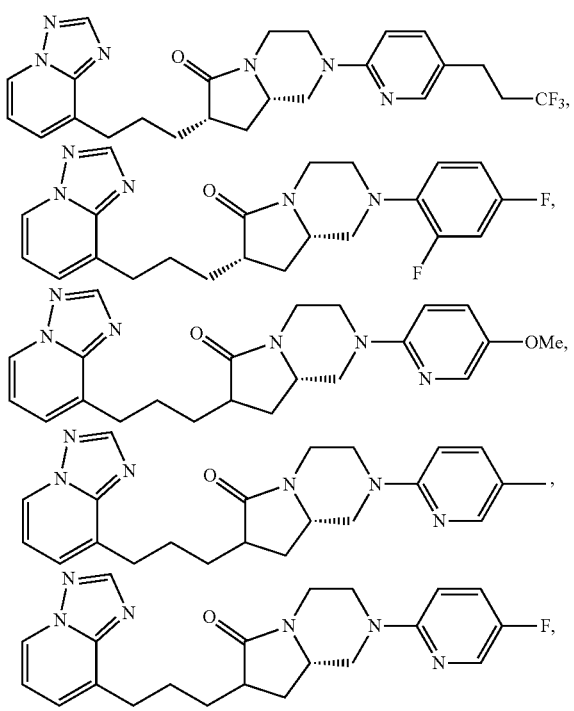
or a pharmaceutically acceptable salt or solvate thereof.
In some embodiments is a compound selected from:
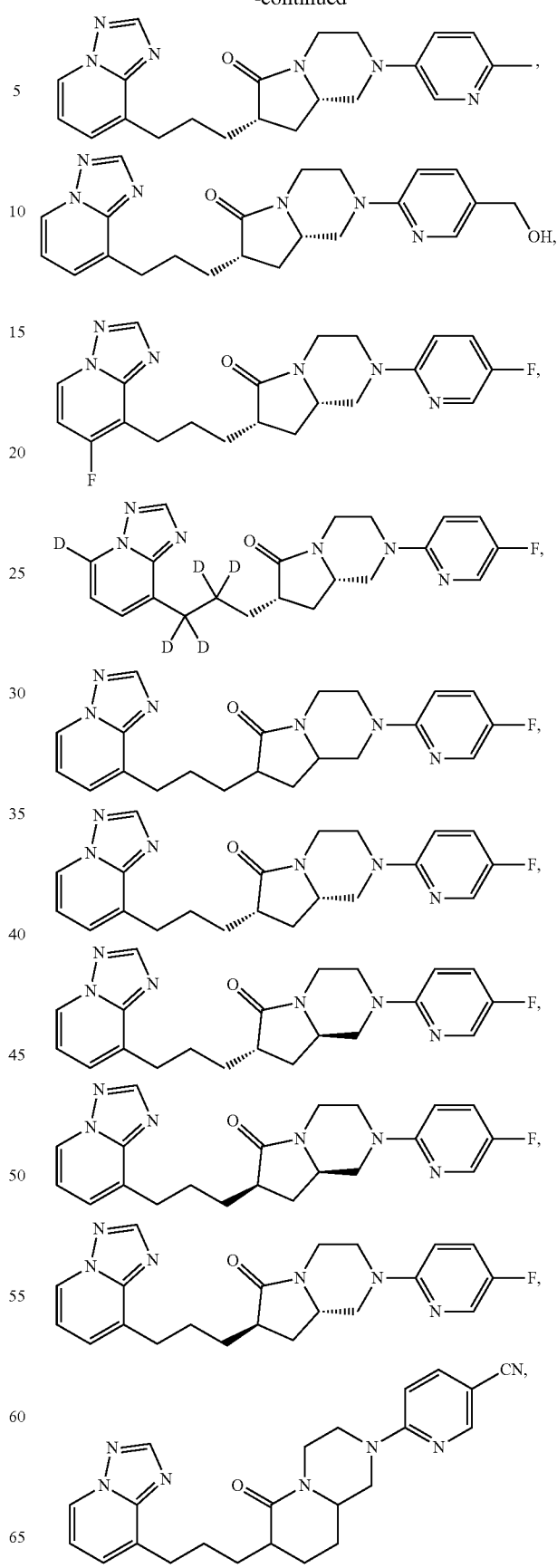

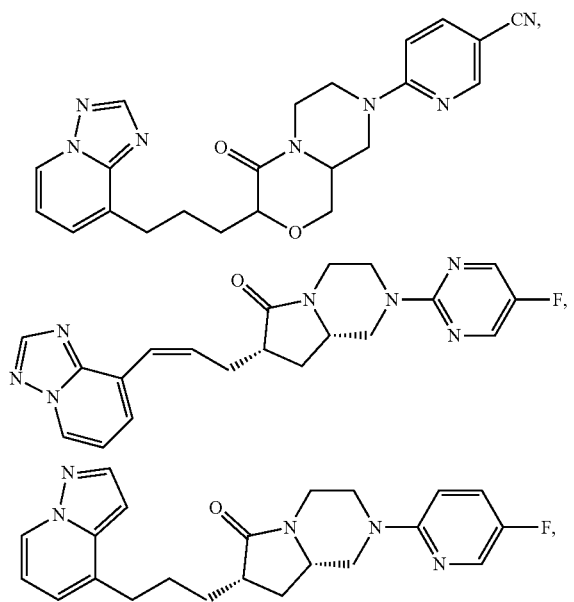
or a pharmaceutically acceptable salt or solvate thereof.
In some embodiments is a compound selected from:
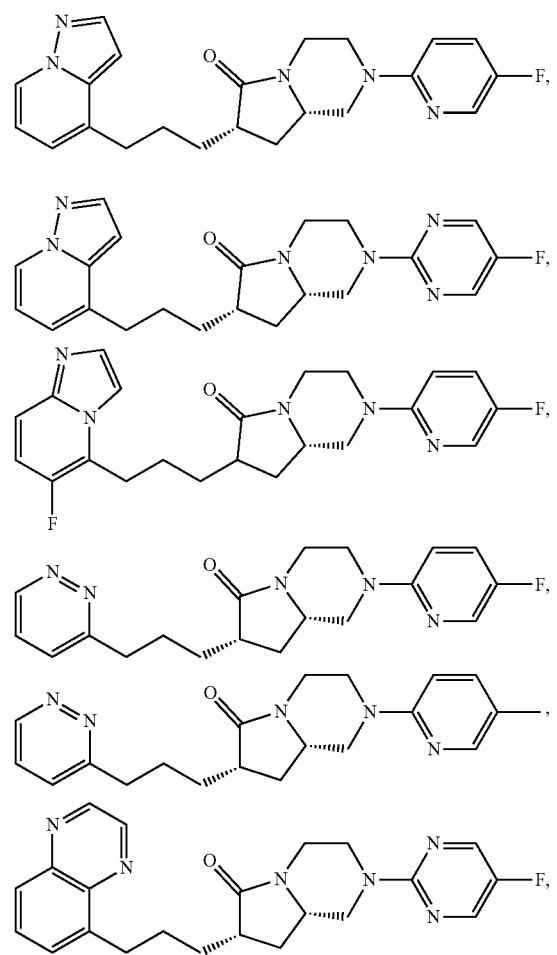
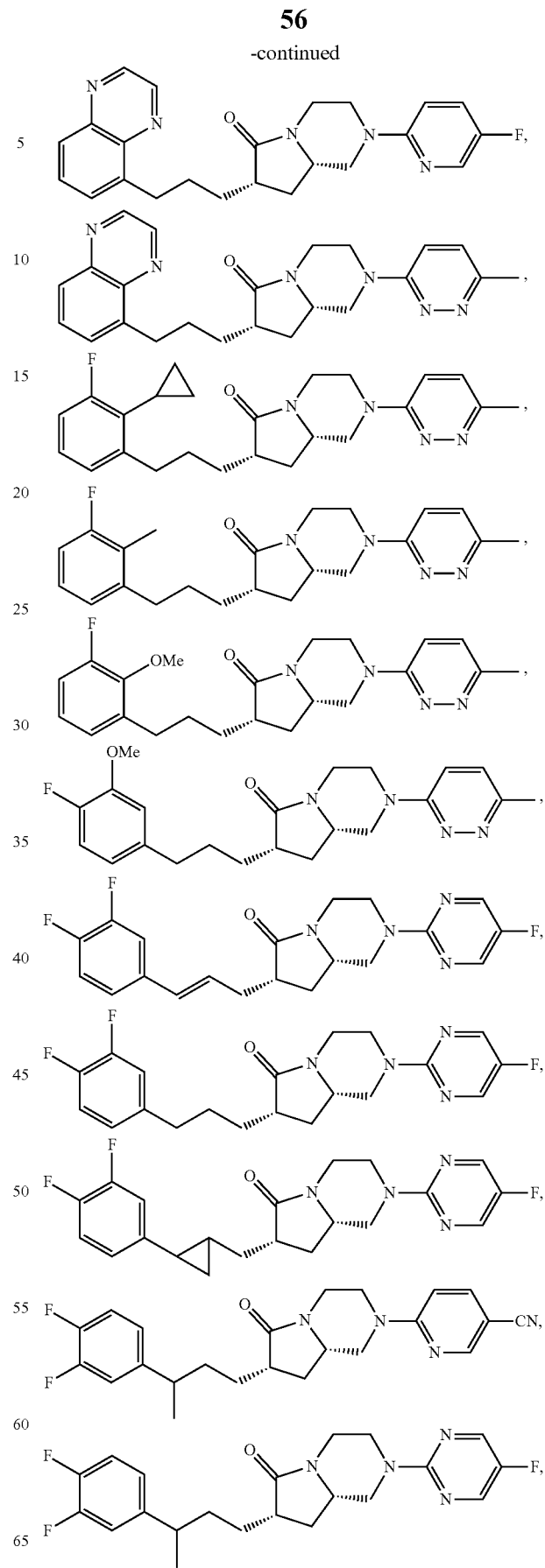

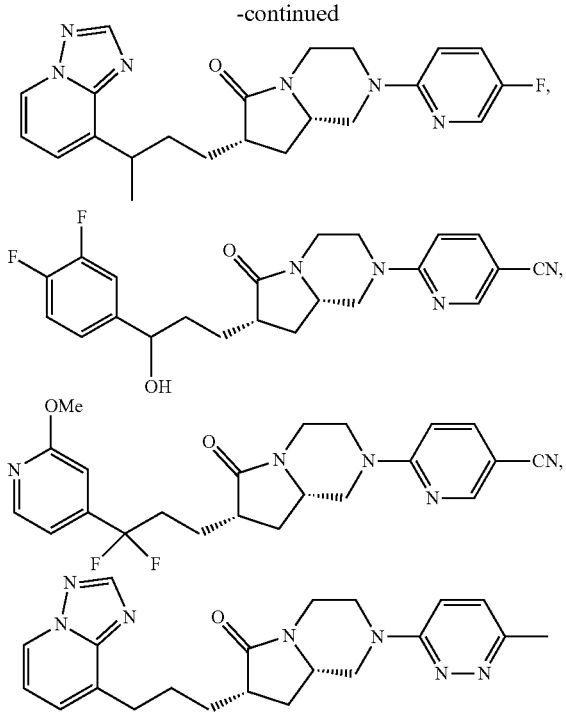

or a pharmaceutically acceptable salt or solvate thereof.
In some embodiments is a compound selected from:

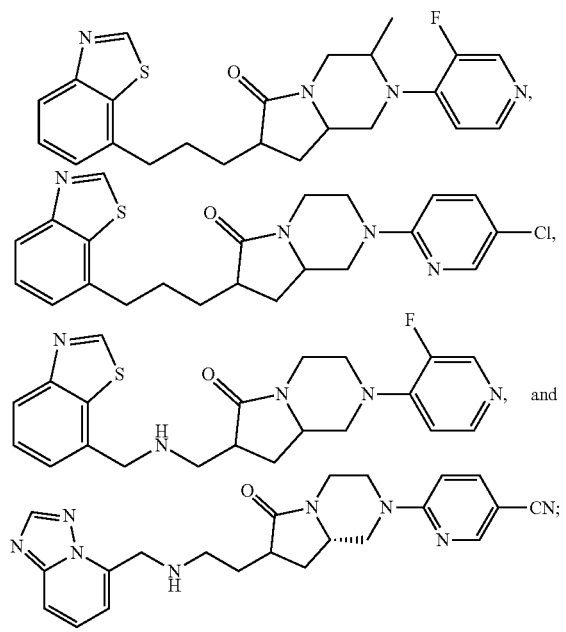

or a pharmaceutically acceptable salt or solvate thereof.

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, WI, including Sigma Chemical and Fluka), Apin Chemicals Ltd. (Milton Park, UK), Ark Pharm, Inc. (Libertyville, IL), Avocado Research (Lancashire, U.K.), BDH Inc. (Toronto, Canada), Bionet (Cornwall, U.K.), Chemservice Inc. (West Chester, PA), Combi-blocks (San Diego, CA), Crescent Chemical Co. (Hauppauge, NY), eMolecules (San Diego, CA), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Matrix Scientific, (Columbia, SC), Maybridge Chemical Co. Ltd. (Cornwall, U.K.), Parish Chemical Co. (Orem, UT), Pfaltz & Bauer, Inc. (Waterbury, CT), Polyorganix (Houston, TX), Pierce Chemical Co. (Rockford, IL), Riedel de Haen AG (Hanover, Germany), Ryan Scientific, Inc. (Mount Pleasant, SC), Spectrum Chemicals (Gardena, CA), Sundia Meditech, (Shanghai, China), TCI America (Portland, OR), Trans World Chemicals, Inc. (Rockville, MD), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of the Compounds

Isomers

The compounds described herein include all possible tautomers within the formulas described herein.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers.

In some situations, the compounds described herein possess one or more chiral centers and each center exists in the (R)-configuration, or (S)-configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

Labeled Compounds

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{17}O$, $^{18}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present disclosure, whether radioactive or not, are encompassed within the scope of the present disclosure.

In certain embodiments, the compounds disclosed herein have some or all of the $^1H$ atoms replaced with $^2H$ atoms. The methods of synthesis for deuterium-containing compounds are known in the art. In some embodiments deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

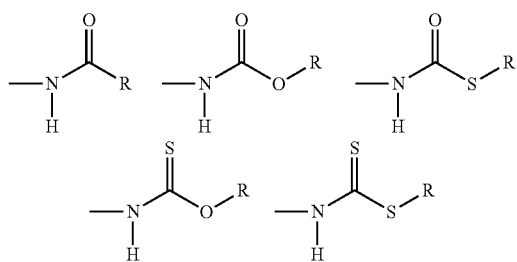

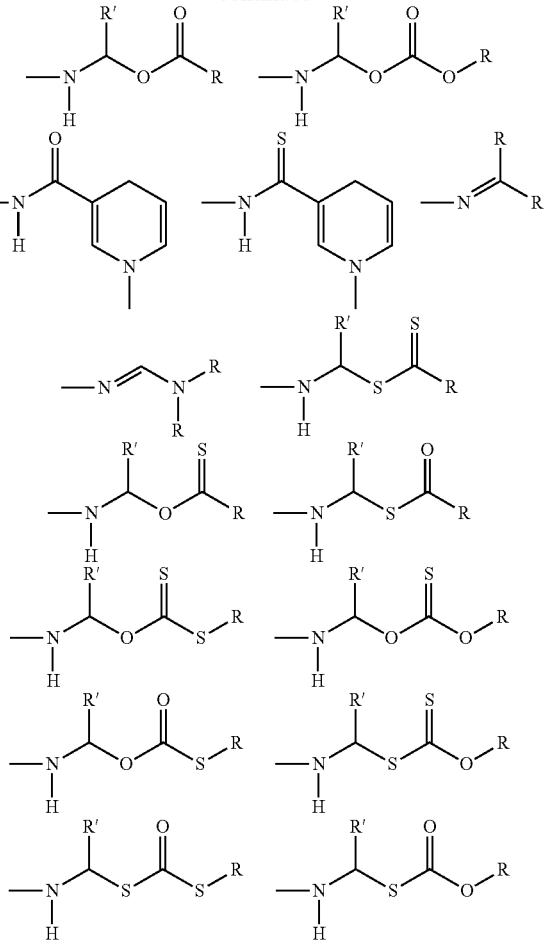

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Pharmaceutical Compositions

In certain embodiments, the compound of Formula (I), (Ia), (Ib), (Ic), (Id), (II), (IIa), (III), or (IIIa) as described herein is administered as a pure chemical. In some embodiments, the compound of Formula (I), (Ia), (Ib), (Ic), (Id), (II), (IIa), (III), or (IIIa) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21st Ed. Mack Pub. Co., Easton, PA (2005)).

Accordingly, provided herein is a pharmaceutical composition comprising at least one compound of Formula (I), (Ia), (Ib), (Ic), (Id), (II), (IIa), (III), or (IIIa) described herein, or a pharmaceutically acceptable salt or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof.

One embodiment provides a pharmaceutical composition comprising a pharmaceutically acceptable excipient and a compound of Formula (Ia), or a pharmaceutically acceptable salt thereof.

One embodiment provides a pharmaceutical composition comprising a pharmaceutically acceptable excipient and a compound of Formula (Ib), or a pharmaceutically acceptable salt thereof.

One embodiment provides a pharmaceutical composition comprising a pharmaceutically acceptable excipient and a compound of Formula (Ic), or a pharmaceutically acceptable salt thereof.

One embodiment provides a pharmaceutical composition comprising a pharmaceutically acceptable excipient and a compound of Formula (Id), or a pharmaceutically acceptable salt thereof.

One embodiment provides a pharmaceutical composition comprising a pharmaceutically acceptable excipient and a compound of Formula (II), or a pharmaceutically acceptable salt thereof.

One embodiment provides a pharmaceutical composition comprising a pharmaceutically acceptable excipient and a compound of Formula (IIa), or a pharmaceutically acceptable salt thereof.

One embodiment provides a pharmaceutical composition comprising a pharmaceutically acceptable excipient and a compound of Formula (III), or a pharmaceutically acceptable salt thereof.

One embodiment provides a pharmaceutical composition comprising a pharmaceutically acceptable excipient and a compound of Formula (IIIa), or a pharmaceutically acceptable salt thereof.

In certain embodiments, the compound of Formula (I), (Ia), (Ib), (Ic), (Id), (II), (IIa), (III), or (IIIa) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These pharmaceutical compositions include those suitable for oral, rectal, topical, buccal, parenteral (e.g., subcutaneous, intramuscular, intradermal, or intravenous) vaginal, ophthalmic, or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I), (Ia), (Ib), (Ic), (Id), (II), (IIa), (III), or (IIIa) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Disclosed compounds are administered to subjects or patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Methods of Using the Compounds and Compositions

Antagonists of MAChR M1

The muscarinic acetylcholine receptor $M_1$ (mAChR $M_1$) is found in both the central and peripheral nervous systems, particularly in the cerebral cortex and sympathetic ganglia. Notably, M1 is expressed on oligodendrocyte precursor cells (OPCs) in the central nervous system. Over time, OPCs will differentiate into myelin-producing oligodendrocytes. Myelin is indispensible for action potential conduction along the axon and its loss has been attributed to neurodegenerative disorders, specifically multiple sclerosis. In some embodiments, non-selective mAChR antagonists accelerate OPC differentiation into oligodendrocytes. In some embodiments, selective mAChR $M_1$ antagonists are useful in the treatment of demyelinating disorders, such as multiple sclerosis. In some embodiments, M1 antagonists are useful in treating epileptic disorders and certain movement disorders, including Parkinson's disease, dystonia, and fragile X syndrome. In one aspect, the compounds disclosed herein are antagonists of the muscarinic acetylcholine $M_1$ receptor (mAChR $M_1$). In some embodiments, the compounds disclosed herein are antagonists of the muscarinic acetylcholine $M_2$ receptor (mAChR $M_2$). In some embodiments, the compounds disclosed herein are antagonists of the muscarinic acetylcholine $M_3$ receptor (mAChR $M_3$). In some embodiments, the compounds disclosed herein are antagonists of the muscarinic acetylcholine $M_4$ receptor (mAChR $M_4$). In some embodiments, the compounds disclosed herein are antagonists of the muscarinic acetylcholine $M_5$ receptor (mAChR $M_5$). In some embodiments, the compounds disclosed herein are antagonists of one or more of mAChR $M_1$, mAChR $M_2$, mAChR $M_3$, mAChR $M_4$, or mAChR $M_5$. In some embodiments, the compounds disclosed herein are selective antagonists of the muscarinic acetylcholine $M_1$ receptor (mAChR $M_1$) over one or more of the mAChR $M_2$, $M_3$, $M_4$, or $M_5$ receptors. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_2$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_3$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_4$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_5$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR M2, M3, M4, or Ms, or combinations thereof.

Treatment Methods

The compounds disclosed herein are useful for treating, preventing, ameliorating, controlling or reducing the risk of a variety of disorders wherein the patient or subject would benefit from antagonism of the muscarinic acetylcholine $M_1$ receptor.

In one aspect, a treatment can include selective $M_1$ receptor antagonism to an extent effective to affect cholinergic activity. Thus, disorders for which the compounds disclosed herein are useful can be associated with cholinergic activity, for example cholinergic hyperfunction. In some embodiments, provided herein is a method of treating or preventing a disorder in a subject comprising the step of administering to the subject a compound disclosed herein, or a pharmaceutically acceptable salt or solvate thereof, or a pharmaceutical composition described herein in a dosage and amount effective to treat the disorder in the subject.

Provided herein is a method for the treatment of one or more disorders, for which muscarinic acetylcholine receptor inhibition is predicted to be beneficial, in a subject comprising the step of administering to the subject a compound disclosed herein, or a pharmaceutically acceptable salt or solvate thereof, or a pharmaceutical composition described herein in a dosage and amount effective to treat the disorder in the subject.

In some embodiments provided herein is a method of treating a neurodegenerative disorder in a subject in need thereof, comprising administering to subject a therapeutically effective amount of a compound of Formula (I), (Ia), (Ib), (Ic), (Id), (II), (IIa), (III), or (IIIa), or a pharmaceutically acceptable salt or solvate thereof.

In some embodiments provided herein is a method of treating neuropathy in a subject in need thereof, comprising administering to the subject a therapeutically effective amount of a compound of Formula (I), (Ia), (Ib), (Ic), or (Id), or a pharmaceutically acceptable salt or solvate thereof. In some embodiments is a method of treating neuropathy in a subject in need thereof, comprising administering to the subject a therapeutically effective amount of a compound of Formula (I), (Ia), (Ib), (Ic), or (Id), or a pharmaceutically acceptable salt or solvate thereof, wherein the neuropathy is peripheral neuropathy. In some embodiments is a method of treating neuropathy in a subject in need thereof, comprising administering to the subject a therapeutically effective amount of a compound of Formula (I), (Ia), (Ib), (Ic), or (Id), or a pharmaceutically acceptable salt or solvate thereof, wherein the neuropathy is diabetic neuropathy.

In some embodiments is a method of treating a demyelinating disease in a subject in need thereof, comprising administering to the subject a therapeutically effective amount of a compound of Formula (I), (Ia), (Ib), (Ic), (Id), (II), (IIa), (III), or (IIIa), or a pharmaceutically acceptable salt or solvate thereof. In some embodiments is a method of treating a demyelinating disease in a subject in need thereof, comprising administering to the subject a therapeutically effective amount of a compound of Formula (I), (Ia), (Ib), (Ic), (Id), (II), (IIa), (III), or (IIIa), or a pharmaceutically acceptable salt or solvate thereof, wherein the demyelinating disease is a demyelinating disease of the central nervous system. In some embodiments is a method of treating a demyelinating disease in a subject in need thereof, comprising administering to the subject a therapeutically effective amount of a compound of Formula (I), (Ia), (Ib), (Ic), (Id), (II), (IIa), (III), or (IIIa), or a pharmaceutically acceptable salt or solvate thereof, wherein the demyelinating disease is multiple sclerosis. In some embodiments is a method of treating a demyelinating disease in a subject in need thereof, comprising administering to the subject a therapeutically effective amount of a compound of Formula (I), (Ia), (Ib), (Ic), (Id), (II), (IIa), (III), or (IIIa), or a pharmaceutically acceptable salt or solvate thereof, wherein the demyelinating disease is a demyelinating disease of the peripheral nervous system.

In some embodiments is a method of modulating muscarinic acetylcholine receptor $M_1$ activity in a subject comprising administering to the subject a compound of Formula (I), (Ia), (Ib), (Ic), (Id), (II), (IIa), (III), or (IIIa), or a pharmaceutically acceptable salt or solvate thereof. In some embodiments, the compound of Formula (I), (Ia), (Ib), (Ic), or (Id), or a pharmaceutically acceptable salt or solvate thereof acts as a selective M1 antagonist.

Combination Therapy

Also contemplated herein are combination therapies, for example, co-administering a disclosed compound and an additional active agent, as part of a specific treatment regimen intended to provide the beneficial effect from the co-action of these therapeutic agents. In some embodiments, a compound described herein is administered in combination with one or more immunomodulatory agents. In some embodiments, a compound described herein is administered in combination with one or more immunomodulatory agents, wherein the immunomodulatory agents are selected from an IFN-β 1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or FTY720 or other SIP1 functional modulator; a dimethyl fumarate; an antibody to the alpha subunit of the IL-2 receptor of T cells (CD25) or daclizumab; an antibody against CD52 or alemtuzumab; an antibody against CD20; and an inhibitor of a dihydroorotate dehydrogenase or teriflunomide. In some embodiments, the immunomodulatory agent is an IFN-β 1 molecule. In some embodiments, the immunomodulatory agent is a corticosteroid. In some embodiments, the immunomodulatory agent is a polymer of glutamic acid, lysine, alanine and tyrosine or glatiramer. In some embodiments, the immunomodulatory agent is an antibody or fragment thereof against alpha-4 integrin or natalizumab. In some embodiments, the immunomodulatory agent is an anthracenedione molecule or mitoxantrone. In some embodiments, the immunomodulatory agent is a fingolimod or FTY720 or other SIP1 functional modulator. In some embodiments, the immunomodulatory agent is a dimethyl fumarate. In some embodiments, the immunomodulatory agent is an antibody to the alpha subunit of the IL-2 receptor of T cells (CD25) or daclizumab. In some embodiments, the immunomodulatory agent is an antibody against CD52 or alemtuzumab. In some embodiments, the immunomodulatory agent is an antibody against CD20. In some embodiments, the immunomodulatory agent is an inhibitor of a dihydroorotate dehydrogenase or teriflunomide.

The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tent-butyl carbamate

CDI 1,1'-carbonyldiimidazole
Cy cyclohexyl
DCE dichloroethane (ClCH$_2$CH$_2$Cl)
DCM dichloromethane (CH$_2$Cl$_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HFIP 1,1,1,3,3,3-hexafluoropropan-2-ol
HPLC high performance liquid chromatography
LAH lithium aluminum hydride
LCMS liquid chromatography-mass spectrometry
Me methyl
MeOH methanol
MS mass spectroscopy
NMM N-methylmorpholine
NMR nuclear magnetic resonance
PMB para-methoxybenzyl
rt room temperature
TEA triethylamine
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Examples 1 and 2: Synthesis of (7R,8aS)-7-(3-(benzo[d]thiazol-7-yl)propyl)-2-(3-fluoropyridin-4-yl)hexahydropyrrolo[1,2-a]pyrazin-6(2H)-one (Example 1) and (7S,8aS)-7-(3-(benzo [d]thiazol-7-yl)propyl)-2-(3-fluoropyridin-4-yl)hexahydropyrrolo[1,2-a]pyrazin-6(2H)-one (Example 2)

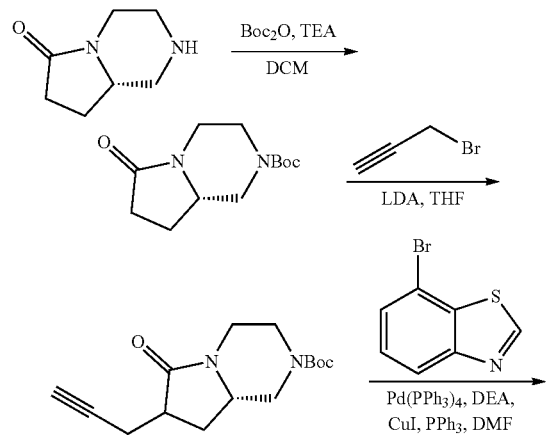

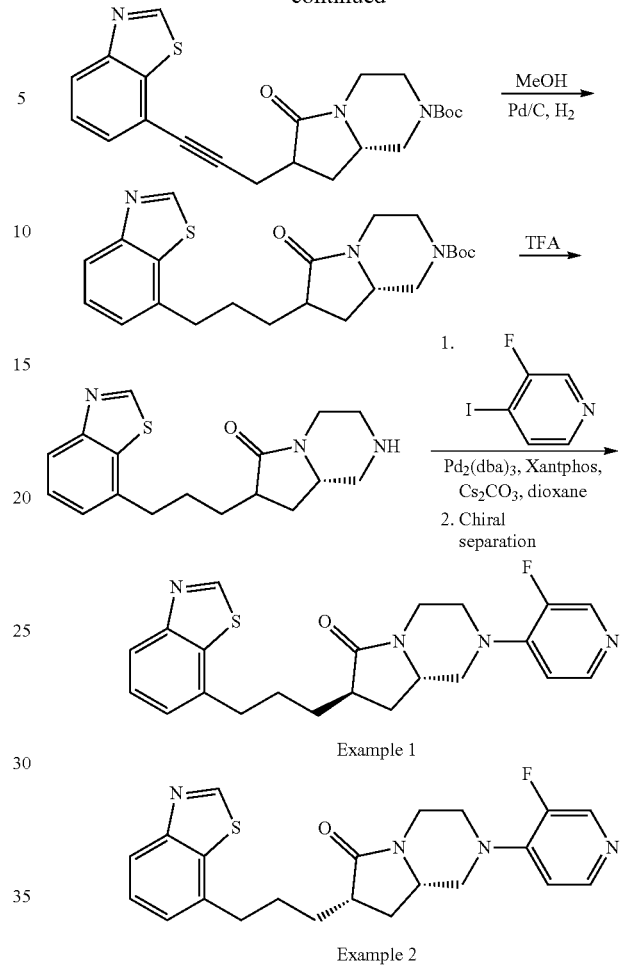

Example 1

Example 2

Step 1: In a 25-mL round-bottom flask was placed (8aS)-octahydropyrrolo[1,2-a]pyrazin-6-one hydrochloride (1000 mg, 5.66 mmol, 1 eq), DCM (10 mL). The resulting solution was stirred at rt. This was followed by the addition of Boc$_2$O (2471 mg, 11.32 mmol, 2 eq) dropwise with stirring at 0° C. in 3 min. To this was added TEA (1718 mg, 16.98 mmol, 3 eq) dropwise with stirring at 0° C. in 3 min. The resulting solution was stirred at room temperature overnight. The resulting mixture was concentrated. The resulting solution was extracted with 2×350 mL of ethyl acetate and the organic layers were combined and dried over anhydrous sodium sulfate. The solids were filtered off. The resulting mixture was concentrated. The residue was chromatographed on a silica gel column to afford tert-butyl (8aS)-6-oxo-octahydropyrrolo[1,2-a]pyrazine-2-carboxylate (850 mg, 62%) as a yellow semi-solid.

Step 2: In a 250 mL 3-necked round-bottom flask purged and maintained with an inert atmosphere of nitrogen, was placed THF (40 mL). The solution was stirred for 5 min at −70° C. in a liquid nitrogen bath. This was followed by the addition of LDA (568 mg, 5.30 mmol, 1.5 eq) dropwise with stirring at −70° C. The resulting solution was stirred for 10 min at −70° C. under nitrogen atmosphere in a liquid nitrogen bath. To this was added a solution of tert-butyl (8aS)-6-oxo-octahydropyrrolo[1,2-a]pyrazine-2-carboxylate (850 mg, 3.53 mmol, 1 eq) in THF (10 mL) dropwise with stirring at −70° C. in 15 min. The resulting solution was stirred for 1 h at −70° C. under nitrogen atmosphere in a liquid nitrogen bath. To the mixture was added 3-bromoprop-1-yne (547 mg, 4.6 mmol, 1.3 eq) dropwise with stirring at −70° C. in 25 min. The resulting solution was stirred for 1 h at −40° C. under nitrogen atmosphere in a liquid nitrogen bath. The reaction was then quenched by the addition of NH$_4$Cl solution. The resulting solution was extracted with ethyl acetate and the organic layers were combined and dried over anhydrous sodium sulfate. The solids were filtered off. The resulting mixture was concentrated. The residue was chromatographed on a silica gel column to afford tert-butyl (8aS)-6-oxo-7-(prop-2-yn-1-yl)-octahydropyrrolo[1,2-a]pyrazine-2-carboxylate (650 mg, 66%) as a yellow semi-solid.

Step 3: In a 20-mL sealed tube was placed tert-butyl (8aS)-6-oxo-7-(prop-2-yn-1-yl)-octahydropyrrolo[1,2-a]pyrazine-2-carboxylate (320 mg, 1.15 mmol, 1 eq), 7-bromo-1,3-benzothiazole (295.3 mg, 1.38 mmol, 1.2 eq), Pd(PPh$_3$)$_4$ (66.4 mg, 0.057 mmol, 0.05 eq), DEA (857.8 mg, 5.74 mmol, 5 eq), CuI (11 mg, 0.057 mmol, 0.05 eq), PPh$_3$ (60.3 mg, 0.230 mmol, 0.2 eq), N,N-dimethylformamide (5 mL). The resulting solution was stirred for 2 h at 80° C. The solids were filtered off and the filtrate was concentrated. The resulting solution was extracted with ethyl acetate and the organic layers were combined and dried over anhydrous sodium sulfate and concentrated. The residue was chromatographed on a silica gel column to afford tert-butyl (8aS)-7-[3-(1,3-benzothiazol-7-yl)prop-2-yn-1-yl]-6-oxo-octahydropyrrolo[1,2-a]pyrazine-2-carboxylate (380 mg, 80%) as a yellow semi-solid.

Step 4: In a 25-mL round-bottom flask purged and maintained with an inert atmosphere of nitrogen, was placed tert-butyl (8aS)-7-[3-(1,3-benzothiazol-7-yl)prop-2-yn-1-yl]-6-oxo-octahydropyrrolo[1,2-a]pyrazine-2-carboxylate (380 mg, 0.92 mmol, 1 eq), Pd/C (500 mg, 4.7 mmol, 5.09 eq), MeOH (8 mL). The resulting solution was stirred at rt for 3 h under hydrogen. The solids were filtered off. The resulting mixture was concentrated. The residue was chromatographed on a silica gel column to afford tert-butyl (7R,8aS)-7-[3-(1,3-benzothiazol-7-yl)propyl]-6-oxo-octahydropyrrolo[1,2-a]pyrazine-2-carboxylate (300 mg, 78%) as a brown semi-solid.

Step 5: In a 25-mL round-bottom flask was placed tert-butyl (7R,8aS)-7-[3-(1,3-benzothiazol-7-yl)propyl]-6-oxo-octahydropyrrolo[1,2-a]pyrazine-2-carboxylate (300 mg, 0.72 mmol, 1 eq), DCM (5 mL). The resulting solution was stirred at rt. This was followed by the addition of TFA (4 mL) dropwise with stirring at 0° C. The resulting solution was stirred for 40 min at rt. The resulting mixture was concentrated. The pH value of the solution was adjusted to 8-9 with NH$_3$—MeOH (7 M). The resulting solution was stirred for 60 min at rt. The resulting mixture was concentrated. The residue was purified by HPLC to afford (8aS)-7-[3-(1,3-benzothiazol-7-yl)propyl]-octahydropyrrolo[1,2-a]pyrazin-6-one (135 mg, 59%) as a yellow semi-solid.

Step 6: In a 20-mL sealed tube purged and maintained with an inert atmosphere of nitrogen, was placed (8aS)-7-[3-(1,3-benzothiazol-7-yl)propyl]-octahydropyrrolo[1,2-a]pyrazin-6-one (135 mg, 0.43 mmol, 1 eq), 3-fluoro-4-iodopyridine (115 mg, 0.52 mmol, 1.21 eq), Pd$_2$(dba)$_3$ (176 mg, 0.19 mmol, 0.45 eq), Xantphos (198 mg, 0.34 mmol, 0.80 eq), Cs$_2$CO$_3$ (404 mg, 1.24 mmol, 2.90 eq), dioxane (4 mL). The resulting solution was stirred for 2 h at 110° C. in an oil bath. The solids were filtered off. The resulting mixture was concentrated. The crude product was purified by Prep-HPLC. This resulted in 80 mg of the racemic as a white solid. The racemic was separated by Chiral-Prep-HPLC. This resulted in 32.8 mg of example 1 and 19.4 mg of example 2.

Example 1: LCMS: m/z=410.8[M+1]$^+$, $^1$H NMR (300 MHz, methanol-d4) δ 9.25 (s, 1H), 8.18 (d, J=3.0 Hz, 1H), 8.10 (d, J=2.85 Hz, 1H), 7.92 (d, J=3.75 Hz, 1H), 7.51 (t, J=8.2, 7.3 Hz, 1H), 7.35 (d, J=7.3 Hz, 1H), 7.02 (m, J=8.2, 5.7 Hz, 1H), 4.03 (d, J=6.0 Hz 1H), 3.92-3.75 (m, 3H), 3.20-2.80 (m, 4H), 2.79-2.50 (m, 2H), 2.02-1.72 (m, 5H), 1.60-1.40 (m, 1H).

Example 2: LCMS: m/z=410.8[M+1]$^+$, $^1$H NMR (300 MHz, methanol-d4) δ 9.25 (s, 1H), 8.18 (d, J=3.0 Hz, 1H), 8.10 (d, J=2.85 Hz, 1H), 7.92 (d, J=3.75 Hz, 1H), 7.51 (t, J=8.2, 7.3 Hz, 1H), 7.35 (d, J=7.3 Hz, 1H), 7.02 (m, J=8.2, 5.7 Hz, 1H), 4.03 (d, J=6.0 Hz 2H), 3.84 (d, J=6.15 Hz, 1H), 3.72 (d, J=4.35 Hz, 1H), 3.03-2.80 (m, 4 H), 2.79-2.40 (m, 3H), 2.15-1.75 (m, 3H), 1.60-1.20 (m, 2H).

Example 3: Synthesis of (7S,8aS)-2-(3-fluoropyridin-4-yl)-7-(3-(imidazo[1,2-a]pyridin-5-yl)propyl)hexahydropyrrolo[1,2-a]pyrazin-6(2H)-one

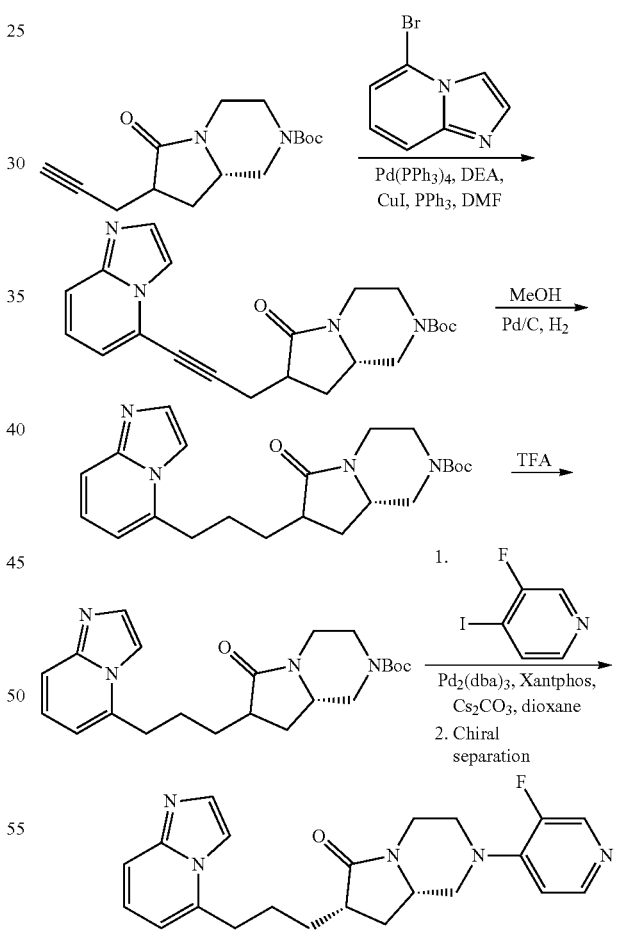

Step 1: In a 30-mL sealed tube was placed tert-butyl (8aS)-6-oxo-7-(prop-2-yn-1-yl)hexahydropyrrolo[1,2-a]pyrazine-2(1H)-carboxylate (340 mg, 1.22 mmol, 1 eq), DMF (5 mL), 5-bromoimidazo[1,2-a]pyridine (288 mg, 1.47 mmol, 1.2 eq), Pd(PPh$_3$)$_4$ (70.6 mg, 0.06 mmol, 0.05 eq), DEA (911.4 mg, 6.11 mmol, 5 eq), CuI (11.6 mg, 0.06 mmol, 0.05 eq), PPh$_3$ (64.1 mg, 0.24 mmol, 0.2 eq). The resulting solution was stirred for 2 h at 80° C. in an oil bath. The solids were filtered off. The resulting solution was extracted with ethoxyethane. The residue was chromatographed on a silica gel column to afford tert-butyl (8aS)-7-(3-[imidazo[1,2-a]pyridin-5-yl]prop-2-yn-1-yl)-6-oxo-octahydropyrrolo[1,2-a]pyrazine-2-carboxylate (300 mg, 62%) as a yellow oil. LCMS: m/z=395.2 [M+H]+.

Step 2: In a 25-mL round-bottom flask was placed tert-butyl (8aS)-7-(3-[imidazo[1,2-a]pyridin-5-yl]prop-2-yn-1-yl)-6-oxo-octahydropyrrolo[1,2-a]pyrazine-2-carboxylate (280 mg, 0.71 mmol, 1 eq), MeOH (4 mL), Pd/C (280 mg, 2.63 mmol, 3.71 eq). The resulting solution was stirred at rt for 3 h under H2. The solids were filtered off. The resulting mixture was concentrated. The residue was chromatographed on a silica gel column to afford tert-butyl (7R,8aS)-7-(3-[imidazo[1,2-a]pyridin-5-yl]propyl)-6-oxo-octahydropyrrolo[1,2-a]pyrazine-2-carboxylate (230 mg, 81%) as a yellow oil. LCMS: m/z=399.2 [M+H]+.

Step 3: In a 25-mL round-bottom flask was placed tert-butyl (7R,8aS)-7-(3-[imidazo[1,2-a]pyridin-5-yl]propyl)-6-oxo-octahydropyrrolo[1,2-a]pyrazine-2-carboxylate (220 mg, 0.55 mmol,1 eq), DCM (6 mL), TFA (3 mL). The resulting solution was stirred at rt for 1 h. The resulting mixture was concentrated. The residue was purified by Flash-Prep-HPLC to afford (8aS)-7-(3-[imidazo[1,2-a]pyridin-5-yl]propyl)-octahydropyrrolo[1,2-a]pyrazin-6-one (150 mg, 92%) as a yellow oil. LCMS: m/z=299.1 [M+H]+.

Step 4: In a 10-mL sealed tube purged and maintained with an inert atmosphere of nitrogen, was placed (8aS)-7-(3-[imidazo[1,2-a]pyridin-5-yl]propyl)-octahydropyrrolo[1,2-a]pyrazin-6-one (70 mg, 0.235 mmol, 1 eq), dioxane (2 mL), 3-fluoro-4-iodopyridine (62.77 mg, 0.282 mmol, 1.2 eq), Pd2(dba)3 (43 mg, 0.047 mmol, 0.2 eq), Xantphos (54.3 mg, 0.094 mmol, 0.4 eq), Cs2CO3 (229 mg, 0.704 mmol, 3 eq). The resulting solution was stirred for 2 h at 110° C. in an oil bath. The solids were filtered off. The resulting mixture was concentrated. The residue was purified by Prep-HPLC to afford (8aS)-2-(3-fluoropyridin-4-yl)-7-(3-[imidazo[1,2-a]pyridin-5-yl]propyl)-octahydropyrrolo [1,2-a]pyrazin-6-one (36 mg, 21%) as a white solid. The product was purified by Chiral-Prep-HPLC to afford the title compound (Example 3) (6 mg). LCMS: m/z=394.2 [M+H]+; 1H NMR (300 MHz, Methanol-d4) δ 8.52 (d, J=8.7 Hz, 1H), 8.37 (d, J=2.2 Hz, 1H), 8.22 (d, J=7.0 Hz, 1H), 8.14 (d, J=2.3 Hz, 1H), 7.98 (m, J=9.0, 7.2 Hz, 1H), 7.86 (d, J=9.0 Hz, 1H), 7.44 (m, J=6.2 Hz, 2H), 4.50 (d, J=13.0 Hz, 1H), 4.38 (d, J=13.6 Hz, 1H), 4.08 (d, J=13.2 Hz, 1H), 3.81 (d, J=7.5 Hz, 1H), 3.35 (s, 1H), 3.32-3.15 (m, 3H), 3.13 (s, 1H), 3.07 (d, J=12.0 Hz, 1H), 2.67 (d, J=9.6 Hz, 1H), 2.55 (m, J=12.1, 7.4 Hz, 1H), 2.07-1.96 (m, 2H), 1.63 (s, 1H), 1.55-1.38 (m, 1H).

Example 4: Synthesis of 6-((7S,8aS)-7-(3-([1,2,4]triazolo [1,5-a] pyridin-5-yl)propyl)-6-oxohexahydropyrrolo [1,2-a] pyrazin-2(1H)-yl)nicotinonitrile

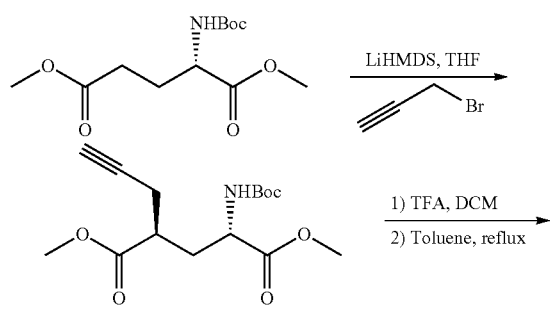

Step 1: Into a 100-mL 3-necked round-bottom flask purged and maintained with an inert atmosphere of nitrogen, was placed dry THF (10 mL). This was followed by the addition of LiHMDS (2N) (5.5 mL, 11 mmol, 1.5 eq) at −78° C. To this was added (S)-dimethyl 2-(tert-butoxycarbonylamino)pentanedioate (2 g, 7.3 mmol, 1 eq) dissolved in dry THF (30 mL) at −78° C. in 10 mins. The resulting solution was stirred for 1 h at −78° C. To the mixture was added 3-bromoprop-1-yne (1.3 g, 11 mmol, 1.5 eq) in 10 min. The resulting solution was stirred for an additional 2 hours while the temperature was maintained at −65° C. The reaction was quenched with saturated NH4Cl aqueous solu-

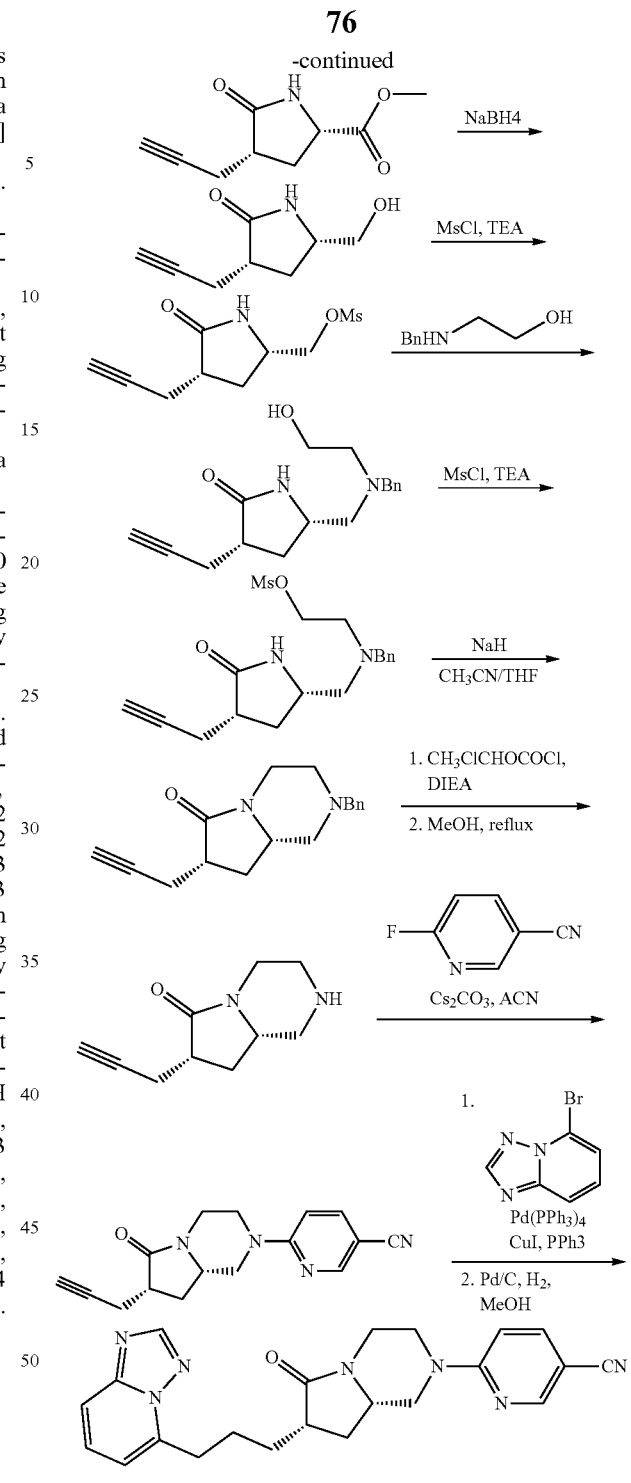

tion. The resulting mixture was concentrated. The resulting solution was extracted with dichloromethane (100 mL). The residue was chromatographed on a silica gel column to afford (2S,4S)-dimethyl 2-(tert-butoxycarbonylamino)-4-(prop-2-ynyl)pentanedioate (1.2 g, 53%) as a yellow solid. LCMS (m/z) 314.1 [M+H]+.

Step 2: To a solution of (2S,4S)-dimethyl 2-(tert-butoxycarbonylamino)-4-(prop-2-ynyl)pentanedioate (1.2 g, 3.8 mmol) in $CH_2Cl_2$ (10 mL) was added TFA (5 mL) and the solution was stirred at room temperature until no trace of starting material remained. After the solution was concentrated under vacuum, the resulting oil was dissolved in toluene (20 mL) and heated at reflux for 1.5 hour. The solution was concentrated under vacuum to give 1.1 g of the corresponding crude lactam. The crude product was chromatographed on a silica gel column to afford (2S,4S)-methyl 5-oxo-4-(prop-2-ynyl)pyrrolidine-2-carboxylate (0.7 g, 100%) as a yellow oil. LCMS (m/z) 182.3 [M+H]+.

Step 3: To a solution of (2S,4S)-methyl 5-oxo-4-(prop-2-ynyl)pyrrolidine-2-carboxylate (0.7 g, 3.8 mmol) in 15 mL of absolute ethanol, $NaBH_4$ (289 mg, 7.6 mmol) was added. After 20 hours at room temperature, acetic acid (2 mL) was slowly added and the mixture stirred for 30 mins. Water (1.5 mL) was added and the mixture was stirred for 10 min at room temperature. The pH value was adjusted to 7 by adding 2N NaOH, and the solvents were evaporated under reduced pressure. The residue was extracted with hot ethyl acetate (5×30 mL) and after evaporation a colorless solid was obtained, which was chromatographed on a silica gel column to afford (3S,5S)-5-(hydroxymethyl)-3-(prop-2-ynyl)pyrrolidin-2-one (0.42 g, 72%) as a colorless solid. LCMS (m/z) 154.5 [M+H]+.

Step 4: To a solution of (3S,5S)-5-(hydroxymethyl)-3-(prop-2-ynyl)pyrrolidin-2-one (0.42 g, 2.73 mmol, 1 eq) in $CH_2Cl_2$ (15 mL), TEA (0.55 g, 5.46 mmol, 2 eq) and MsCl (0.47 g, 4.1 mmol, 1.5 eq) were added dropwise at 0° C. The mixture was stirring at room temperature for 2 hours, then it was diluted with DCM (60 mL) and washed with a saturated $NaHCO_3$ (3×30 mL) aqueous solution. After drying ($Na_2SO_4$) the solvent was removed under reduced pressure and the residue was purified by reverse phase with $NH_4HCO_3$ in water/$CH_3CN$ (40%) to give ((2S,4S)-5-oxo-4-(prop-2-ynyl)pyrrolidin-2-yl)methyl methanesulfonate as a yellow oil (0.43 g, 68% yield). LCMS (m/z) 232.5 [M+H]+.

Step 5: A mixture of ((2S,4S)-5-oxo-4-(prop-2-ynyl)pyrrolidin-2-yl)methyl methanesulfonate (430 mg, 1.85 mmol, 1 eq) and 2-(benzylamino)ethanol (1.12 g, 7.4 mmol, 4 eq) was heated at 130° C. in a microwave oven (Personal Chemistry Emrys® Optimizer) for 40 minutes. The residue was partitioned between water and DCM, the organic phase was washed with brine, dried ($Na_2SO_4$) and evaporated under vacuum. The residue was chromatographed on a silica gel column to afford (3S,5S)-5-((benzyl(2-hydroxyethyl)amino)methyl)-3-(prop-2-ynyl)pyrrolidin-2-one as a yellow oil (320 mg, 60% yield). LCMS (m/z) 287 [M+H]+.

Step 6: To a solution of (3S,5S)-5-((benzyl(2-hydroxyethyl)amino)methyl)-3-(prop-2-ynyl)pyrrolidin-2-one (0.32 g, 1.1 mmol, 1 eq) in DCM (15 mL), TEA (222 mg, 2.2 mmol, 2 eq) and MsCl (190 mg, 1.65 mmol, 1.5 eq) were added at 0° C. The mixture was warmed to room temperature and stirred for 20 hours, then it was diluted with DCM (60 mL) and washed with saturated $NaHCO_3$ (3×30 mL) aqueous solution. After drying ($Na_2SO_4$) and removal of the solvent, the crude product (0.31 g) was used directly for next step. LCMS (m/z) 365 [M+H]+.

Step 7: The crude product of step 6 (0.31 g) was dissolved in a mixture of $CH_3CN$/THF (1/1, 10 mL) and then 60% NaH (66 mg, 1.65 mmol, 1.5 eq) was added in portion at room temperature under a nitrogen atmosphere. After stirring for 16 hours, the solvent was removed under vacuum and the residue was taken up with water and extracted with DCM. The organic phase was washed with brine, dried ($Na_2SO_4$) and concentrated. The residue was purified by reverse phase with $NH_4HCO_3$ in water/$CH_3CN$ (45%) to afford (7S,8aS)-2-benzyl-7-(prop-2-ynyl)-hexahydropyrrolo[1,2-a]pyrazin-6(7H)-one (90 mg, 30% yield) as a colorless solid. LCMS (m/z) 269 [M+H]+. $^1H$ NMR (400 MHz, MeOD): δ 7.36-7.28 (m, 5H), 3.90-3.86 (m, 1H), 3.61-3.53 (m, 3H), 3.06-3.03 (m, 1H), 2.90-2.87 (m, 2H), 2.71-2.69 (m, 1H), 2.51-2.48 (m, 2H), 2.34-2.30 (m, 1H), 2.28.-2.26 (m, 1H), 1.98-1.96 (m, 1H), 1.82-1.77 (m, 1H), 1.59-1.56 (m, 1H).

Step 8: 1-chloroethyl carbonochloridate (6.4 mL, 59.6 mmol, 8 eq) was added to a solution of (7S,8aS)-2-benzyl-7-(prop-2-ynyl)-hexahydropyrrolo[1,2-a]pyrazin-6(7H)-one (2 g, 7.45 mmol, 1 eq), DIEA (10.4 mL, 59.6 mmol, 8 eq) in toluene (40 mL). The reaction mixture was stirred for 2 hours at 100° C. The reaction solution was concentrated under reduced pressure. The obtained residue was dissolved in methanol (40 mL) and heated to 65° C. for 30 min. The reaction solution was cooled to room temperature then concentrated under reduced pressure. The obtained residue was dissolved in acetonitrile (40 mL). 6-Fluoronicotinonitrile (910 mg, 7.45 mmol, 1 eq) and cesium carbonate (7.3 g, 22.4 mmol, 3 eq) were added. The reaction mixture was stirred for 8 hours at 80° C. The reaction mixture was partitioned between ethyl acetate and water. The organic phase was washed with saturated NaCl, dried over $MgSO_4$, filtered and concentrated. The residue was chromatographed on a silica gel column to give 6-((7S,8aS)-6-oxo-7-(prop-2-yn-1-yl)hexahydropyrrolo[1,2-a]pyrazin-2(1H)-yl)nicotinonitrile (1.3 g). LCMS (m/z) 281 [M+H]+.

Step 9: DIEA (0.27 mL, 1.52 mmol, 5 eq), CuI (3 mg, 0.015 mmol, 5 mol %), and $PPh_3$ (16 mg, 0.061 mmol, 0.2 eq) were added to a sealed tube containing a solution of 6-((7S,8aS)-6-oxo-7-(prop-2-yn-1-yl)hexahydropyrrolo[1,2-a]pyrazin-2(1H)-yl)nicotinonitrile (85 mg, 0.304 mmol, 1 eq) and 5-bromo-[1,2,4]triazolo[1,5-a]pyridine (72 mg, 0.365 mmol, 1.2 eq) in DMF (1 mL). The resulting mixture was sparged with nitrogen. $Pd(PPh_3)_4$ (18 mg, 0.015 mmol, 5 mol %) was added. The vessel was capped and heated to 80° C. for 23 h. The reaction mixture was loaded directly onto a prep HPLC column eluting with 0.1% formic acid in water/acetonitrile (5-100% gradient). Product-containing fractions were combined and concentrated to give 6-((7S,8aS)-7-(3-([1,2,4]triazolo [1,5-a]pyridin-5-yl)prop-2-yn-1-yl)-6-oxohexahydropyrrolo[1,2-a]pyrazin-2(1H)-yl)nicotinonitrile (67 mg). The material was dissolved in MeOH and Pd/C (5 wt %, 50 mg) was added. The reaction was stirred under an atmosphere of $H_2$ for 2 h. The reaction was filtered through celite, concentrated, and purified by prep HPLC to give 6-((7S,8aS)-7-(3-([1,2,4]triazolo[1,5-a]pyridin-5-yl)propyl)-6-oxohexahydropyrrolo[1,2-a]pyrazin-2(1H)-yl)nicotinonitrile (35 mg). LCMS (m/z) 402 [M+H]+.

Example 5: Synthesis of 6-((7R,8aS)-7-((([1,2,4]triazolo[1,5-a]pyridin-5-ylmethyl)amino)methyl)-6-oxohexahydropyrrolo[1,2-a]pyrazin-2(1H)-yl)nicotinonitrile

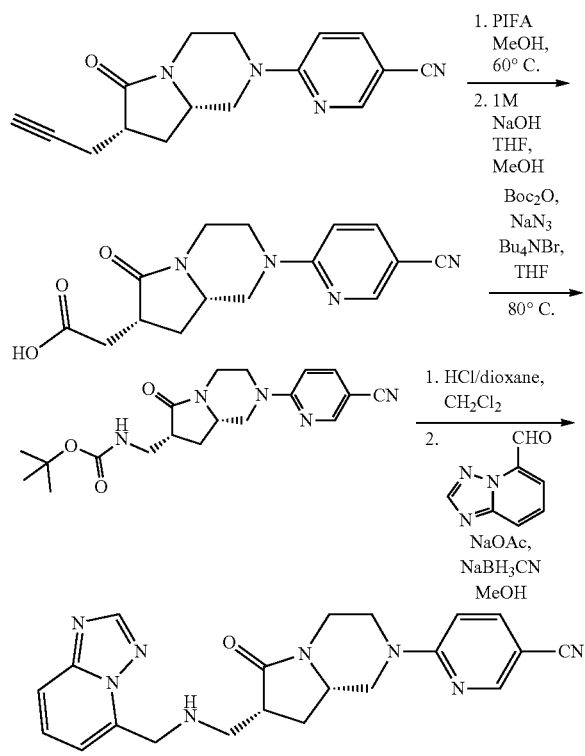

Step 1: To a sealed tube containing a solution of 6-((7S,8aS)-6-oxo-7-(prop-2-yn-1-yl)hexahydropyrrolo[1,2-a]pyrazin-2(1H)-yl)nicotinonitrile (819 mg, 2.92 mmol, 1.0 eq) in MeOH (10 mL) was added phenyliodine bis(trifluoroacetate) (PIFA, 4.4 g, 10.2 mmol, 3.5 eq). The vessel was capped and heated to 60° C. for 56 h. The reaction mixture was concentrated and then purified on silica gel to give methyl 2-((7R,8aS)-2-(5-cyanopyridin-2-yl)-6-oxooctahydropyrrolo[1,2-a]pyrazin-7-yl)acetate (173 mg, 19% yield). The material was dissolved in MeOH (2 mL) and THF (2 mL), 1M NaOH (1.7 mL, 1.65 mmol, 3.0 eq) was added and the reaction was stirred at ambient temperature for 1.5 h. The reaction was acidified with 1M HCl (1.8 mL) and extracted with ethyl acetate. The organic phase was washed with brine, dried over MgSO₄, filtered, and concentrated to give 2-((7R,8aS)-2-(5-cyanopyridin-2-yl)-6-oxooctahydropyrrolo[1,2-a]pyrazin-7-yl)acetic acid (135 mg, 82% yield). LCMS (m/z) 301 [M+H]⁺.

Step 2: To a sealed tube containing a solution of 2-((7R,8aS)-2-(5-cyanopyridin-2-yl)-6-oxooctahydropyrrolo[1,2-a]pyrazin-7-yl)acetic acid (135 mg, 0.450 mmol, 1.0 eq) in THF (4.5 mL) was added NaN₃ (102 mg, 1.57 mmol, 3.5 eq), Bu₄NBr (22 mg, 0.067 mmol, 15 mol %), and Boc₂O (108 mg, 0.494 mmol, 1.1 eq). The vessel was capped and heated to 80° C. for 45 h. The reaction was quenched with 10% Na₂S₂O₃ and then partitioned between ethyl acetate and aq. NH₄Cl. The organic layer was washed with brine, dried over MgSO₄, filtered, and concentrated. The crude residue was purified on silica gel to give tert-butyl (((7R,8aS)-2-(5-cyanopyridin-2-yl)-6-oxooctahydropyrrolo[1,2-a]pyrazin-7-yl)methyl)carbamate (22 mg, 13% yield). LCMS (m/z) 272 [M−Boc+H]⁺.

Step 3: To a solution of tert-butyl (((7R,8aS)-2-(5-cyanopyridin-2-yl)-6-oxooctahydropyrrolo[1,2-a]pyrazin-7-yl)methyl)carbamate (22 mg, 0.06 mmol, 1.0 eq) in CH₂Cl₂ (1 mL) was added 4M HCl in dioxane (150 µL, 0.60 mmol, 10 eq). The reaction was stirred for 30 min then concentrated. To the obtained residue was added MeOH (2 mL), NaOAc (10 mg, 0.12 mmol, 2.0 eq), [1,2,4]triazolo[1,5-a]pyridine-5-carbaldehyde (11 mg, 0.072 mmol, 1.2 eq), and NaBH₃CN (6 mg, 0.09 mmol, 1.5 eq). The reaction was stirred at ambient temperature for 16 h, then concentrated and purified by prep HPLC to give 6-((7R,8aS)-7-((([1,2,4]triazolo[1,5-a]pyridin-5-ylmethyl)amino)methyl)-6-oxohexahydropyrrolo[1,2-a]pyrazin-2(1H)-yl)nicotinonitrile as the formate salt (15 mg, 54% yield). LCMS (m/z) 403 [M+H]⁺.

Examples 6-9 were prepared in a similar manner as described in Examples 1-5.

Example 6: Synthesis of 7-(3-(benzo[d]thiazol-7-yl)propyl)-2-(3-fluoropyridin-4-yl)hexahydropyrrolo[1,2-a]pyrazin-6(2H)-one

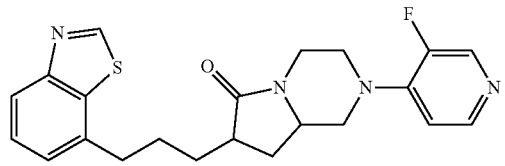 [SMILES: O=C1C(CCCc2cccc3ncsc23)CC2CN(c3ccncc3F)CCN12]

The title compound was obtained as a racemic mixture of diastereomers from racemic tert-butyl 6-oxohexahydropyrrolo[1,2-a]pyrazine-2(1H)-carboxylate in a similar manner as described for Examples 1 and 2. LCMS: m/z=411.1 [M+H]⁺

Examples 7 and 8: Synthesis of (7S,8aR)-7-(3-(benzo[d]thiazol-7-yl)propyl)-2-(3-fluoropyridin-4-yl)hexahydropyrrolo[1,2-a]pyrazin-6(2H)-one (example 7) and (7R,8aR)-7-(3-(benzo[d]thiazol-7-yl)propyl)-2-(3-fluoropyridin-4-yl)hexahydropyrrolo[1,2-a]pyrazin-6(2H)-one (example 8)

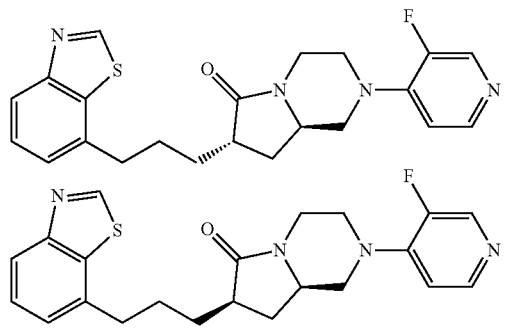

The title compounds were prepared from tert-butyl (R)-6-oxohexahydropyrrolo[1,2-a]pyrazine-2(1H)-carboxylate in a similar manner as described for Examples 1 and 2. LCMS example 7: m/z=410.8 [M+H]⁺; LCMS example 8: m/z=410.8 [M+H]⁺.

Example 9: Synthesis of (8aS)-7-(3-(benzo[d]thiazol-7-yl)propyl)-2-(3-fluoropyridin-4-yl)hexahydropyrrolo[1,2-a]pyrazin-6(2H)-one

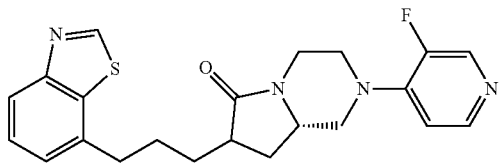 [SMILES: O=C1C(CCCc2cccc3ncsc23)C[C@H]2CN(c3ccncc3F)CCN12]

The title compound was isolated as a mixture of diastereomers prior to the chiral HPLC separation performed in Examples 1 and 2, step 6.

Example 10: Synthesis of 6-((7S,8aS)-7-(3-(benzo[d]thiazol-7-yl)propyl)-6-oxohexahydropyrrolo[1,2-a]pyrazin-2(1H)-yl)nicotinonitrile

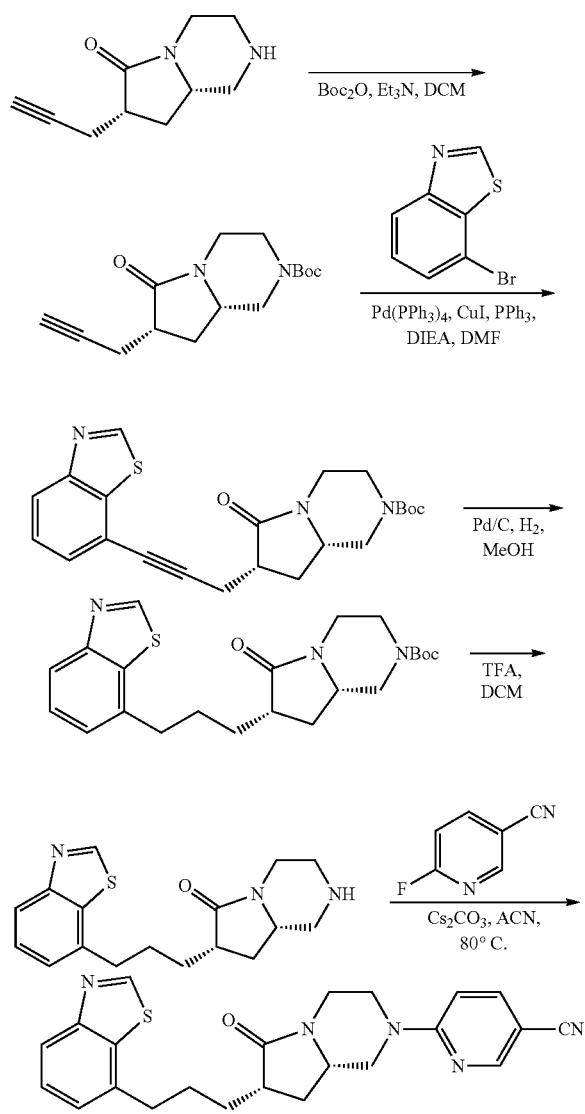

Step 1: To a solution (7S,8aS)-7-(prop-2-yn-1-yl)hexahydropyrrolo[1,2-a]pyrazin-6(2H)-one (100 mg, 0.56 mmol, 1.0 equiv.) in DCM (10 mL) was added Boc$_2$O (610 mg, 2.8 mmol, 5.0 equiv.) and Et$_3$N (283 mg, 2.8 mmol, 5.0 equiv.). The reaction mixture was stirred for 2 h at rt. The mixture was concentrated under reduced pressure. The obtained residue was purified by reverse phase HPLC with NH$_4$HCO$_3$ in water/CH$_3$CN (45%). which gave (7S, 8aS)-tert-butyl 6-oxo-7-(prop-2-ynyl)-hexahydropyrrolo [1,2-a]pyrazine-2(1H)-carboxylate as a white solid. LCMS: m/z=279.1 [M+H]$^+$.

Step 2: Into a 30-mL sealed tube purged and maintained with an inert atmosphere of nitrogen, was placed tert-butyl (7S,8aS)-6-oxo-7-(prop-2-yn-1-yl)-octahydropyrrolo[1,2-a]pyrazine-2-carboxylate (110 mg, 0.395 mmol, 1.0 equiv), DMF (3 mL), 7-bromo-1,3-benzothiazole (101 mg, 0.474 mmol, 1.2 equiv), Pd(PPh$_3$)$_4$ (23 mg, 0.020 mmol, 0.05 equiv.), CuI (3.8 mg, 0.020 mmol, 0.05 equiv.), PPh$_3$ (21 mg, 0.079 mmol, 0.2 equiv.), DIEA (294 mg, 1.98 mmol, 5.0 equiv.). The resulting solution was stirred for 2 h at 80° C. in an oil bath. The mixture was filtered and the filtrates were concentrated in vacuo. The residue was purified by silica gel chromatography which gave tert-butyl (7S,8aS)-7-[3-(1,3-benzothiazol-7-yl)prop-2-yn-1-yl]-6-oxo-octahydropyrrolo [1,2-a]pyrazine-2-carboxylate as light yellow oil. LCMS: m/z=412.1 [M+H]$^+$.

Step 3: Into a 100-mL round-bottom flask, was placed tert-butyl (7S,8aS)-7-[3-(1,3-benzothiazol-7-yl)prop-2-yn-1-yl]-6-oxo-octahydropyrrolo[1,2-a]pyrazine-2-carboxylate (140 mg, 0.341 mmol, 1.0 equiv.), MeOH (5 mL), and 10% Pd/C (73 mg). The mixture was stirred for 3 h at rt under H$_2$ atmosphere. The mixture was filtered through celite and concentrated in vacuo. Purification by silica gel chromatography gave tert-butyl (7S,8aS)-7-[3-(1,3-benzothiazol-7-yl)propyl]-6-oxo-octahydropyrrolo[1,2-a]pyrazine-2-carboxylate as light yellow oil. LCMS: m/z=416.1 [M+H]$^+$.

Step 4: Into a 25-mL round-bottom flask, was placed tert-butyl (7S,8aS)-7-[3-(1,3-benzothiazol-7-yl)propyl]-6-oxo-octahydropyrrolo[1,2-a]pyrazine-2-carboxylate (130 mg, 0.313 mmol, 1.0 equiv.), DCM (3 mL), and TFA (2 mL). The resulting solution was stirred for 1 h at rt followed by concentration in vacuo. Purification by silica gel chromatography gave (7S,8aS)-7-[3-(1,3-benzothiazol-7-yl)propyl]-octahydropyrrolo[1,2-a]pyrazin-6-one as light yellow oil. LCMS: m/z=316.1 [M+H]$^+$.

Step 5: Into a 30-mL sealed tube, was placed (7S,8aS)-7-[3-(1,3-benzothiazol-7-yl)propyl]-octahy dropyrrolo [1,2-a]pyrazin-6-one (90 mg, 0.29 mmol, 1.0 equiv.), ACN (3 mL), 6-fluoropyridine-3-carbonitrile (62 mg, 0.34 mmol, 1.2 equiv.), and Cs$_2$CO$_3$ (280 mg, 0.858 mmol, 3.0 equiv.). The resulting solution was stirred for 2 h at 80° C. in an oil bath. The mixture was coolet to rt, filtered, and concentrated. Purification by silica gel chromatography followed by further purification by reverse phase HPLC gave the title compound, 6-[(7S,8aS)-7-[3-(1,3-benzothiazol-7-yl)propyl]-6-oxo-octahydropyrrolo [1,2-a]pyrazin-2-yl]pyridine-3-carbonitrile, as an off-white solid. LCMS: m/z=418.1 [M+H]$^+$.

The following examples were prepared from (7S,8aS)-7-(3-(benzo[d]thiazol-7-yl)propyl)hexahydropyrrolo[1,2-a]pyrazin-6(2H)-one and the appropriate corresponding heteroaryl halide using the same procedure as described for Example 10, step 5.

| Example | Structure | Name | LCMS (m/z) [M + H]+ |
|---|---|---|---|
| 11 | 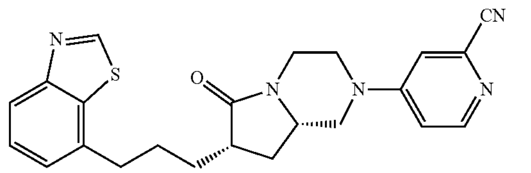 [SMILES: N#Cc1cc(N2CCN3C(=O)[C@@H](CCCc4cccc5ncsc45)C[C@H]3C2)ccn1] | 4-((7S,8aS)-7-(3-(benzo[d]thiazol-7-yl)propyl)-6-oxohexahydropyrrolo[1,2-a]pyrazin-2(1H)-yl)picolinonitrile | 418.0 |
| 12 | 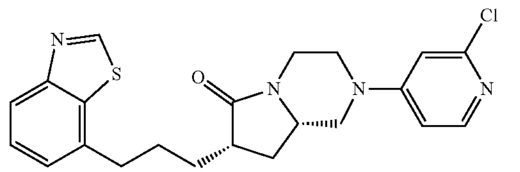 [SMILES: O=C1[C@@H](CCCc2cccc3ncsc23)C[C@H]2CN(c3ccnc(Cl)c3)CCN12] | (7S,8aS)-7-(3-benzo[d]thiazol-7-yl)propyl)-2-(2-chloropyridin-4-yl)hexahydropyrrolo[1,2-a]pyrazin-6(2H)-one | 427.2 |
| 13 | 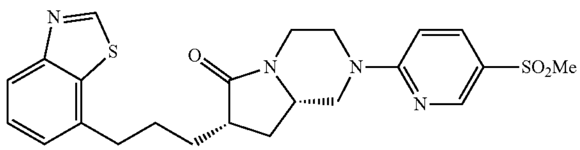 [SMILES: CS(=O)(=O)c1ccc(N2CCN3C(=O)[C@@H](CCCc4cccc5ncsc45)C[C@H]3C2)nc1] | (7S,8aS)-7-(3-(benzo[d]thiazol-7-yl)propyl)-2-(5-(methylsulfonyl)pyridin-2-yl)hexahydropyrrolo[1,2-a]pyrazin-6(2H)-one | 470.9 |

The following examples were prepared from 6-((7S,8aS)-6-oxo-7-(prop-2-yn-1-yl)hexahydropyrrolo[1,2-a]pyrazin-2(1H)-yl)nicotinonitrile and the appropriate corresponding aryl bromide using the same procedure as described for Example 4, step 9.

| Example | Structure | Name | LCMS (m/z) [M + H]+ |
|---|---|---|---|
| 14 | 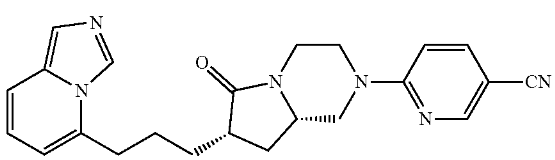 [SMILES: N#Cc1ccc(N2CCN3C(=O)[C@@H](CCCc4cccc5cncn45)C[C@H]3C2)nc1] | 6-((7S,8aS)-7-(3-(imidazo[1,5-a]pyridin-5-yl)propyl)-6-oxohexahydropyrrolo[1,2-a]pyrazin-2(1H)-yl)nicotinonitrile | 401.1 |
| 15 | 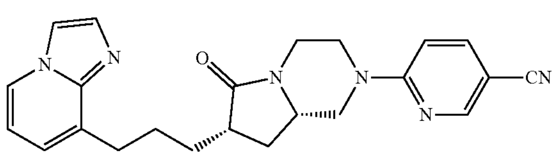 [SMILES: N#Cc1ccc(N2CCN3C(=O)[C@@H](CCCc4cccn5ccnc45)C[C@H]3C2)nc1] | 6-((7S,aS)-7-(3-imidazo[1,2-a]pyridin-8-yl)propyl)-6-oxohexahydropyrrolo[1,2-a]pyrazin-2(1H)-yl)nicotinonitrile | 401.2 |
| 16 | 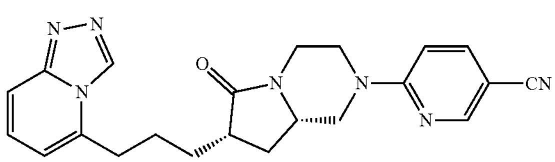 [SMILES: N#Cc1ccc(N2CCN3C(=O)[C@@H](CCCc4cccc5nncn45)C[C@H]3C2)nc1] | 6-((7S,8aS)-7-(3-([1,2,4]triazolo[4,3-a]pyridin-5-yl)propyl)-6-oxohexahydropyrrolo[1,2-a]pyrazin-2(1H)-yl)nicotinonitrile | 402.2 |
| 17 | 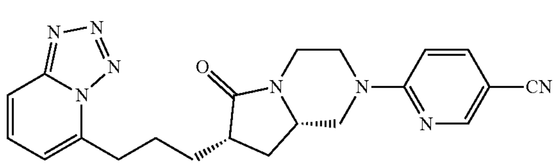 [SMILES: N#Cc1ccc(N2CCN3C(=O)[C@@H](CCCc4cccc5nnnn45)C[C@H]3C2)nc1] | 6-((7S,8aS)-6-oxo-7-(3-(tetrazolo[1,5-a]pyridin-5-yl)propyl)hexahydropyrrolo[1,2-a]pyrazin-2(1H)-yl)nicotinonitrile | 403.2 |

-continued

| Example | Structure | Name | LCMS (m/z) [M + H]+ |
|---|---|---|---|
| 18 | 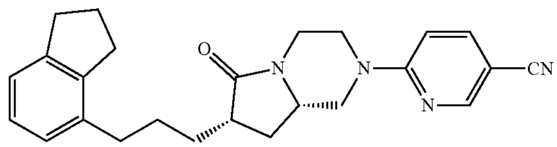 [SMILES: N#Cc1ccc(N2CCN3C(=O)[C@@H](CCCc4cccc5c4CCC5)C[C@H]3C2)nc1] | 6-((7S,8aS)-7-(3-(2,3-dihydro-1H-inden-4-yl)propyl)-6-oxohexahydropyrrolo[1,2-a]pyrazin-2(1H)-yl)nicotinonitrile | 401.2 |
| 19 | 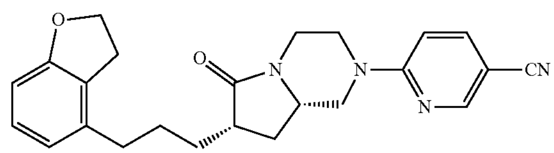 [SMILES: N#Cc1ccc(N2CCN3C(=O)[C@@H](CCCc4cccc5c4CCO5)C[C@H]3C2)nc1] | 6-((7S,8aS)-7-(3-(2,3-dihydrobenzofuran-4-yl)propyl)-6-oxohexahydropyrrolo[1,2-a]pyrazin-2(1H)-yl)nicotinonitrile | 403.2 |
| 20 | 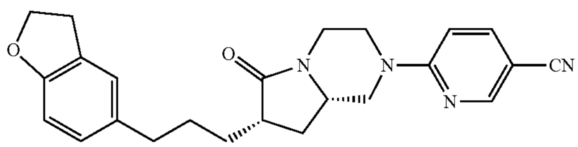 [SMILES: N#Cc1ccc(N2CCN3C(=O)[C@@H](CCCc4ccc5c(c4)CCO5)C[C@H]3C2)nc1] | 6-((7S,8aS)-7-(3-(2,3-dihydrobenzofuran-5-yl)propyl)-6-oxohexahydropyrrolo[1,2-a]pyrazin-2(1H)-yl)nicotinonitrile | 403.2 |
| 21 | 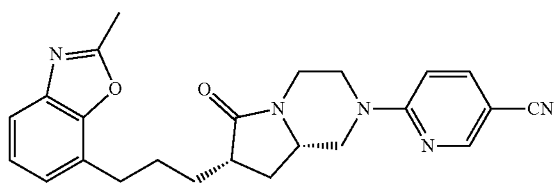 [SMILES: Cc1nc2cccc(CCC[C@H]3C[C@H]4CN(c5ccc(C#N)cn5)CCN4C3=O)c2o1] | 6-((7S,8aS)-7-(3-(2-methylbenzo[d]oxazol-7-yl)propyl)-6-oxohexahydropyrrolo[1,2-a]pyrazin-2(1H)-yl)nicotinonitrile | 416.2 |
| 22 | 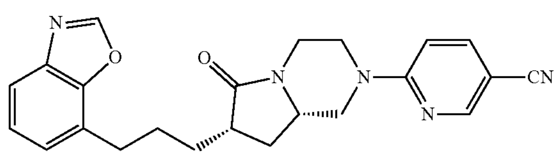 [SMILES: N#Cc1ccc(N2CCN3C(=O)[C@@H](CCCc4cccc5ncoc45)C[C@H]3C2)nc1] | 6-((7S,8aS)-7-(3-(benzo[d]oxazol-7-yl)propyl)-6-oxohexahydropyrrolo[1,2-a]pyrazin-2(1H)-yl)nicotinonitrile | 402.2 |
| 23 | 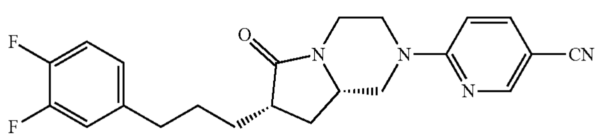 [SMILES: N#Cc1ccc(N2CCN3C(=O)[C@@H](CCCc4ccc(F)c(F)c4)C[C@H]3C2)nc1] | 6-((7S,8aS)-7-(3-(3,4-difluorophenyl)propyl)-6-oxohexahydropyrrolo[1,2-a]pyrazin-2(1H)-yl)nicotinonitrile | 397.1 |
| 24 | 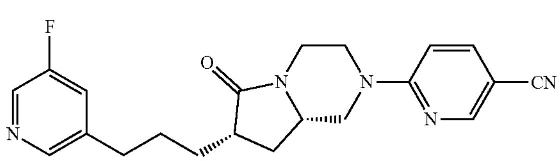 [SMILES: N#Cc1ccc(N2CCN3C(=O)[C@@H](CCCc4cncc(F)c4)C[C@H]3C2)nc1] | 6-((7S,8aS)-7-(3-(5-fluoropyridin-3-yl)propyl)-6-oxohexahydropyrrolo[1,2-a]pyrazin-2(1H)-yl)nicotinonitrile | 380.1 |
| 25 | 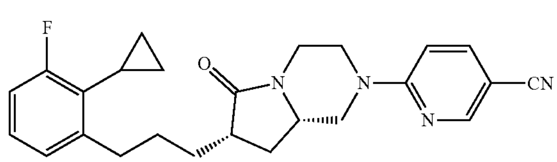 [SMILES: N#Cc1ccc(N2CCN3C(=O)[C@@H](CCCc4cccc(F)c4C4CC4)C[C@H]3C2)nc1] | 6-((7S,8aS)-7-(3-(2-cyclopropyl-3-fluorophenyl)propyl)-6-oxohexahydropyrrolo[1,2-a]pyrazin-2(1H)-yl)nicotinonitrile | 419.3 |

Example 26: Synthesis of (7S,8aS)-7-(3-(benzo[d]thiazol-7-yl)propyl)-2-(pyridin-3-yl)hexahydropyrrolo[1,2-a]pyrazin-6(2H)-one

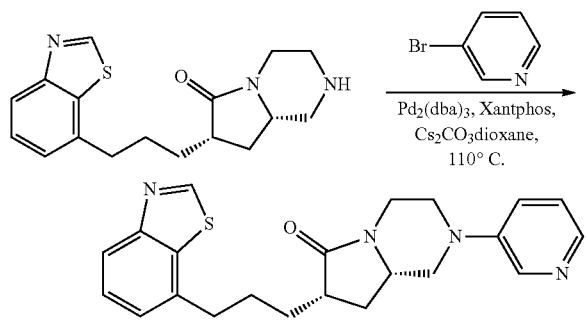

Into a 30-mL sealed tube purged and maintained with an inert atmosphere of nitrogen, was placed (7S,8aS)-7-[3-(1,3-benzothiazol-7-yl)propyl]-octahydropyrrolo[1,2-a]pyrazin-6-one (40 mg, 0.13 mmol, 1.0 equiv.), dioxane (2 mL), 3-bromopyridine (30 mg, 0.190 mmol, 1.5 equiv.), $Pd_2(dba)_3$ (23 mg, 0.025 mmol, 0.2 equiv.), Xantphos (29 mg, 0.051 mmol, 0.4 equiv.), $Cs_2CO_3$ (124 mg, 0.380 mmol, 3.0 equiv.). The resulting mixture was stirred for 3 h at 110° C. in an oil bath. The mixture was cooled to rt, filtered, and concentrated in vacuo. Purification by silica gel chromatography followed by further purification by reverse phase HPLC gave the title compound, (7S,8aS)-7-[3-(1,3-benzothiazol-7-yl)propyl]-2-(pyridin-3-yl)-octahydropyrrolo[1,2-a]pyrazin-6-one, as a white solid. LCMS: m/z=393.1 $[M+H]^+$.

The following examples were prepared from (7S,8aS)-7-(3-(benzo[d]thiazol-7-yl)propyl)hexahydropyrrolo[1,2-a]pyrazin-6(2H)-one and the appropriate corresponding heteroaryl bromide using the same procedure as described for Example 26.

| Example | Structure | Name | LCMS (m/z) [M + H]+ |
|---|---|---|---|
| 27 | 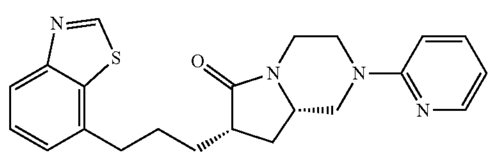 [SMILES: O=C1[C@@H](CCCc2cccc3ncsc23)C[C@H]2CN(c3ccccn3)CCN12] | (7S,8aS)-7-(3-(benzo[d]thiazol-7-yl)propyl)-2-(pyridin-2-yl)hexahydropyrrolo[1,2-a]pyrazin-6(2H)-one | 393.0 |
| 28 | 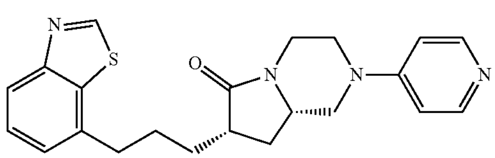 [SMILES: O=C1[C@@H](CCCc2cccc3ncsc23)C[C@H]2CN(c3ccncc3)CCN12] | (7S,8aS)-7-(3-(benzo[d]thiazol-7-yl)propyl)-2-(pyridin-4-yl)hexahydropyrrolo[1,2-a]pyrazin-6(2H)-one | 392.9 |
| 29 | 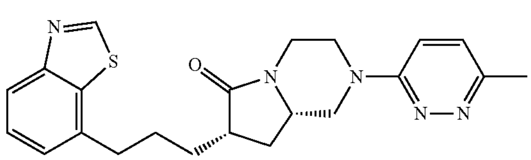 [SMILES: Cc1ccc(N2CCN3C(=O)[C@@H](CCCc4cccc5ncsc45)C[C@H]3C2)nn1] | (7S,8aS)-7-(3-(benzo[d]thiazol-7-yl)propyl)-2-(6-methylpyridazin-3-yl)hexahydropyrrolo[1,2-a]pyrazin-6(2H)-one | 408.1 |

Example 30: Synthesis of (7S,8aS)-2-(2-aminopyridin-4-yl)-7-(3-(benzo[d]thiazol-7-yl)propyl)hexahydropyrrolo[1,2-a]pyrazin-6(2H)-one

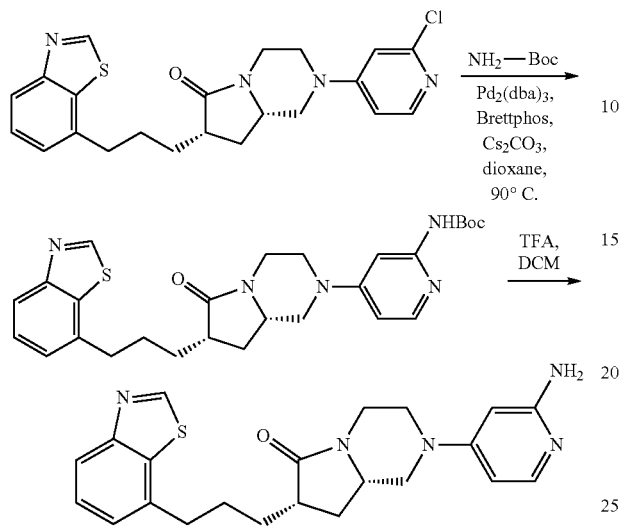

Step 1: Into a 10-mL sealed tube purged and maintained with an inert atmosphere of nitrogen, was placed (7S,8aS)-7-[3-(1,3-benzothiazol-7-yl)propyl]-2-(2-chloropyridin-4-yl)-octahydropyrrolo[1,2-a]pyrazin-6-one (30 mg, 0.070 mmol, 1.0 equiv), dioxane (2 mL), tert-butyl carbamate (247 mg, 2.11 mmol, 3.0 equiv), $Pd_2(dba)_3$ (13 mg, 0.014 mmol, 0.2 equiv.), Brettphos (15 mg, 0.028 mmol, 0.4 equiv.), and $Cs_2CO_3$ (69 mg, 0.21 mmol, 3.0 equiv.). The mixture was stirred for 3 h at 90° C. in an oil bath. The solids were filtered out and the filtrates were concentrated. The crude product was purified by Flash-Prep-HPLC which gave tert-butyl N-[4-[(7S,8aS)-7-[3-(1,3-benzothiazol-7-yl)propyl]-6-oxo-octahydropyrrolo[1,2-a]pyrazin-2-yl]pyridin-2-yl]carbamate as a white solid. LCMS: m/z=508.1 $[M+H]^+$.

Step 2: Into a 8-mL vial, was placed tert-butyl N-[4-[(7S,8aS)-7-[3-(1,3-benzothiazol-7-yl)propyl]-6-oxo-octahydropyrrolo[1,2-a]pyrazin-2-yl]pyridin-2-yl]carbamate (10 mg, 0.020 mmol, 1.0 equiv.), DCM (1 mL), and TFA (0.5 mL). The resulting solution was stirred for 1 h at rt. The resulting mixture was concentrated and purified reverse phase HPLC which gave the title compound, (7S,8aS)-2-(2-aminopyridin-4-yl)-7-[3-(1,3-benzothiazol-7-yl)propyl]-octahydropyrrolo[1,2-a]pyrazin-6-one, as a white solid. LCMS: m/z=408.1 $[M+H]^+$.

Example 31: Synthesis of (7S,8aS)-7-(3-([1,2,4]triazolo[1,5-a]pyridin-5-yl)propyl)-2-(6-(trifluoromethyl)pyridin-2-yl)hexahydropyrrolo[1,2-a]pyrazin-6(2H)-one

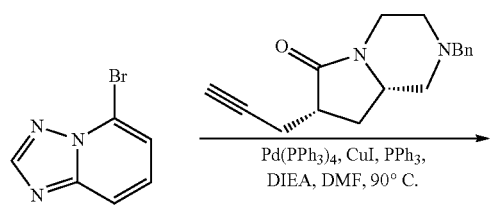

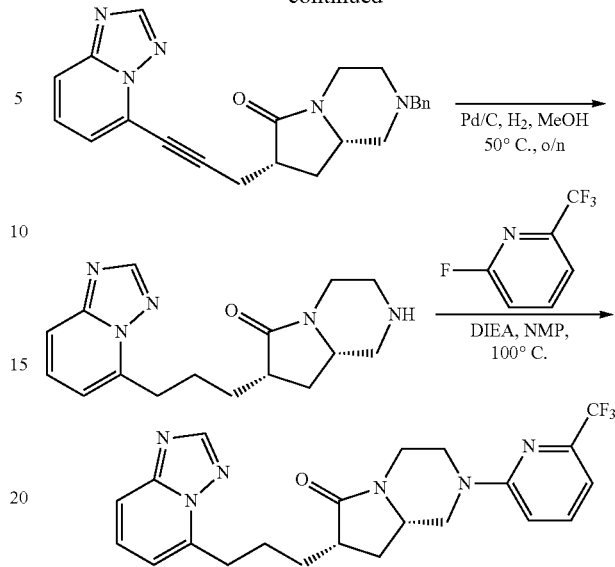

Step 1: Into a 30-mL sealed tube purged and maintained with nitrogen, was placed 5-bromo-[1,2,4]triazolo[1,5-a]pyridine (1.00 g, 5.05 mmol, 1.0 equiv.), DMF (10 mL), (7S,8aS)-2-benzyl-7-(prop-2-yn-1-yl)-octahydropyrrolo[1,2-a]pyrazin-6-one (1.36 g, 5.05 mmol, 1.0 eq), $Pd(PPh_3)_4$ (292 mg, 0.252 mmol, 0.05 equiv.), CuI (48 mg, 0.25 mmol, 0.05 equiv.), $PPh_3$ (265 mg, 1.01 mmol, 0.2 equiv.), DEA (3.77 g, 25.3 mmol, 5.0 eq). The mixture was stirred for 2 h at 90° C. in an oil bath. The mixture was cooled to rt, diluted with EtOAc, filtered and concentrated in vacuo. Purification by silica gel chromatography gave (7S,8aS)-2-benzyl-7-(3-[[1,2,4]triazolo[1,5-a]pyridin-5-yl]prop-2-yn-1-yl)-octahydropyrrolo[1,2-a]pyrazin-6-one as a yellow oil. LCMS: m/z=386.1 $[M+H]^+$ Step 2: Into a 100-mL round-bottom flask, was placed (7S,8aS)-2-benzyl-7-(3-[[1,2,4]triazolo[1,5-a]pyridin-5-yl]prop-2-yn-1-yl)-octahydropyrrolo[1,2-a]pyrazin-6-one (700 mg, 1.82 mmol, 1.0 equiv.), MeOH (10 mL), and 10% Pd/C(193 mg). The mixture was stirred overnight at 50° C. in an oil bath under $H_2$ atmosphere. The mixture was cooled to rt, filtered through celite, and concentrated. Purification by silica gel chromatography gave (7S,8aS)-7-(3-[[1,2,4]triazolo[1,5-a]pyridin-5-yl]propyl)-octahydropyrrolo[1,2-a]pyrazin-6-one as yellow oil. LCMS: m/z=300.1 $[M+H]^+$ Step 3: Into a 10-mL sealed tube, was placed (7S,8aS)-7-(3-[[1,2,4]triazolo[1,5-a]pyridin-5-yl]propyl)-octahydropyrrolo[1,2-a]pyrazin-6-one (40 mg, 0.13 mmol, 1.0 equiv.), NMP (0.5 mL), 2-fluoro-6-(trifluoromethyl)pyridine (33 mg, 0.20 mmol, 1.5 equiv.), and DIEA (0.5 mL). The resulting solution was stirred for 2 h at 100° C. in an oil bath. The crude product was purified by reverse phase HPLC which gave the title compound, (7S,8aS)-7-(3-[[1,2,4]triazolo[1,5-a]pyridin-5-yl]propyl)-2-[6-(trifluoromethyl)pyridin-2-yl]-octahydropyrrolo[1,2-a]pyrazin-6-one, as a white solid. LCMS: m/z=445.1 $[M+H]^+$.

The following examples were prepared from (7S,8aS)-7-(3-([1,2,4]triazolo[1,5-a]pyridin-5-yl)propyl)hexahydropyrrolo[1,2-a]pyrazin-6(2H)-one and the appropriate corresponding heteroaryl halide using the same procedure as described for Example 31, step 3.

| Example | Structure | Name | LCMS (m/z) [M + H]+ |
|---|---|---|---|
| 32 | 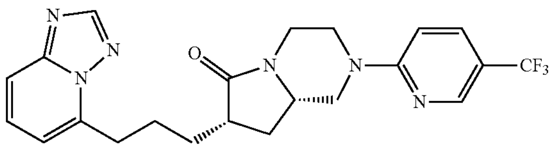 [SMILES: O=C1[C@@H](CCCc2cccc3ncnn23)C[C@H]2CN(c3ccc(C(F)(F)F)cn3)CCN12] | (7S,8aS)-7-(3-([1,2,4]triazolo[1,5-a]pyridin-5-yl)propyl)-2-(5-(trifluoromethyl)pyridin-2-yl)hexahydropyrrolo[1,2-a]pyrazin-6(2H)-one | 445.0 |
| 33 | 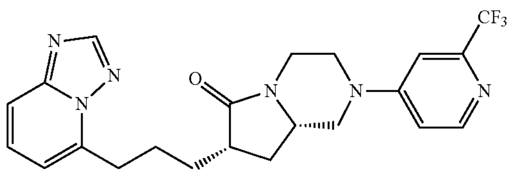 [SMILES: O=C1[C@@H](CCCc2cccc3ncnn23)C[C@H]2CN(c3ccnc(C(F)(F)F)c3)CCN12] | (7S,8aS)-7-(3-([1,2,4]triazolo[1,5-a]pyridin-5-yl)propyl)-2-(2-(trifluoromethyl)pyridin-4-yl)hexahydropyrrolo[1,2-a]pyrazin-6(2H)-one | 445.1 |
| 34 | 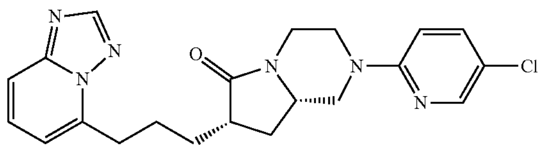 [SMILES: O=C1[C@@H](CCCc2cccc3ncnn23)C[C@H]2CN(c3ccc(Cl)cn3)CCN12] | (7S,8aS)-7-(3-([1,2,4]triazolo[1,5-a]pyridin-5-yl)propyl)-2-(5-chloropyridin-2-yl)hexahydropyrrolo[1,2-a]pyrazin-6(2H)-one | 411.1 |
| 35 | 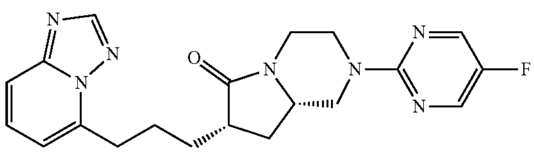 [SMILES: O=C1[C@@H](CCCc2cccc3ncnn23)C[C@H]2CN(c3ncc(F)cn3)CCN12] | (7S,8aS)-7-(3-([1,2,4]triazolo[1,5-a]pyridin-5-yl)propyl)-2-(5-fluoropyrimidin-2-yl)hexahydropyrrolo[1,2-a]pyrazin-6(2H)-one | 396.1 |
| 36 | 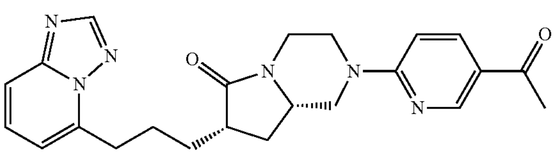 [SMILES: CC(=O)c1ccc(N2CCN3C(=O)[C@@H](CCCc4cccc5ncnn45)C[C@H]3C2)nc1] | (7S,8aS)-7-(3-([1,2,4]triazolo[1,5-a]pyridin-5-yl)propyl)-2-(5-acetylpyridin-2-yl)hexahydropyrrolo[1,2-a]pyrazin-6(2H)-one | 419.1 |

Example 37: Synthesis of (7S,8aS)-2-(2-methoxypyridin-4-yl)-7-(3-{[1,2,4]triazolo[1,5-a]pyridin-5-yl}propyl)-octahydropyrrolo[1,2-a]pyrazin-6-one

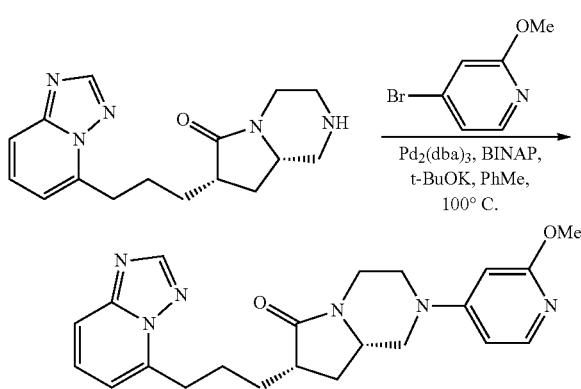

Into a 10-mL sealed tube purged and maintained with nitrogen, was placed (7S,8aS)-7-(3-[[1,2,4]triazolo[1,5-a]pyridin-5-yl]propyl)-octahydropyrrolo[1,2-a]pyrazin-6-one (40 mg, 0.13 mmol, 1.0 equiv.), PhMe (2 mL), 4-bromo-2-methoxypyridine (28 mg, 0.15 mmol, 1.1 equiv.), Pd$_2$(dba)$_3$ (15 mg, 0.016 mmol, 0.12 equiv.), BINAP (100 mg, 0.16 mmol, 1.2 equiv.), t-BuOK (45 mg, 0.40 mmol, 3.0 equiv.). The resulting solution was stirred for 2 h at 100° C. in an oil bath. The solids were filtered out and the filtrates were concentrated. Purification by silica gel chromatography gave the title compound, (7S,8aS)-2-(2-methoxypyridin-4-yl)-7-(3-[[1,2,4]triazolo[1,5-a]pyridin-5-yl]propyl)-octahydropyrrolo[1,2-a]pyrazin-6-one, as a yellow solid. LCMS: m/z=407.2 [M+H]$^+$.

The following examples were prepared from (7S,8aS)-7-(3-([1,2,4]triazolo[1,5-a]pyridin-5-yl)propyl)hexahydropyrrolo[1,2-a]pyrazin-6(2H)-one and the appropriate corresponding aryl or heteroaryl bromide using the same procedure as described for example 37. Examples 41, 42, 43, 44, and 46 were obtained as mixtures of diastereomers.

| Example | Structure | Name | LCMS (m/z) [M + H]+ |
|---|---|---|---|
| 38 | 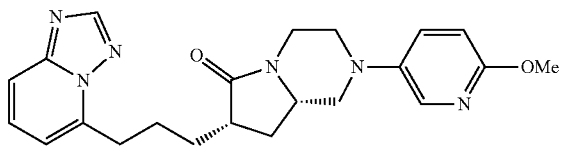 [SMILES: COc1ccc(N2CCN3C(=O)[C@@H](CCCc4cccc5ncnn45)C[C@H]3C2)cn1] | (7S,8aS)-7-(3-([1,2,4]triazolo[1,5-a]pyridin-5-yl)propyl)-2-(6-methoxypyridin-3-yl)hexahydropyrrolo[1,2-a]pyrazin-6(2H)-one | 407.2 |
| 39 | 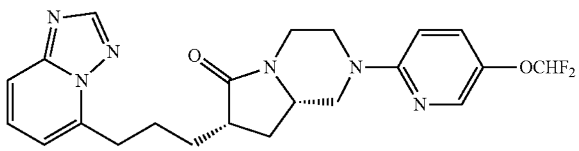 [SMILES: O=C1[C@@H](CCCc2cccc3ncnn23)C[C@H]2CN(c3ccc(OC(F)F)cn3)CCN12] | (7S,8aS)-7-(3-([1,2,4]triazolo[1,5-a]pyridin-5-yl)propyl)-2-(5-(difluoromethoxy)pyridin-2-yl)hexahydropyrrolo[1,2-a]pyrazin-6(2H)-one | 443.2 |
| 40 | 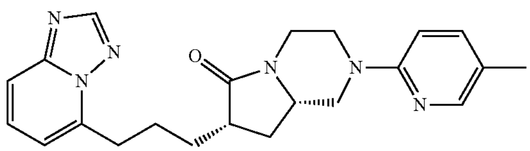 [SMILES: Cc1ccc(N2CCN3C(=O)[C@@H](CCCc4cccc5ncnn45)C[C@H]3C2)nc1] | (7S,8aS)-7-(3-([1,2,4]triazolo[1,5-a]pyridin-5-yl)propyl)-2-(5-methylpyridin-2-yl)hexahydropyrrolo[1,2-a]pyrazin-6(2H)-one | 391.2 |
| 41 | 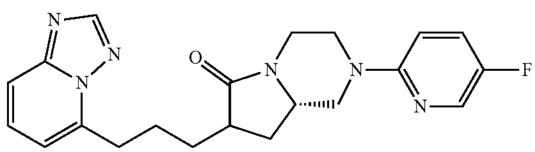 [SMILES: O=C1C(CCCc2cccc3ncnn23)C[C@H]2CN(c3ccc(F)cn3)CCN12] | (7S,8aS)-7-(3-([1,2,4]triazolo[1,5-a]pyridin-5-yl)propyl)-2-(5-fluoropyridin-2-yl)hexahydropyrrolo[1,2-a]pyrazin-6(2H)-one | 395.1 |
| 42 | 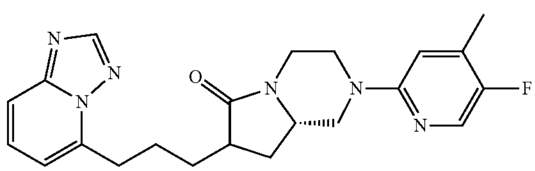 [SMILES: Cc1cc(N2CCN3C(=O)C(CCCc4cccc5ncnn45)C[C@H]3C2)ncc1F] | (7S,8aS)-7-(3-([1,2,4]triazolo[1,5-a]pyridin-5-yl)propyl)-2-(5-fluoro-4-methylpyridin-2-yl)hexahydropyrrolo[1,2-a]pyrazin-6(2H)-one | 409.1 |
| 43 | 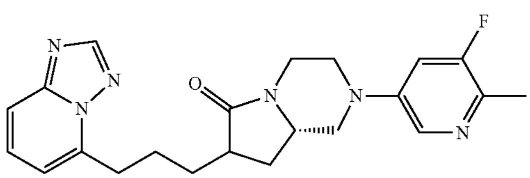 [SMILES: Cc1ncc(N2CCN3C(=O)C(CCCc4cccc5ncnn45)C[C@H]3C2)cc1F] | (7S,8aS)-7-(3-([1,2,4]triazolo[1,5-a]pyridin-5-yl)propyl)-2-(5-fluoro-6-methylpyridin-3-yl)hexahydropyrrolo[1,2-a]pyrazin-6(2H)-one | 409.2 |
| 44 | 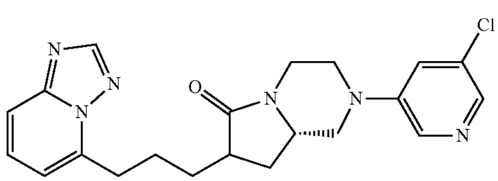 [SMILES: O=C1C(CCCc2cccc3ncnn23)C[C@H]2CN(c3cncc(Cl)c3)CCN12] | (8aS)-7-(3-([1,2,4]triazolo[1,5-a]pyridin-5-yl)propyl)-2-(5-chloropyridin-3-yl)hexahydropyrrolo[1,2-a]pyrazin-6(2H)-one | 411.1 |
| 45 | 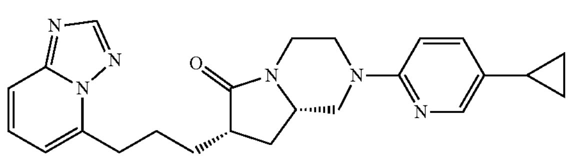 [SMILES: O=C1[C@@H](CCCc2cccc3ncnn23)C[C@H]2CN(c3ccc(C4CC4)cn3)CCN12] | (8aS)-7-(3-([1,2,4]triazolo[1,5-a]pyridin-5-yl)propyl)-2-(5-cyclopropylpyridin-2-yl)hexahydropyrrolo[1,2-a]pyrazin-6(2H)-one | 417.2 |
| 46 | 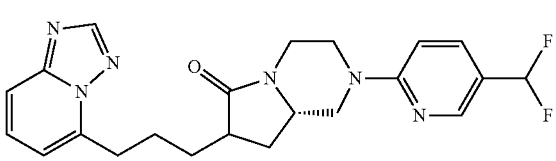 [SMILES: O=C1C(CCCc2cccc3ncnn23)C[C@H]2CN(c3ccc(C(F)F)cn3)CCN12] | (8aS)-7-(3-([1,2,4]triazolo[1,5-a]pyridin-5-yl)propyl)-2-(5-(difluoromethyl)pyridin-2-yl)hexahydropyrrolo[1,2-a]pyrazin-6(2H)-one | 427.2 |

| Example | Structure | Name | LCMS (m/z) [M + H]+ |
|---|---|---|---|
| 47 | 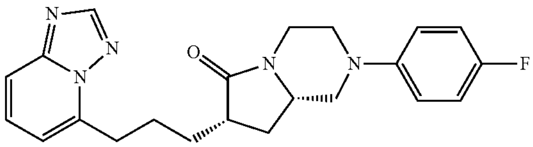 [SMILES: O=C1[C@@H](CCCc2cccc3ncnn23)C[C@H]2CN(c3ccc(F)cc3)CCN12] | (7S,8aS)-7-(3-([1,2,4]triazolo[1,5-a]pyridin-5-yl)propyl)-2-(4-fluorophenyl)hexahydropyrrolo[1,2-a]pyrazin-6(2H)-one | 394.1 |
| 48 | 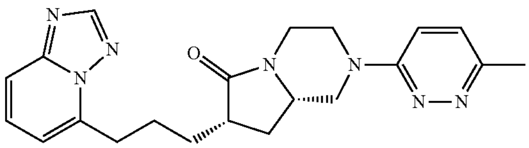 [SMILES: Cc1ccc(N2CCN3C(=O)[C@@H](CCCc4cccc5ncnn45)C[C@H]3C2)nn1] | (7S,8aS)-7-(3-([1,2,4]triazolo[1,5-a]pyridin-5-yl)propyl)-2-(6-methylpyridazin-3-yl)hexahydropyrrolo[1,2-a]pyrazin-6(2H)-one | 392.2 |
| 49 | 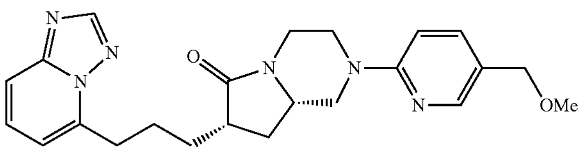 [SMILES: COCc1ccc(N2CCN3C(=O)[C@@H](CCCc4cccc5ncnn45)C[C@H]3C2)nc1] | (7S,8aS)-7-(3-([1,2,4]triazolo[1,5-a]pyridin-5-yl)propyl)-2-(5-(methoxymethyl)pyridin-2-yl)hexahydropyrrolo[1,2-a]pyrazin-6(2H)-one | 421.2 |

Examples 50 and 51: Synthesis of (7S,8aS)-7-(3-([1,2,4]triazolo[1,5-a]pyridin-5-yl)propyl)-2-(5-fluoropyridin-2-yl)hexahydropyrrolo[1,2-a]pyrazin-6(2H)-one and (7R,8aS)-7-(3-([1,2,4]triazolo[1,5-a]pyridin-5-yl)propyl)-2-(5-fluoropyridin-2-yl)hexahydropyrrolo[1,2-a]pyrazin-6(2H)-one

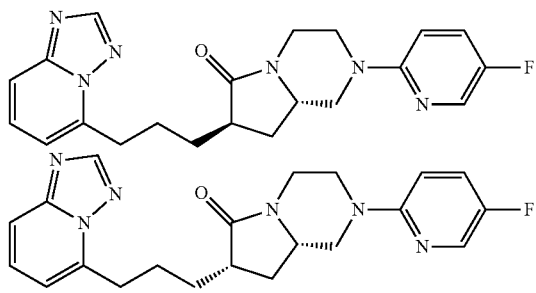

Example 41 was purified by chiral chromatography (chiralpak IF-3) to give Example 51, LCMS: m/z=417.4 [M+Na]+, followed by 50, LCMS: m/z=395.1 [M+H]+.

Example 52: Synthesis of 5-((7S,8aS)-7-(3-([1,2,4]triazolo[1,5-a]pyridin-5-yl)propyl)-6-oxohexahydropyrrolo[1,2-a]pyrazin-2(1H)-yl)-2-fluorobenzonitrile

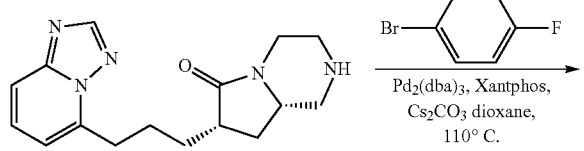

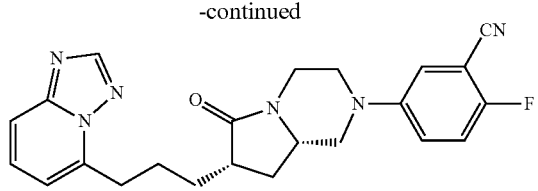

Into a 10-mL sealed tube purged and maintained with an inert atmosphere of nitrogen, was placed (7S,8aS)-7-(3-[[1,2,4]triazolo[1,5-a]pyridin-5-yl]propyl)-octahydropyrrolo[1,2-a]pyrazin-6-one (30 mg, 0.100 mmol, 1.0 equiv.), dioxane (2 mL), 5-bromo-2-fluorobenzonitrile (24 mg, 0.12 mmol, 1.2 equiv.), Pd$_2$(dba)$_3$ (18 mg, 0.02 mmol, 0.2 equiv.), Xantphos (23 mg, 0.04 mmol, 0.4 equiv.), Cs$_2$CO$_3$ (98 mg, 0.30 mmol, 3.0 equiv.). The resulting solution was stirred for 2 h at 110° C. in an oil bath. The mixture was filtered, concentrated, and purified by silica gel chromatography. Additional purification by reverse phase HPLC gave the title compound, 5-((7S,8aS)-7-(3-([1,2,4]triazolo[1,5-a]pyridin-5-yl)propyl)-6-oxohexahydropyrrolo[1,2-a]pyrazin-2(1H)-yl)-2-fluorobenzonitrile, as a white solid. LCMS: m/z=419.1 [M+H]+.

Example 53: Synthesis of (7S,8aS)-7-(3-([1,2,4]triazolo[1,5-a]pyridin-5-yl)propyl)-2-(5-(hydroxymethyl)pyridin-2-yl)hexahydropyrrolo[1,2-a]pyrazin-6(2H)-one

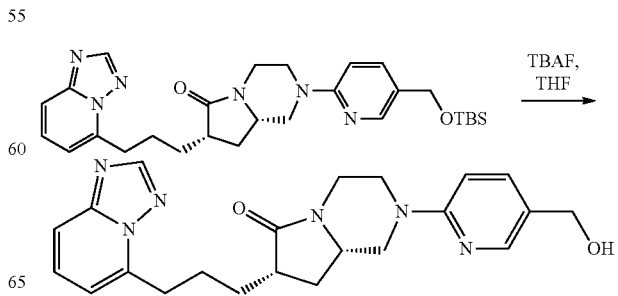

Step 1: (7S, 8aS)-7-(3-([1,2,4]triazolo[1,5-a]pyridin-5-yl)propyl)-2-(5-(((tert-butyldimethylsilyl)oxy)methyl)pyridin-2-yl)hexahydropyrrolo[1,2-a]pyrazin-6(2H)-one was prepared from (7S,8aS)-7-(3-([1,2,4]triazolo[1,5-a]pyridin-5-yl)propyl)hexahydropyrrolo[1,2-a]pyrazin-6(2H)-one (99 mg, 0.33 mmol, 1.0 equiv.) and 2-bromo-5-(((tert-butyldimethylsilyl)oxy)methyl)pyridine as described for the synthesis of example 37. LCMS: m/z=521.2 [M+H]$^+$.

Step 2: Into a 25-mL round-bottom flask, was placed (7S,8aS)-2-(5-[[(tert-butyldimethylsilyl)oxy]methyl]pyridin-2-yl)-7-(3-[[1,2,4]triazolo[1,5-a]pyridin-5-yl]propyl)-hexahydropyrrolo[1,2-a]pyrazin-6-one (70 mg, 0.13 mmol, 1.0 equiv.), THF (3 mL), TBAF (53 mg, 0.20 mmol, 1.5 equiv.). The resulting solution was stirred for 1 h at rt and concentrated in vacuo. The crude product was purified by silica gel chromatography followed by reverse phase HPLC which gave (7S,8aS)-2-[5-(hydroxymethyl)pyridin-2-yl]-7-(3-[[1,2,4]triazolo[1,5-a]pyridin-5-yl]propyl)-hexahydropyrrolo[1,2-a]pyrazin-6-one as a white solid. LCMS: m/z=407.2 [M+H]$^+$.

Example 54: Synthesis of 6-((7S,8aS)-7-(3-(1-methyl-1H-benzo[d]imidazol-7-yl)propyl)-6-oxo-hexahydropyrrolo[1,2-a]pyrazin-2(1H)-yl)nicotinonitrile

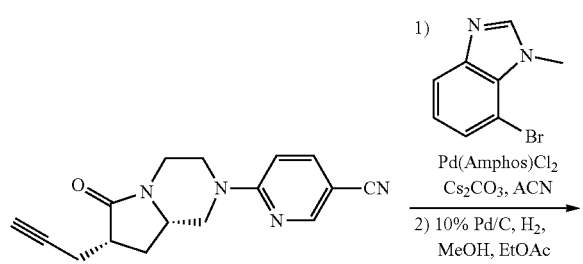

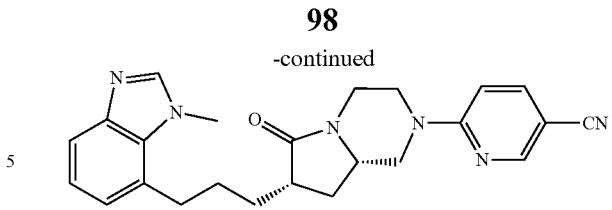

A mixture of 6-((7S,8aS)-6-oxo-7-(prop-2-yn-1-yl)hexahydropyrrolo[1,2-a]pyrazin-2(1H)-yl)nicotinonitrile (132 mg, 0.47 mmol, 1 eq), 7-bromo-1-methyl-1H-benzo[d]imidazole (100 mg, 0.47 mmol, 1 eq), Cs$_2$CO$_3$ (307 mg, 0.942 mmol, 2 eq), and Pd(Amphos)Cl$_2$ (4.0 mg, 0.047 mmol, 0.1 eq) in ACN (1.0 mL) was heated at 80° C. for 6 h in a sealed vial purged with N$_2$. The mixture was cooled to rt and partitioned between EtOAc and water. The layers were separated. The organics were dried over MgSO$_4$, filtered and concentrated. The material was dissolved in MeOH (1.0 ml) and EtOAc (1.0 mL). 10% Pd/C (50 mg) was added. The reaction was stirred under an atmosphere of H$_2$ for 23 h. The reaction was filtered through celite, concentrated, and purified by silica gel chromatography (0% MeOH in DCM gradient to 10% MeOH in DCM) which gave the title compound. LCMS: m/z=415.1 [M+H]$^+$. $^1$H NMR (400 MHz, d6-DSMO): δ 8.50 (dd, J=2.0, 0.4 Hz, 1H), 8.07 (s, 1H), 7.88 (dd, J=7.6, 2.0 Hz, 1H), 7.46 (dd, J=6.4, 1.2 Hz, 1H), 7.08 (app t, J=5.6 Hz, 1H), 7.03-7.00 (m, 2H), 4.67 (m, 1H), 4.51 (m, 1H), 4.03 (s, 3H), 3.83 (dd, J=10.4, 1.6 Hz, 1H), 3.43 (m, 1H), 3.06-3.02 (m, 2H), 2.91 (td, J=10.0, 2.8 Hz, 1H), 2.78 (td, J=9.6, 2.0 Hz, 1H), 2.65 (dd, J=10.4, 8.8 Hz, 1H), 2.42 (m, 1H), 2.34 (m, 1H), 1.89 (m, 1H), 1.73-1.67 (m, 2H), 1.41 (m, 1H), 1.26 (m, 1H).

The following examples were prepared from 6-((7S,8aS)-6-oxo-7-(prop-2-yn-1-yl)hexahydropyrrolo[1,2-a]pyrazin-2(1H)-yl)nicotinonitrile and the appropriate corresponding aryl or heteroaryl bromide using the same procedure as described for Example 54.

| Example | Structure | Name | LCMS (m/z) [M + H]+ |
|---|---|---|---|
| 55 | 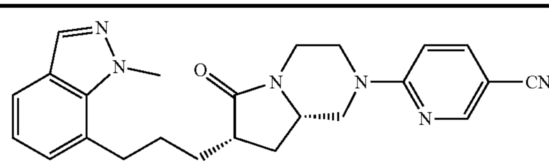 | 6-((7S,8aS)-7-(3-(1-methyl-1H-indazol-7-yl)propyl)-6-oxohexahydropyrrolo[1,2-a]pyrazin-2(1H)-yl)nicotinonitrile | 415.2 |
| 56 | 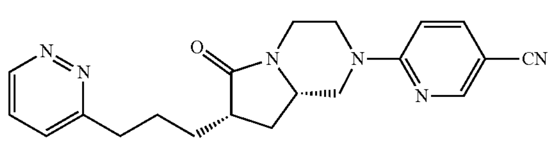 [SMILES: N#Cc1ccc(N2CCN3C(=O)[C@@H](CCCc4cccnn4)C[C@H]3C2)nc1] | 6-((7S,8aS)-6-oxo-7-(3-(pyridazin-3-yl)propyl)hexahydropyrrolo[1,2-a]pyrazin-2(1H)-yl)nicotinonitrile | 363.2 |
| 57 | 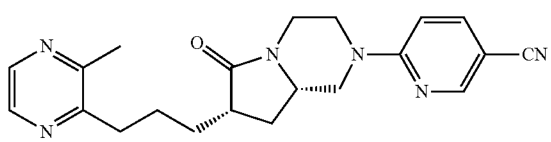 [SMILES: Cc1nccnc1CCC[C@H]1C[C@H]2CN(c3ccc(C#N)cn3)CCN2C1=O] | 6-((7S,8aS)-7-(3-(3-methylpyrazin-2-yl)propyl)-6-oxohexahydropyrrolo[1,2-a]pyrazin-2(1H)-yl)nicotinonitrile | 377.2 |
| 58 | 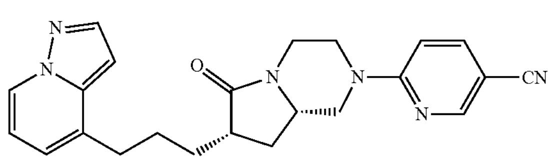 [SMILES: N#Cc1ccc(N2CCN3C(=O)[C@@H](CCCc4cccn5nccc45)C[C@H]3C2)nc1] | 6-((7S,8aS)-6-oxo-7-(3-(pyrazolo[1,5-a]pyridin-4-yl)propyl)hexahydropyrrolo[1,2-a]pyrazin-2(1H)-yl)nicotinonitrile | 401.2 |

| Example | Structure | Name | LCMS (m/z) [M + H]+ |
|---|---|---|---|
| 59 | 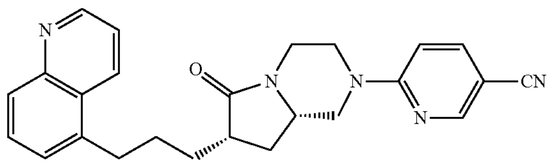 [SMILES: N#Cc1ccc(N2CCN3C(=O)[C@@H](CCCc4cccc5ncccc45)C[C@H]3C2)nc1] | 6-((7S,8aS)-6-oxo-7-(3-(quinolin-5-yl)propyl)hexahydropyrrolo[1,2-a]pyrazin-2(1H)-yl)nicotinonitrile | 412.2 |
| 60 | 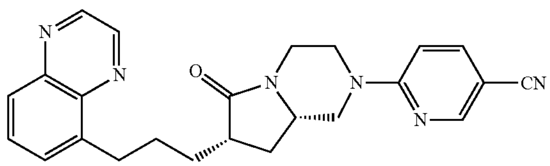 [SMILES: N#Cc1ccc(N2CCN3C(=O)[C@@H](CCCc4cccc5nccnc45)C[C@H]3C2)nc1] | 6-((7S,8aS)-6-oxo-7-(3-(quinoxalin-5-yl)propyl)hexahydropyrrolo[1,2-a]pyrazin-2(1H)-yl)nicotinonitrile | 413.2 |

Example 61: Synthesis of 6-((7S,8aS)-6-oxo-7-(3-(1,2,3,4-tetrahydroquinoxalin-5-yl)propyl)hexahydropyrrolo[1,2-a]pyrazin-2(1H)-yl)nicotinonitrile

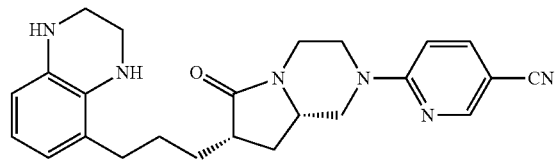 [SMILES: N#Cc1ccc(N2CCN3C(=O)[C@@H](CCCc4cccc5c4NCCN5)C[C@H]3C2)nc1]

The title compound was isolated as the minor product from the synthesis of Example 60. LCMS: m/z=417.2 [M+H]+.

Example 62: Synthesis of (7S,8aS)-2-(5-fluoropyridin-2-yl)-7-(3-{[1,2,4]triazolo[1,5-a]pyridin-8-yl}propyl)-octahydropyrrolo[1,2-a]pyrazin-6-one

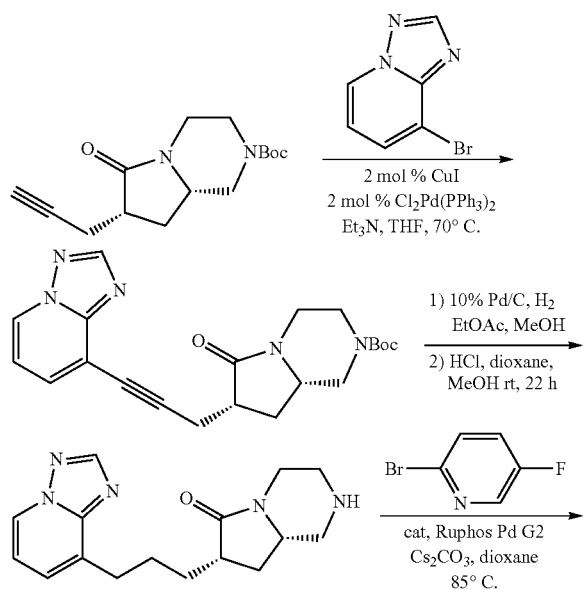

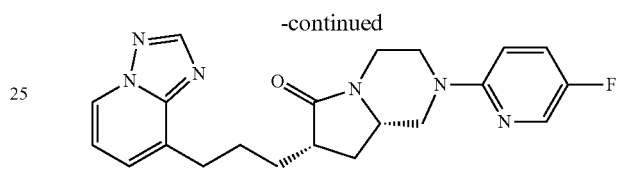

Step 1: A 3000 mL 3-neck RBF fitted with a mechanical stirrer, JKem thermocoupler, and reflux condenser was charged with tert-butyl (7S,8aS)-6-oxo-7-(prop-2-yn-1-yl)hexahydropyrrolo[1,2-a]pyrazine-2(1H)-carboxylate (129.0 g of 95 wt. % purity and 90% diastereomeric excess, 439 mmol, 1.0 equiv.) and 8-bromo-[1,2,4]triazolo[1,5-a]pyridine (86.8 g, 439 mmol, 1.0 equiv.). The solids were dissolved in a 1:1 vol/vol mixture of triethylamine/THF (1200 mL). Copper Iodide (2.78 g, 8.77 mmol, 0.02 equiv.) was added followed by Bis(triphenylphosphine)palladium (II)chloride (6.16 g, 8.77 mmol, 0.02 equiv.). The mixture heated (heating mantle) to 70° C. and mechanically stirred for 5 min. at which time heating mantle was turned off. As the reaction cooled, a brownish precipitate emerged. As cooling continued the precipitate grew larger, eventually turning the mixture to a solid tan sludge. The sludge was diluted with water (1 L) and stirred gently with a stirring rod. The liquid was decanted off and filtered. This process was repeated with an additional 500 mL of water. The remaining solid was set aside. The filtered liquid was concentrated to remove volatiles (triethylamine and THF). The resultant aqueous brown sludge was diluted with brine and extracted with EtOAc (2×). The reaction flask containing precipitates was partitioned between EtOAc and brine. The layers were separated, and all EtOAc extracts were combined, washed sequentially with sat. aq. NH4Cl (2×,) and brine. The organics were dried over MgSO4, filtered, and concentrated. The concentrates were treated with MTBE/MeOH (10:1, 750 mL) and heated gently with a heat gun to promote solvation of impurities. The dark brown liquid was filtered through a coarse filter and all remaining solids were washed with MTBE (2×). The remaining solids were vacuum oven dried overnight which gave tert-butyl (7S,8aS)-7-(3-([1,2,4]triazolo[1,5-a]pyridin-8-yl)prop-2-yn-1-yl)-6-oxohexahydropyrrolo[1,2-a]pyrazine-2(1H)-carboxylate as a light brown solid. LCMS: m/z=396.2 [M+H]+.

Step 2: To a solution of tert-butyl (7S,8aS)-7-(3-([1,2,4]triazolo[1,5-a]pyridin-8-yl)prop-2-yn-1-yl)-6-oxohexahydropyrrolo[1,2-a]pyrazine-2(1H)-carboxylate (163 g of 95 wt. % purity material, 390 mmol) in MeOH/EtOAc (4:1, 800 mL) was added a slurry of 10% Pd/C (50 wt. % $H_2O$, 30 g) in MeOH/EtOAc (2:1, 500 mL). Hydrogen gas was bubbled through the reaction mixture via balloon and the balloon was refilled as needed. At 26 h, additional 10% Pd/C (50 wt. % $H_2O$, 25 g) was added and hydrogen bubbling process was continued. Additional 10% Pd/C (50 wt. % $H_2O$) was added at 74 h (25 g) and 126 h (10 g) until the reaction was determined complete by LCMS @168 h. Nitrogen gas was bubbled through the reaction mixture for 20 min and the mixture was diluted with DCM (500 mL). The mixture was filtered through celite and the filter cake was rinsed with DCM. The filtrates were concentrated in vacuo to give tert-butyl (7S,8aS)-7-(3-([1,2,4]triazolo[1,5-a]pyridin-8-yl)propyl)-6-oxohexahydropyrrolo[1,2-a]pyrazine-2(1H)-carboxylate as a brown viscous oil. LCMS: m/z=400.2 [M+H]$^+$. The concentrated oil was dissolved in MeOH/dioxane (1:1, 500 mL) and transferred to a 2000 mL RBF. The flask was placed in an ice bath and 4N HCl/dioxane (300 mL) was added via addition funnel over 2 h. After the addition was complete the cooling bath was removed and the mixture was stirred for a total of 22 h. The mixture, which contained an off-white precipitate, was filtered. The filtrate washed with EtOAc and all filtrates were set aside. The solid was placed in dish and oven-dried under vacuum to give 115.4 g of an off-white powder. The dried solid was dissolved/suspended in 600 mL of water and 600 mL of DCM. 3N aqueous NaOH (400 mL) was added (pH>11) followed by the addition of brine (200 mL). The layers were separated, and the aqueous phase was extracted with additional DCM (5×500 mL). The combined organics were dried over MgSO4, filtered, and concentrated to give ((7S,8aS)-7-(3-([1,2,4]triazolo[1,5-a]pyridin-8-yl)propyl)hexahydropyrrolo[1,2-a]pyrazin-6 (2H)-one as a light orange oil.

Step 3: A mixture containing (7S,8aS)-7-(3-([1,2,4]triazolo[1,5-a]pyridin-8-yl)propyl)hexahydropyrrolo[1,2-a]pyrazin-6(2H)-one (3.27 g, 10.9 mmol, 1.0 equiv.), 2-bromo-5-fluoropyridine (2.88 g, 16.4 mmol, 1.5 equiv.), Ruphos Pd G2 (505 mg, 0.65 mmol, 0.06 equiv.), and cesium carbonate (7.11 g, 21.8 mmol, 2.0 equiv.) in dioxane (25 mL) was stirred in heavy-walled sealed vessel at 80° C. for 24 h. The mixture was cooled to rt, filtered, and concentrated in vacuo. The concentrate was partitioned between sat. NH4Cl and EtOAc. The organics were washed with additional sat. NH4Cl, dried over MgSO4, filtered, and concentrated. Purification by silica gel chromatography (0% MeOH in EtOAc gradient to 10% MeOH in EtOAc) gave (7S,8aS)-2-(5-fluoropyridin-2-yl)-7-(3-[[1,2,4]triazolo[1,5-a]pyridin-8-yl]propyl)-hexahydropyrrolo[1,2-a]pyrazin-6-one as a white solid. LCMS: m/z=395.1 [M+H]$^+$ $^1$H NMR (300 MHz, Methanol-d$_4$) δ 8.66 (dd, J=6.9, 1.2 Hz, 1H), 8.41 (s, 1H), 8.02 (d, J=3.1 Hz, 1H), 7.54 (dd, J=7.1, 1.1 Hz, 1H), 7.46-7.38 (m, 1H), 7.17 (t, J=7.0 Hz, 1H), 6.91 (dd, J=9.2, 3.4 Hz, 1H), 4.54-4.43 (m, 1H), 4.34-4.24 (m, 1H), 4.01-3.90 (m, 1H), 3.63 (m, 1H), 3.07 (t, J=7.2 Hz, 3H), 3.01-2.89 (m, 1H), 2.87-2.75 (m, 2H), 2.63-2.40 (m, 2H), 2.05-1.82 (m, 3H), 1.56-1.30 (m, 1H).

Example 63: Synthesis of (7S,8aS)-7-(3-([1,2,4]triazolo[1,5-a]pyridin-8-yl)propyl)-2-(5-fluoropyrimidin-2-yl)hexahydropyrrolo[1,2-a]pyrazin-6(2H)-one

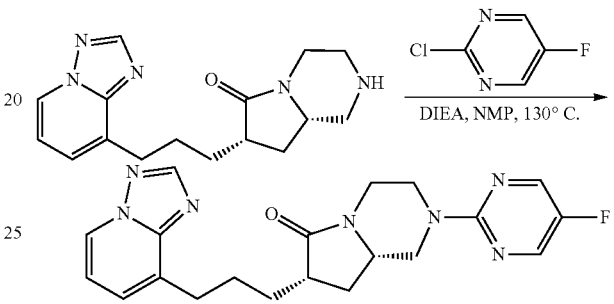

Into a 10-mL sealed tube purged and maintained with an inert atmosphere of nitrogen, was placed (7S,8aS)-7-(3-[[1,2,4]triazolo[1,5-a]pyridin-8-yl]propyl)-hexahydro-1H-pyrrolo[1,2-a]pyrazin-6-one (60 mg, 0.20 mmol, 1.0 equiv.), NMP (1 mL), 2-chloro-5-fluoropyrimidine (32 mg, 0.24 mmol, 1.2 equiv.), DIEA (1 mL). The resulting solution was stirred for 2 h at 130° C. in an oil bath. The mixture was cooled to rt and purified by silica gel chromatography followed by additional purification by reverse phase HPLC which gave (7S, 8aS)-2-(5-fluoropyrimidin-2-yl)-7-(3-[[1,2,4]triazolo[1,5-a]pyridin-8-yl]propyl)-hexahy dropyrrolo[1,2-a]pyrazin-6-one as an off-white solid. LCMS: m/z=396.1 [M+H]$^+$. $^1$H NMR (300 MHz, Methanol-d4) δ 8.66 (m, 1H), 8.41 (s, 1H), 8.32 (s, 2H), 7.54 (dd, J=7.2, 0.9 Hz, 1H), 7.17 (t, J=7.2 Hz, 1H), 4.92 (m, 1H), 4.87 (m, 1H), 3.96 (m, 1H), 3.56 (m, 1H), 3.10-3.05 (m, 2H), 2.90-2.84 (m, 2H), 2.66-2.44 (m, 3H), 1.96-1.89 (m, 3H), 1.43-1.36 (m, 2H).

The following examples were prepared from (7S,8aS)-7-(3-([1,2,4]triazolo[1,5-a]pyridin-8-yl)propyl)hexahydropyrrolo[1,2-a]pyrazin-6(2H)-one and the appropriate corresponding heteroaryl halide using the same procedure as described for Example 63.

| Example | Structure | Name | LCMS (m/z) [M + H]+ |
|---|---|---|---|
| 64 | 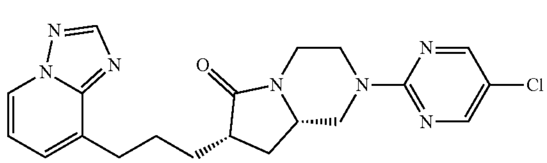 [SMILES: O=C1[C@@H](CCCc2cccn3ncnc23)C[C@H]2CN(c3ncc(Cl)cn3)CCN12] | (7S,8aS)-7-(3-([1,2,4]triazolo[1,5-a]pyridin-8-yl)propyl)-2-(5-chloropyrimidin-2-yl)hexahydropyrrolo[1,2-a]pyrazin-6(2H)-one | 412.4 |

| Example | Structure | Name | LCMS (m/z) [M + H]+ |
|---|---|---|---|
| 65 | 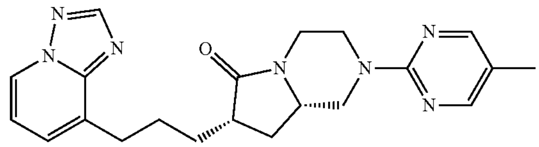 | (7S,8aS)-7-(3-([1,2,4]triazolo[1,5-a]pyridin-8-yl)propyl)-2-(5-methylpyrimidin-2-yl)hexahydropyrrolo[1,2-a]pyrazin-6(2H)-one | 392.4 |
| 66 | 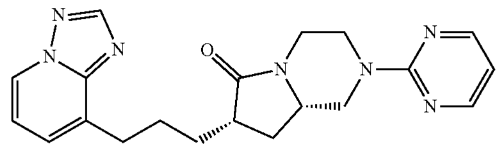 [SMILES: O=C1[C@@H](CCCc2cccn3ncnc23)C[C@H]2CN(c3ncccn3)CCN12] | (7S,8aS)-7-(3-([1,2,4]triazolo[1,5-a]pyridin-8-yl)propyl)-2-(pyrimidin-2-yl)hexahydropyrrolo[1,2-a]pyrazin-6(2H)-one | 378.4 |
| 67 | 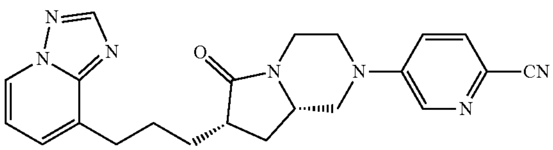 [SMILES: N#Cc1ccc(N2CCN3C(=O)[C@@H](CCCc4cccn5ncnc45)C[C@H]3C2)cn1] | 5-((7S,8aS)-7-(3-([1,2,4]triazolo[1,5-a]pyridin-8-yl)propyl)-6-oxohexahydropyrrolo[1,2-a]pyrazin-2(1H)-yl)picolinonitrile | 402.2 |
| 68 | 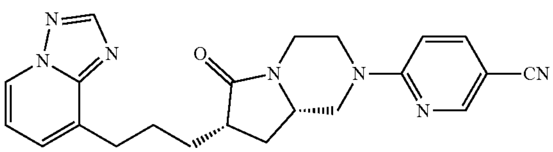 [SMILES: N#Cc1ccc(N2CCN3C(=O)[C@@H](CCCc4cccn5ncnc45)C[C@H]3C2)nc1] | 6-((7S,8aS)-7-(3-([1,2,4]triazolo[1,5-a]pyridin-8-yl)propyl)-6-oxohexahydropyrrolo[1,2-a]pyrazin-2(1H)-yl)nicotinonitrile | 402.2 |
| 69 | 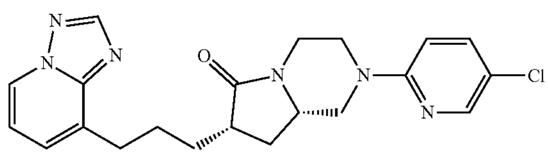 [SMILES: O=C1[C@@H](CCCc2cccn3ncnc23)C[C@H]2CN(c3ccc(Cl)cn3)CCN12] | (7S,8aS)-7-(3-([1,2,4]triazolo[1,5-a]pyridin-8-yl)propyl)-2-(5-chloropyridin-2-yl)hexahydropyrrolo[1,2-a]pyrazin-6(2H)-one | 411.1 |

Example 70: Synthesis of (7S,8aS)-7-(3-{7-fluoro-[1,2,4]triazolo[1,5-a]pyridin-8-yl}propyl)-2-(5-fluoropyridin-2-yl)-octahydropyrrolo[1,2-a]pyrazin-6-one

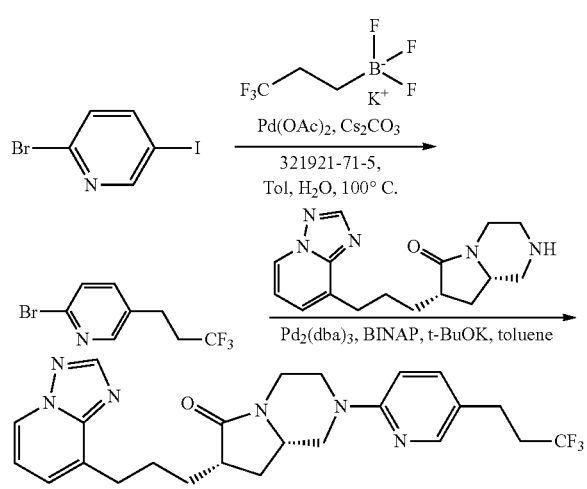

Step 1: Into a 10-mL sealed tube purged and maintained with nitrogen, was placed 2-bromo-5-iodopyridine (180 mg, 0.634 mmol, 1 eq), toluene (3.00 mL), trifluoro(3,3,3-trifluoropropyl)boranuide (126 mg, 0.761 mmol, 1.2 equiv.), Pd(OAc)$_2$ (29 mg, 0.12 mmol, 0.2 equiv.), Cs$_2$CO$_3$ (517 mg, 1.56 mmol, 2.5 equiv.), H$_2$O (1.5 mL). The resulting solution was stirred for 2 h at 100° C. in an oil bath. The mixture was cooled rt, filtered, and concentrated. Purification by silica gel chromatography gave 2-bromo-5-(3,3,3-trifluoropropyl)pyridine as yellow oil. LCMS: m/z=254.1[M+H]$^+$.

Step 2: Into a 10-mL sealed tube purged and maintained with an inert atmosphere of nitrogen, was placed (7S,8aS)-7-(3-[[1,2,4]triazolo[1,5-a]pyridin-8-yl]propyl)-hexahydro-1H-pyrrolo[1,2-a]pyrazin-6-one (20 mg, 0.067 mmol, 1.0 equiv.), PhMe (1 mL), 2-bromo-5-(3,3,3-trifluoropropyl)pyridine (21 mg, 0.08 mmol, 1.2 equiv.), Pd$_2$(dba)$_3$ (12 mg, 0.013 mmol, 0.2 equiv.), BINAP (17 mg, 0.027 mmol, 0.4 equiv.), t-BuOK (23 mg, 0.20 mmol, 3.0 equiv.). The mixture was stirred for 2 h at 100° C. in an oil bath. The mixture was cooled rt, filtered, and concentrated. Purification by silica gel chromatography gave (7S,8aS)-7-(3-[[1,2,4]triazolo[1,5-a]pyridin-8-yl]propyl)-2-[5-(3,3,3-trifluorproyl)yridin-2-yl]-hexahydropyrrolo[1,2-a]pyrazin-6-one as an off-white solid. LCMS: m/z=473.1[M+H]$^+$.

The following examples were prepared from (7S,8aS)-7-(3-([1,2,4]triazolo[1,5-a]pyridin-8-yl)propyl)hexahydropyrrolo[1,2-a]pyrazin-6(2H)-one and the appropriate corresponding aryl or heteroaryl bromide using the same procedure as described for example Example 70, step 2. Examples 72, 73, and 74 were obtained as mixtures of diastereomers.

| Example | Structure | Name | LCMS (m/z) [M + H]+ |
|---|---|---|---|
| 71 | 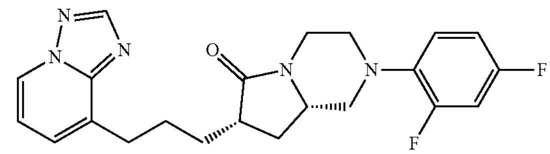 [SMILES: O=C1[C@@H](CCCc2cccn3ncnc23)C[C@H]2CN(c3ccc(F)cc3F)CCN12] | (7S,8aS)-7-(3-([1,2,4]triazolo[1,5-a]pyridin-8-yl)propyl)-2-(2,4-difluorophenyl)hexahydropyrrolo[1,2-a]pyrazin-6(2H)-one | 412.4 |
| 72 | 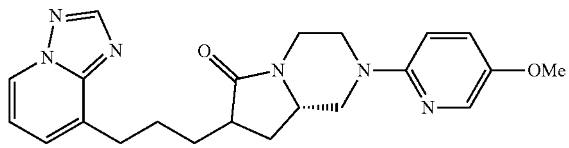 [SMILES: COc1ccc(N2CCN3C(=O)C(CCCc4cccn5ncnc45)C[C@H]3C2)nc1] | (7S,8aS)-7-(3-([1,2,4]triazolo[1,5-a]pyridin-8-yl)propyl)-2-(5-methoxypyridin-2-yl)hexahydropyrrolo[1,2-a]pyrazin-6(2H)-one | 407.2 |
| 73 | 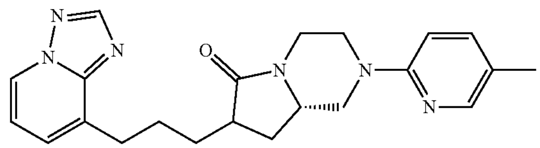 [SMILES: Cc1ccc(N2CCN3C(=O)C(CCCc4cccn5ncnc45)C[C@H]3C2)nc1] | (8aS)-7-(3-([1,2,4]triazolo[1,5-a]pyridin-8-yl)propyl)-2-(5-methylpyridin-2-yl)hexahydropyrrolo[1,2-a]pyrazin-6(2H)-one | 391.2 |
| 74 | 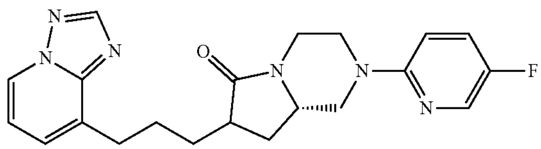 [SMILES: O=C1C(CCCc2cccn3ncnc23)C[C@H]2CN(c3ccc(F)cn3)CCN12] | (8aS)-7-(3-([1,2,4]triazolo[1,5-a]pyridin-8-yl)propyl)-2-(5-fluoropyridin-2-yl)hexahydropyrrolo[1,2-a]pyrazin-6(2H)-one | 395.1 |
| 75 | 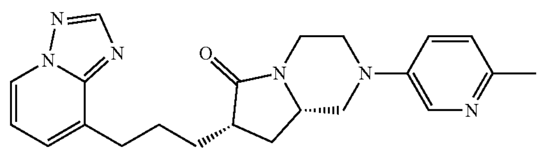 [SMILES: Cc1ccc(N2CCN3C(=O)[C@@H](CCCc4cccn5ncnc45)C[C@H]3C2)cn1] | (7S,8aS)-7-(3-([1,2,4]triazolo[1,5-a]pyridin-8-yl)propyl)-2-(6-methylpyridin-3-yl)hexahydropyrrolo[1,2-a]pyrazin-6(2H)-one | 391.2 |
| 76 | 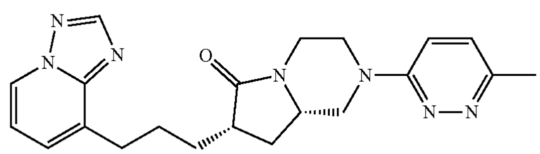 | (7S,8aS)-7-(3-([1,2,4]triazolo[1,5-a]pyridin-8-yl)propyl)-2-(6-methylpyridazin-3-yl)hexahydropyrrolo[1,2-a]pyrazin-6(2H)-one | 392.1 |

Example 77: Synthesis of (7S,8aS)-7-(3-([1,2,4]triazolo[1,5-a]pyridin-8-yl)propyl)-2-(5-(hydroxymethyl)pyridin-2-yl)hexahydropyrrolo[1,2-a]pyrazin-6(2H)-one

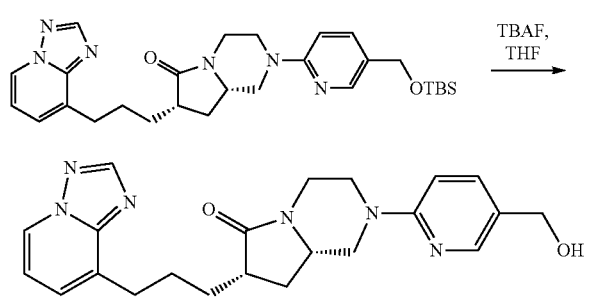

Step 1: (7S,8aS)-7-(3-([1,2,4]triazolo[1,5-a]pyridin-8-yl)propyl)-2-(5-(((tert-butyldimethylsilyl)oxy)methyl)pyridin-2-yl)hexahydropyrrolo[1,2-a]pyrazin-6(2H)-one was prepared from (7S,8aS)-7-(3-([1,2,4]triazolo[1,5-a]pyridin-8-yl)propyl)hexahydropyrrolo[1,2-a]pyrazin-6(2H)-one (90 mg, 0.30 mmol, 1.0 equiv.) and 2-bromo-5-((((tert-butyldimethylsilyl)oxy)methyl)pyridine as described for the synthesis of Example 37. LCMS: m/z=521.1 [M+H]+.

Step 2: The title compound was prepared from: (7S,8aS)-7-(3-([1,2,4]triazolo[1,5-a]pyridin-8-yl)propyl)-2-(5-(((tert-butyldimethylsilyl)oxy)methyl)pyridin-2-yl)hexahydropyrrolo[1,2-a]pyrazin-6(2H)-one as described for the synthesis of Example 53, step 2. LCMS: m/z=407.2 [M+H]+.

Example 78: Synthesis of (7S,8aS)-7-(3-{7-fluoro-[1,2,4]triazolo[1,5-a]pyridin-8-yl}propyl)-2-(5-fluoropyridin-2-yl)-octahydropyrrolo[1,2-a]pyrazin-6-one

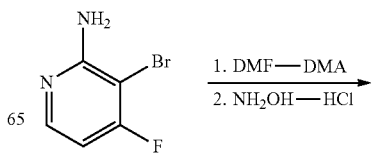

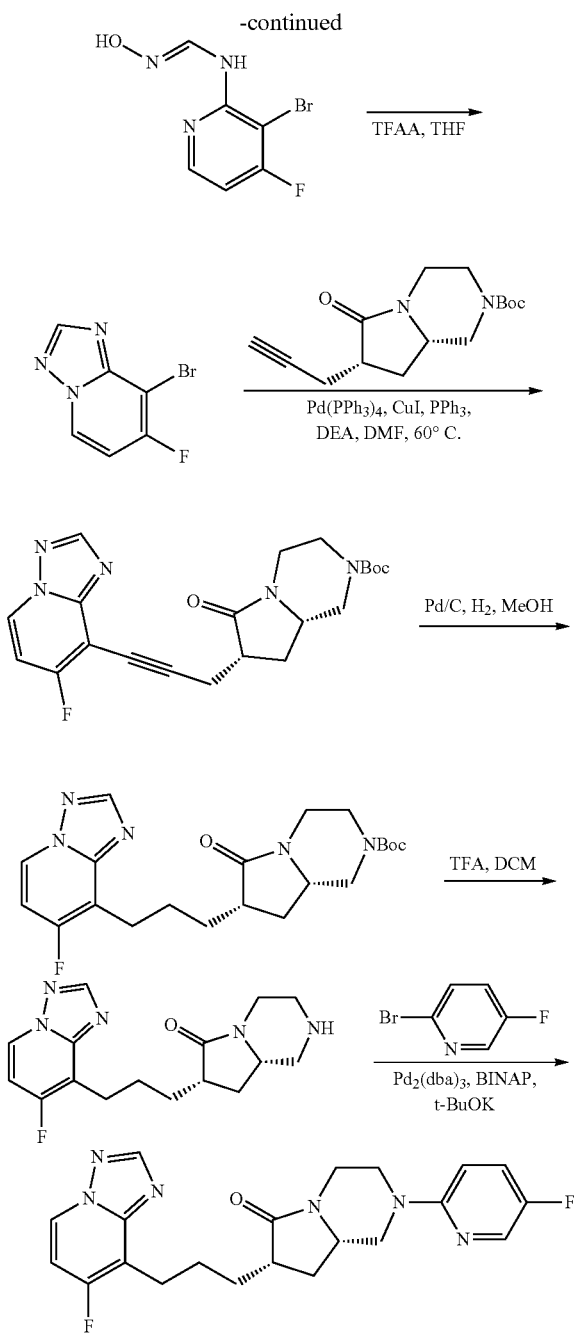

Step 1: Into a 100-mL round-bottom flask purged and maintained with nitrogen, was placed 3-bromo-4-fluoropyridin-2-amine (900 mg, 4.71 mmol, 1.0 equiv.), IPA (15 mL), N,N-Dimethylformamide dimethyl acetal (730 mg, 6.13 mmol, 1.3 equiv.). The resulting solution was stirred for 2 h at 85° C. in an oil bath at which time the mixture was cooled to 50° C. and NH₂OH·HCl (426 mg, 6.13 mmol, 1.3 equiv.) was added. The resulting solution was stirred for an additional 2 h at 50° C. in an oil bath. The mixture was cooled to rt and concentrated in vacuo. The resulting residue purified by silica gel chromatography which gave (E)-N-(3-bromo-4-fluoropyridin-2-yl)-N-hydroxymethanimidamide as an off-white solid. LCMS: m/z=234.1 [M+H]⁺

Step 2: Into a 100-mL round-bottom flask, was placed (E)-N-(3-bromo-4-fluoropyridin-2-yl)-N-hydroxymethanimidamide (1.00 g, 4.27 mmol, 1.0 equiv.) and THF (15 mL). The solution was cooled to 0° C. and TFAA (2.69 g, 13 mmol, 3.0 eq) was added. The mixture was slowly warmed to rt and stirred for 5 h. The pH value of the solution was adjusted to pH-7 by the addition of aqueous sodium hydroxide and the mixture was extracted with dichloromethane. The extracts were concentrated and purified by silica gel chromatography which gave 8-bromo-7-fluoro-[1,2,4]triazolo[1,5-a]pyridine as yellow oil. LCMS: m/z=216.1 [M+H]⁺.

Step 3: Into a 30-mL sealed tube purged and maintained with nitrogen, was placed 8-bromo-7-fluoro-[1,2,4]triazolo[1,5-a]pyridine (200 mg, 0.926 mmol, 1.0 equiv.), DMF (4 mL), tert-butyl (7S,8aS)-6-oxo-7-(prop-2-yn-1-yl)-hexahydropyrrolo[1,2-a]pyrazine-2-carboxylate (258 mg, 0.926 mmol, 1.0 equiv.), Pd(PPh₃)₄ (54 mg, 0.046 mmol, 0.05 equiv.), CuI (9 mg, 0.046 mmol, 0.05 equiv.), PPh₃ (49 mg, 0.19 mmol, 0.2 equiv.), and DIEA (691 mg, 4.63 mmol, 5.0 equiv.). The resulting solution was stirred for 2 h at 60° C. in an oil bath. The resulting solution was partitioned between water and ethyl acetate. The layers were separated and the organics were concentrated and purified by silica gel chromatography which gave tert-butyl (7S,8aS)-7-(3-[7-fluoro-[1,2,4]triazolo[1,5-a]pyridin-8-yl]prop-2-yn-1-yl)-6-oxo-hexahydropyrrolo [1,2-a]pyrazine-2-carboxylate as yellow oil. LCMS: m/z=414.1 [M+H]⁺.

Step 4: Into a 25-mL round-bottom flask, was placed tert-butyl (7S,8aS)-7-(3-[7-fluoro-[1,2,4]triazolo[1,5-a]pyridin-8-yl]prop-2-yn-1-yl)-6-oxo-hexahydropyrrolo[1,2-a]pyrazine-2-carboxylate (180 mg, 0.435 mmol, 1.0 equiv.), MeOH (5 mL), and 10% Pd/C (93 mg). The mixture was stirred overnight at rt under H₂ atmosphere. The mixture was filtered through celite, concentrated, and purified by silica gel chromatography which gave tert-butyl (7S,8aS)-7-(3-[7-fluoro-[1,2,4]triazolo[1,5-a]pyridin-8-yl]propyl)-6-oxo-hexahydropyrrolo [1,2-a]pyrazine-2-carboxylate as yellow oil. LCMS: m/z=418.2 [M+H]⁺

Step 5: Into a 25-mL round-bottom flask, was placed tert-butyl (7S,8aS)-7-(3-[7-fluoro-[1,2,4]triazolo[1,5-a]pyridin-8-yl]propyl)-6-oxo-hexahydropyrrolo[1,2-a]pyrazine-2-carboxylate (150 mg, 0.359 mmol, 1.0 equiv.), DCM (3 mL), and TFA (2 mL). The resulting solution was stirred for 1 h at rt. The pH value of the solution was adjusted to 7. The crude product was purified by silica gel chromatography which gave (7S,8aS)-7-(3-[7-fluoro-[1,2,4]triazolo [1,5-a]pyridin-8-yl]propyl)-hexahydro-1H-pyrrolo [1,2-a]pyrazin-6-one as yellow oil. LCMS: m/z=318.2 [M+H]⁺.

Step 6: Into a 10-mL sealed tube purged and maintained with nitrogen, was placed (7S,8aS)-7-(3-[7-fluoro-[1,2,4]triazolo[1,5-a]pyridin-8-yl]propyl)-hexahydro-1H-pyrrolo [1,2-a]pyrazin-6-one (50 mg, 0.16 mmol, 1.0 equiv.), PhMe (3 mL), 2-bromo-5-fluoropyridine (33 mg, 0.19 mmol, 1.2 equiv.), Pd₂(dba)₃ (29 mg, 0.032 mmol, 0.2 equiv.), BINAP (39 mg, 0.063 mmol, 0.4 equiv.), and t-BuOK (53 mg, 0.47 mmol, 3.0 equiv.). The mixture was stirred for 2 h at 100° C. in an oil bath. The solids were filtered and the resulting mixture was concentrated. The residue was purified by silica gel chromatography followed by further purification by reverse phase HPLC which gave the title compound, (7S,8aS)-7-(3-[7-fluoro-[1,2,4]triazolo[1,5-a]pyridin-8-yl]propyl)-2-(5-fluoropyridin-2-yl)-hexahydropyrrolo [1,2-a]pyrazin-6-one, as a white solid. LCMS: m/z=413.2 [M+H]⁺.

Example 79: Synthesis of (7S,8aS)-7-(3-([1,2,4]triazolo[1,5-a]pyridin-8-yl-5-d)propyl-2,2,3,3-d4)-2-(5-fluoropyridin-2-yl)hexahydropyrrolo[1,2-a]pyrazin-6(2H)-one

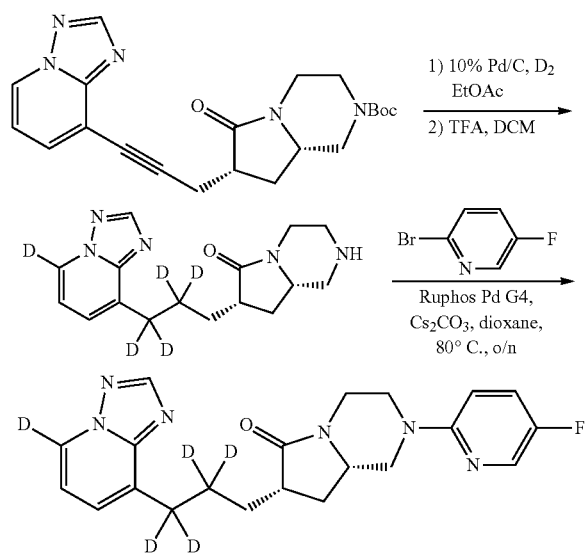

Step 1: (7S,8aS)-7-(3-([1,2,4]triazolo[1,5-a]pyridin-8-yl-5-d)propyl-2,2,3,3-d4)hexahydropyrrolo[1,2-a]pyrazin-6(2H)-one was prepared from tert-butyl (7S,8aS)-7-(3-([1,2,4]triazolo [1,5-a]pyridin-8-yl)prop-2-yn-1-yl)-6-oxohexahydropyrrolo[1,2-a]pyrazine-2(1H)-carboxylate (180 mg, 0.455 mmol, 1.0 equiv.) in similar fashion as described for the synthesis of Example 78 steps 4 and 5 with the exception that $D_2$ gas was substituted for $H_2$ gas in step 4. LCMS: m/z=305 [M+H]$^+$.

Step 2: The title compound was prepared from (7S,8aS)-7-(3-([1,2,4]triazolo[1,5-a]pyridin-8-yl-5-d)propyl-2,2,3,3-d4)hexahydropyrrolo[1,2-a]pyrazin-6(2H)-one (40 mg, 0.13 mmol, 1.0 equiv.) in similar fashion as described for the synthesis of Example 62, step 3 with the exception that Ruphos Pd G4 was used as catalyst. LCMS: m/z=399.2 [M]$^+$.

Example 80: Synthesis of 7-(3-([1,2,4]triazolo[1,5-a]pyridin-8-yl)propyl)-2-(5-fluoropyridin-2-yl)hexahydropyrrolo [1,2-a] pyrazin-6(2H)-one

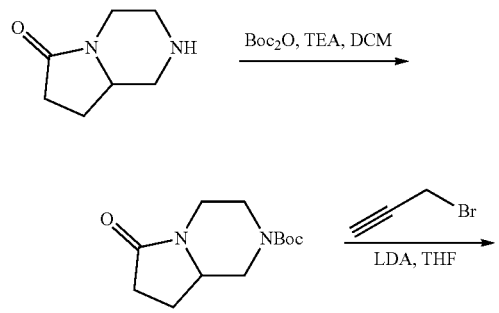

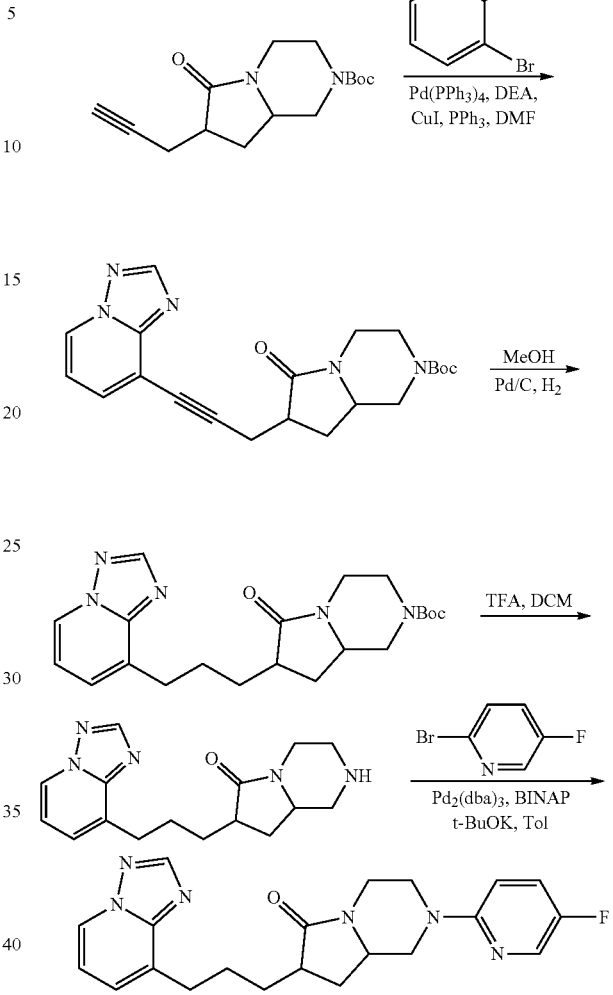

Step 1: tert-butyl 6-oxo-7-(prop-2-yn-1-yl)hexahydropyrrolo[1,2-a]pyrazine-2(1H)-carboxylate was prepared from hexahydropyrrolo[1,2-a]pyrazin-6(2H)-one (1.59 g, 11.3 mmol, 1.0 equiv.) in two steps in similar fashion as described for the synthesis of tert-butyl (8aS)-6-oxo-7-(prop-2-yn-1-yl)hexahydropyrrolo[1,2-a]pyrazine-2(1H)-carboxylate in examples 1 and 2, steps 1 and 2.

Step 2: 7-(3-([1,2,4]triazolo[1,5-a]pyridin-8-yl)propyl)hexahydropyrrolo[1,2-a]pyrazin-6(2H)-one was prepared from tert-butyl 6-oxo-7-(prop-2-yn-1-yl)hexahydropyrrolo[1,2-a]pyrazine-2(1H)-carboxylate (330 mg, 1.19 mmol, 1.0 equiv.), and 8-bromo-[1,2,4]triazolo[1,5-a]pyridine as described for the synthesis of example 31, steps 1-2. LCMS: m/z=300.1 [M+H]$^+$.

Step 3: 7-(3-([1,2,4]triazolo [1,5-a]pyridin-8-yl)propyl)-2-(5-fluoropyridin-2-yl)hexahydropyrrolo[1,2-a]pyrazin-6(2H)-one was obtained as a mixture of stereoisomers from 7-(3-([1,2,4]triazolo [1,5-a]pyridin-8-yl)propyl)hexahydropyrrolo[1,2-a]pyrazin-6(2H)-one carboxylate (158 mg, 0.53 mmol, 1.0 equiv.) and 2-bromo-5-fluoropyridine as described for the synthesis of Example 78, step 6. LCMS: m/z=395.2 [M+H]$^+$.

Examples 81, 82, and 83: Synthesis of (7S,8aR)-7-(3-([1,2,4]triazolo[1,5-a]pyridin-8-yl)propyl)-2-(5-fluoropyridin-2-yl)hexahydropyrrolo[1,2-a]pyrazin-6(2H)-one, (7R,8aR)-7-(3-([1,2,4]triazolo[1,5-a]pyridin-8-yl)propyl)-2-(5-fluoropyridin-2-yl)hexahydropyrrolo[1,2-a]pyrazin-6(2H)-one, and (7R,8aS)-7-(3-([1,2,4]triazolo[1,5-a]pyridin-8-yl)propyl)-2-(5-fluoropyridin-2-yl)hexahydropyrrolo[1,2-a]pyrazin-6(2H)-one

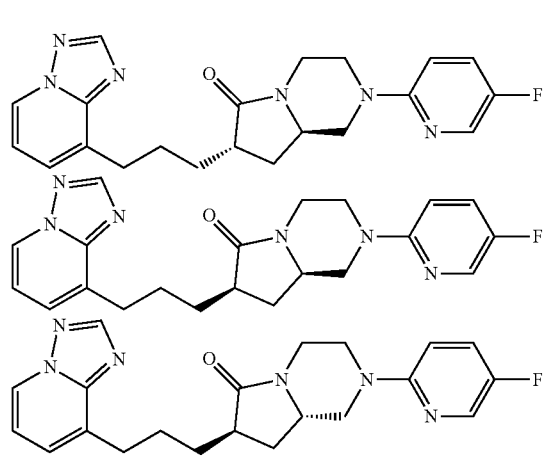

The title compounds were prepared as pure stereoisomers from 7-(3-([1,2,4]triazolo[1,5-a]pyridin-8-yl)propyl)-2-(5-fluoropyridin-2-yl)hexahydropyrrolo[1,2-a]pyrazin-6(2H)-one (Example 80) via chiral chromatography (chiralpak IF-3). LCMS: m/z=395.2; 395.2; 395.2 [M+H]+.

Example 84: Synthesis of 6-(7-(3-([1,2,4]triazolo[1,5-a]pyridin-8-yl)propyl)-6-oxooctahydro-2H-pyrido[1,2-a]pyrazin-2-yl)nicotinonitrile

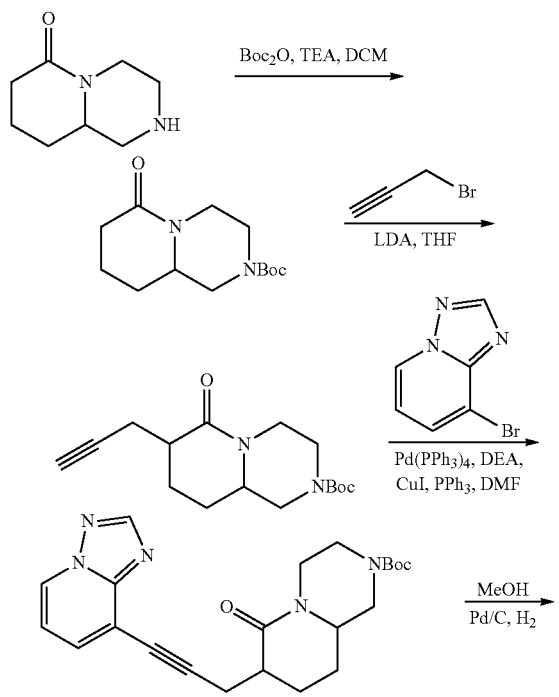

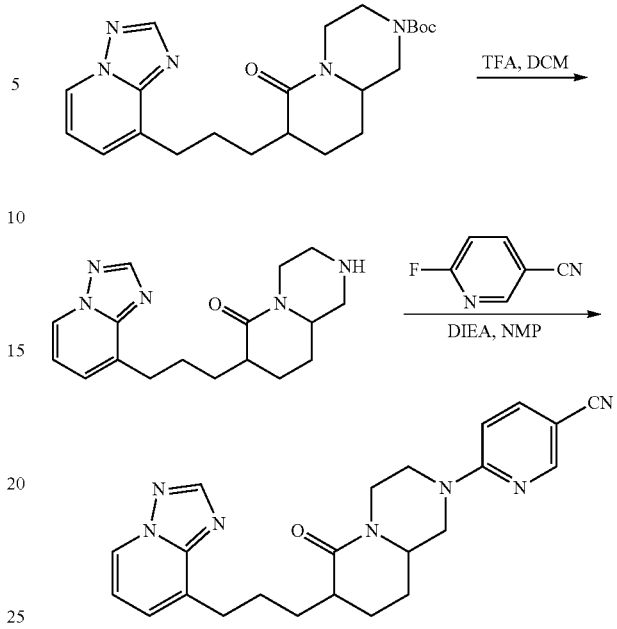

Step 1: 7-(3-([1,2,4]triazolo[1,5-a]pyridin-8-yl)propyl)octahydro-6H-pyrido[1,2-a]pyrazin-6-one was obtained as a mixture of stereoisomers in 5 steps from octahydro-6H-pyrido[1,2-a]pyrazin-6-one (404 mg, 2.62 mmol, 1.0 equiv.) in similar fashion as described for the synthesis of Example 80, steps 1 and 2. LCMS: m/z=312.4 [M+H]+.

Step 2: The title compound was prepared as a mixture of stereoisomers from 7-(3-([1,2,4]triazolo[1,5-a]pyridin-8-yl)propyl)octahydro-6H-pyrido[1,2-a]pyrazin-6-one (60 mg, 0.19 mmol, 1.0 equiv.) and 6-fluoronicotinonitrile in similar fashion as described for the synthesis of Example 63. LCMS: m/z=416.2 [M+H]+.

Example 85: Synthesis of 6-(3-(3-([1,2,4]triazolo[1,5-a]pyridin-8-yl)propyl)-4-oxohexahydropyrazino[2,1-c][1,4]oxazin-8(1H)-yl)nicotinonitrile

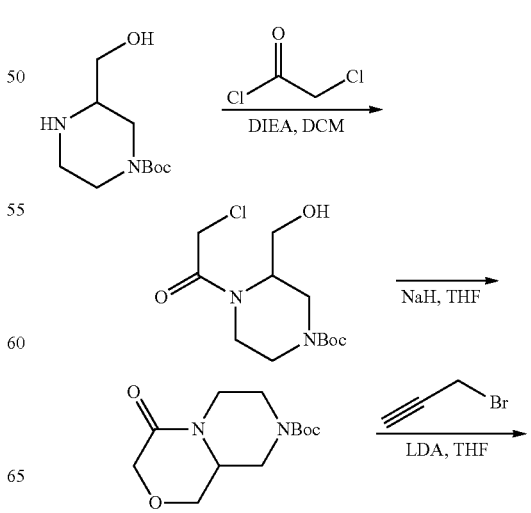

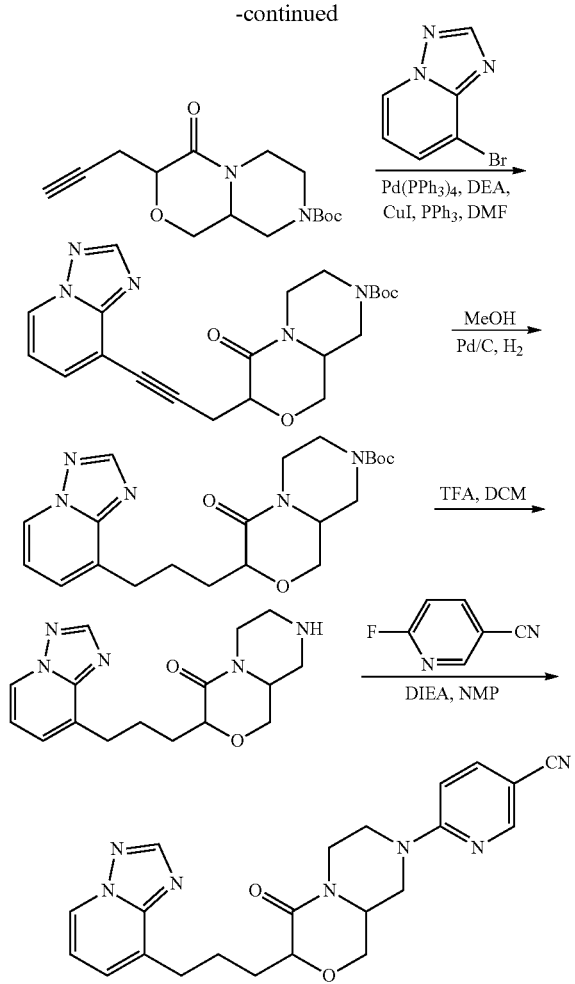

Step 1: Into a 250-mL round-bottom flask, was placed tert-butyl 3-(hydroxymethyl)piperazine-1-carboxylate (5.00 g mg, 23.1 mmol, 1.0 equiv.), DCM (50 mL). This was followed by the addition of DIEA (7.47 g, 57.8 mmol 2.5 equiv.). The flask was cooled to 0° C. and a solution of chloroacetyl chloride (3.14 g, 27.7 mmol, 1.2 equiv.) in DCM (10 mL) was added dropwise. The resulting solution was stirred while warming to rt over 1 h. The mixture was diluted with DCM and washed with water (3×). The organcis were dried over MgSO4, filtered, and concentrated to give tert-butyl 4-(2-chloroacetyl)-3-(hydroxymethyl)piperazine-1-carboxylate as brown oil. LCMS: m/z=293.1 [M+H]+.

Step 2: Into a 250-mL 3-necked round-bottom flask purged and maintained with an inert atmosphere of nitrogen, was placed tert-butyl 4-(2-chloroacetyl)-3-(hydroxymethyl) piperazine-1-carboxylate (6.00 g, 20.47 mmol, 1.0 equiv.) in THF (60 mL). The mixture was cooled to 0° C. and NaH (1.48 g, 61.5 mmol, 3.0 equiv.) was added. The ice bath was removed and the resulting mixture was stirred for 30 min at rt. The reaction was quenched with water. The resulting solution was extracted with 500 mL of DCM. The organics were washed with water (2×), dried over Na2SO4, filtered, and concentrated. Purification by silica gel chromatography (15% MeOH in DCM) gave tert-butyl 4-oxo-hexahydropyrazino[2,1-c][1,4]oxazine-8-carboxylate as a yellow solid. LCMS: m/z=257.1 [M+H]+

Step 3: 3-(3-([1,2,4]triazolo[1,5-a]pyridin-8-yl)propyl) hexahydropyrazino[2,1-c][1,4]oxazin-4(3H)-one was obtained as a mixture of stereoisomers from tert-butyl 4-oxo-3-(prop-2-yn-1-yl)hexahydropyrazino[2,1-c][1,4] oxazine-8(1H)-carboxylate (280 mg, 0.951 mmol, 1.0 equiv.) and 8-bromo-[1,2,4]triazolo[1,5-a]pyridine in similar fashion as described for the synthesis of example 80, Step 2. LCMS: m/z=316.1 [M+H]+.

Step 4: The title compound was prepared as a mixture of stereoisomers from 3-(3-([1,2,4]triazolo[1,5-a]pyridin-8-yl) propyl)hexahydropyrazino[2,1-c][1,4]oxazin-4(3H)-one (60 mg, 0.19 mmol, 1.0 equiv.) and 6-fluoronicotinonitrile in similar fashion as described for the synthesis of Example 63. LCMS: m/z=418.1 [M+H]+.

Example 86: Synthesis of (7S,8aS)-7-((Z)-3-([1,2,4]triazolo[1,5-a]pyridin-8-yl)allyl)-2-(5-fluoropyrimidin-2-yl)hexahydropyrrolo[1,2-a]pyrazin-6(2H)-one

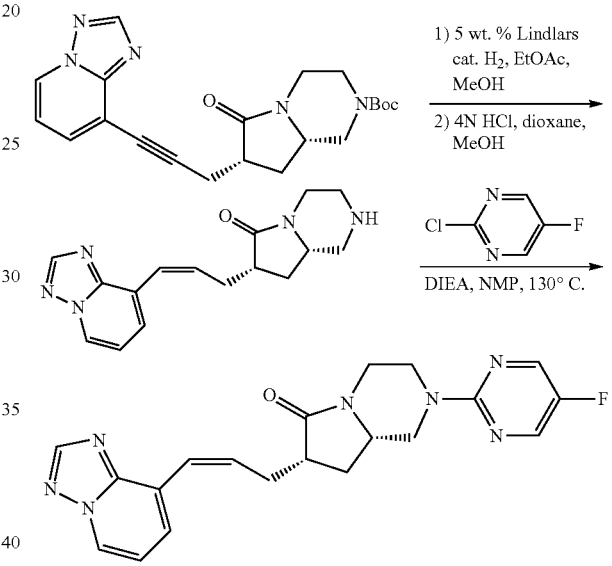

Step 1: To a solution of tert-butyl (7S,8aS)-7-(3-([1,2,4] triazolo[1,5-a]pyridin-8-yl)prop-2-yn-1-yl)-6-oxohexahydropyrrolo[1,2-a]pyrazine-2(1H)-carboxylate (250 mg, 0.632 mmol, 1.0 equiv.) and quionoline (12 mg, 0.095 mmol, 0.15 equiv.) in EtOAc/MeOH (3:1, 6 mL) was added 5 wt. % Lindlar catalyst (50 mg). The mixture was stirred under H2 atmosphere for 16 h and filtered through celite. Purificaiton by reverse phase HPLC gave tert-butyl (7S, 8aS)-7-((Z)-3-([1,2,4]triazolo[1,5-a]pyridin-8-yl)allyl)-6-oxohexahydropyrrolo[1,2-a]pyrazine-2(1H)-carboxylate. LCMS: m/z=398.2 [M+H]+.

Step 2: To a solution of tert-butyl (7S,8aS)-7-((Z)-3-([1, 2,4]triazolo[1,5-a]pyridin-8-ypallyl)-6-oxohexahydropyrrolo[1,2-a]pyrazine-2(1H)-carboxylate (37 mg, 0.093 mmol, 1.0 equiv.) in MeOH (1.0 mL) was added a solution of 4N HCl in dioxane (2.0 mL). The mixture was stirred at rt for 3 h and concentrated in vacuo. to give the amine, (7S,8aS)-7-(Z)-3-([1,2,4]triazolo[1,5-a]pyridin-8-yl)allyl)hexahydropyrrolo[1,2-a]pyrazin-6(2H)-one as an HCl salt. LCMS: m/z=298.2 [M+H]+.

Step 3: A mixture of (7S,8aS)-7-((Z)-3-([1,2,4]triazolo[1, 5-a]pyridin-8-yl)allyl)hexahydropyrrolo[1,2-a]pyrazin-6 (2H)-one HCl salt (from above), 2-chloro-5-fluoropyrimidine (19 mg, 0.15 mmol, 1.5 equiv.), and DIEA (24 mg, 0.19 mmol, 2.0 equiv.) in NMP (1.5 mL) was heated to 130 C by microwave irradiation for 1 h. The mixture was cooled to rt, and partitioned between EtOAc and water. The layers were separated and the aqueous phase was back-extracted w/EtOAc. The organics were dried over MgSO4, filtered, and concentrated. Purification by silica gel chromatography (0% MeOH in EtOAc gradient to 10% MeOH in EtOAc) gave the title compound as a white solid. LCMS: m/z=395.1 [M+H]$^+$.

Example 87: Synthesis of (7S,8aS)-2-(5-fluoropyridin-2-yl)-7-(3-(pyrazolo[1,5-a]pyridin-4-yl)propyl)hexahydropyrrolo[1,2-a]pyrazin-6(2H)-one

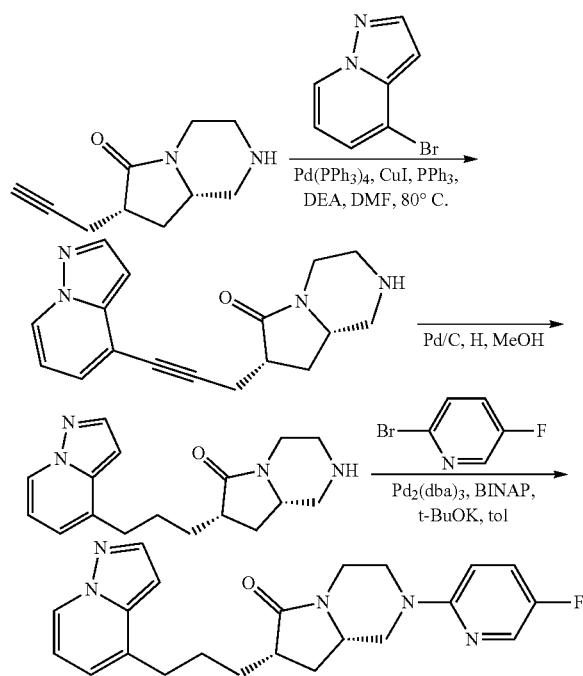

Step 1: (7S,8aS)-7-(3-(pyrazolo[1,5-a]pyridin-4-yl)propyl)hexahydropyrrolo[1,2-a]pyrazin-6(2H)-one was prepared from (7S,8aS)-7-(prop-2-yn-1-yl)hexahydropyrrolo[1,2-a]pyrazin-6(2H)-one (99 mg, 0.56 mmol, 1.0 equiv.) and 4-bromopyrazolo[1,5-a]pyridine as described for the synthesis of Example 31, steps 1-2. LCMS: m/z=299.1 [M+H]$^+$.

Step 2: The title compound was prepared from (7S,8aS)-7-(3-(pyrazolo[1,5-a]pyridin-4-yl)propyl)hexahydropyrrolo[1,2-a]pyrazin-6(2H)-one (30 mg, 0.10 mmol, 1.0 equiv.) and 2-bromo-5-fluoropyridine as described for the synthesis of Example 78, step 6. LCMS: m/z=394.1 [M+H]$^+$.

Example 88: (7S,8aS)-2-(5-fluoropyrimidin-2-yl)-7-(3-(pyrazolo[1,5-a]pyridin-4-yl)propyl)hexahydropyrrolo[1,2-a]pyrazin-6(2H)-one

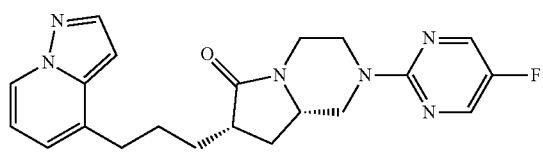 [SMILES: O=C1[C@@H](CCCc2cccn3nccc23)C[C@H]2CN(c3ncc(F)cn3)CCN12]

The title compound was prepared from (7S,8aS)-7-(3-(pyrazolo[1,5-a]pyridin-4-yl)propyl)hexahydropyrrolo[1,2-a]pyrazin-6(2H)-one (70 mg, 0.24 mmol, 1.0 equiv.) and 2-chloro-5-fluoropyrimidine in a similar fashion as described for Example 63. LCMS: m/z=395.4 [M+H]$^+$.

Example 89: Synthesis of (8aS)-7-(3-(6-fluoroimidazo[1,2-a]pyridin-5-yl)propyl)-2-(5-fluoropyridin-2-yl)hexahydropyrrolo[1,2-a]pyrazin-6(2H)-one

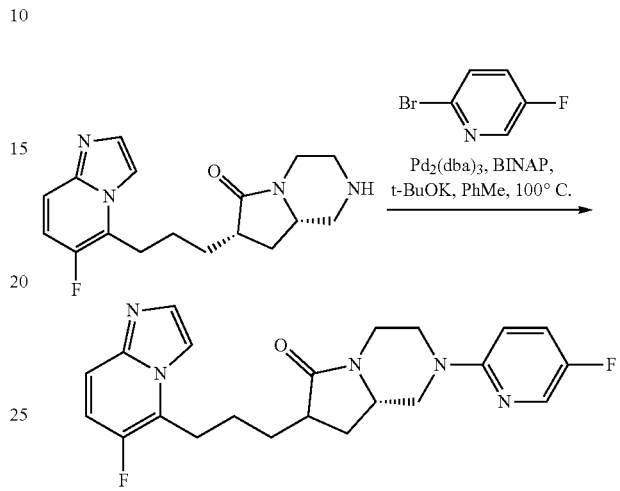

Step 1: (7S,8aS)-7-(3-(6-fluoroimidazo[1,2-a]pyridin-5-yl)propyl)hexahydropyrrolo[1,2-a]pyrazin-6(2H)-one was prepared from tert-butyl (7S,8aS)-6-oxo-7-(prop-2-yn-1-yl)hexahydropyrrolo[1,2-a]pyrazine-2(1H)-carboxylate (136 mg, 0.488 mmol, 1.0 equiv.) and 5-bromo-6-fluoroimidazo[1,2-a]pyridine in similar fashion as described for the synthesis of Example 78, steps 3-5. LCMS: m/z=317.2 [M+H]$^+$.

Step 2: The title compound was prepared from (7S,8aS)-7-(3-(6-fluoroimidazo[1,2-a]pyridin-5-yl)propyl)hexahydropyrrolo[1,2-a]pyrazin-6(2H)-one (38 mg, 0.12 mmol, 1.0 equiv.) and 2-bromo-5-fluoropyridine as described for the synthesis of Example 78, step 6. LCMS: m/z=412.1 [M+H]$^+$.

Example 90: Synthesis of (7S,8aS)-2-(5-fluoropyridin-2-yl)-7-(3-(pyridazin-3-yl)propyl)hexahydropyrrolo[1,2-a]pyrazin-6(2H)-one

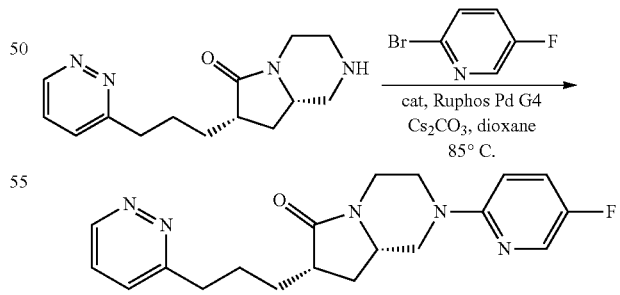

Step 1: (7S,8aS)-7-(3-(pyridazin-3-yl)propyl)hexahydropyrrolo[1,2-a]pyrazin-6(2H)-one was prepared from tert-butyl (7S,8aS)-6-oxo-7-(prop-2-yn-1-yl)hexahydropyrrolo[1,2-a]pyrazine-2(1H)-carboxylate (335 mg, 1.20 mmol, 1.0 equiv.) and 3,6-dibromopyridazine in similar fashion as described for the synthesis of Example 78, steps 3-5. LCMS: m/z=317.2 [M+H]$^+$.

Step 2: The title compound was prepared from (7S,8aS)-7-(3-(pyridazin-3-yl)propyl)hexahydropyrrolo[1,2-a]pyrazin-6(2H)-one (50 mg, 0.19 mmol, 1.0 equiv.) and 2-bromo-5-fluoropyridine as described for the synthesis of Example 62, step 3 with the exception that RuPhos Pd G4 was employed as catalyst. LCMS: m/z=356.1 [M+H]⁺.

Example 91: Synthesis of (7S,8aS)-2-(5-methylpyridin-2-yl)-7-(3-(pyridazin-3-yl)propyl)hexahydropyrrolo[1,2-a]pyrazin-6(2H)-one

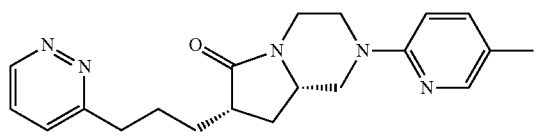 [SMILES: Cc1ccc(N2CCN3C(=O)[C@@H](CCCc4cccnn4)C[C@H]3C2)nc1]

The title compound was prepared from (7S,8aS)-7-(3-(pyridazin-3-yl)propyl)hexahydropyrrolo[1,2-a]pyrazin-6(2H)-one (50 mg, 0.19 mmol, 1.0 equiv.) and 2-bromo-5-methylpyridine as described for the synthesis of Example 90. LCMS: m/z=352.2 [M+H]⁺.

Example 92: Synthesis of (7S,8aS)-2-(5-fluoropyrimidin-2-yl)-7-(3-(quinoxalin-5-yl)propyl)hexahydropyrrolo[1,2-a]pyrazin-6(2H)-one

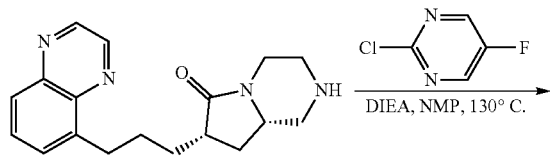

Step 1 (7S,8aS)-7-(3-(quinoxalin-5-yl)propyl)hexahydropyrrolo[1,2-a]pyrazin-6(2H)-one was prepared from tert-butyl (7S,8aS)-6-oxo-7-(prop-2-yn-1-yl)hexahydropyrrolo[1,2-a]pyrazine-2(1H)-carboxylate (250 mg, 0.898 mmol, 1.0 equiv.), and 5-bromoquinoxaline in similar fashion as described for the synthesis of Example 77, steps 3-5. LCMS: m/z=311.1 [M+H]⁺.

Step 2: The title compound was prepared from (7S,8aS)-7-(3-(quinoxalin-5-yl)propyl)hexahydropyrrolo[1,2-a]pyrazin-6(2H)-one (60 mg, 0.193 mmol, 1.0 equiv,) and 2-chloro-5-fluoropyrimidine in a similar fashion as described for Example 63. LCMS: m/z=407.1 [M+H]⁺.

Example 93: Synthesis of (7S,8aS)-2-(5-fluoropyridin-2-yl)-7-(3-(quinoxalin-5-yl)propyl)hexahydropyrrolo[1,2-a]pyrazin-6(2H)-one

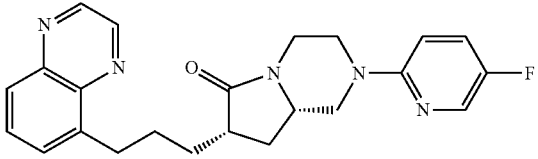 [SMILES: O=C1[C@@H](CCCc2cccc3nccnc23)C[C@H]2CN(c3ccc(F)cn3)CCN12]

The title compound was prepared from (7S,8aS)-7-(3-(quinoxalin-5-yl)propyl)hexahydropyrrolo[1,2-a]pyrazin-6(2H)-one (38 mg, 0.122 mmol, 1.0 equiv,) and 2-bromo-5-fluoropyridine as described for the synthesis of Example 78, step 6. LCMS: m/z=406.1 [M+H]⁺.

Example 94: Synthesis of (7S,8aS)-2-(6-methylpyridazin-3-yl)-7-(3-(quinoxalin-5-yl)propyl)hexahydropyrrolo[1,2-a]pyrazin-6(2H)-one

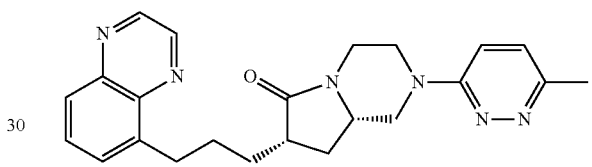

The title compound was prepared from (7S,8aS)-7-(3-(quinoxalin-5-yl)propyl)hexahydropyrrolo[1,2-a]pyrazin-6(2H)-one (60 mg, 0.19 mmol, 1.0 equiv,) and 3-bromo-6-methylpyridazine as described for the synthesis of Example 78, step 6. LCMS: m/z=403.1 [M+H]⁺.

Example 95: Synthesis of (7S,8aS)-7-(3-(2-cyclopropyl-3-fluorophenyl)propyl)-2-(6-methylpyridazin-3-yl)hexahydropyrrolo[1,2-a]pyrazin-6(2H)-one

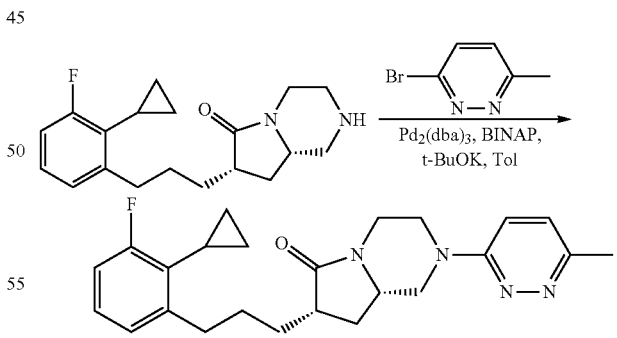

Step 1: (7S,8aS)-7-(3-(2-cyclopropyl-3-fluorophenyl)propyl)hexahydropyrrolo[1,2-a]pyrazin-6(2H)-one was prepared from tert-butyl (7S, 8aS)-6-oxo-7-(prop-2-yn-1-yl)hexahydropyrrolo[1,2-a]pyrazine-2(1H)-carboxylate (582 mg, 2.09 mmol, 1.0 equiv,) and 1-bromo-2-cyclopropyl-3-fluorobenzene in similar fashion as described for the synthesis of Example 78, steps 3-5. LCMS: m/z=317.1 [M+H]⁺.

Step 2: The title compound was prepared from (7S,8aS)-7-(3-(2-cyclopropyl-3-fluorophenyl)propyl)hexahydropyrrolo[1,2-a]pyrazin-6(2H)-one (60 mg, 0.19 mmol, 1.0 equiv,) and 3-bromo-6-methylpyridazine in a similar fashion as described for Example 78, step 6. LCMS: m/z=409.1 [M+H]⁺.

Example 96: Synthesis of (7S,8aS)-7-(3-(3-fluoro-2-methylphenyl)propyl)-2-(6-methylpyridazin-3-yl)hexahydropyrrolo [1,2-a] pyrazin-6(2H)-one

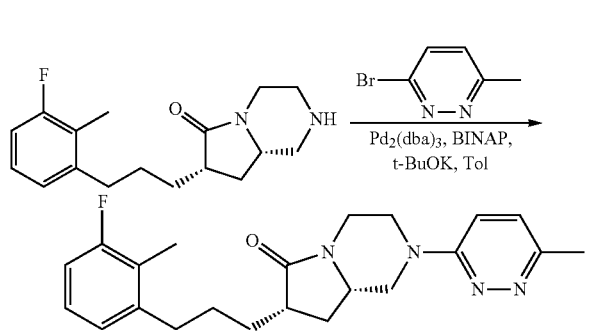

Step 1: (7S, 8aS)-7-(3-(3-fluoro-2-methylphenyl)propyl) hexahydropyrrolo[1,2-a]pyrazin-6(2H)-one was prepared from tert-butyl (7S,8aS)-6-oxo-7-(prop-2-yn-1-yl)hexahydropyrrolo[1,2-a]pyrazine-2(1H)-carboxylate (300 mg, 1.08 mmol, 1.0 equiv,) and 1-bromo-3-fluoro-2-methylbenzene in similar fashion as described for the synthesis of Example 78, steps 3-5. LCMS: m/z=307.1 [M+H]⁺.

Step 2: The title compound was prepared from (7S,8aS)-7-(3-(3-fluoro-2-methylphenyl)propyl)hexahydropyrrolo[1,2-a]pyrazin-6(2H)-one (60 mg, 0.21 mmol, 1.0 equiv,) and 3-bromo-6-methylpyridazine in a similar fashion as described for Example 78, step 6. LCMS: m/z=383.1 [M+H]⁺.

Example 97: Synthesis of (7S,8aS)-7-(3-(3-fluoro-2-methylphenyl)propyl)-2-(6-methylpyridazin-3-yl)hexahydropyrrolo[1,2-a]pyrazin-6(2H)-one

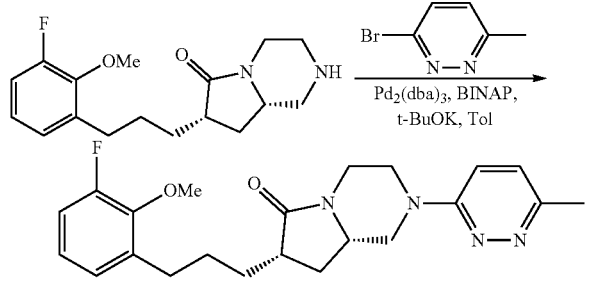

Step 1: (7S,8aS)-7-(3-(3-fluoro-2-methoxyphenyl)propyl)hexahydropyrrolo[1,2-a]pyrazin-6(2H)-one was prepared from tert-butyl (7S,8aS)-6-oxo-7-(prop-2-yn-1-yl)hexahydropyrrolo pyrazine-2(1H)-carboxylate (300 mg, 1.08 mmol, 1.0 equiv,) and 1-bromo-3-fluoro-2-methoxybenzene in similar fashion as described for the synthesis of Example 78, steps 3-5. LCMS: m/z=307.1 [M+H]⁺.

Step 2: The title compound was prepared from (7S,8aS)-7-(3-(3-fluoro-2-methoxyphenyl)propyl)hexahydropyrrolo[1,2-a]pyrazin-6(2H)-one (60 mg, 0.19 mmol, 1.0 equiv,) and 3-bromo-6-methylpyridazine in a similar fashion as described for Example 78, step 6. LCMS: m/z=399.1 [M+H]⁺.

Example 98: Synthesis of (7S,8aS)-7-(3-(4-fluoro-3-methoxyphenyl)propyl)-2-(6-methylpyridazin-3-yl)hexahydropyrrolo[1,2-a]pyrazin-6(2H)-one

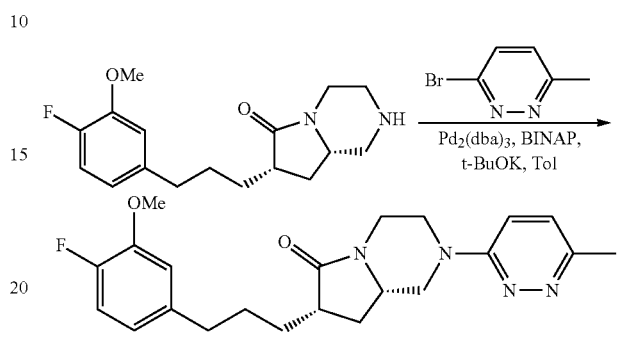

Step 1: (7S,8aS)-7-(3-(4-fluoro-3-methoxyphenyl)propyl)hexahydropyrrolo[1,2-a]pyrazin-6(2H)-one was prepared from tert-butyl (7S,8aS)-6-oxo-7-(prop-2-yn-1-yl)hexahydropyrrolo pyrazine-2(1H)-carboxylate (300 mg, 1.08 mmol, 1.0 equiv,) and 4-bromo-1-fluoro-2-methoxybenzene in similar fashion as described for the synthesis of Example 78, steps 3-5. LCMS: m/z=307.1 [M+H]⁺.

Step 2: The title compound was prepared from (7S,8aS)-7-(3-(4-fluoro-3-methoxyphenyl)propyl)hexahydropyrrolo[1,2-a]pyrazin-6(2H)-one (60 mg, 0.19 mmol, 1.0 equiv,) and 3-bromo-6-methylpyridazine in a similar fashion as described for Example 78, step 6. LCMS: m/z=399.1 [M+H]⁺.

Example 99: Synthesis of (7S,8aS)-7-((E)-3-(3,4-difluorophenyl)allyl)-2-(5-fluoropyrimidin-2-yl)hexahydropyrrolo[1,2-a]pyrazin-6(2H)-one

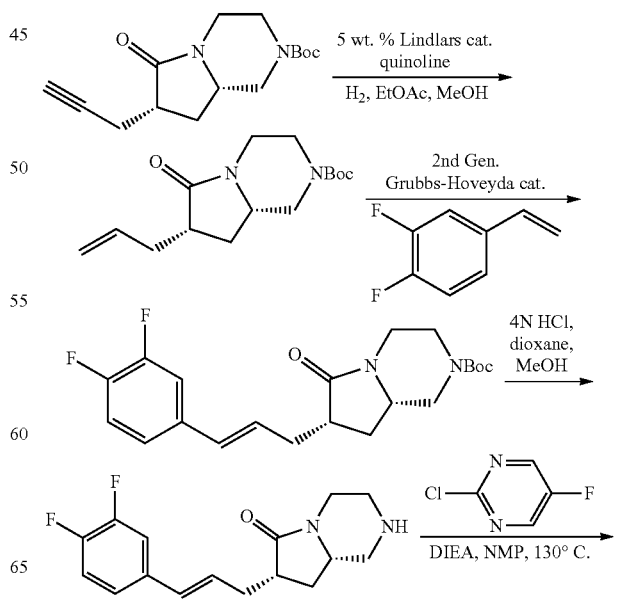

121

-continued

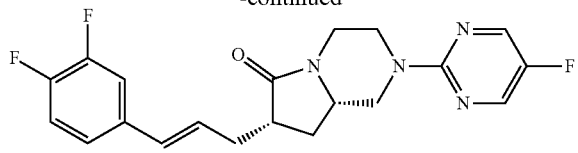

Step 1: To a solution tert-butyl (7S,8aS)-6-oxo-7-(prop-2-yn-1-yl)hexahydropyrrolo[1,2-a]pyrazine-2(1H)-carboxylate (2.00 g, 7.19 mmol, 1 equiv.) in EtOAc/MeOH (1:1, 20 mL) containing quinoline (186 mg, 1.44 mmol, 0.2 equiv.) was added 5 wt. % Lindlar catalyst. The mixture was placed under H2 atmosphere and stirred at rt for 2.5. The mixture was filtered through celite and concentrated. Purification by silica gel chromatography (30% EtOAc in hexanes gradient to 85% EtOAc in hexanes) gave tert-butyl (7S,8aS)-7-allyl-6-oxohexahydropyrrolo[1,2-a]pyrazine-2(1H)-carboxylate as a yellow solid. LCMS: m/z=281.2 [M+H]+.

Step 2: A mixture of tert-butyl (7S,8aS)-7-allyl-6-oxohexahydropyrrolo[1,2-a]pyrazine-2(1H)-carboxylate (150 mg, 0.54 mmol, 1.0 equiv.), 1,2-difluoro-4-vinylbenzene (150 mg, 1.07 mmol, 2.0 equiv.), and 2nd Generation Grubbs-Hoveyda catalyst (16.8 mg, 0.027 mmol, 0.05 equiv.) in DCE (2.5 mL) was stirred in a sealed vial at 70° C. for 4 h at which time additional catalyst (16.8 mg, 0.027 mmol, 0.05 equiv.) was added. Stirring was continued for an additional 14 h and the mixture was warmed to rt and concentrated. Purification by silica gel chromatography (30% EtOAc in hexanes gradient to 90% EtOAc in hexanes) gave tert-butyl (7S,8aS)-7-((E)-3-(3,4-difluorophenyl)allyl)-6-oxohexahydropyrrolo[1,2-a]pyrazine-2(1H)-carboxylate as a dark red oil. LCMS: m/z=393.1 [M+H]+.

Step 3: To a solution of tert-butyl (7S,8aS)-7-((E)-3-(3,4-difluorophenyl)allyl)-6-oxohexahydropyrrolo[1,2-a]pyrazine-2(1H)-carboxylate (125 mg, 0.319 mmol, 2.0 equiv.) in MeOH (1.0 mL) was added a solution of 4N HCl in dioxane (2.0 mL). The mixture was stirred at rt for 3 h and concentrated in vacuo. The resultant solid was dissolved in MeOH and loaded column containing on strong cation exchange resin. The column was eluted with MeOH (2 column volumes) and the eluants discarded. Elution with 2N NH3 in MeOH gave the product, (7S,8aS)-7-((E)-3-(3,4-difluorophenyl)allyl)hexahydropyrrolo[1,2-a]pyrazin-6(2H)-one, as the free base after concentration. LCMS: m/z=293.0 [M+H]+.

Step 4: The title compound was prepared from (7S,8aS)-7-((E)-3-(3,4-difluorophenyl)allyl)hexahydropyrrolo[1,2-a]pyrazin-6(2H)-one (67 mg, 0.23 mmol, 1.0 equiv.) and 2-chloro-5-fluoropyrimidine in a similar fashion as described for Example 63. LCMS: m/z=389.1 [M+H]+.

Example 100: Synthesis of (7S,8aS)-7-(3-(3,4-difluorophenyl)propyl)-2-(5-fluoropyrimidin-2-yl)hexahydropyrrolo[1,2-a]pyrazin-6(2H)-one

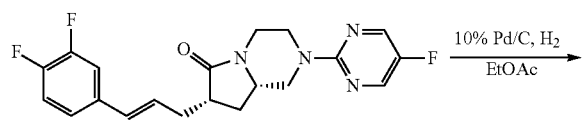

122

-continued

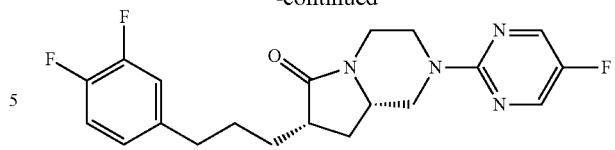

To a solution of (7S,8aS)-7-((E)-3-(3,4-difluorophenyl)allyl)-2-(5-fluoropyrimidin-2-yphexahydropyrrolo[1,2-a]pyrazin-6(2H)-one (20 mg, 0.052 mmol, 1.0 equiv.) in EtOAc (1.5 mL) was added 10% Pd/C (10 mg). The mixture was stirred under H2 atmosphere at rt for 1.5 h and conentrated in vacuo. Purification by silica gel chromatography (30% EtOAc in hexanes gradient to 75% EtOAc in hexanes) the title compound as a white solid. LCMS: m/z=391.1 [M+H]+.

Example 101: Synthesis of (7S,8aS)-7-((2-(3,4-difluorophenyl)cyclopropyl)methyl)-2-(5-fluoropyrimidin-2-yl)hexahydropyrrolo[1,2-a]pyrazin-6(2H)-one

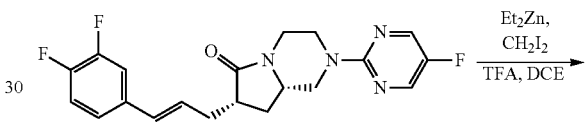

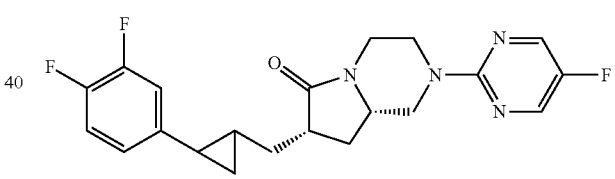

To an ice/salt cooled solution of Et2Zn solution (15 wt. % in PhMe, 417 uL, 0.46 mmol, 5.0 equiv.) further diluted with DCE (0.75 mL) under N2 atmosphere was added a solution of TFA (35 uL, 0.46 mmol, 5.0 equiv.) in DCE (0.75 mL) dropwise. After stirring for 20 min a solution of CH2I2 (37 uL, 0.46 mmol, 5.0 equiv.) in DCE (0.75 mL) was added. After another 20 min, (7S,8aS)-7-((E)-3-(3,4-difluorophenyl)allyl)-2-(5-fluoropyrimidin-2-yl)hexahydropyrrolo[1,2-a]pyrazin-6(2H)-one (36 mg, 0.093 mmol, 1.0 equiv.) in DCE (1.0 mL) was added to the mxture. The mixture was warmed to rt and stirred for 72 h at which time the reaction was quenched with 1N aqueous HCl (1.0 mL). After stirring for 20 min the mixture was partitioned between DCM and sat. NaHCO3. The phases were separated and the organics were washed with brine, dried (MgSO4), filtered and concentrated. Purification by silica gel chromatography (30% EtOAc in hexanes gradient to 80% EtOAc in hexanes) followed by purification with rev. phase HPLC gave (7S,8aS)-7-((2-(3,4-difluorophenyl)cyclopropyl)methyl)-2-(5-fluoropyrimidin-2-yl)hexahydropyrrolo[1,2-a]pyrazin-6(2H)-one as a mixture of stereoisomers. LCMS: m/z=403.1 [M+H]+.

Example 102: Synthesis of 6-((7S,8aS)-7-(3-(3,4-difluorophenyl)butyl)-6-oxohexahydropyrrolo[1,2-a]pyrazin-2(1H)-yl)nicotinonitrile

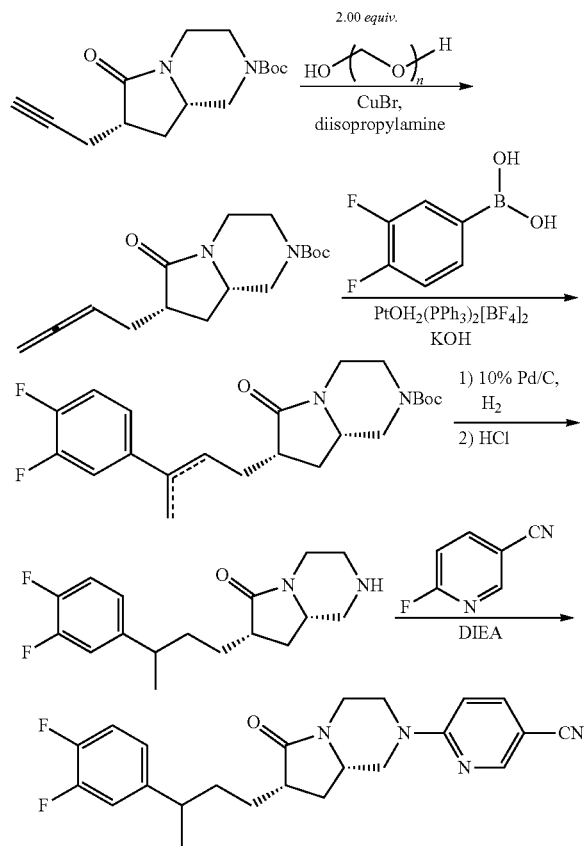

Step 1: A solution of tert-butyl (7S,8aS)-6-oxo-7-(prop-2-yn-1-yl)hexahydropyrrolo[1,2-a]pyrazine-2(1H)-carboxylate (500 mg, 1.80 mmol, 1.0 eq), diisopropylamine (365 mg, 3.60 mmol, 2.0 eq), Copper (I) bromide (90 mg, 0.63 mmol, 0.35 eq), and paraformaldehyde (108 mg, 2.0 eq with respect to monomer) in dioxane (2.5 mL) was heated in a sealed tube at 100° C. for 18 h. The mixture was cooled to rt and partitioned between EtOAc and 1N aq. HCl. The layers were separated and the organics were washed sequentially with 1N aq. HCl and brine. The organics were dried over MgSO4, filtered, and concentrated. Purification by silica gel chromatography (45% EtOAc in hexanes gradient to 85% EtOAc in hexanes) gave tert-butyl (7S,8aS)-7-(3λ⁵-buta-2,3-dien-1-yl)-6-oxohexahydropyrrolo[1,2-a]pyrazine-2(1H)-carboxylate as a yellow solid. LCMS: m/z=293.1 [M+1]$^+$.

Step 2: A mixture of the allene (85 mg, 0.29 mmol, 1.0 eq), (3,4-difluorophenyl)boronic acid (92 mg, 0.58 mmol, 2.0 equiv.), PtOH$_2$(PPh$_3$)$_2$[BF$_4$]$_2$ (24 mg, 0.15 mmol, 0.05 eq), KOH (82 mg, 1.45 mmol, 5.0 eq) in dioxane (2.5 mL) containing H$_2$O (0.125 mL) was stirred in a sealed vial at 100° C. for 16 h. After cooling to rt the mixture was diluted with EtOAc, and MgSO$_4$ was added. The mixture was filtered and concentrated. Purification by silica gel chromatography (30% EtOAc in hexanes gradient to 75% EtOAc in hexanes gave a mixture of tert-butyl (7S,8aS)-7-((E)-3-(3,4-difluorophenyl)but-2-en-1-yl)-6-oxohexahydropyrrolo[1,2-a]pyrazine-2(1H)-carboxylate and tert-butyl (7S,8aS)-7-(3-(3,4-difluorophenyl)but-3-en-1-yl)-6-oxohexahydropyrrolo pyrazine-2(1H)-carboxylate LCMS: m/z=407.2 [M+1]$^+$.

Step 3: To a solution of the alkene isomers from step 2 in EtOAc/MeOH (2: 1, 4 mL) was added 10% Pd/C (25 mg). The heterogeneous mixture was stirred under H$_2$ balloon for 1 h. The mixture was filtered and concentrated. The concentrate was dissolved in MeOH (0.5 mL) and treated with 4N HCl dioxane (1.0 mL). The mixture was stirred at rt for 1 h and concentrated to give the resultant amine, (7S,8aS)-7-(3-(3,4-difluorophenyl)butyphexahydropyrrolo[1,2-a]pyrazin-6(2H)-one hydrochloride as a white solid LCMS: m/z=309.2 [M+1]$^+$.

Step 4: A mixture of (7S,8aS)-7-(3-(3,4-difluorophenyl)butyl)hexahydropyrrolo[1,2-a]pyrazin-6(2H)-one hydrochloride (17 mg, 0.05 mmol, 1.0 eq), 6-fluoronicotinonitrile (18 mg, 0.15 mmol, 3.0 eq), DIEA (25 mg, 0.20 mmol, 4.0 eq) in NMP (1.0 mL) was stirred in a sealed vial at 120° C. for 72 h. The mixture was purified by rev. phase HPLC. Further purification by silica gel chromatography (40% EtOAc in hexanes to 85% EtOAc in hexanes gave 6-((7S,8aS)-7-(3-(3,4-difluorophenyl)butyl)-6-oxohexahydropyrrolo[1,2-a]pyrazin-2(1H)-yl)nicotinonitrile as a white solid LCMS: m/z=411.1 [M+1]$^+$.

Example 103: Synthesis of (7S,8aS)-7-(3-(3,4-difluorophenyl)butyl)-2-(5-fluoropyrimidin-2-yl)hexahydropyrrolo[1,2-a] pyrazin-6(2H)-one

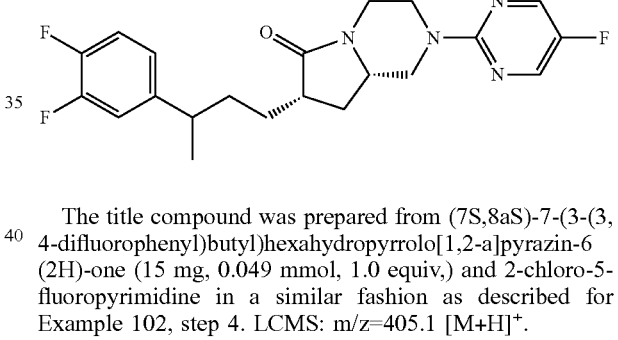

The title compound was prepared from (7S,8aS)-7-(3-(3,4-difluorophenyl)butyl)hexahydropyrrolo[1,2-a]pyrazin-6(2H)-one (15 mg, 0.049 mmol, 1.0 equiv,) and 2-chloro-5-fluoropyrimidine in a similar fashion as described for Example 102, step 4. LCMS: m/z=405.1 [M+H]$^+$.

Example 104: Synthesis of (7S,8aS)-7-(3-([1,2,4]triazolo[1,5-a]pyridin-8-yl)butyl)-2-(5-fluoropyridin-2-yl)hexahydropyrrolo [1,2-a] pyrazin-6(2H)-one

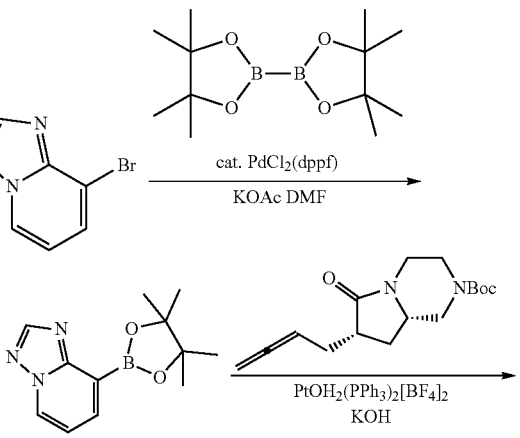

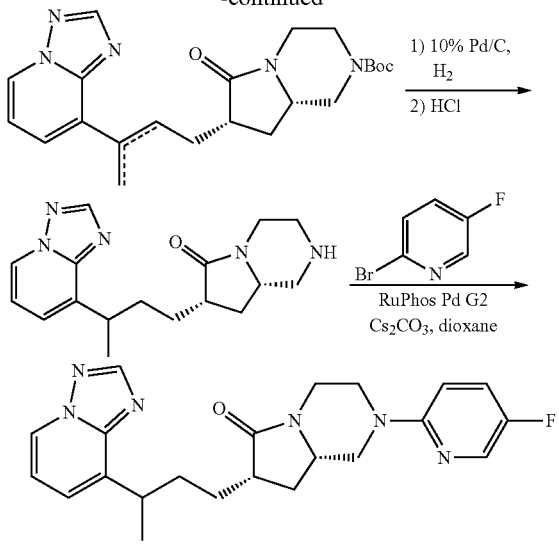

Step 1: A mixture of 8-bromo-[1,2,4]triazolo[1,5-a]pyridine (1.00 g, 5.05 mmol, 1.0 equiv.), 4,4,4',4',5,5,5',5'-octamethyl-2,2'-bi(1,3,2-dioxaborolane) (1.60 g, 6.31 mmol, 1.25 equiv.), potassium acetate (991 mg, 10.1 mmol, 2.0 equiv.), and $PdCl_2$ (dppf).DCM (206 mg, 0.252 mmol, 0.05 equiv.) in DMF (8.0 ml) was heated to 100° C. for 20 h. The mixture was diluted with EtOAc and plugged through celite to give 8-(4,4,5,5-tetramethyl-1,3,2-dioxaborolan-2-yl)-[1,2,4]triazolo[1,5-a]pyridine as a black sludge after concentration. LCMS: m/z=164.1 [M+H−86]$^+$.

Step 2: (7S,8aS)-7-(3-([1,2,4]triazolo[1,5-a]pyridin-8-yl)butyl)hexahydropyrrolo[1,2-a]pyrazin-6(2H)-one was prepared from tert-butyl (7S,8aS)-7-(315-buta-2,3-dien-1-yl)-6-oxohexahydropyrrolo[1,2-a]pyrazine-2(1H)-carboxylate (130 mg, 0.444 mmol, 1.0 equiv.) and 8-(4,4,5,5-tetramethyl-1,3,2-dioxaborolan-2-yl)-[1,2,4]triazolo[1,5-a]pyridine (153 mg of isomer mixture, 0.623 mmol, 1.40 equiv.) in similar fashion as described for the synthesis of Example 102 steps 2 and 3. LCMS: m/z=314.2 [M+H]$^+$.

Step 3: The title compound was prepared from (7S,8aS)-7-(3-([1,2,4]triazolo[1,5-a]pyridin-8-yl)butyphexahydropyrrolo[1,2-a]pyrazin-6(2H)-one (1.7 mg, 0.0054 mmol, 1.0 equiv.) and 2-bromo-5-fluoropyridine in similar fashion as described for the synthesis of Example 62, step 3. LCMS: m/z=409.1 [M+H]$^+$.

Example 105: Synthesis of 6-((7S,8aS)-7-(3-(3,4-difluorophenyl)-3-hydroxypropyl)-6-oxohexahydropyrrolo[1,2-a]pyrazin-2(1H)-yl)nicotinonitrile

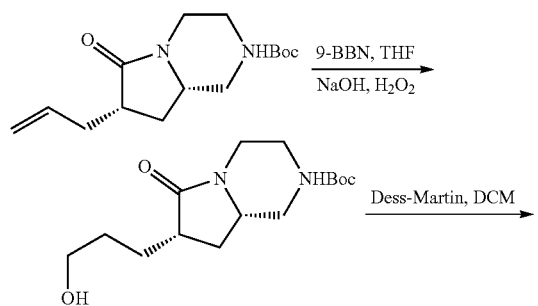

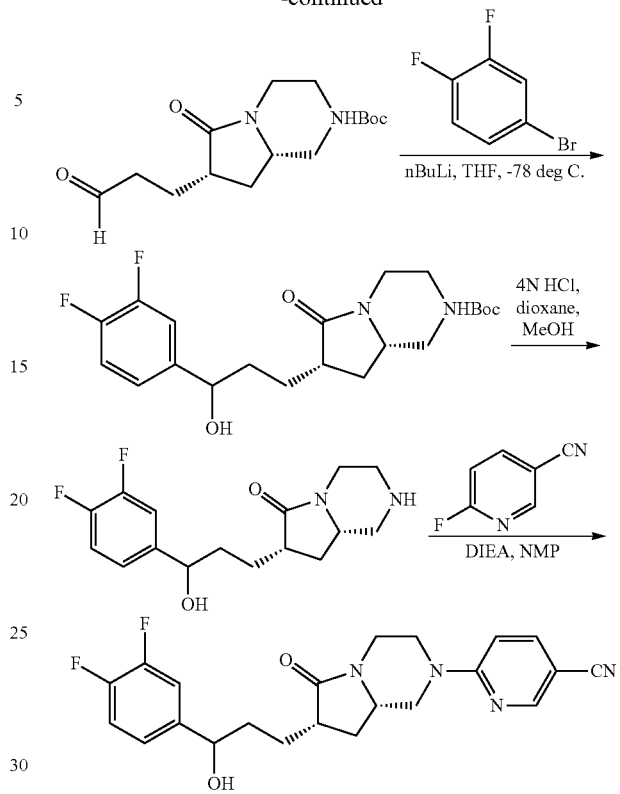

Step 1: To a solution of tert-butyl (7S,8aS)-7-allyl-6-oxohexahydropyrrolo[1,2-a]pyrazine-2(1H)-carboxylate (1.87 g, 6.68 mmol, 1.0 equiv.) in THF (3.5 mL) under $N_2$ was added 9-BBN solution (0.5M in THF, 20.0 mL, 10.0 mmol, 1.5 equiv.). The mixture was stirred for 20 h at rt, cooled to 0° C. and 1N aq. NaOH (1.5 mL) was added followed by the dropwise addition of 30% aq. $H_2O_2$ (1.5 mL). Stirring was continued for 1 h while the mixture slowly warmed to rt. The mixture was diluted with brine and extracted sequentially with EtOAc and DCM. The combined organics were dried over $MgSO_4$, filtered, and concentrated. Purification by silica gel chromatography (0% MeOH in EtOAc gradient to 15% MeOH in EtOAc) gave tert-butyl (7S,8aS)-7-(3-hydroxypropyl)-6-oxohexahydropyrrolo[1,2-a]pyrazine-2(1H)-carboxylate as a clear oil. LCMS: m/z=299.2 [M+H]$^+$.

Step 2: A mixture of gave tert-butyl (7S,8aS)-7-(3-hydroxypropyl)-6-oxohexahydropyrrolo[1,2-a]pyrazine-2(1H)-carboxylate (400 mg, 1.34 mmol, 1.0 equiv.) and Dess-Martin periodinane (682 mg, 1.61 mol, 1.2 equiv.) in DCM (3.5 mL) was stirred at rt for 3.5 h and concentrated in vacuo. Purification by silica gel chromatography (EtOAc) gave tert-butyl (7S,8aS)-6-oxo-7-(3-oxopropyl)hexahydropyrrolo[1,2-a]pyrazine-2(1H)-carboxylate as a clear oil. LCMS: m/z=297.1 [M+H]$^+$.

Step 3: To a solution of the 4-bromo-1,2-difluorobenzene (111 mg, 0.574 mmol, 2.0 equiv.) in THF (2.0 mL) cooled to −78° C. under $N_2$ was added a solution of n-BuLi (1.6M in hexanes, 0.359 mL, 0.574 mmol, 2.0 equiv.). The mixture was stirred for 20 min at which time a solution of the tert-butyl (7S,8aS)-6-oxo-7-(3-oxopropyl)hexahydropyrrolo[1,2-a]pyrazine-2(1H)-carboxylate (85 mg, 0.287 mmol, 1.0 equiv.) in THF (2.0 mL) was added slowly. The mixture was stirred for 1 h at −78° C., quenched by the addition of sat.

NH₄Cl, and extracted with EtOAc. Purification by silica gel chromatography (30% EtOAc in hexanes gradient to 80% EtOAc in hexanes) gave tert-butyl (7S,8aS)-7-(3-(3,4-difluorophenyl)-3-hydroxypropyl)-6-oxohexahydropyrrolo[1,2-a]pyrazine-2(1H)-carboxylate as a mixture of diastereomers. LCMS: m/z=411.2 [M+H]⁺.

Step 4: To a solution of tert-butyl (7S,8aS)-7-(3-(3,4-difluorophenyl)-3-hydroxypropyl)-6-oxohexahydropyrrolo[1,2-a]pyrazine-2(1H)-carboxylate (18 mg, 0.044 mmol, 1.0 equiv.) in MeOH (0.5 mL) was added 4N HCl in dioxane (1.5 mL). The mixture was stirred at rt for 2 h and concentrated in vacuo. The concentrate was dissolved in NMP (1.0 mL). DIEA (28 mg, 0.22 mmol, 5.0 equiv.) and 6-fluoronicotinonitrile (19 mg, 0.15 mmol, 3.5 equiv.) were added and the mixture was stirred in a sealed vial at 120° C. for 72 h. Purification by reverse phase HPLC gave the title compound as a mixture of diastereomers. LCMS: m/z=457.3 [M+H]⁺.

Example 106: Synthesis of 6-((7S,8aS)-7-(3,3-difluoro-3-(2-methoxypyridin-4-yl)propyl)-6-oxohexahydropyrrolo[1,2-a]pyrazin-2(1H)-yl)nicotinonitrile

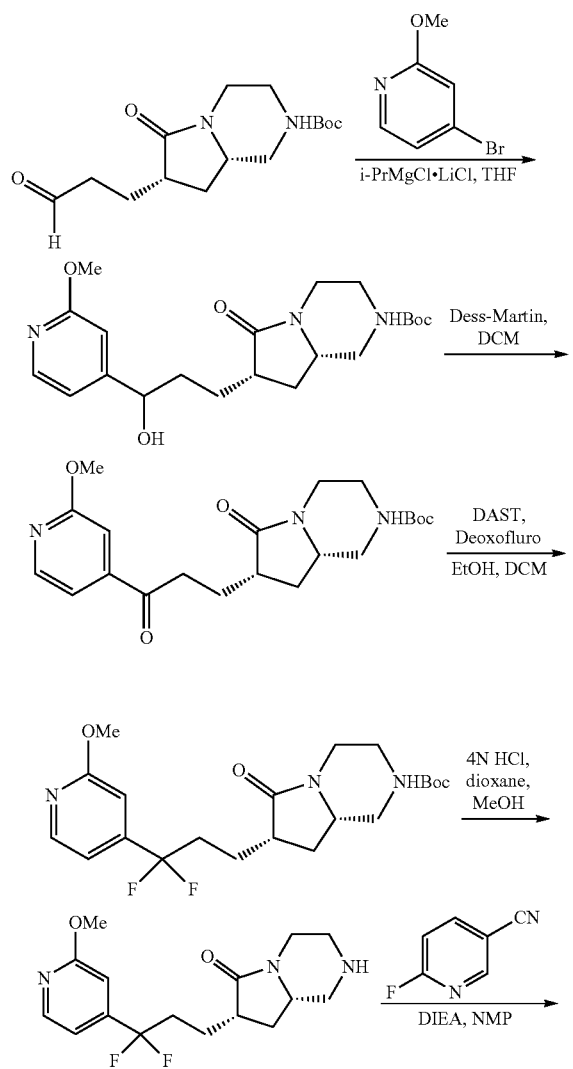

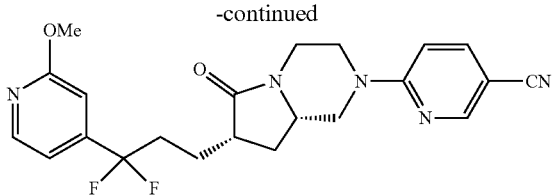

Step 1: To a solution of 4-iodo-2-methoxypyridine (174 mg, 0.739 mmol, 1.1 equiv.) in THF (2.0 mL) under N₂ cooled to −15° C. was added i-PrMgCl—LiCl solution (1.3M in THF, 0.568 mL, 0.739 mmol, 1.1 equiv.). After stirring for 20 min a solution of tert-butyl (7S,8aS)-6-oxo-7-(3-oxopropyl)hexahydropyrrolo[1,2-a]pyrazine-2(1H)-carboxylate (199 mg, 0.671 mmol, 1.0 equiv.) in THF (2.0 mL) was added. The mixture was stirred for 1 h while warming to rt, quenched by the addition of sat. aqueous NH₄Cl, and extracted with EtOAc (2×). The organics were dried over MgSO₄, filtered, and concentrated. Purification by silical gel chromatography (0% EtOAc in EtOAc gradient to 5% MeOH in EtOAc) gave tert-butyl (7S, 8aS)-7-(3-hydroxy-3-(2-methoxypyridin-4-yl)propyl)-6-oxohexahydropyrrolo[1,2-a]pyrazine-2(1H)-carboxylate as a clear oil. LCMS: m/z=406.2 [M+H]⁺.

Step 2: To a solution of tert-butyl (7S,8aS)-7-(3-hydroxy-3-(2-methoxypyridin-4-yl)propyl)-6-oxohexahydropyrrolo[1,2-a]pyrazine-2(1H)-carboxylate (105 mg, 0.258 mmol, 1.0 equiv.) in DCM (3 mL) was added Dess-Martin periodinane (164 mg, 0.387 mmol, 1.5 equiv.). The mixture was stirred at rt for 3 h and concentrated in vacuo. Purification by silica gel chromatography (60% EtOAc in hexanes gradient to 100% EtOAc in hexanes) gave tert-butyl (7S, 8aS)-7-(3-hydroxy-3-(2-methoxypyridin-4-yl)propyl)-6-oxohexahydropyrrolo[1,2-a]pyrazine-2(1H)-carboxylate as a white solid. LCMS: m/z=404.2 [M+H]⁺.

Step 3: To a solution of tert-butyl (7S,8aS)-7-(3-hydroxy-3-(2-methoxypyridin-4-yl)propyl)-6-oxohexahydropyrrolo[1,2-a]pyrazine-2(1H)-carboxylate (90 mg, 0.22 mmol, 1.0 equiv.) in DCM (2.0 ml) was added DAST (90 mg, 0.56 mmol, 2.5 equiv.). EtOH (5.1 mg, 0.11 mmol, 0.5 equiv.) was added and the mixture was stirred at rt for 26 h at which time a solution of DeoxoFluor (2.7M in PhMe, 0.16 mL, 0.44 mmol, 2.0 equiv.) was added and stirring was continued for 96 h. Additional DeoxoFluor (2.7M in PhMe, 0.20 mL, 0.55 mmol, 2.5 equiv.). The mixture was stirred heated to 60° C. and stirred for 24 h. The mixture was cooled to rt and washed with sat. aq. NaHCO₃. The organics were dried over MgSO₄, filtered, and concentrated. Purification by silica gel chromatography (0% MeOH in hexanes gradient to 5% MeOH in hexanes) gave tert-butyl (7S,8aS)-7-(3,3-difluoro-3-(2-methoxypyridin-4-yl)propyl)-6-oxohexahydropyrrolo[1,2-a]pyrazine-2(1H)-carboxylate. LCMS: m/z=426.1 [M+H]⁺.

Step 4: The title compound was prepared from tert-butyl (7S,8aS)-7-(3,3-difluoro-3-(2-methoxypyridin-4-yl)propyl)-6-oxohexahydropyrrolo[1,2-a]pyrazine-2(1H)-carboxylate (3 mg, 0.007 mmol, 1.0 equiv.) and 6-fluoronicotinonitrile in similar fashion as described for the synthesis of Example 10, step 5. LCMS: m/z=428.1 [M+H]⁺.

Examples 107-110: Examples 107-110 are prepared in a similar manner as described in Examples 1-5.

| Example | Structure | Name |
|---|---|---|
| 107 | 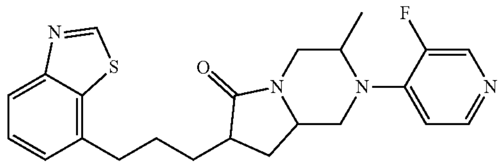 [SMILES: CC1CN2C(=O)C(CCCc3cccc4ncsc34)CC2CN1c1ccncc1F] | 7-(3-(benzo[d]thiazol-7-yl)propyl)-2-(3-fluoropyridin-4-yl)-3-methylhexahydropyrrolo[1,2-a]pyrazin-6(2H)-one |
| 108 | 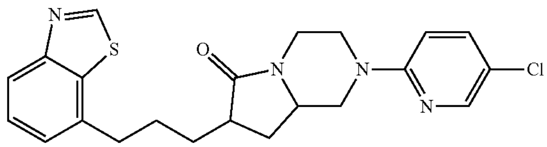 [SMILES: O=C1C(CCCc2cccc3ncsc23)CC2CN(c3ccc(Cl)cn3)CCN12] | 7-(3-(benzo[d]thiazol-7-yl)propyl)-2-(5-chloropyridin-2-yl)hexahydropyrrolo[1,2-a]pyrazin-6(2H)-one |
| 109 | 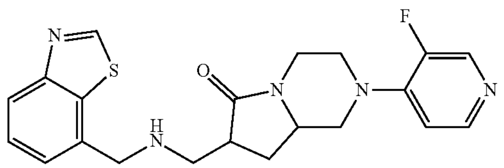 [SMILES: O=C1C(CNCc2cccc3ncsc23)CC2CN(c3ccncc3F)CCN12] | 7-(((benzo[d]thiazol-7-ylmethyl)amino)methyl)-2-(3-fluoropyridin-4-yl)hexahydropyrrolo[1,2-a]pyrazin-6(2H)-one |
| 110 | 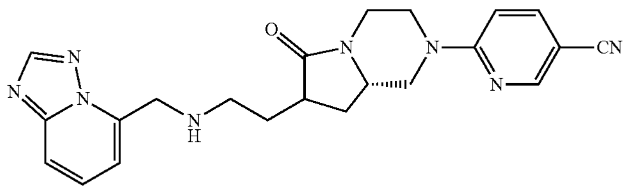 [SMILES: N#Cc1ccc(N2CCN3C(=O)C(CCNCc4cccc5ncnn45)C[C@H]3C2)nc1] | 6-((8aS)-7-(2-(([1,2,4]triazolo[1,5-a]pyridin-5-ylmethyl)amino)ethyl)-6-oxohexahydropyrrolo[1,2-a]pyrazin-2(1H)-yl)nicotinonitrile |

II. Biological Evaluation

Example 111: In Vitro Functional Assay of Muscarinic Acetylcholine Receptor Activity CHO-K1 cells stably expressing human M1 receptor with Aequorin (Perkin Elmer) were grown in F12 media, 10% FBS with 0.4 mg/mL geneticin and 0.25 mg/mL. Cells were grown to confluence and frozen down to be assayed at a later date. On the day of the experiment cells were thawed in a 37° C. water bath, resuspended in DMEM/HAM's F12 with HEPES (Invitrogen)+0.1% protease-free BSA (assay buffer), and spun down to remove freezing media. After centrifugation, supernatant was removed and 12 mL of assay buffer was added. Coelenterazine h (Promega) was added to the cells at a final concentration of 5 uM and incubated for 4 hours at room temperature in the dark. Compound master plate-96 deep well (Corning) were formatted in a 8-point DRC in assay buffer with 0.2% DMSO at a starting concentration of 60 uM (2×). After 4 hours of incubation, cells were plated at a concentration of 5×10$^5$ cells/well in 96 well white-walled, tissue culture-treated, clear-bottom plates (VWR). Compounds were added to the daughter plate, and cells plus compound were incubated at room temperature for 30 minutes in the dark.

Calcium flux was measured using the FlexStation 3 (Molecular Devices). To measure the antagonist dose-response, the EC80 of Acetylcholine was injected to the daughter plate using the automated compound transfer function of the Flex Station, and the increase in luminescence was measured over time. Antagonist activity was analyzed as a concentration dependent decrease in the EC80 acetylcholine response. Dose response curves were generated using Prism (GraphPad Software). The IC$_{50}$ of the compounds was calculated from the dose response curve. Results are shown in Table 1.

TABLE 1

| Example # | M1 IC$_{50}$ | M2 IC$_{50}$ | M3 IC$_{50}$ |
|---|---|---|---|
| 1 | D | D | D |
| 2 | A | C | C |
| 3 | B | D | C |
| 4 | A | B | B |
| 5 | B | C | D |
| 6 | B | C | D |
| 7 | C | C | D |
| 8 | D | D | D |
| 9 | B | C | D |
| 10 | A | B | C |
| 11 | B | B | B |
| 12 | B | C | C |
| 13 | A | B | B |
| 14 | B | C | C |
| 15 | B | D | C |
| 16 | B | B | B |
| 17 | A | C | C |
| 18 | C | C | D |
| 19 | A | B | C |
| 20 | B | C | C |
| 21 | A | C | C |
| 22 | A | B | C |
| 25 | A | C | B |
| 26 | B | D | C |
| 27 | B | D | C |
| 28 | A | B | B |
| 30 | A | C | C |
| 31 | C | D | D |
| 32 | A | B | C |
| 33 | B | C | C |
| 34 | A | C | C |
| 35 | A | D | D |
| 37 | A | C | C |
| 38 | C | D | D |
| 39 | B | D | C |

TABLE 1-continued

| Example # | M1 IC$_{50}$ | M2 IC$_{50}$ | M3 IC$_{50}$ |
|---|---|---|---|
| 40 | A | D | D |
| 41 | A | C | C |
| 42 | D | C | D |
| 43 | C | C | C |
| 44 | C | C | D |
| 45 | A | A | B |
| 46 | A | C | C |
| 47 | B | D | D |
| 48 | A | C | C |
| 49 | A | C | C |
| 50 | B | D | D |
| 52 | B | B | C |
| 53 | A | C | D |
| 54 | A | B | C |
| 55 | B | C | C |
| 56 | A | B | B |
| 57 | C | C | D |
| 58 | A | B | B |
| 59 | A | B | C |
| 60 | A | A | B |
| 61 | B | C | D |
| 62 | A | C | C |
| 63 | A | D | C |
| 64 | A | B | C |
| 65 | B | C | D |
| 66 | B | D | D |
| 67 | A | B | A |
| 68 | A | B | A |
| 71 | C | C | D |
| 72 | A | C | C |
| 78 | A | C | C |
| 87 | B | C | C |
| 88 | A | C | C |
| 89 | A | C | C |
| 93 | A | D | C |

A=IC$_{50}$ of less than 100 nM; B=IC$_{50}$ less than 1 uM (1000 nM) but greater than or equal to 100 nM; C=IC$_{50}$ less than 10 uM (10000 nM) but greater than or equal to 1 uM (1000 nM); D=IC$_{50}$ greater than 10 uM (10000 nM); NT=not tested.

Exemplary Compounds, Pharmaceutical Compositions, and Methods

Compound 1: A compound of Formula (IA):

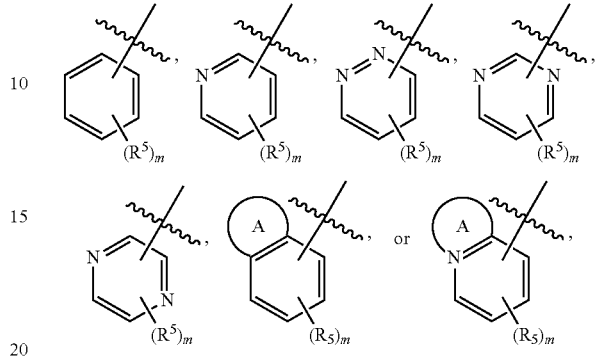

Formula (IA)

wherein: E is —CH$_2$—, —CH$_2$CH$_2$—, —O—CH$_2$—, or —CH$_2$—O—; X is a bond,

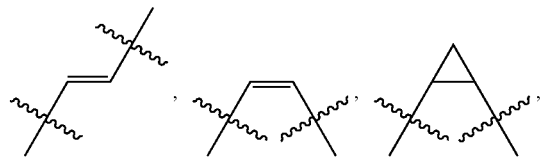

—C≡C—, —C(═O)—, —CH$_2$O—, —CH$_2$CH$_2$O—, —O—, —N(R$^7$)—, —S(O)$_2$—, —CH$_2$N(R$^7$)—, or —CH$_2$CH$_2$N(R$^7$)—; Y is a bond, —O—, or —N(R$^8$)—; R$^1$ is

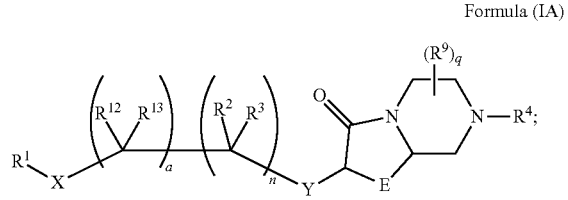

wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy; each R$^2$ is independently selected from hydrogen, deuterium, halogen, —OH, and C$_{1-6}$ alkyl; each R$^3$ is independently selected from hydrogen, deuterium, halogen, —OH, and C$_{1-6}$ alkyl; R$^4$ is

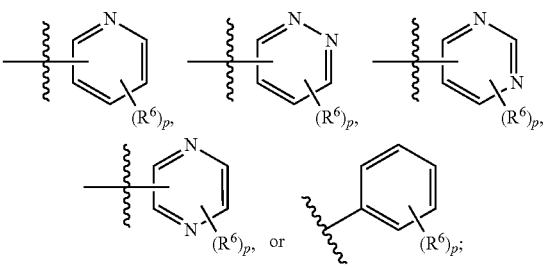

each R$^5$ is independently selected from halogen, —CN, C$_{1-6}$ alkyl, C$_{1-6}$ cycloalkyl, C$_{1-6}$ alkoxy, C$_{1-6}$ haloalkyl, and C$_{1-6}$ haloalkoxy; each R$^6$ is independently selected from hydrogen, deuterium, halogen, —CN, —N(R$^{10}$)$_2$, C$_{1-6}$ alkyl, C$_{1-6}$ alkyl-OH, C$_{1-6}$ cycloalkyl, C$_{1-6}$ alkoxy, C$_{1-6}$ haloalkyl, C$_{1-6}$ haloalkoxy, —C(═O)(C$_{1-6}$ alkyl), —(C(R$^{10}$)$_2$)$_q$—O—(C$_{1-6}$ alkyl) and —S(O)$_2$R$^{11}$; R$^7$ is hydrogen or C$_{1-6}$ alkyl; R$^8$ is hydrogen or C$_{1-6}$ alkyl; R$^9$ is hydrogen or C$_{1-6}$ alkyl; each R$^{10}$ is independently selected from H and C$_{1-6}$ alkyl; R$^{11}$ is C$_{1-6}$ alkyl; each R$^{12}$ is independently selected from hydrogen, deuterium, halogen, —OH, and C$_{1-6}$ alkyl; each R$^{13}$ is independently selected from hydrogen, deuterium, halogen, —OH, and C$_{1-6}$ alkyl; a is 1, 2, 3, 4, or 5; m is 0, 1, 2, or 3; n is 1, 2, 3, 4, or 5; p is 0, 1, 2, or 3; and each q is independently 0, 1, 2, 3, or 4;

or a pharmaceutically acceptable salt or solvate thereof.

Compound 2: Compound 1, or a pharmaceutically acceptable salt or solvate thereof, wherein: E is —CH$_2$—; X is a bond, —CH$_2$O—, —CH$_2$CH$_2$O—, —O—, —N(R$^7$)—, —S(O)$_2$—, —CH$_2$N(R$^7$)—, or —CH$_2$CH$_2$N(R$^7$)—; Y is a bond, —O—, or —N(R$^8$)—; R$^1$ is

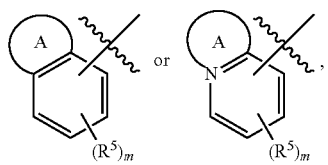

wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy; each R$^2$ is independently selected from H and C$_{1-6}$ alkyl; each R$^3$ is independently selected from H and C$_{1-6}$ alkyl; R$^4$ is

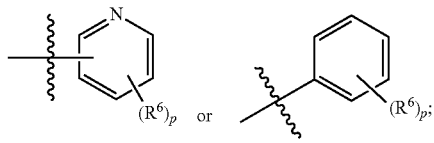

each R$^5$ is independently selected from halogen, —CN, C$_{1-6}$ alkyl, C$_{1-6}$ alkoxy, C$_{1-6}$ haloalkyl, and C$_{1-6}$ haloalkoxy; each R$^6$ is independently selected from halogen, —CN, —N(R$^{10}$)$_2$, C$_{1-6}$ alkyl, C$_{1-6}$ alkoxy, C$_{1-6}$ haloalkyl, C$_{1-6}$ haloalkoxy, and —S(O)$_2$R$^{11}$; and R$^9$ is C$_{1-6}$ alkyl.

Compound 2: Compound 1, or a pharmaceutically acceptable salt or solvate thereof, having the structure of Formula (Ia):

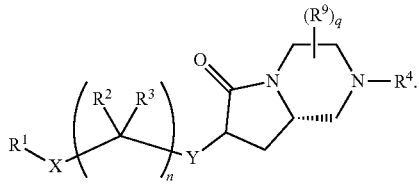

Formula (Ia)

Compound 4: Compound 1, or a pharmaceutically acceptable salt or solvate thereof, having the structure of Formula (Ib):

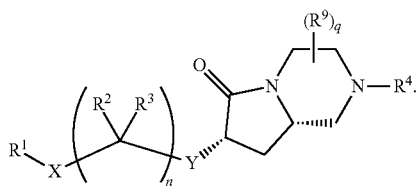

Formula (Ib)

Compound 5: Compound 1, or a pharmaceutically acceptable salt or solvate thereof, having the structure of Formula (Ic):

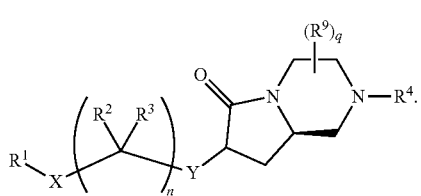

Formula (Ic)

Compound 6: Compound 1, or a pharmaceutically acceptable salt or solvate thereof, having the structure of Formula (Id):

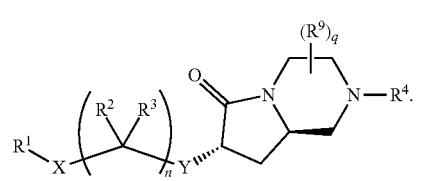

Formula (Id)

Compound 7: Compound 1, or a pharmaceutically acceptable salt or solvate thereof, having the structure of Formula (Ie):

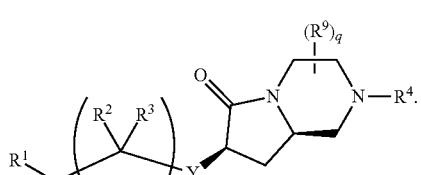

Formula (Ie)

Compound 8: Any one of Compounds 1 through 7, or a pharmaceutically acceptable salt or solvate thereof, wherein R$^1$ is

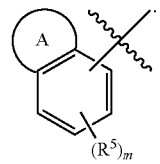

Compound 9: Any one of Compounds 1 through 8, or a pharmaceutically acceptable salt or solvate thereof, wherein ring A is a 4-, 5-, or 6-membered cycloalkyl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy.

Compound 10: Any one of Compounds 1 through 8, or a pharmaceutically acceptable salt or solvate thereof, wherein ring A is a 5- or 6-membered heteroaryl ring optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy.

Compound 11: Any one of Compounds 1 through 8 or 10, or a pharmaceutically acceptable salt or solvate thereof, wherein R$^1$ is

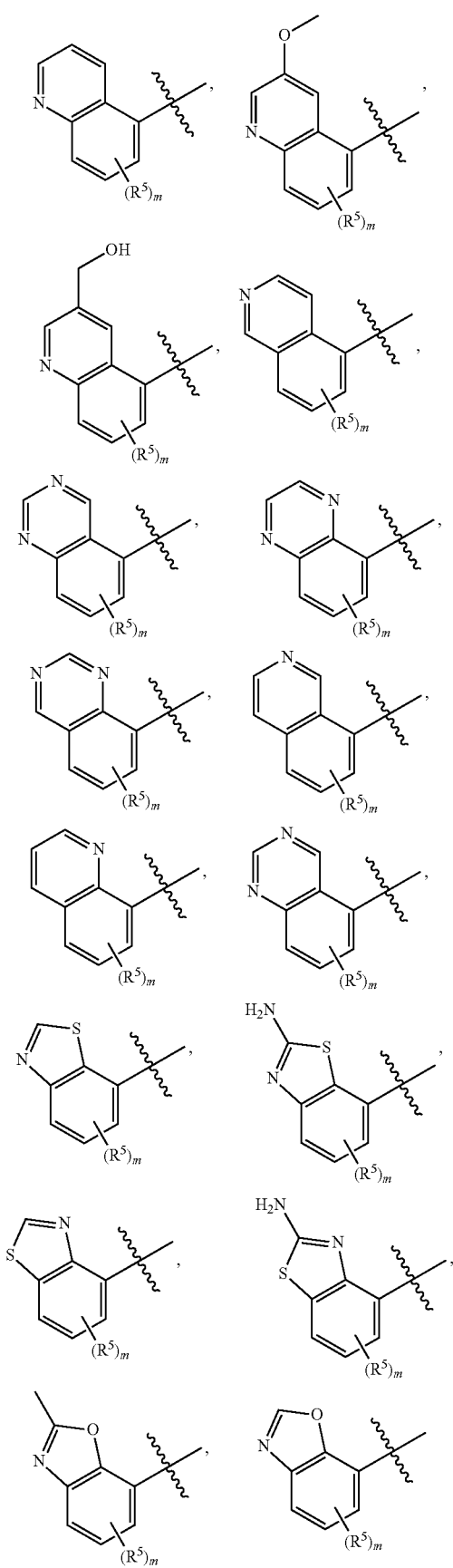

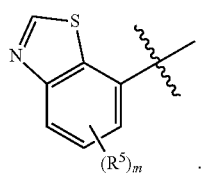

Compound 12: Any one of Compounds 1 through 8 or 10, or a pharmaceutically acceptable salt or solvate thereof, wherein $R^1$ is

Compound 13: Any one of Compounds 1 through 8, or a pharmaceutically acceptable salt or solvate thereof, wherein ring A is a 5- or 6-membered heterocycloalkyl ring or a 4-, 5-, or 6-membered cycloalkyl ring optionally substituted with halogen, —CN, —N($R^{10}$)$_2$, $C_{1-6}$ alkyl, $C_{1-6}$ alkyl-OH, $C_{1-6}$ alkoxy, $C_{1-6}$ haloalkyl, or $C_{1-6}$ haloalkoxy.

Compound 14: Compound 13, or a pharmaceutically acceptable salt or solvate thereof, wherein $R^1$ is

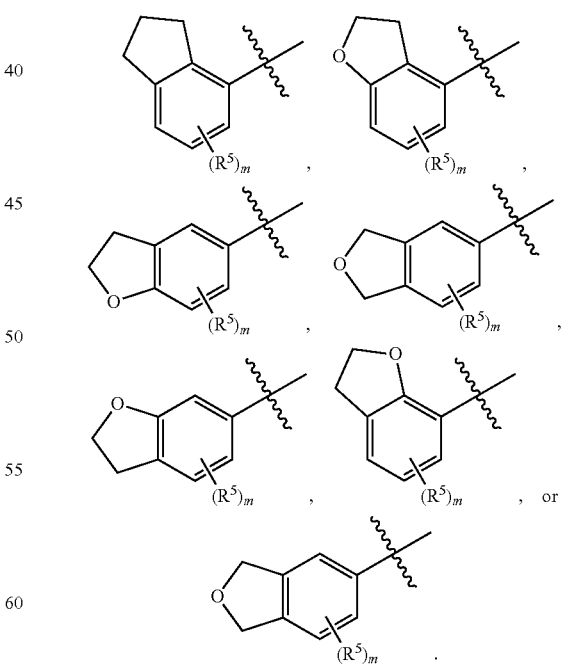

Compound 15: Any one of Compounds 1 through 7, or a pharmaceutically acceptable salt or solvate thereof, wherein $R^1$ is

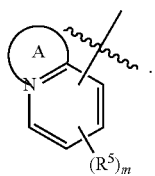

Compound 16: Compound 15, or a pharmaceutically acceptable salt or solvate thereof, wherein $R^1$ is

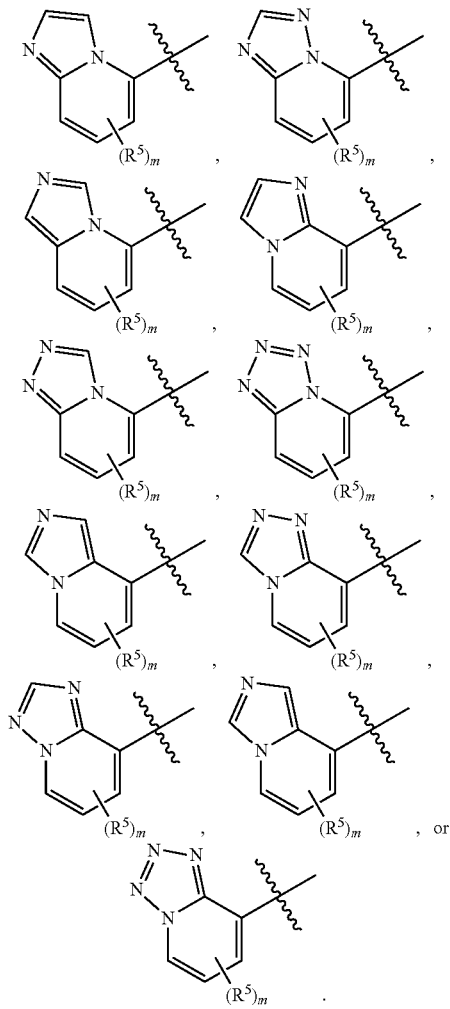

, or

Compound 17: Compound 15, or a pharmaceutically acceptable salt or solvate thereof, wherein $R^1$ is

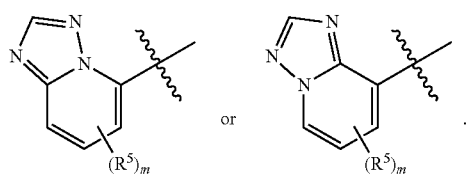

Compound 18: Any one of Compounds 1 through 17, or a pharmaceutically acceptable salt or solvate thereof, wherein m is 0.

Compound 19: Any one of Compounds 1 through 18, or a pharmaceutically acceptable salt or solvate thereof, wherein q is 0.

Compound 20: Any one of Compounds 1 through 19, or a pharmaceutically acceptable salt or solvate thereof, wherein X is a bond and Y is a bond.

Compound 21: Any one of Compounds 1 through 19, or a pharmaceutically acceptable salt or solvate thereof, wherein X is a bond and Y is —O—.

Compound 22: Any one of Compounds 1 through 16, or a pharmaceutically acceptable salt or solvate thereof, wherein X is a bond and Y is —N(H)—.

Compound 23: Any one of Compounds 1 through 20, or a pharmaceutically acceptable salt or solvate thereof, wherein X is —CH$_2$N(H)— and Y is a bond.

Compound 24: Any one of Compounds 1 through 20, or a pharmaceutically acceptable salt or solvate thereof, wherein X is —S(O)$_2$— and Y is a bond.

Compound 25: Any one of Compounds 1 through 24, or a pharmaceutically acceptable salt or solvate thereof, wherein each $R^2$ and each $R^3$ are H.

Compound 26: Any one of Compounds 1 through 25, or a pharmaceutically acceptable salt or solvate thereof, wherein n is 1, 2, or 3.

Compound 27: Compound 26, or a pharmaceutically acceptable salt or solvate thereof, wherein n is 3.

Compound 28: Compound 26, or a pharmaceutically acceptable salt or solvate thereof, wherein n is 2.

Compound 29: Compound 26, or a pharmaceutically acceptable salt or solvate thereof, wherein n is 1.

Compound 30: Any one of Compounds 1 through 29, or a pharmaceutically acceptable salt or solvate thereof, wherein $R^4$ is

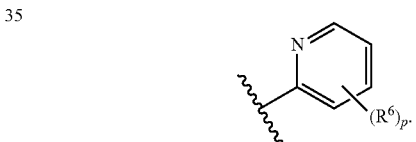

Compound 31: Any one of Compounds 1 through 29, or a pharmaceutically acceptable salt or solvate thereof, wherein $R^4$ is

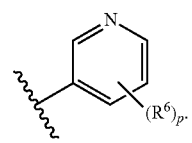

Compound 32: Any one of Compounds 1 through 29, or a pharmaceutically acceptable salt or solvate thereof, wherein $R^4$ is

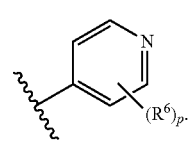

Compound 33: Any one of Compounds 1 through 29, or a pharmaceutically acceptable salt or solvate thereof, wherein $R^4$ is

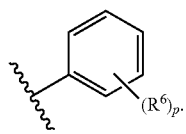

Compound 34: Any one of Compounds 1 through 33, or a pharmaceutically acceptable salt or solvate thereof, wherein each $R^6$ is independently selected from halogen, —CN, —N$(R^{10})_2$, and —S(O)$_2R^{11}$.

Compound 35: Any one of Compounds 1 through 34, or a pharmaceutically acceptable salt or solvate thereof, wherein each $R^6$ is independently selected from halogen and —CN.

Compound 36: Any one of Compounds 1 through 35, or a pharmaceutically acceptable salt or solvate thereof, wherein p is 1 or 2.

Compound 37: Compound 36, or a pharmaceutically acceptable salt or solvate thereof, wherein p is 2.

Compound 38: Compound 36, or a pharmaceutically acceptable salt or solvate thereof, wherein p is 1.

Compound 39: Any one of Compounds 1 through 33, or a pharmaceutically acceptable salt or solvate thereof, wherein p is 0.

Compound 40: Compound 1 selected from:

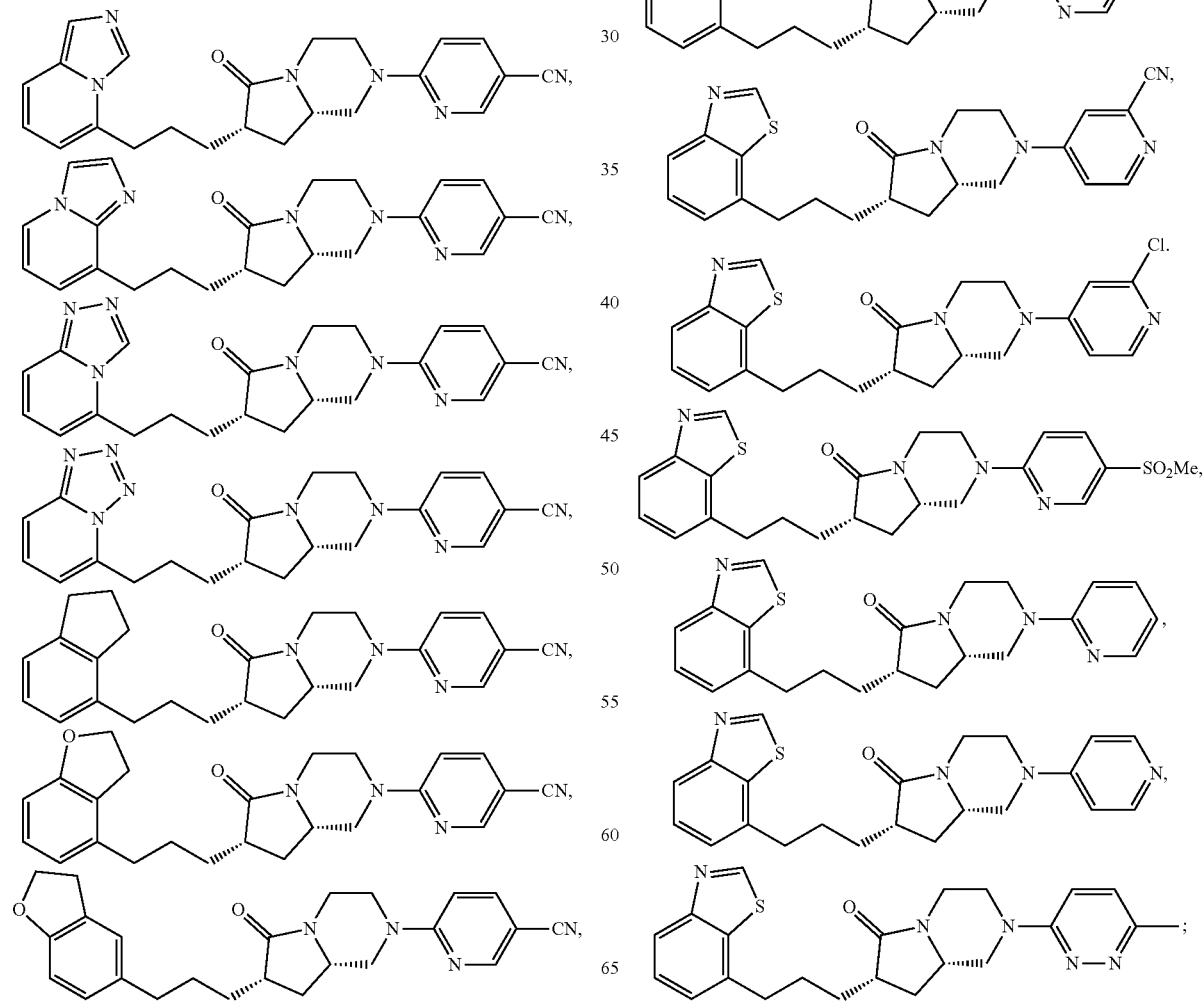

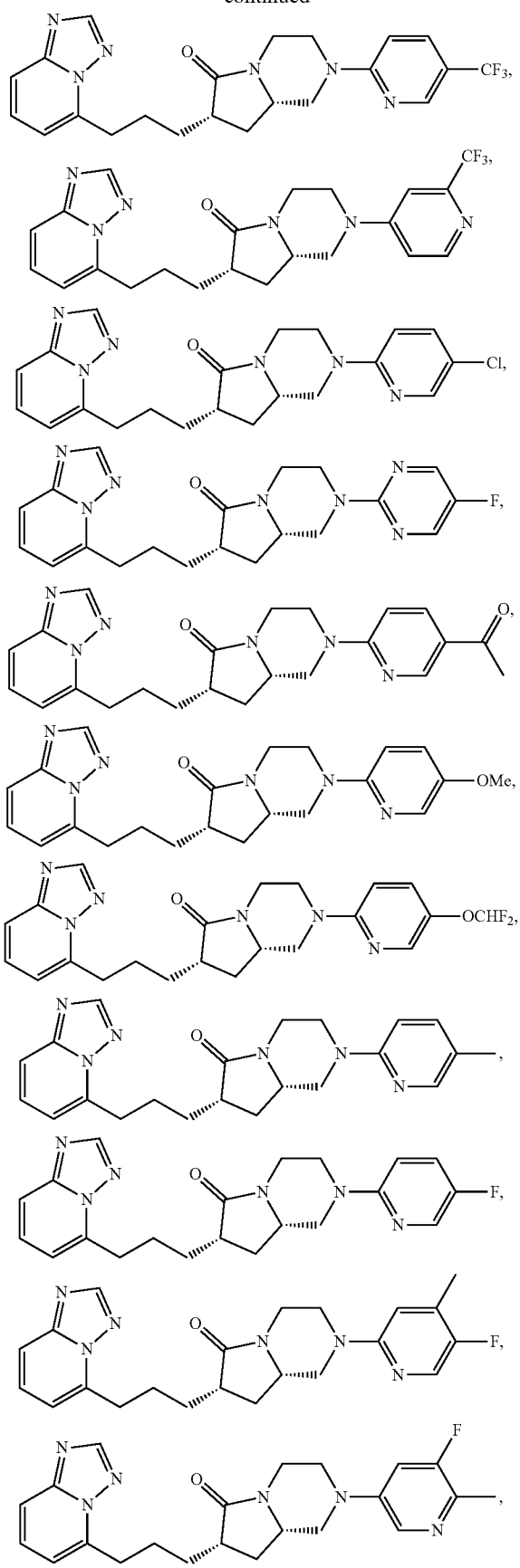
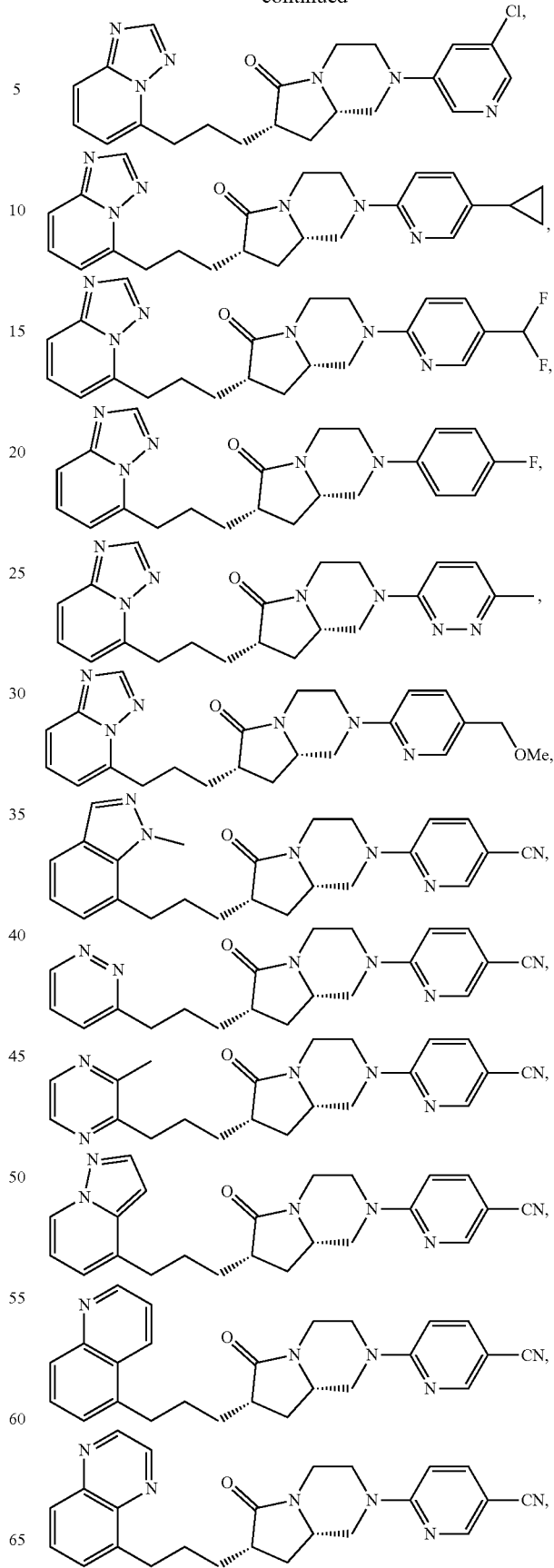

-continued
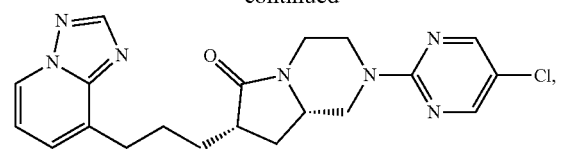
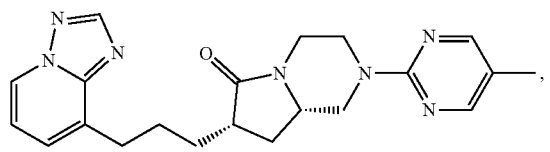
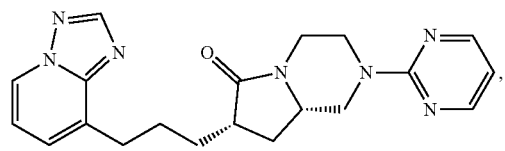
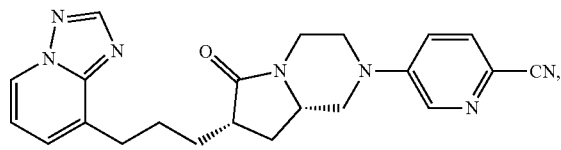
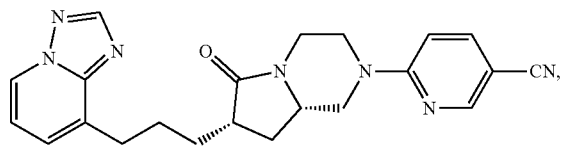
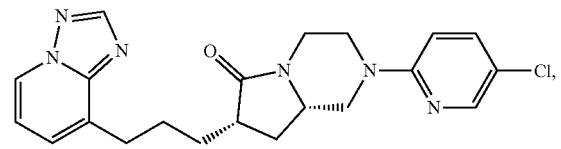
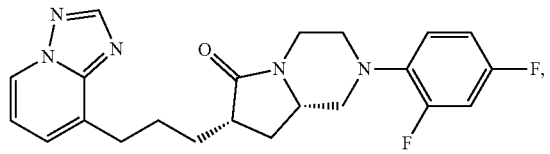
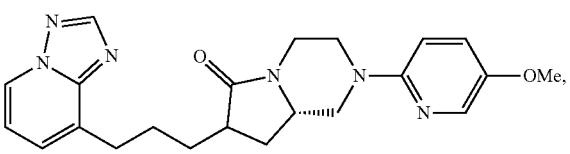
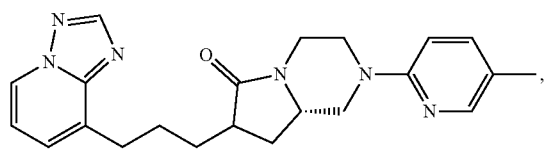
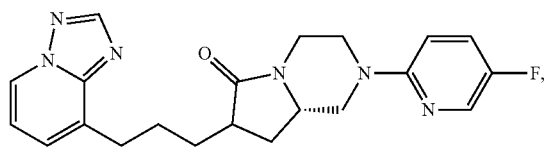
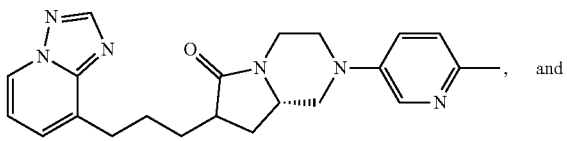, and
-continued
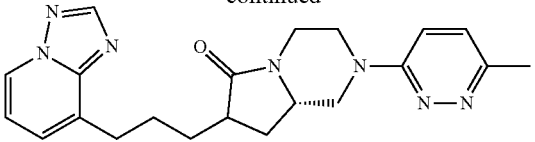
or a pharmaceutically acceptable salt or solvate thereof.
Compound 41: Compound 1 selected from:
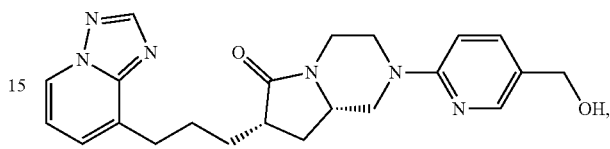
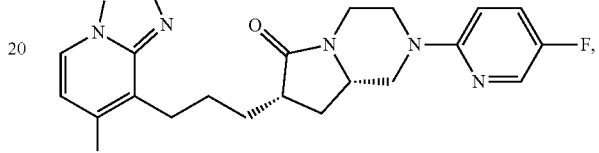
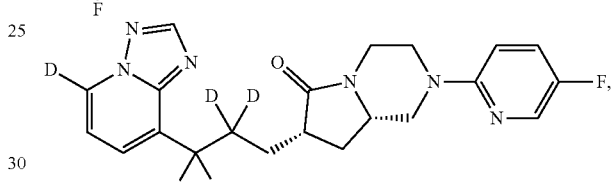
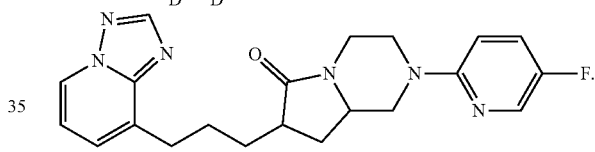
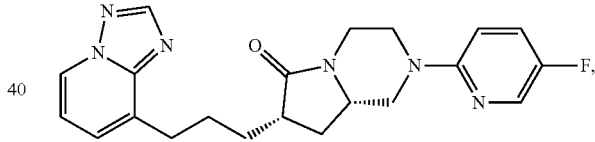
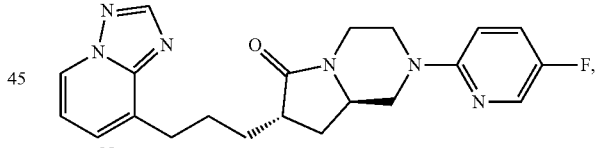
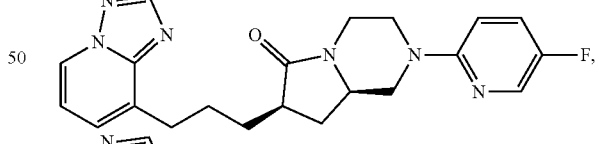
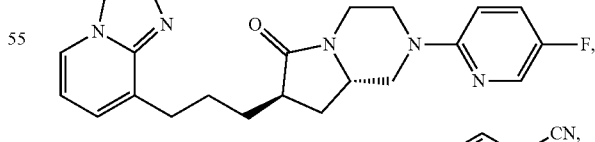
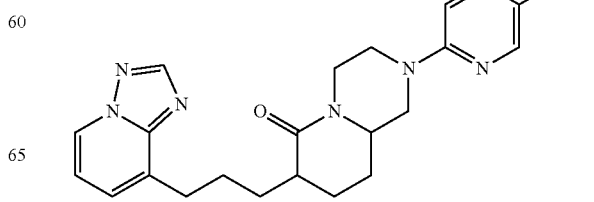

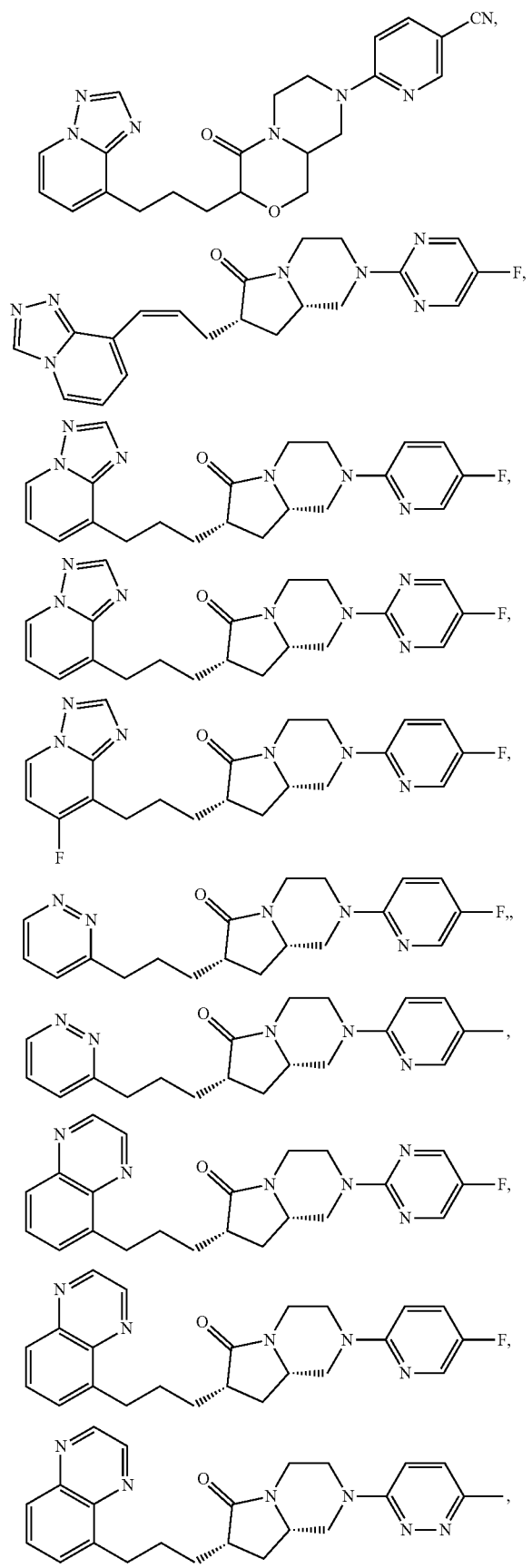
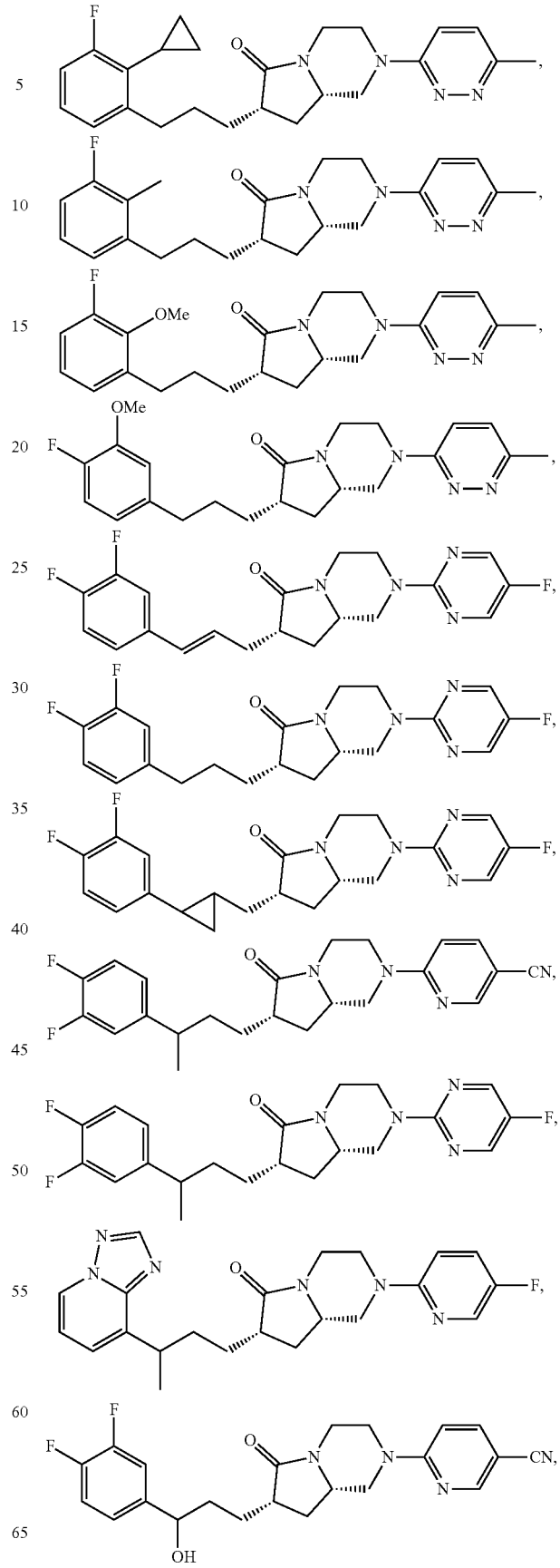

147
-continued
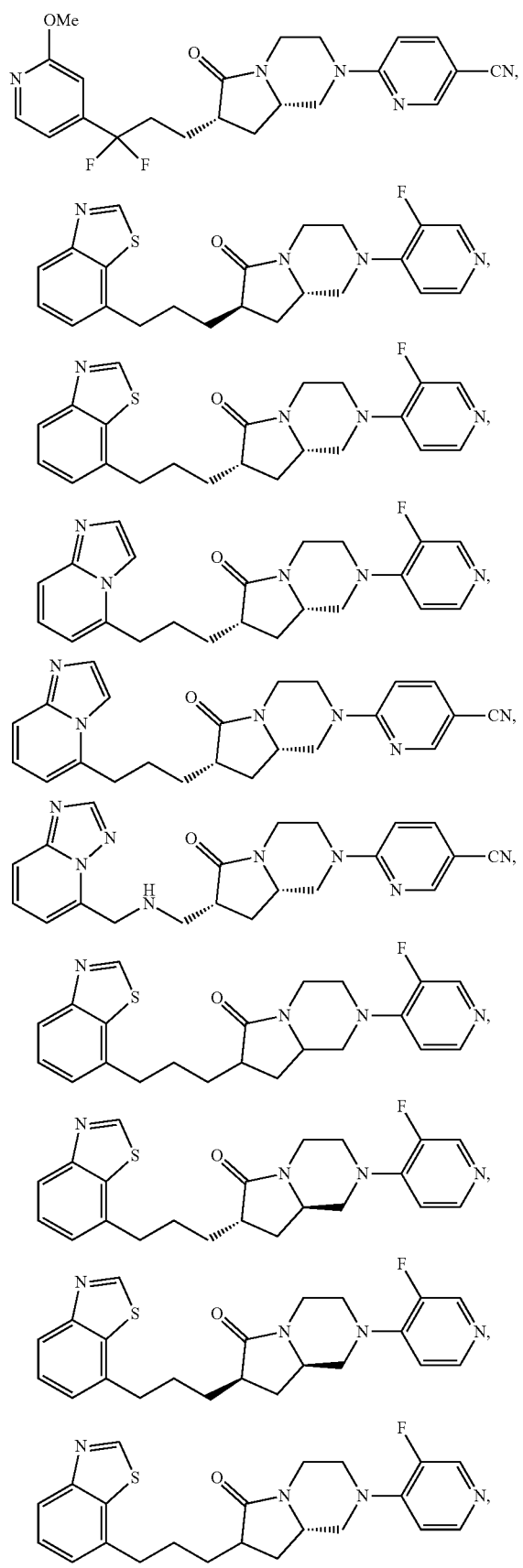
148
-continued
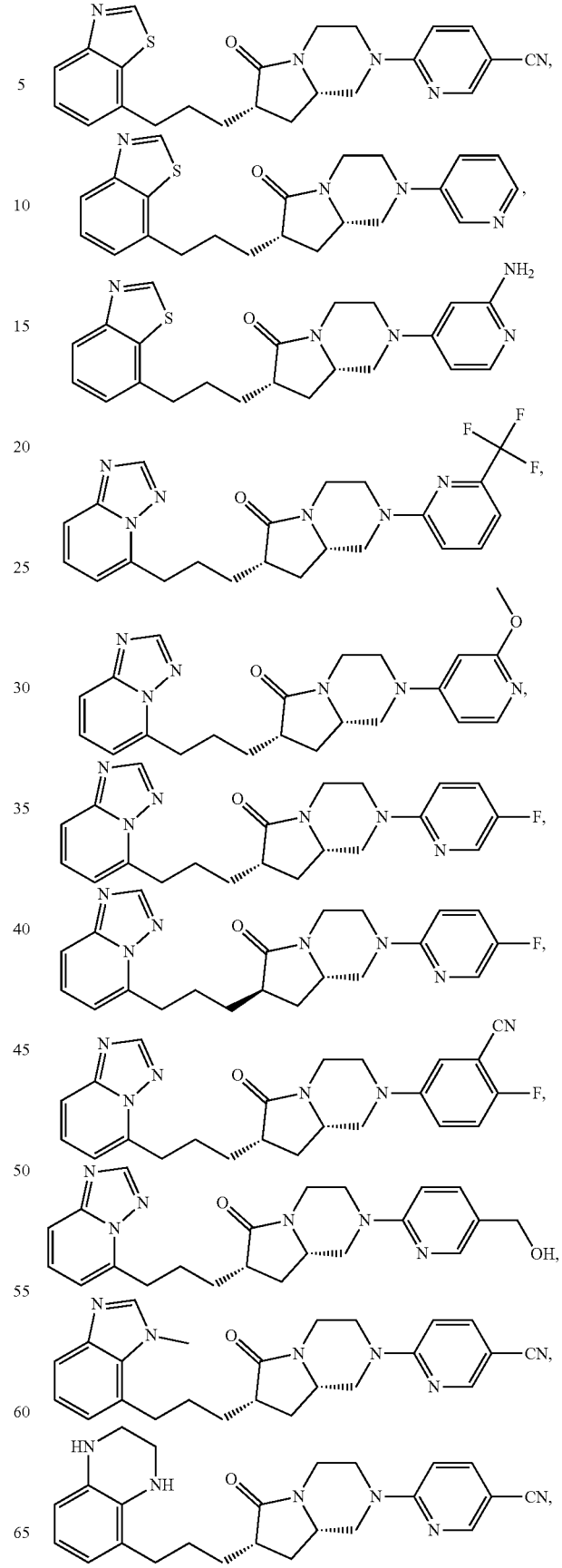

-continued

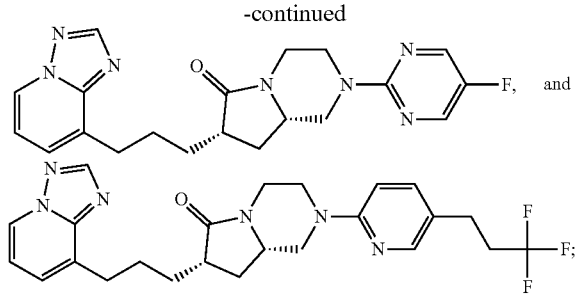

or a pharmaceutically acceptable salt or solvate thereof.

Compound 42: Compound 1 selected from:

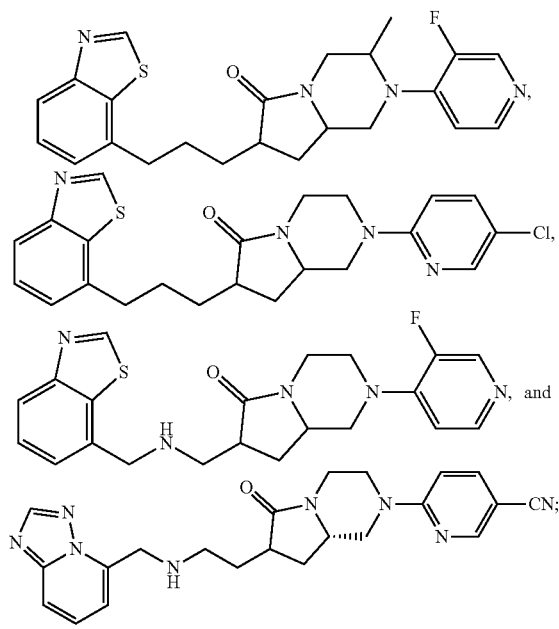

or a pharmaceutically acceptable salt thereof.

Pharmaceutical Composition 43: A pharmaceutical composition comprising any one of Compounds 1 through 42, or a pharmaceutically acceptable salt or solvate thereof, and at least one pharmaceutically acceptable excipient.

Method 44: A method of treating a neurodegenerative disorder in a subject in need thereof, comprising administering to the subject a therapeutically effective amount of any one of Compounds 1 through 42, or a pharmaceutically acceptable salt or solvate thereof.

Method 45: A method of treating a demyelinating disease in a subject in need thereof, comprising administering to the subject a therapeutically effective amount of any one of Compounds 1 through 42, or a pharmaceutically acceptable salt or solvate thereof.

Method 46: Method 45, wherein the demyelinating disease is a demyelinating disease of the central nervous system.

Method 47: Method 46, wherein the disease is multiple sclerosis.

Method 48: Method 45, wherein the demyelinating disease is a demyelinating disease of the peripheral nervous system.

Method 49: A method of treating a neuropathic disease, optionally a peripheral neuropathy, in a subject in need thereof, comprising administering to the subject a therapeutically effective amount of any one of Compounds 1 through 41, or a pharmaceutically acceptable salt or solvate thereof.

Method 50: Method 49, wherein the neuropathic disease is diabetic neuropathy.

Method 51: Any one of Methods 44 through 50, further comprising the administration of one or more immunomodulatory agents.

Method 52: Method 51, wherein the one or more immunomodulatory agents are selected from: an IFN-β 1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or FTY720 or other SIP1 functional modulator; a dimethyl fumarate; an antibody to the alpha subunit of the IL-2 receptor of T cells (CD25) or daclizumab; an antibody against CD52 or alemtuzumab; an antibody against CD20; and an inhibitor of a dihydroorotate dehydrogenase or teriflunomide.

Method 53: A method of modulating muscarinic acetylcholine receptor M1 activity in a subject comprising administering to the subject a any one of Compounds 1 through 41, or a pharmaceutically acceptable salt or solvate thereof.

Method 54: Method 53, wherein the compound acts as a selective M1 antagonist.

Compound 55: Compound 1, or a pharmaceutically acceptable salt or solvate thereof, wherein $R^4$ is

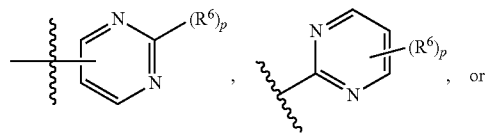

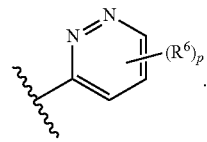

Any of the features of any of the exemplary compounds, pharmaceutical compositions, or methods is applicable to any or all other compounds, pharmaceutical compositions, or methods identified herein. Moreover, any of the features of the exemplary compounds, pharmaceutical compositions, or methods is independently combinable, partly or wholly, with other compounds, pharmaceutical compositions, or methods described herein in any way, e.g., the features of one, two, or three or more exemplary compounds, pharmaceutical compositions, or methods may be combinable in whole or in part. Further, any of the features of the exemplary compounds, pharmaceutical compositions, or methods may be made optional. Any method as described herein can be performed using any compound or composition described herein, and any compound or pharmaceutical composition described herein can be used to perform a method as described herein.

What is claimed is:

1. A compound of Formula (IA):

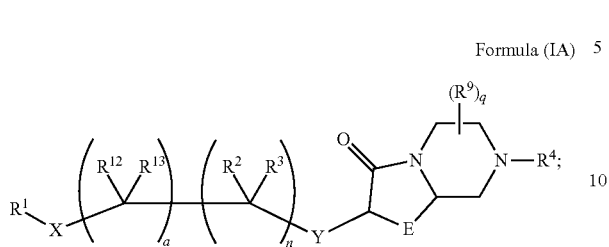

Formula (IA)

wherein:

E is —CH$_2$—, —CH$_2$CH$_2$—, —O—CH$_2$—, or —CH$_2$—O—;

X is a bond,

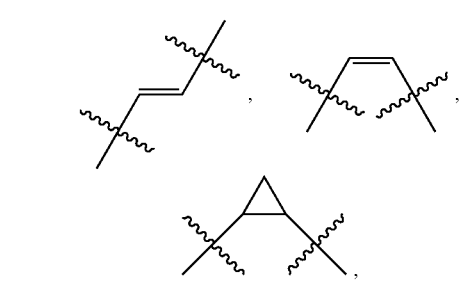

—C≡C—, —C(=O)—, —CH$_2$O—, —CH$_2$CH$_2$O—, —O—, —N(R$^7$)—, —S(O)$_2$—, —CH$_2$N(R$^7$)—, or —CH$_2$CH$_2$N(R$^7$)—;

Y is a bond, —O—, or —N(R$^8$)—;

R$^1$ is

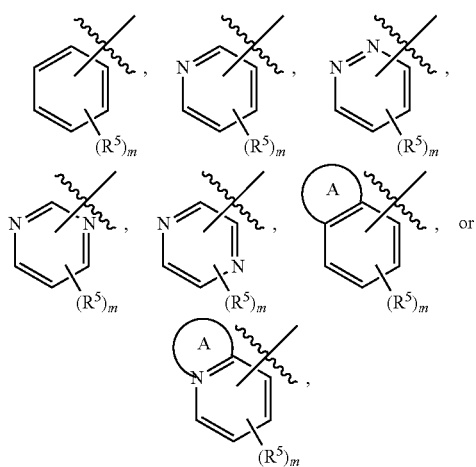

wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N(R$^{10}$)$_2$, C$_{1-6}$ alkyl, C$_{1-6}$ alkyl-OH, C$_{1-6}$ alkoxy, C$_{1-6}$ haloalkyl, or C$_{1-6}$ haloalkoxy;

each R$^2$ is independently selected from hydrogen, deuterium, halogen, —OH, and C$_{1-6}$ alkyl;

each R$^3$ is independently selected from hydrogen, deuterium, halogen, —OH, and C$_{1-6}$ alkyl;

R$^4$ is

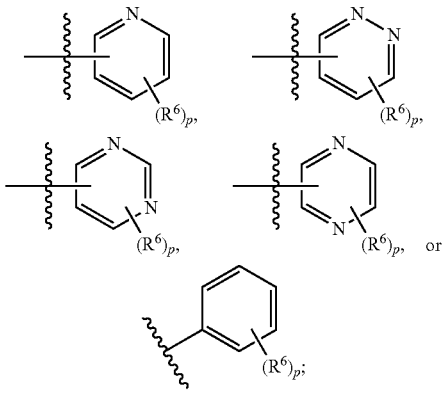

each R$^5$ is independently selected from halogen, —CN, C$_{1-6}$ alkyl, C$_{1-6}$ cycloalkyl, C$_{1-6}$ alkoxy, C$_{1-6}$ haloalkyl, and C$_{1-6}$ haloalkoxy;

each R$^6$ is independently selected from deuterium, halogen, —CN, —N(R$^{10}$)$_2$, C$_{1-6}$ alkyl, C$_{1-6}$ alkyl-OH, C$_{3-6}$ cycloalkyl, C$_{1-6}$ alkoxy, C$_{1-6}$ haloalkyl, C$_{1-6}$ haloalkoxy, —C(=O)(C$_{1-6}$ alkyl), —(C(R$^{10}$)$_2$)$_q$—O—(C$_{1-6}$ alkyl) and —S(O)$_2$R$^{11}$;

R$^7$ is hydrogen or C$_{1-6}$ alkyl;

R$^8$ is hydrogen or C$_{1-6}$ alkyl;

each R$^9$ is independently C$_{1-6}$ alkyl;

each R$^{10}$ is independently selected from H and C$_{1-6}$ alkyl;

R$^{11}$ is C$_{1-6}$ alkyl;

each R$^{12}$ is independently selected from hydrogen, deuterium, halogen, —OH, and C$_{1-6}$ alkyl;

each R$^{13}$ is independently selected from hydrogen, deuterium, halogen, —OH, and C$_{1-6}$ alkyl;

a is 1, 2, 3, 4, or 5;

m is 0, 1, 2, or 3;

n is 1, 2, 3, 4, or 5;

p is 0, 1, 2, or 3; and each q is independently 0, 1, 2, 3, or 4;

or a pharmaceutically acceptable salt or solvate thereof.

2. A compound of Formula (Ib):

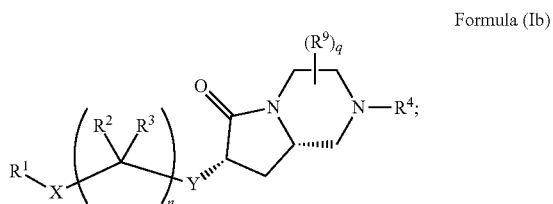

Formula (Ib)

wherein:

X is a bond,

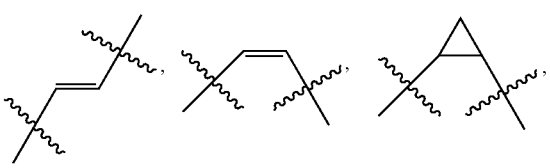

—C≡C—, —C(═O)— —CH₂O—, —CH₂CH₂O—, —O—, —N(R⁷)—, —S(O)₂—, —CH₂N(R⁷)—, or —CH₂CH₂N(R⁷)—;

Y is a bond, —O—, or —N(R⁸)—;

R¹ is

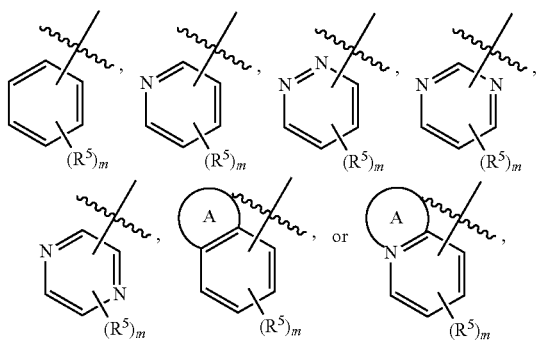

wherein ring A is a 5- or 6-membered heteroaryl ring, a 5- or 6-membered heterocycloalkyl ring, or a 4-, 5-, or 6-membered cycloalkyl ring, wherein ring A is optionally substituted with halogen, —CN, —N(R¹⁰)₂, C₁₋₆ alkyl, C₁₋₆ alkyl-OH, C₁₋₆ alkoxy, C₁₋₆ haloalkyl, or C₁₋₆ haloalkoxy;

each R² is independently selected from hydrogen, deuterium, halogen, —OH, and C₁₋₆ alkyl;

each R³ is independently selected from hydrogen, deuterium, halogen, —OH, and C₁₋₆ alkyl;

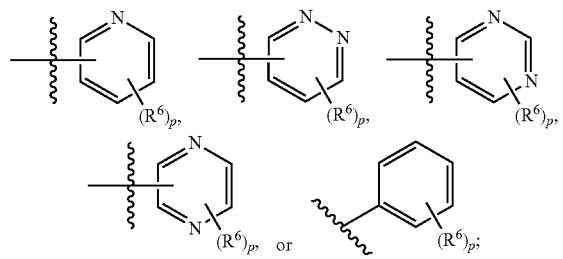

R⁴ is each R⁵ is independently selected from halogen, —CN, C₁₋₆ alkyl, C₃₋₆ cycloalkyl, C₁₋₆ alkoxy, C₁₋₆ haloalkyl, and C₁₋₆ haloalkoxy;

each R⁶ is independently selected from deuterium, halogen, —CN, —N(R¹⁰)₂, C₁₋₆ alkyl, C₁₋₆ alkyl-OH, C₃₋₆ cycloalkyl, C₁₋₆ alkoxy, C₁₋₆ haloalkyl, C₁₋₆ haloalkoxy, —C(═O)(C₁₋₆ alkyl), —(C(R¹⁰)₂)_q—O—(C₁₋₆ alkyl) and —S(O)₂R¹¹;

R⁷ is hydrogen or C₁₋₆ alkyl;

R⁸ is hydrogen or C₁₋₆ alkyl;

each R⁹ is independently C₁₋₆ alkyl;

each R¹⁰ is independently selected from H and C₁₋₆ alkyl;

R¹¹ is C₁₋₆ alkyl;

m is 0, 1, 2, or 3;

n is 1, 2, 3, 4, or 5;

p is 0, 1, 2, or 3; and each q is independently 0, 1, 2, 3, or 4;

or a pharmaceutically acceptable salt or solvate thereof.

3. The compound of claim 1, or a pharmaceutically acceptable salt or solvate thereof, wherein R¹ is

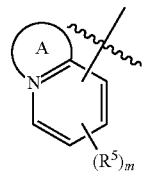

4. The compound of claim 3, or a pharmaceutically acceptable salt or solvate thereof, wherein R¹ is

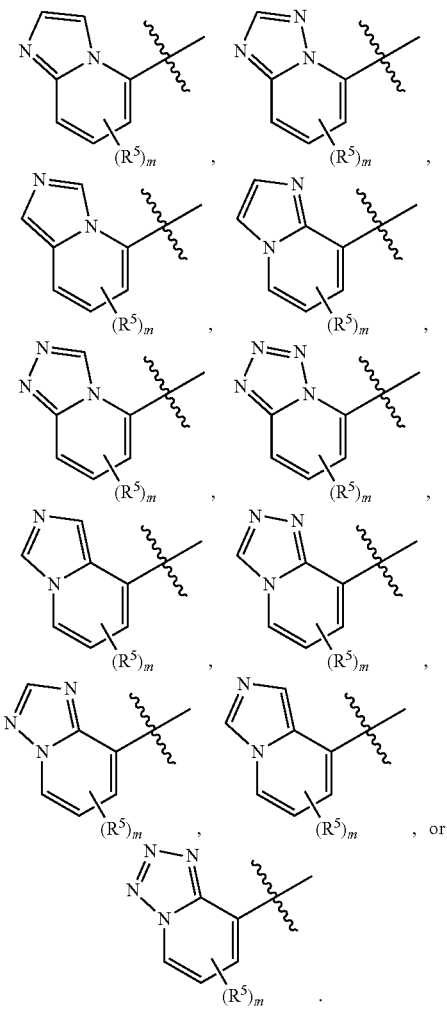

5. The compound of claim 3, or a pharmaceutically acceptable salt or solvate thereof, wherein R¹ is

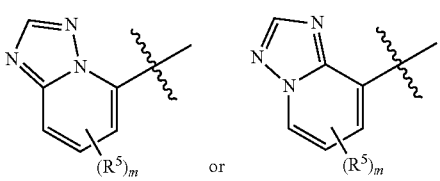

6. The compound of claim 1, or a pharmaceutically acceptable salt or solvate thereof, wherein m is 0.

7. The compound of claim 1, or a pharmaceutically acceptable salt or solvate thereof, wherein q is 0.

8. The compound of claim 1, or a pharmaceutically acceptable salt or solvate thereof, wherein X is a bond and Y is a bond.

9. The compound of claim 1, or a pharmaceutically acceptable salt or solvate thereof, wherein each $R^2$ and each $R^3$ are H.

10. The compound of claim 1, or a pharmaceutically acceptable salt or solvate thereof, wherein n is 3.

11. The compound of claim 1, or a pharmaceutically acceptable salt or solvate thereof, wherein $R^4$ is

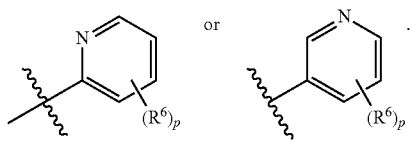

12. The compound of claim 1, or a pharmaceutically acceptable salt or solvate thereof, wherein each $R^6$ is independently selected from halogen and —CN.

13. The compound of claim 1, or a pharmaceutically acceptable salt or solvate thereof, wherein p is 1.

14. The compound of claim 1, selected from:

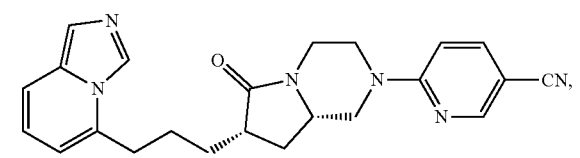

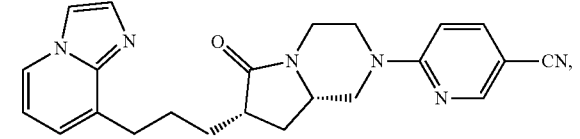

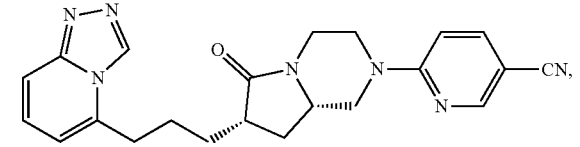

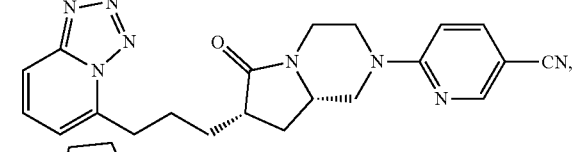

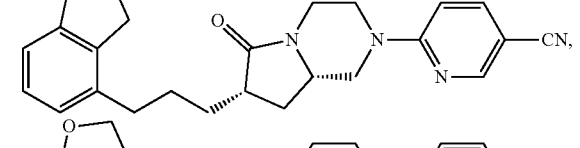

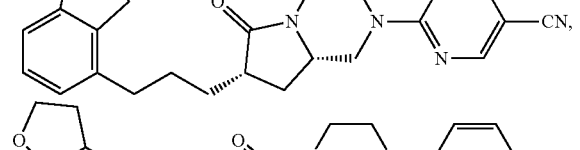

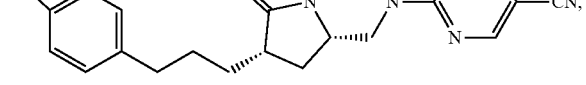

-continued

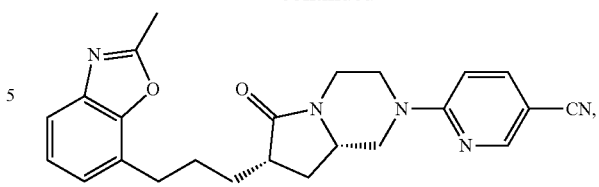

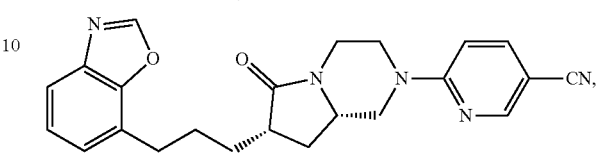

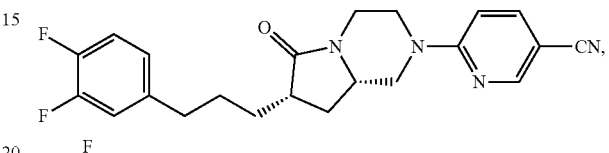

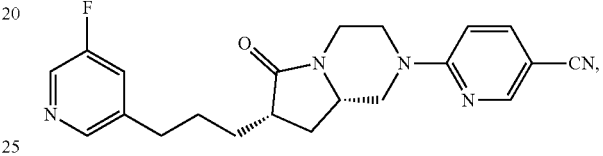

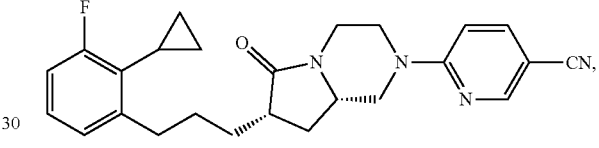

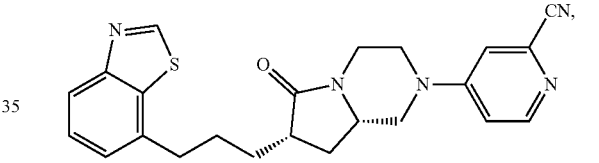

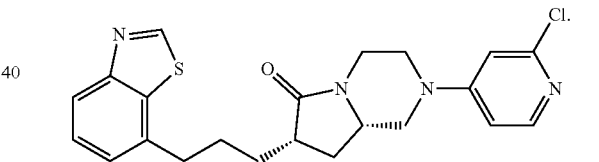

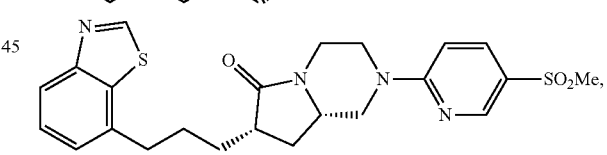

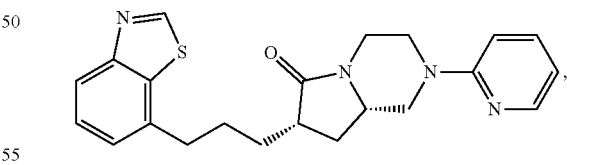

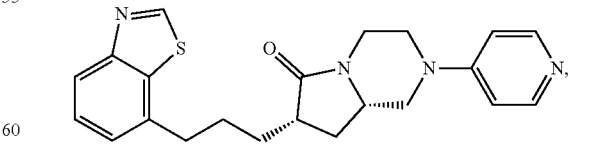

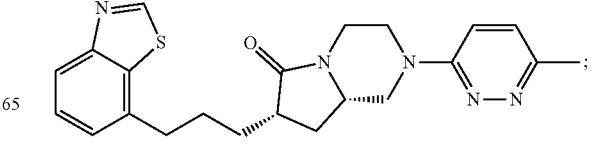

157
-continued
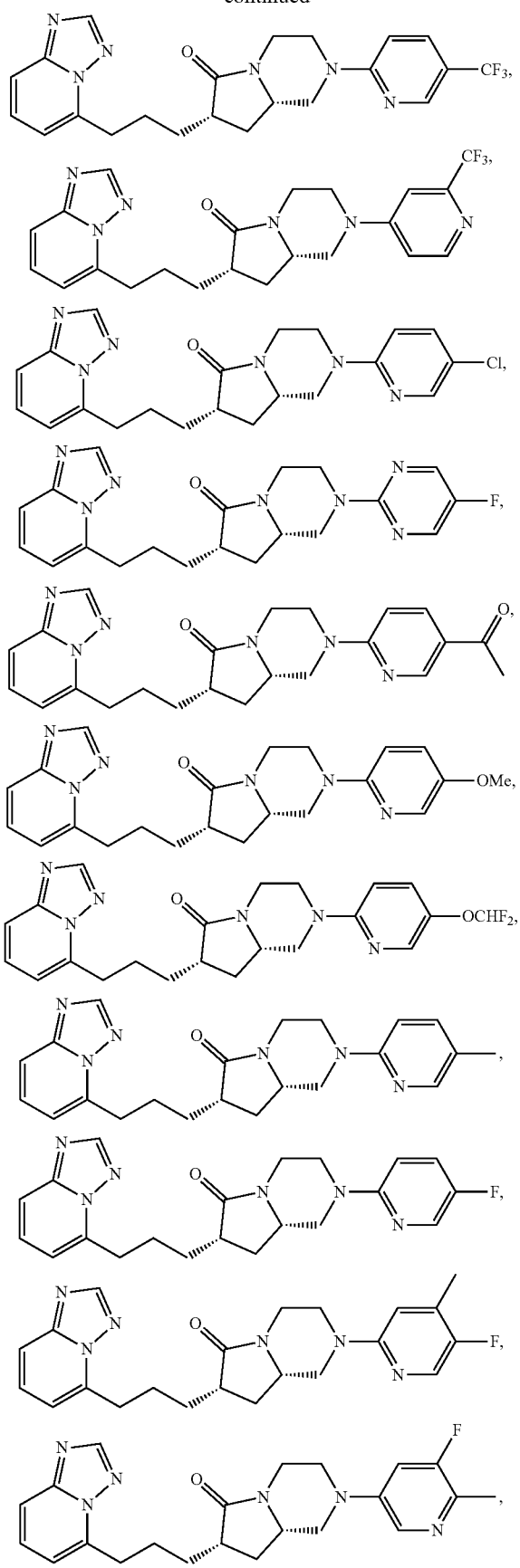
158
-continued
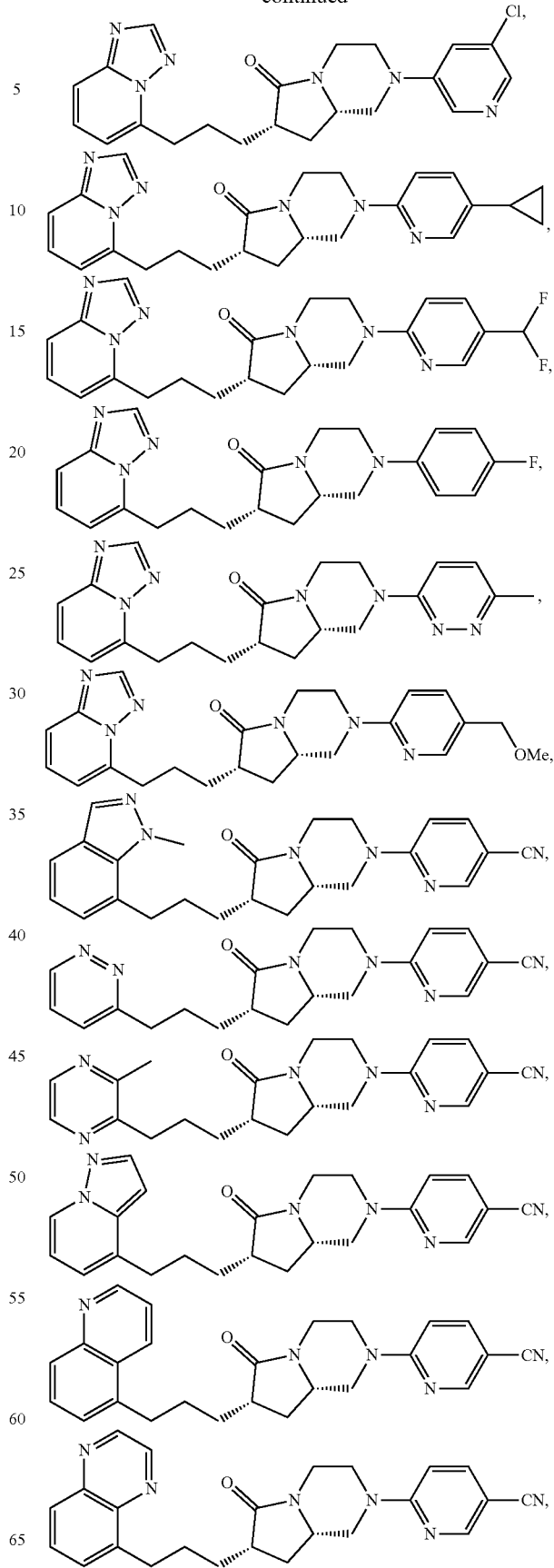

-continued
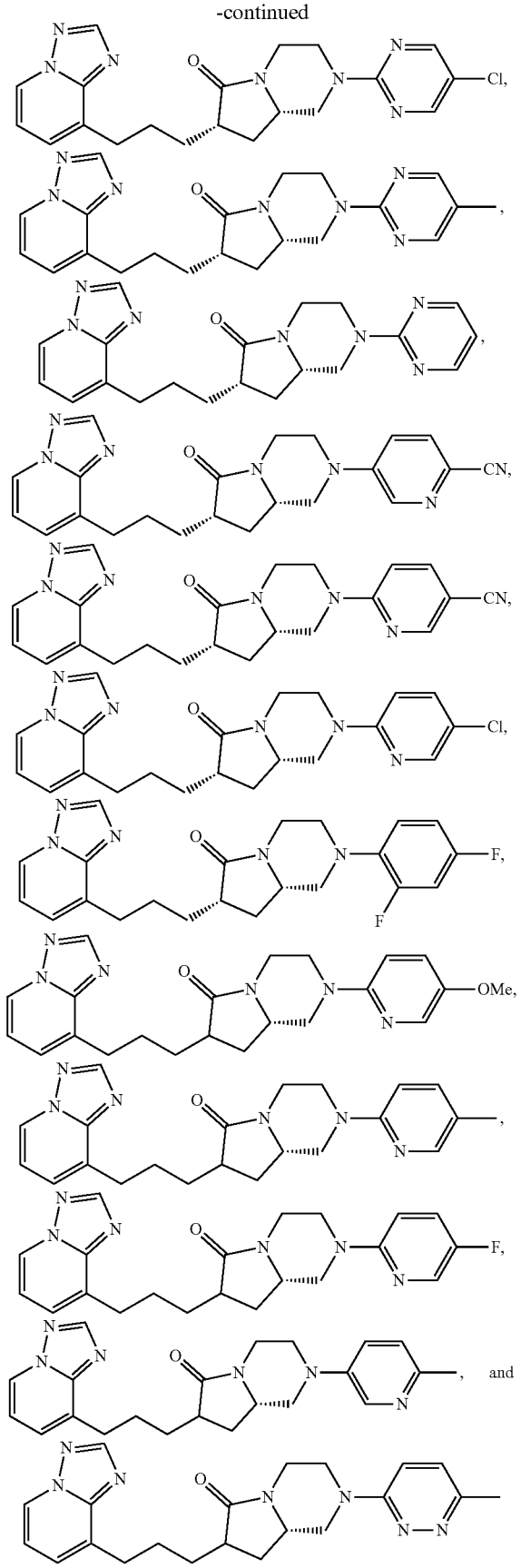
or a pharmaceutically acceptable salt or solvate thereof.
15. A compound, selected from:
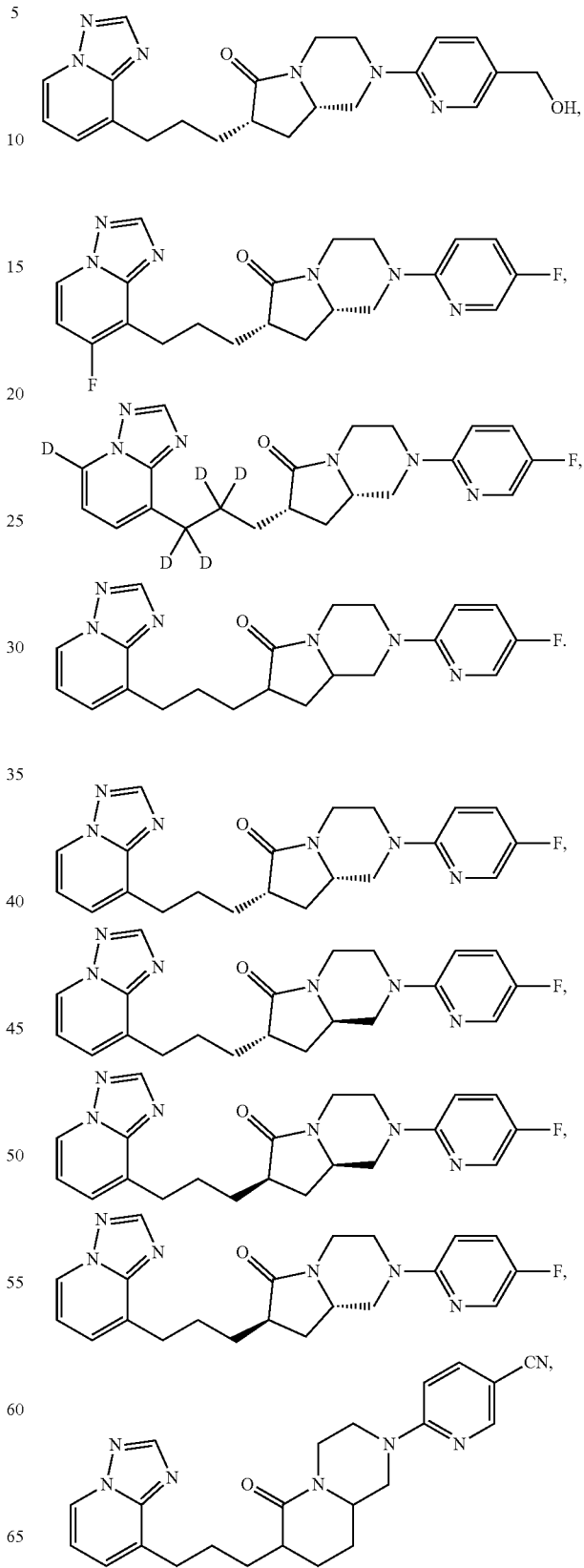

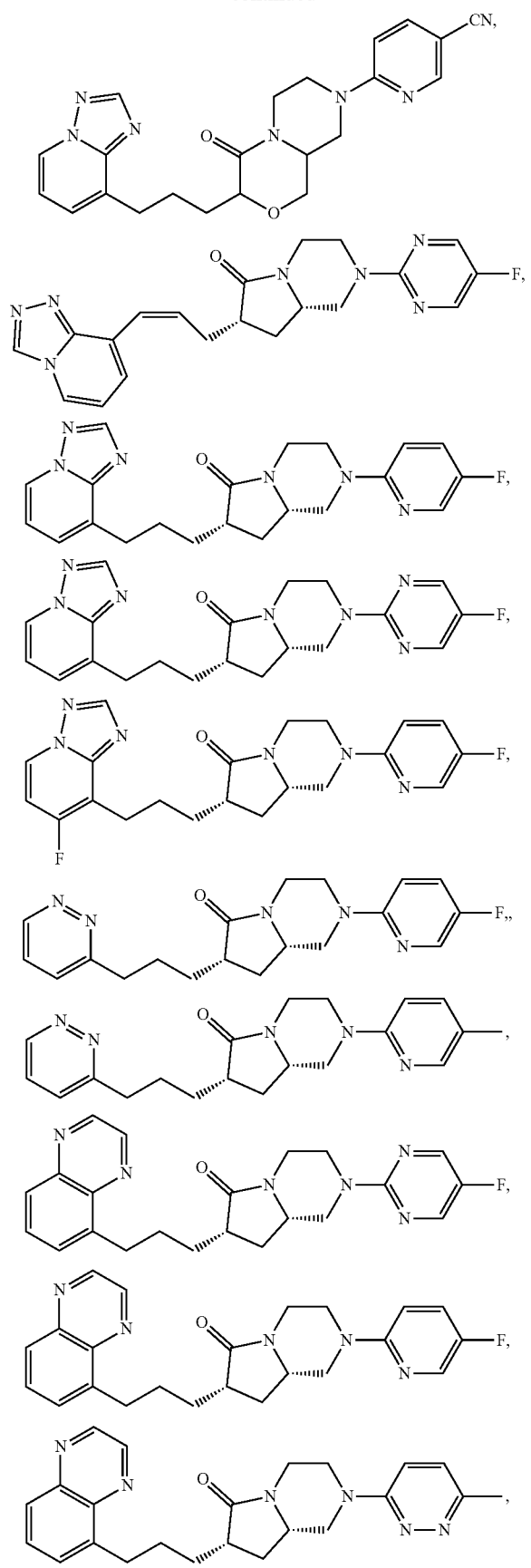
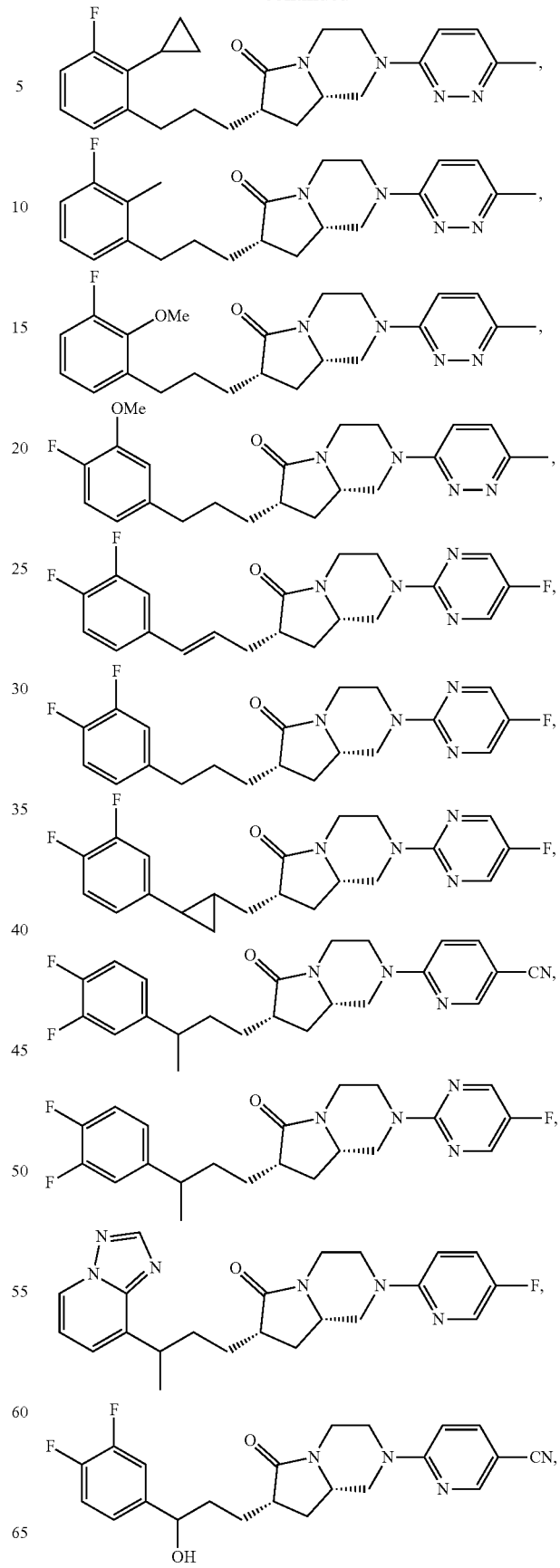

163
-continued
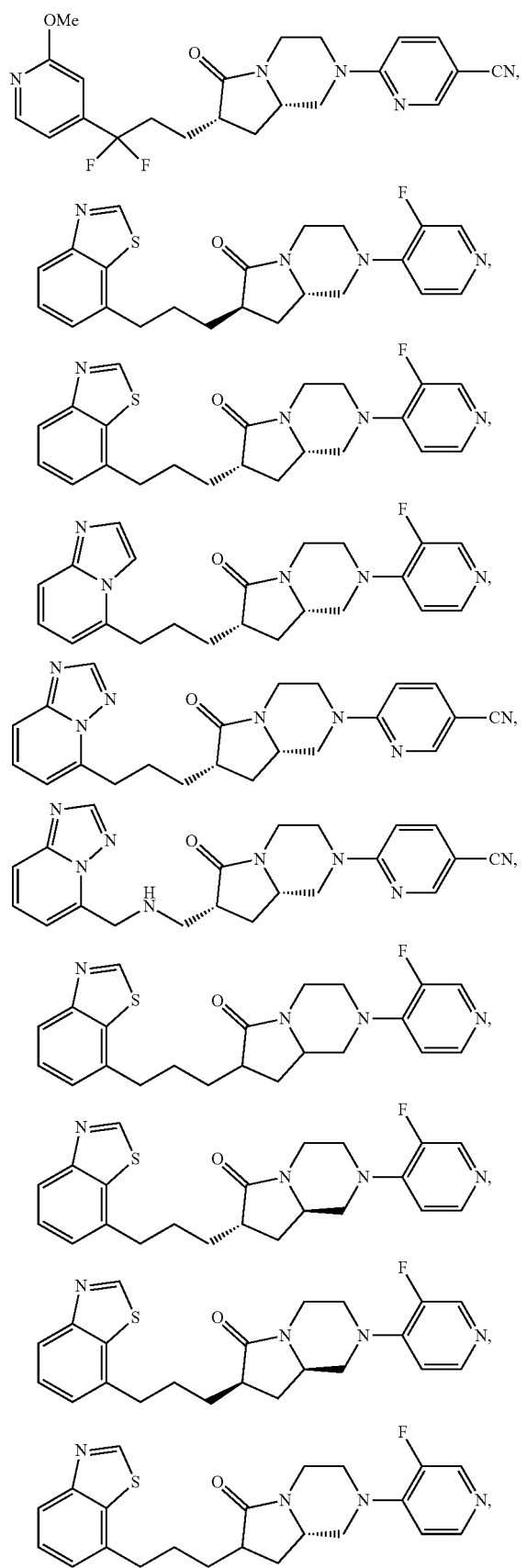
164
-continued
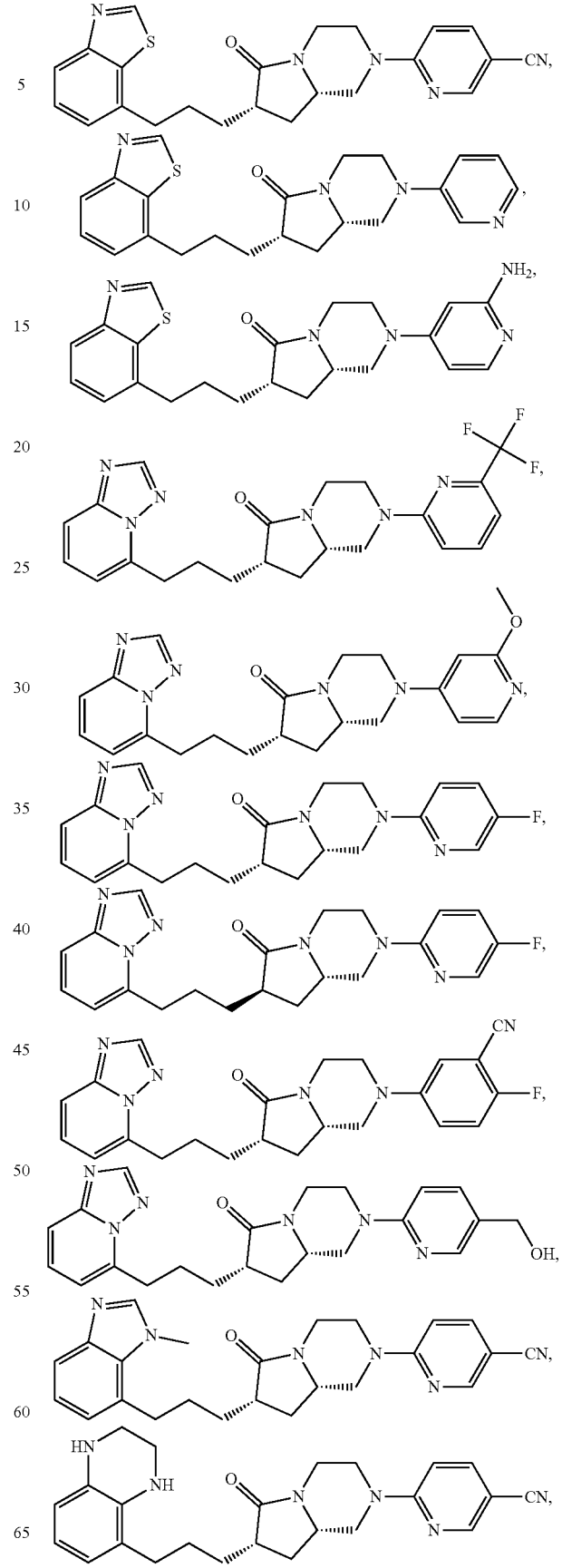

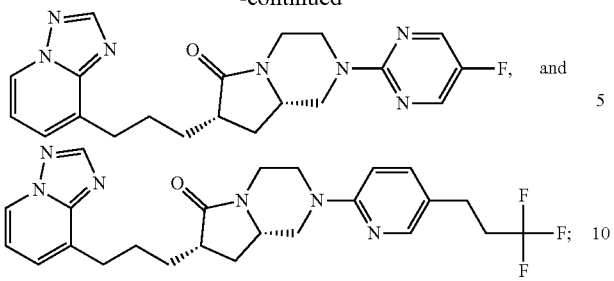

or a pharmaceutically acceptable salt or solvate thereof.

16. A pharmaceutical composition comprising a compound of claim 1, or a pharmaceutically acceptable salt or solvate thereof, and at least one pharmaceutically acceptable excipient.

17. A method of modulating muscarinic acetylcholine receptor $M_1$ activity in a subject comprising administering to the subject a compound of claim 1, or a pharmaceutically acceptable salt or solvate thereof.

18. The method of claim 17, wherein the compound acts as a selective $M_1$ antagonist.

* * * * *